US012558435B2

(12) United States Patent
Genovese et al.

(10) Patent No.: US 12,558,435 B2
(45) Date of Patent: Feb. 24, 2026

(54) TRANSIENT INHIBITION OF P53 IN GENE THERAPY

(71) Applicants: Ospedale San Raffaele S.R.L., Milan (IT); Fondazione Telethon, Rome (IT)

(72) Inventors: Pietro Genovese, Milan (IT); Giulia Schiroli, Milan (IT); Luigi Naldini, Milan (IT); Aurelien Jacob, Milan (IT); Samuele Ferrari, Milan (IT)

(73) Assignees: Ospedale San Raffaele S.R.L., Milan (IT); Fondazione Telethon ETS, Rome (IT)

(*) Notice: Subject to any disclaimer, the term of this patent is extended or adjusted under 35 U.S.C. 154(b) by 1175 days.

(21) Appl. No.: 17/255,362

(22) PCT Filed: Jun. 25, 2019

(86) PCT No.: PCT/EP2019/066915
§ 371 (c)(1),
(2) Date: Dec. 22, 2020

(87) PCT Pub. No.: WO2020/002380
PCT Pub. Date: Jan. 2, 2020

(65) Prior Publication Data
US 2021/0260216 A1 Aug. 26, 2021

(30) Foreign Application Priority Data

Jun. 25, 2018 (EP) .................................... 18305807

(51) Int. Cl.
A61K 48/00 (2006.01)
C07K 14/005 (2006.01)
C12N 15/86 (2006.01)
C12N 15/90 (2006.01)

(52) U.S. Cl.
CPC .......... A61K 48/005 (2013.01); C07K 14/005 (2013.01); C12N 15/86 (2013.01); C12N 15/907 (2013.01); C12N 2310/20 (2017.05); C12N 2710/10022 (2013.01); C12N 2750/14143 (2013.01)

(58) Field of Classification Search
CPC .......... C12N 15/86; C12N 2750/14143; C12N 2510/00; C07K 14/4746
See application file for complete search history.

(56) References Cited

U.S. PATENT DOCUMENTS

| | | | |
|---|---|---|---|
| 4,797,368 A | 1/1989 | Carter et al. | |
| 5,139,941 A | 8/1992 | Muzyczka et al. | |
| 8,586,354 B2 | 11/2013 | Holm | |
| 8,951,772 B2 | 2/2015 | Holm | |
| 10,155,930 B2 | 12/2018 | Holm | |
| 10,300,096 B2 | 5/2019 | Holm | |
| 10,519,425 B2 | 12/2019 | Yamanaka et al. | |

| | | | |
|---|---|---|---|
| 2016/0333377 A1 | 11/2016 | Scharenberg et al. | |
| 2018/0245065 A1* | 8/2018 | Ihry .................. | C07K 14/4746 |
| 2019/0175764 A1 | 6/2019 | Kajaste-Rudnitski et al. | |

FOREIGN PATENT DOCUMENTS

| | | |
|---|---|---|
| CN | 1655827 A | 8/2005 |
| CN | 101843641 A | 9/2010 |
| WO | WO-98/01563 A2 | 1/1998 |
| WO | WO-98/05635 A1 | 2/1998 |
| WO | WO-98/07859 A2 | 2/1998 |
| WO | WO-98/09985 A2 | 3/1998 |
| WO | WO-98/17815 A1 | 4/1998 |
| WO | WO-03/099859 A2 | 12/2003 |
| WO | WO-2004/035616 A2 | 4/2004 |
| WO | WO-2005/051430 A1 | 6/2005 |
| WO | WO-2005/052143 A2 | 6/2005 |
| WO | WO-2013/176233 A1 | 11/2013 |
| WO | WO-2016/183345 A1 | 11/2016 |
| WO | WO-2018/083606 A1 | 5/2018 |

OTHER PUBLICATIONS

Dai C, Gu W. p53 post-translational modification: deregulated in tumorigenesis. Trends Mol Med. Nov. 2010; 16(11):528-36. doi: 10.1016/j.molmed.2010.09.002. PMID: 20932800; PMCID: PMC2978905. (Year: 2010).*

Mittelman JM, Gudkov AV. Generation of p53 suppressor peptide from the fragment of p53 protein. Somat Cell Mol Genet. May 1999;25(3):115-28. doi: 10.1023/a:1018822121890. PMID: 11441532. (Year: 1999).*

Ossovskaya VS, Mazo IA, Chernov MV, Chernova OB, Strezoska Z, Kondratov R, Stark GR, Chumakov PM, Gudkov AV. Use of genetic suppressor elements to dissect distinct biological effects of separate p53 domains. Proc Natl Acad Sci U S A. Sep. 17, 1996; 93(19):10309-14. (Year: 1996).*

Thai M, Graham NA, Braas D, Nehil M, Komisopoulou E, Kurdistani SK, McCormick F, Graeber TG, Christofk HR. Adenovirus E4ORF1-induced MYC activation promotes host cell anabolic glucose metabolism and virus replication. Cell Metab. Apr. 1, 2014;19(4):694-701. (Year: 2014).*

Soussi T, Caron de Fromentel C, Breugnot C, May E. Nucleotide sequence of a cDNA encoding the rat p53 nuclear oncoprotein. Nucleic Acids Res. Dec. 9, 1988;16(23):11384. doi: 10.1093/nar/16.23.11384. PMID: 3060862; PMCID: PMC339034. (Year: 1988).*

Aiuti et al., Gene therapy for immunodeficiency due to adenosine deaminase deficiency, N. Engl. J. Med., 360(5):447-58 (Jan. 2009).

Aiuti et al., Lentiviral hematopoietic stem cell gene therapy in patients with Wiskott-Aldrich syndrome, Science, 341(6148):1233151 (Aug. 2013).

(Continued)

Primary Examiner — Fereydoun G Sajjadi
Assistant Examiner — Qinhua Gu
(74) Attorney, Agent, or Firm — MARSHALL, GERSTEIN & BORUN LLP

(57) ABSTRACT

An agent which promotes homology directed DNA repair for use in haematopoietic stem and/or progenitor cell gene therapy, wherein said haematopoietic stem cells are gene edited. Use of an agent which promotes homology directed DNA repair, for increasing the survival and/or engraftment of gene edited haematopoietic stemand/or progenitorcells or for increasing the efficiency of gene editing of haematopoietic stem and/or progenitor cells.

16 Claims, 58 Drawing Sheets

Specification includes a Sequence Listing.

(56)                    References Cited

OTHER PUBLICATIONS

Ausubel et al. (eds.), Short Protocols in Molecular Biology, Third Edition, John Wiley & Sons, Inc. (1995).

Biffi et al., Lentiviral hematopoietic stem cell gene therapy benefits metachromatic leukodystrophy, Science, 341(6148):1233158 (Aug. 2013).

Boztug et al., Stem-cell gene therapy for the Wiskott-Aldrich syndrome, N. Engl. J. Med., 363(20):1918-27 (Nov. 2010).

Butler et al., Integrating single-cell transcriptomic data across different conditions, technologies, and species, Nat. Biotechnol., 36(5):411-20 (Jun. 2018).

Cartier et al., Hematopoietic stem cell gene therapy with a lentiviral vector in X-linked adrenoleukodystrophy, Science, 326(5954):818-23 (Nov. 2009).

Chang et al., The genetic engineering of hematopoietic stem cells: the rise of lentiviral vectors, the conundrum of the LTR, and the promise of lineage-restricted vectors, Mol. Ther., 15(3):445-56 (Mar. 2007).

Coffin et al., Retorviruses, Cold Spring Harbor Laboratory Press, pp. 758-763 (1997).

Dahlman et al., Orthogonal gene knockout and activation with a catalytically active Cas9 nuclease, Nat. Biotechnol., 33(11):1159-61 (2015).

Diez et al., Therapeutic gene editing in CD34 + hematopoietic progenitors from Fanconi anemia patients, EMBO Mol. Med., 9(11):1574-88 (Nov. 2017).

Elbashir et al., Functional anatomy of siRNAs for mediating efficient RNAi in *Drosophila melanogaster* embryo lysate, EMBO J., 20(23):6877-88 (Dec. 2001).

Esvelt et al., Orthogonal Cas9 proteins for RNA-guided gene regulation and editing, Nat. Methods, 10(11):1116-21 (2013).

Fares et al., Integrating single-cell transcriptomic data across different conditions, technologies, and species, Blood, 129(25):3344-51 (Jun. 2017).

Finak et al., MAST: a flexible statistical framework for assessing transcriptional changes and characterizing heterogeneity in single-cell RNA sequencing data, Genome Biol., 16:278 (Dec. 2015).

Fragkos et al., H2AX is required for cell cycle arrest via the p53/p21 pathway, Mol. Cell Biol., 29(10):2828-40 (May 2009).

Gait (ed.), Oligonucleotide Synthesis: A Practical Approach, Oxford, England: IRL Press Limited (1984).

Gaj et al, ZFN, TALEN and CRISPR/Cas-based methods for genome engineering, Trends Biotechnol., vol. 31, pp. 397-405 (2013).

Gwiazda et al., High Efficiency CRISPR/Cas9-mediated Gene Editing in Primary Human T-cells Using Mutant Adenoviral E4orf6/E1b55k "Helper" Proteins, Mol. Ther., 24(9):1570-80 (Sep. 2016).

Haapaniemi et al., CRISPR-Cas9 genome editing induces a p53-mediated DNA damage response, Nat. Med., 24(7):927-30 (Jun. 2018).

Hacien-Bey-Abina et al., Efficacy of gene therapy for X-linked severe combined immunodeficiency, N. Engl. J. Med., 363(4):355-64 (Jul. 2010).

Hsu et al., DNA targeting specificity of RNA-guided Cas9 nucleases, Nat. Biotechnol., 31(9):827-32 (Sep. 2013).

Huang et al., The adenovirus early region 4 open reading frame 6/7 protein regulates the DNA binding activity of the cellular transcription factor, E2F, through a direct complex, Genes Dev., 3(11):1699-710 (Nov. 1989).

Hutvágner et al., A cellular function for the RNA-interference enzyme Dicer in the maturation of the let-7 small temporal RNA, Science, 293(5531):834-8 (Aug. 2001).

International Application No. PCT/EP2019/066915, International Search Report and Written Opinion, mailed Nov. 15, 2019.

Komarov et al., A chemical inhibitor of p53 that protects mice from the side effects of cancer therapy, Science, 285(5434):1733-7 (Sep. 1999).

Leavitt et al., Human immunodeficiency virus type 1 integrase mutants retain in vitro integrase activity yet fail to integrate viral DNA efficiently during infection, J. Virol., 70(2):721-8 (Feb. 1996).

Leonova et al., A small molecule inhibitor of p53 stimulates amplification of hematopoietic stem cells but does not promote tumor development in mice, Cell Cycle, 9(7):1434-43 (Apr. 2010).

Lewis et al., Human immunodeficiency virus infection of cells arrested in the cell cycle, EMBO J., 11(8):3053-8 (Aug. 1992).

Lewis et al., Passage through mitosis is required for oncoretroviruses but not for the human immunodeficiency virus, J. Virol., 68(1):510-6 (Jan. 1994).

Lilley et al. (eds.), DNA Structures, Part A, Synthesis and Physical Analysis of DNA, vol. 211 in Methods in Enzymology, San Diego, California: Academic Press, Inc. (1992).

Lu et al., Tracking single hematopoietic stem cells in vivo using high-throughput sequencing in conjunction with viral genetic barcoding, Nat. Biotechnol., 29(10):928-33 (Oct. 2011).

Milyavsky et al., A distinctive DNA damage response in human hematopoietic stem cells reveals an apoptosis-independent role for p53 in self-renewal, Cell Stem Cell, 7(2):186-97 (Aug. 2010).

Naldini et al., Efficient transfer, integration, and sustained long-term expression of the transgene in adult rat brains injected with a lentiviral vector, Proc. Natl. Acad. Sci. USA, 93(12):11382-8 (Oct. 1996).

Naldini et al., In vivo gene delivery and stable transduction of nondividing cells by a lentiviral vector, Science, 272(5259):263-7 (Apr. 1996).

Nightingale et al., Transient gene expression by nonintegrating lentiviral vectors, Mol Ther, vol. 13, pp. 1121-1132 (2006).

Notredame et al., T-Coffee: A novel method for fast and accurate multiple sequence alignment, J. Mol. Biol., 302(1):205-17 (Sep. 2000).

Paix et al., High Efficiency, Homology-Directed Genome Editing in Caenorhabditis elegans Using CRISPR-Cas9 Ribonucleoprotein Complexes, Genetics, 201(1):47-54 (2015).

Pant et al., The p53 pathway in hematopoiesis: lessons from mouse models, implications for humans, Blood, 120(26):5118-27 (Dec. 2012).

Polak et al. (eds.), In Situ Hybridization: Principles and Practice, New York: Oxford University Press (1990).

Roe et al., DNA Isolation and Sequencing: Essential Techniques, Chichester, West Sussex: John Wiley & Sons (1996).

Sambrook et al., Molecular Cloning: a Laboratory Manual, Cold Harbor Laboratory, 2nd edition (1989).

Sander et al., CRISPR-Cas systems for editing, regulating and targeting genomes, Nat. Biotechnol., 32(4):347-55 (Apr. 2014).

Schiroli et al., Precise Gene Editing Preserves Hematopoietic Stem Cell Function following Transient p53-Mediated DNA Damage Response, Cell Stem Cell, 24(4):551-65 (Apr. 2019).

Schiroli et al., Preclinical modeling highlights the therapeutic potential of hematopoietic stem cell gene editing for correction of SCID-X1, Sci. Transl. Med., 9(411):eaan0820 (Oct. 2017).

Silve et al., Meganucleases and other tools for targeted genome engineering: perspectives and challenges for gene therapy, Curr. Gene Ther., 11(1):11-27 (Feb. 2011).

Stark et al., How cells respond to interferons, Annu. Rev. Biochem., 67:227-64 (1998).

Van der Oost et al., Unravelling the structural and mechanistic basis of CRISPR-Cas systems, Nat. Rev. Microbiol., 12(7):479-92 (2014).

Wang et al., Homology-driven genome editing in hematopoietic stem and progenitor cells using ZFN mRNA and AAV6 donors, Nat. Biotechnol., 33(12):1256-63 (Dec. 2015).

Zalatan et al., Engineering complex synthetic transcriptional programs with CRISPR RNA scaffolds, Cell, 160(1):339-50 (2015).

Zetsche et al., Cpf1 is a single RNA-guided endonuclease of a class 2 CRISPR-Cas system, Cell, 163(3):759-71 (2015).

Zheng et al., Massively parallel digital transcriptional profiling of single cells, Nat. Commun., 8:14049 (Jan. 2017).

Chu et al., Increasing the efficiency of homology-directed repair for CRISPR-Cas9-induced precise gene editing in mammalian cells, Nature Biotechnology, May 2015, vol. 33, No. 5, pp. 543-548.

De Ravin et al., CRISPR-Cas9 gene repair of hematopoietic stem cells from patients with X-linked chronic granulomatous disease, Science Translational Medicine, 2017, vol. 9(372) :eaaah3480.

Fischer, Census and evaluation of p53 target genes, Oncogene, 2017, vol. 36, pp. 3943-3956.

(56)          References Cited

OTHER PUBLICATIONS

Haapaniemi et al., Inhibition of p53 improves CRISPR/Cas-mediated precision genome editing, bioRXiv, 2017, doi: https://doi.org/10.1101/180943.

Hastie et al., Assay of protein kinases using radiolabeled ATP: a Protocol, Nature Protocols, 2006, vol. 1, No. 2, pp. 968-971.

Ihry et al., p53 inhibits CRISPR-Cas9 engineering in human pluripotent stem cells, Nature Medicine, 2018, https://doi.org/10.1038/s41591-018-0050-6.

Kruse et al., SnapShot: p53 Posttranslational Modifications Cell, 2008, vol. 133, pp. 930-931.

NCBI Database accession No. NP 001175.2, serine/threonine-protein kinase ATR isoform 1, Jan. 18, 2021.

Ralph et al., Silencing mutant SOD1 using RNAi protects against neurodegeneration and extends survival in an ALS model, Nature Medicine, 2005, vol. 11, pp. 429-433.

Weber et al., ATM and ATR as therapeutic targets in cancer, Pharmacology & Therapeutics, 2015, vol. 149, pp. 124-138.

Kuo et al., Site-Specific Gene Editing of Human Hematopoietic Stem Cells for X-Linked Hyper-IgM Syndrome, Cell Rep., May 29, 2018 vol. 23 No. 9 pp. 2606-2616.

Sacchetti et al., Targeted genome editing of recombination activating gene 1 to potentially treat severe combined immunodeficiency, Human Gene Therapy, 2017, vol. 28, No. 12, p. A8, Abstract OR19.

Cavazza et al., Targeted gene correction of Wiskott-Aldrich Syndrome in human haematopoietic stem and progenitor cells, Human Gene Therapy, 2017, vol. 28, No. 12, p. A53 (Abstract P131).

Sun et al., Tumor-specific cell deaths induced by the adenovirus E4orf4 protein and its application in cancer therapy, Chinese Journal of Biochemistry and Molecular Biology, 34(10):1045-51 (2018).

Qin et al., Potential novel ideas in targeted therapy for cancer, Chinese Journal of Cancer Biotherapy, Issue 6, pp. 712-720 (2014). [abstract only].

Chinese Patent Application No. 201980055217.3, Office Action, dated Jan. 24, 2024.

Nii et al., Roles of p53 in Various Biological Aspects of Hematopoietic Stem Cells, J. Biomed. Biotechnol., vol. 2012, Article 903435, 10 pp. (Jun. 20, 2012).

Kamada et al., Tetramerization of tumor suppressor protein p53, Japanese Biochemical Society, 2010, vol. 82(6), 484-493.

Japanese Office Action for U.S. Appl. No. 17/255,362, mailed Feb. 6, 2024.

Osborn et al., CRISPR/Cas9 Targeted Gene Editing and Cellular Engineering in Fanconi Anemia, Stem cells and development, 2016, vol. 25, No. 20, 1591-1603.

* cited by examiner

A

C p21 induction upon editing

D

Reactome

| Index | Name | P-value | Adjusted p-value | Z-score | Combined score |
|---|---|---|---|---|---|
| 1 | Transcriptional Regulation by TP53_Homo sapiens_R-HSA-3700989 | 4.670e-12 | 1.378e-9 | -2.31 | 60.15 |
| 2 | TP53 Regulates Transcription of Cell Death Genes_Homo sapiens_R-HSA-5633008 | 2.828e-9 | 4.172e-7 | -1.98 | 39.05 |
| 3 | Generic Transcription Pathway_Homo sapiens_R-HSA-212436 | 0.000001411 | 0.0001387 | -2.25 | 30.28 |
| 4 | TP53 Regulates Transcription of Genes Involved in Cytochrome C Release_Homo sapiens_R-HSA-6803204 | 0.000002821 | 0.0002081 | -1.84 | 23.45 |
| 5 | TP53 Regulates Transcription of Cell Cycle Genes_Homo sapiens_R-HSA-6791312 | 0.000005688 | 0.0003356 | -1.93 | 23.26 |
| 6 | TNFs bind their physiological receptors_Homo sapiens_R-HSA-5669034 | 0.0002777 | 0.01365 | -2.19 | 17.95 |
| 7 | Apoptosis_Homo sapiens_R-HSA-109581 | 0.001842 | 0.04180 | -2.06 | 12.94 |
| 8 | Programmed Cell Death_Homo sapiens_R-HSA-5357801 | 0.001995 | 0.04186 | -2.07 | 12.86 |
| 9 | Gene Expression_Homo sapiens_R-HSA-74160 | 0.002469 | 0.04294 | -2.04 | 12.23 |
| 10 | CASP8 activity is inhibited_Homo sapiens_R-HSA-5218900 | 0.001511 | 0.04180 | -1.65 | 10.69 |

Human Adenovirus C serotype 5 (E4 gene)
*35-36 kbp*

A

Electroporation of Nucleases
± E4orf1 ± E4orf6/7 mRNA

B

D

A

B

A

CB derived CD34+ cells

RNP-Cas9 + protein(s) mRNA

Prestimulation time

Days 0    1    2    3    4    7

Early active cytokines
+ *SR1*
+ *dmPGE2*
+ *UM171*

AAV6

Molecular Assays
Gene expression
Flow cytometry
CFU-C assay

Legend:
- ▨ RNP + AAV6
- ▩ + GSE56
- ▨ + Ad5-E4orf6/7
- ▩ + GSE56/Ad5-E4orf6/7

C

%GFP w/in subpopulations (y-axis, 20 to 80)

*fold increase to RNP + AAV6*

CD34-: 1.00, 1.05, 1.25, 1.37 (*   **)
CD34+CD133-: 1.00, 1.05, 1.12, 1.13 (**  **)
CD34+CD133+: 1.00, 1.08, 1.27, 1.27 (**  **)
CD34+CD133+CD90+: 1.00, 1.16, 1.40, 1.50 (**  **)

B

C

F

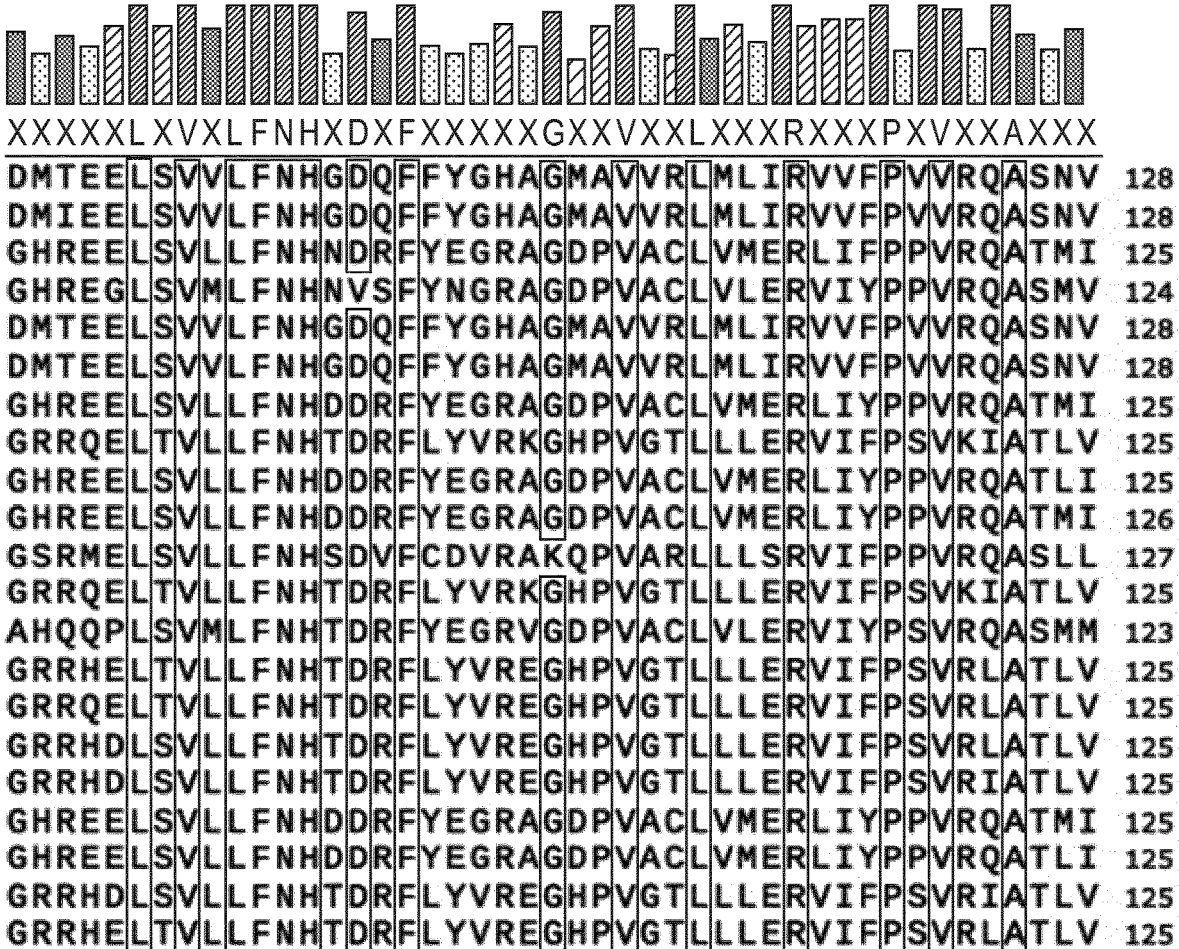

XXXXXLXVXLFNHXDXFXXXXXGXXVXXLXXXRXXXPXVXXAXXX
```
DMTEELSVVLFNHGDQFFYGHAGMAVVRLMLIRVVFPVVRQASNV  128
DMIEELSVVLFNHGDQFFYGHAGMAVVRLMLIRVVFPVVRQASNV  128
GHREELSVLLFNHNDRFYEGRAGDPVACLVMERLIFPPVRQATMI  125
GHREGLSVMLFNHNVSFYNGRAGDPVACLVLERVIYPPVRQASMV  124
DMTEELSVVLFNHGDQFFYGHAGMAVVRLMLIRVVFPVVRQASNV  128
DMTEELSVVLFNHGDQFFYGHAGMAVVRLMLIRVVFPVVRQASNV  128
GHREELSVLLFNHDDRFYEGRAGDPVACLVMERLIYPPVRQATMI  125
GRRQELTVLLFNHTDRFLYVRKGHPVGTLLLERVIFPSVKIATLV  125
GHREELSVLLFNHDDRFYEGRAGDPVACLVMERLIYPPVRQATLI  125
GHREELSVLLFNHDDRFYEGRAGDPVACLVMERLIYPPVRQATMI  126
GSRMELSVLLFNHSDVFCDVRAKQPVARLLLSRVIFPPVRQASLL  127
GRRQELTVLLFNHTDRFLYVRKGHPVGTLLLERVIFPSVKIATLV  125
AHQQPLSVMLFNHTDRFYEGRVGDPVACLVLERVIYPSVRQASMM  123
GRRHELTVLLFNHTDRFLYVREGHPVGTLLLERVIFPSVRLATLV  125
GRRQELTVLLFNHTDRFLYVREGHPVGTLLLERVIFPSVRLATLV  125
GRRHDLSVLLFNHTDRFLYVREGHPVGTLLLERVIFPSVRLATLV  125
GRRHDLSVLLFNHTDRFLYVREGHPVGTLLLERVIFPSVRIATLV  125
GHREELSVLLFNHDDRFYEGRAGDPVACLVMERLIYPPVRQATMI  125
GHREELSVLLFNHDDRFYEGRAGDPVACLVMERLIYPPVRQATLI  125
GRRHDLSVLLFNHTDRFLYVREGHPVGTLLLERVIFPSVRIATLV  125
GRRHELTVLLFNHTDRFLYVREGHPVGTLLLERVIFPSVRLATLV  125
```

FIG. 21A (Continued)

Phylogenetic Tree

Ad1-E4orf1 0.00453
Ad5-E4orf1 0.00328
Ad2-E4orf1 0.00586
Ad6-E4orf1 0.00654
Ad18-E4orf1 0.46875
Ad16-E4orf1 0.43625
Ad4-E4orf1 0.45085
Ad21-E4orf1 0.44033
Ad14-E4orf1 0.0032
Ad55-E4orf1 0.0048
Ad3-E4orf1 0.01314
Ad50-E4orf1 0.005
Ad7-E4orf1 0.003
Ad30-E4orf1 0.00598
Ad36-E4orf1 0.00062
Ad62-E4orf1 0.00738
Ad20-E4orf1 0.012
Ad9-E4orf1 0.004
Ad23-E4orf1 0.0095
Ad71-E4orf1 0.0065
Ad25-E4orf1 0.02934

FIG. 22A

Phylogenetic Tree

A

TRANSIENT INHIBITION OF P53 IN GENE THERAPY

CROSS-REFERENCE TO RELATED APPLICATIONS

This application is a U.S. National Phase of International Patent Application No. PCT/EP2019/066915, filed Jun. 25, 2019, incorporated herein by reference, which claims priority under § 119 to European Patent Application No. 18305807.2, filed on Jun. 25, 2018.

INCORPORATION BY REFERENCE OF MATERIAL SUBMITTED ELECTRONICALLY

Incorporated by reference in its entirety is a computer-readable nucleotide/amino acid sequence listing filed on Dec. 22, 2020, and identified as follows: name of ASCII text file: Sequence_listing.TXT, date of creation: Dec. 21, 2020, file size: 178,950 bytes. The specification is controlling in the event of any discrepancies between sequences in the specification and sequences in the electronic sequence listing.

FIELD OF THE INVENTION

The present invention relates to the genetic modification of cells. More specifically, the present invention relates to the use of agents to improve the efficiency of gene editing and to improve the survival and/or engraftment of haematopoietic stem cells which have been gene edited.

BACKGROUND TO THE INVENTION

The haematopoietic system is a complex hierarchy of cells of different mature cell lineages. These include cells of the immune system that offer protection from pathogens, cells that carry oxygen through the body and cells involved in wound healing. All these mature cells are derived from a pool of haematopoietic stem cells (HSCs) that are capable of self-renewal and differentiation into any blood cell lineage. HSCs have the ability to replenish the entire haematopoietic system.

Haematopoietic cell transplantation (HCT) is a curative therapy for several inherited and acquired disorders. However, allogeneic HCT is limited by the poor availability of matched donors, the mortality associated with the allogeneic procedure which is mostly related to graft-versus-host disease (GvHD), and infectious complications provoked by the profound and long-lasting state of immune dysfunction.

Gene therapy approaches based on the transplantation of genetically modified autologous HSCs offer potentially improved safety and efficacy over allogeneic HCT. They are particularly relevant for patients lacking a matched donor.

The concept of stem cell gene therapy is based on the genetic modification of a relatively small number of stem cells. These persist long-term in the body by undergoing self-renewal, and generate large numbers of genetically "corrected" progeny. This ensures a continuous supply of corrected cells for the rest of the patient's lifetime. HSCs are particularly attractive targets for gene therapy since their genetic modification will be passed to all the blood cell lineages as they differentiate. Furthermore, HSCs can be easily and safely obtained, for example from bone marrow, mobilised peripheral blood and umbilical cord blood.

Efficient long-term gene modification of HSCs and their progeny requires a technology which permits stable integration of the corrective DNA into the genome, without affecting HSC function. Accordingly, the use of integrating recombinant viral systems such as γ-retroviruses, lentiviruses and spumaviruses has dominated this field (Chang, A. H. et al. (2007) Mol. Ther. 15: 445-456). Therapeutic benefits have already been achieved in γ-retrovirus-based clinical trials for Adenosine Deaminase Severe Combined Immunodeficiency (ADA-SCID; Aiuti, A. et al. (2009) N. Engl. J. Med. 360: 447-458), X-linked Severe Combined Immunodeficiency (SCID-X1; Hacein-Bey-Abina, S. et al. (2010) N. Engl. J. Med. 363: 355-364) and Wiskott-Aldrich syndrome (WAS; Boztug, K. et al. (2010) N. Engl. J. Med. 363: 1918-1927). In addition, lentiviruses have been employed as delivery vehicles in the treatment of X-linked adrenoleukodystrophy (ALD; Cartier, N. et al. (2009) Science 326: 818-823), and very recently for metachromatic leukodystrophy (MLD; Biffi, A. et al. (2013) Science 341: 1233158) and WAS (Aiuti, A. et al. (2013) Science 341: 1233151).

In addition to the use of retro- and lentiviral-based vectors, vectors derived from other viruses, such as adenoviruses and adeno-associated viruses (AAV), may also be utilised for the modification of haematopoietic stem and progenitor cells.

The scope of genetic engineering has recently broadened from gene replacement to targeted gene editing using engineered nucleases, which enable precise sequence modification of a locus of interest. Gene editing applications encompass targeted disruption of a gene coding sequence, precise sequence substitution for in situ correction of mutations and targeted transgene insertion into a predetermined locus. Gene editing is based on the design of artificial endonucleases that target a double-strand break (DSB) or nick into the sequence of interest in the genome. Cells repair the DSB through two major mechanisms, Non-Homologous End-Joining (NHEJ) or Homology Directed Repair (HDR), although other repair mechanisms might be eventually exploited. NHEJ often creates small insertions or deletions ("indels") at the target site that may disrupt the coding sequence of a gene, whereas HDR can be exploited to precisely introduce a novel sequence at the target site by providing an exogenous template DNA bearing homology to the sequences flanking the DSB.

Multiple platforms of artificial endonucleases can be used to target a locus of interest, including Zinc Finger Nucleases (ZFNs), TAL effector nucleases (TALENs) and the more recently developed RNA-based CRISPR/Cas9 nucleases. Viral vectors are the most efficient delivery vehicle for a DNA template, for example, the AAV6 vector is able to achieve a high transduction efficiency in human primary cells, such as Hematopoietic Stem/Progenitor (HSPC) cells and T lymphocytes.

Despite recent advance in the generation of gene edited primary cells, several hurdles need to be solved before we can fully benefit from the predicted safety and precision of genetic engineering afforded by these new technologies. A major issue is that gene editing in primary cells, and in particular in the primitive HSPC subset, is constrained by gene transfer efficiency and limited proficiency of homology directed DNA repair (HDR), likely due to HSC quiescence, to low levels of expression of the HDR machinery and conversely to high activity of the error-prone non homologous end joining (NHEJ) pathway. Thus, it will be crucial to enhance the efficiency of HDR in HSC while fully preserving their long-term repopulating activity.

Similarly, the impact of adeno-associated virus (AAV) as a source of donor template for HDR-mediated gene editing remains poorly investigated, and no clinical application of this vector in HSPC has been reported yet. AAV dose-dependent toxicity has been observed, which is directly related to G-rich regions of ITRs that induce cells accumulation in early S-phase due to p53-mediated induction of apoptosis, as described in a hESCs model.

Substantial difficulties remain with the methods employed for the genetic modification of haematopoietic stem and progenitor cells. In particular, the multiple hits of high vector doses required and prolonged ex vivo transduction times associated with existing methods give rise to problems with survival of the transduced haematopoietic stem and progenitor cells during culture and potentially impact their biological properties. Furthermore, improvements in the engraftment of transduced cells will greatly benefit clinical applications.

SUMMARY OF THE INVENTION

The inventors have surprisingly found that the use of an agent which promotes homology directed DNA repair, (such as an inhibitor of p53 activation, or an adenoviral protein) improves gene editing efficiency of haematopoietic cells, haematopoietic stem cells and/or haematopoietic progenitor cells and improves the survival and/or engraftment of treated gene edited haematopoietic cells, haematopoietic stem cells and/or haematopoietic progenitor cells.

The inventors determined that advantageously, the agent which promotes homology directed DNA repair enhanced gene targeting efficiency in haematopoietic stem and progenitor cells, particularly in the more primitive CD34+CD133+CD90+ fraction. Furthermore, the agent does not significantly affect the differentiation status of the haematopoietic stem and/or progenitor cells, thus preserving their long-term re-population capacity.

In one aspect, the present invention provides an agent which promotes homology directed DNA repair for use in haematopoietic cell gene therapy, haematopoietic stem cell gene therapy, and/or haematopoietic progenitor cell gene therapy, wherein said gene therapy comprises gene editing.

In a preferred embodiment, the haematopoietic cells, haematopoietic stem cells and haematopoietic progenitor cells are human cells.

In one embodiment, the cells are HSCs. In one embodiment the cells are HSPCs. In one embodiment, the haematopoietic stem and/or progenitor cells are CD34+ cells.

In one embodiment, the population of haematopoietic stem and/or progenitor cells comprises, is enriched in or substantially consists of CD34+ cells. The population of cells may be further enriched for a particular sub-population of cells, for example CD34+CD38− cells. The population of cells may be further enriched for a particular sub-population of cells, for example CD34+CD133+ and CD90+ cells.

In a preferred embodiment, the gene therapy is haematopoietic stem cell therapy and haematopoietic stem cells are gene edited.

In one aspect, the present invention provides an agent which promotes homology directed DNA repair, for use in increasing the survival and/or engraftment of gene edited haematopoietic cells, haematopoietic stem cells and/or haematopoietic progenitor cells.

In one embodiment, at least 1%, 2%, 3%, 4%, 5%, 6%, 7%, 8%, 9%, 10%, 15%, 20%, 25%, 30%, 50%, 75% or 90%, preferably at least 70%, more cells survive in culture for a period of time (e.g. about 6 or 12 hours, or 1, 2, 3, 4, 5, 6, 7 or more days, preferably about 2 days) when the cells have been exposed to the agent rather than in its absence. Preferably, the period of time begins with transduction of the cells with a viral vector.

The present invention may allow the timing of the pre-treatment/conditioning of cells with cytokines to prime the cells (otherwise quiescent) for transduction to be reduced. Standard timing is 3 days. This time may be reduced to less than 3 days, or less than 2 days, or less than 1 day, for example 0, 1 or 2 days.

In one embodiment, the agent substantially prevents or reduces apoptosis in the haematopoietic stem and/or progenitor cells, in particular during in vitro culture.

In one embodiment, at least 1%, 2%, 3%, 4%, 5%, 6%, 7%, 8%, 9%, 10%, 15%, 20%, 25%, 30%, 40%, 50% or 75%, preferably at least 25%, fewer cells become apoptotic following culture for a period of time (e.g. about 6 or 12 hours, or 1, 2, 3, 4, 5, 6, 7 or more days, preferably about 2 days) when the cells have been exposed to the agent rather than in its absence. Preferably, the period of time begins with the transduction of the cells with a viral vector.

In one embodiment, at least 1%, 2%, 3%, 4%, 5%, 6%, 7%, 8%, 9%, 10%, 15%, 20%, 25%, 30%, 40%, 50% or 75%, preferably at least 10%, more transplanted haematopoietic stem cells and/or haematopoietic progenitor cells and/or their descendant cells (e.g. graft-derived cells) engraft in a host subject when the cells have been exposed to the agent rather than in its absence.

In another aspect, the present invention provides the use of an agent which promotes homology directed DNA repair, for increasing the survival and/or engraftment of gene edited haematopoietic stem and/or progenitor cells or for increasing the efficiency of gene editing of haematopoietic stem and/or progenitor cells.

In one embodiment, the agent is an inhibitor of p53 activation, preferably wherein the inhibitor is an inhibitor of p53 phosphorylation, more preferably an inhibitor of p53 Serine 15 phosphorylation.

In one embodiment, the inhibitor is a p53 dominant negative peptide, an ataxia telangiectasia mutated (ATM) kinase inhibitor, and/or an ataxia telangiectasia and Rad3-related protein (ATR) inhibitor.

In one embodiment, the inhibitor is pifithrin-α or a derivative thereof. In one embodiment, the inhibitor is pifithrin-α cyclic. In one embodiment, the inhibitor is pifithrin-α p-nitro. KU-55933 or a derivative thereof; GSE56 or a fragment or variant thereof; KU-60019, BEZ235, wortmannin, CP-466722, Torin 2, CGK 733, KU-559403, AZD6738 or derivatives thereof; or an siRNA, shRNA, miRNA or antisense DNA/RNA.

In one embodiment, the inhibition of p53 in the haematopoietic cells, haematopoietic stem cells and/or haematopoietic progenitor cells is transient.

In one embodiment, the inhibitor is a transient inhibitor (e.g. has an inhibitory action lasting less than about 1, 2, 3, 4, 5, 6, 7 or 14 days), such as a reversible inhibitor. Preferably, the cells are exposed to the inhibitor for about 1-48 or 1-24 hours, preferably 1-24 hours. The cells may be, for example, exposed to the inhibitor at the same time as the viral vector or before the viral vector.

In one embodiment, the agent is administered before, at the same time as, and/or after the gene editing machinery is introduced into the cell.

In one embodiment, the transient inhibition of p53 occurs during gene editing of the haematopoietic cells, haematopoietic stem cells and/or progenitor cells.

In one embodiment, the inhibitor is added to the haematopoietic cells, haematopoietic stem cells and/or haematopoietic progenitor cells at a concentration of about 1-5 µM.

In one embodiment, the inhibitor is added to the haematopoietic cells, haematopoietic stem cells and/or haematopoietic progenitor cells (e.g. in an in vitro or ex vivo culture) at a concentration of about 1-50, 1-40, 1-30, 1-20 or 1-15 µM, preferably about 1-15 µM. In another embodiment, the inhibitor is added to the haematopoietic cells, haematopoietic stem cells and/or haematopoietic progenitor cells at a concentration of about 5-50, 5-40, 5-30, 5-20 or 5-15 µM, preferably about 5-15 µM.

In one embodiment, the inhibitor is added to the haematopoietic cells, haematopoietic stem cells and/or haematopoietic progenitor cells (e.g. in an in vitro or ex vivo culture) at a concentration of about 1, 2, 3, 4, 5, 6, 7, 8, 9, 10, 11, 12, 13, 14, 15, 20, 25, 30, 35, 40, 45 or 50 µM, preferably about 10 µM.

In one embodiment, the agent comprises at least one adenoviral protein.

In one embodiment, the agent comprises a nucleic acid sequence encoding at least one adenoviral protein.

Preferably, the at least one adenoviral protein is E4ORF1, preferably wherein the amino acid sequence of E4ORF1 is set forth in SEQ ID No. 1, or SEQ ID Nos. 57-76. The at least one adenoviral protein may be a variant or fragment of E4ORF1, when the variant or fragment substantially retains the biological activity of the full length E4ORF1, e.g. the ability to increase the survival and/or engraftment of gene edited haematopoietic stem/progenitor cells defined herein.

Preferably, the at least one adenoviral protein is E4ORF6/7, preferably wherein the amino acid sequence of E4ORF6/7 is set forth in SEQ ID No. 2, or SEQ ID Nos. 77-107. The at least one adenoviral protein may be a variant or fragment of E4ORF6/7, when the variant or fragment substantially retains the biological activity of the full length E4ORF6/7, e.g. the ability to increase the survival and/or engraftment of gene edited haematopoietic stem/progenitor cells defined herein.

In one embodiment, the agent comprises adenoviral protein E4ORF1, preferably wherein the amino acid sequence of E4ORF1 is set forth in SEQ ID No. 1, or SEQ ID Nos. 57-76; and adenoviral protein E4ORF6/7, preferably wherein the amino acid sequence of E4ORF6/7 is set forth in SEQ ID No. 2, or SEQ ID Nos. 77-107.

In one embodiment, the agent comprises a nucleic acid sequence encoding adenoviral protein E4ORF1, preferably wherein the amino acid sequence of E4ORF1 is set forth in SEQ ID No. 1, or SEQ ID Nos. 57-76; and a nucleic acid sequence adenoviral protein E4ORF6/7, preferably wherein the amino acid sequence of E4ORF6/7 is set forth in SEQ ID No. 2, or SEQ ID Nos. 77-107.

The adenoviral protein is not limited to a particular Adenovirus serotype. For example, in one embodiment, the at least one adenoviral proteins is from an Adenovirus of serotype 4, Adenovirus of serotype 5, Adenovirus of serotype 7 and/or Adenovirus of serotype 9. In one embodiment, the at least one adenoviral protein is from an Adenovirus of serotype 5.

In one embodiment, the agent comprises two compounds as defined herein that promote homology directed repair. In one embodiment, the agent comprises the inhibitor of p53 activation and the adenoviral protein, or a nucleotide sequence encoding therefor. Preferably, the inhibitor of p53 activation is GSE56 or a variant thereof.

In one embodiment, the agent comprises:
(a) the inhibitor of p53 activation and adenoviral protein E4ORF1 (or a nucleotide sequence encoding therefor). In one embodiment, the E4ORF1 has the amino acid sequence of E4ORF1 set forth in SEQ ID No. 1, or SEQ ID Nos. 57-76.;
(b) the inhibitor of p53 activation and adenoviral protein E4ORF6/7 (or a nucleotide sequence encoding therefor). In one embodiment, the E4ORF6/7 has the amino acid sequence of E4ORF6/7 set forth in SEQ ID No. 2; or SEQ ID Nos. 77-107.
(c) the inhibitor of p53 activation, adenoviral protein E4ORF1 (or a nucleotide sequence encoding therefor), preferably wherein the amino acid sequence of E4ORF1 is set forth in SEQ ID No. 1, or SEQ ID Nos. 57-76, and adenoviral protein E4ORF6/7 (or a nucleotide sequence encoding therefor), preferably wherein the amino acid sequence of E4ORF6/7 is set forth in SEQ ID No. 2; or SEQ ID Nos. 77-107. Preferably, the inhibitor of p53 activation is GSE56 or a variant thereof.

In one embodiment, the agent is a composition comprising the inhibitor of p53 activation and the adenoviral protein, or a nucleotide sequence encoding therefor.

In one embodiment, the inhibitor of p53 activation is administered simultaneously, sequentially or separately in combination with the adenoviral protein, or a nucleotide sequence encoding therefor.

In one embodiment, the adenoviral protein, or a nucleotide sequence encoding therefor, is administered simultaneously, sequentially or separately in combination with the inhibitor of p53 activation.

In one aspect, the invention provides a product comprising (a) the inhibitor of p53 activation of the invention; and (b) the adenoviral protein of the invention, as a combined preparation for simultaneous, separate or sequential use in therapy, wherein the use is a use of the disclosure.

The term "combination", or terms "in combination", "used in combination with" or "combined preparation" as used herein may refer to the combined administration of two or more entities simultaneously, sequentially or separately.

The term "simultaneous" as used herein means that the entities are administered concurrently, i.e. at the same time.

The term "sequential" as used herein means that the entities are administered one after the other.

The term "separate" as used herein means that the entities are administered independently of each other but within a time interval that allows the entities to show a combined, preferably synergistic, effect. Thus, administration "separately" may permit one entity to be administered, for example, within 1 minute, 5 minutes or 10 minutes after the other.

In one embodiment, the nucleic acid encoding the adenoviral protein is an mRNA.

In one embodiment, the adenoviral protein is expressed transiently in the haematopoietic cell, haematopoietic stem cell and/or haematopoietic progenitor cell, preferably the transient expression occurs during gene editing of the haematopoietic cell, haematopoietic stem cell and/or progenitor cell.

In one embodiment, the target of the gene editing is selected from the group consisting of CD40L, RAG-1, IL-2RG, CYBA, CYBB, NCF1, NCF2, and NCF4. In one embodiment, the target of the gene editing is a gene mutated in chronic granulomatous disease or the gene mutated SCID, atypical SCID and Omenn syndrome, or Hyper IgM syndrome.

Preferably the target of the gene editing is CD40L.

In another aspect, the present invention provides a method of gene editing a population of haematopoietic cells, haematopoietic stem cells and/or haematopoietic progenitor cells comprising introducing gene editing machinery to the population of haematopoietic cells, haematopoietic stem cells and/or haematopoietic progenitor cells; and wherein prior to, at the same time as, or after the introducing of the gene editing machinery to the population of haematopoietic cells, haematopoietic stem cells and/or haematopoietic progenitor cells, the population of haematopoietic cells, haematopoietic stem cells and/or haematopoietic progenitor cells is contacted with an agent which promotes homology directed DNA repair;

In another aspect, the present invention provides a method of gene editing a population of haematopoietic cells, haematopoietic stem cells and/or haematopoietic progenitor cells comprising the steps:

(a) contacting the population of haematopoietic cells, haematopoietic stem cells and/or haematopoietic progenitor cells with an agent which promotes homology directed DNA repair;

(b) introducing gene editing machinery to the population of haematopoietic cells, haematopoietic stem cells and/or haematopoietic progenitor cells; and (c) editing the genome of said haematopoietic cells, haematopoietic stem cells and/or haematopoietic progenitor cells.

In another aspect, the present invention provides a method of gene editing a population of haematopoietic cells, haematopoietic stem cells and/or haematopoietic progenitor cells comprising the steps:

(a) introducing gene editing machinery to the population of haematopoietic cells, haematopoietic stem cells and/or haematopoietic progenitor cells;

(b) contacting the population of haematopoietic cells, haematopoietic stem cells and/or haematopoietic progenitor cells with an agent which promotes homology directed DNA repair; and (c) editing the genome of said haematopoietic cells, haematopoietic stem cells and/or haematopoietic progenitor cells.

In another aspect, the present invention provides a method of gene editing a population of haematopoietic cells, haematopoietic stem cells and/or haematopoietic progenitor cells comprising the steps:

(a) introducing gene editing machinery and an agent which promotes homology directed DNA repair to the population of haematopoietic cells, haematopoietic stem cells and/or haematopoietic progenitor cells;

(b) editing the genome of said haematopoietic cells, haematopoietic stem cells and/or haematopoietic progenitor cells.

In one embodiment, the method steps (a) and (b) are carried out ex vivo or in vitro. Thus, in one embodiment of the method of gene editing a population of haematopoietic cells, haematopoietic stem cells and/or haematopoietic progenitor cells, steps (a) and (b) are carried out ex vivo or in vitro. In one embodiment steps (a) and (b) may be carried out simultaneously. In another embodiment, steps (a) and (b) are carried out sequentially, either step (a) before step (b) or step (b) before step (a).

In one embodiment, the gene editing machinery may comprise a nuclease such as a zinc finger nuclease (ZFNs), a transcription activator like effector nucleases (TALENs), meganucleases, or the clustered regularly interspaced short palindromic repeats (CRISPR)/Cas system.

The gene editing machinery (e.g. CRISPR/Cas system) may comprise one or more guide RNAs complementary to at least one target gene in a cell, an RNA-guided DNA endonuclease enzyme or nucleotide sequence encoding said endonuclease (e.g. Cas9 protein or a nucleotide sequence encoding a Cas9). In one embodiment, the gene editing machinery may be a CRISPR/Cas system.

In one embodiment, the gene editing machinery may be provided by one or more nucleotide sequences. Suitably, the nucleotide sequences encoding the gene editing machinery may be introduced to the cell sequentially or simultaneously. In one embodiment, the agent which promotes HDR may be contacted with the cell simultaneously with the introduction of gene editing machinery to the cell. In one embodiment, one or more nucleotide sequences encoding gene editing machinery is introduced to the cell by electroporation. In one embodiment, one or more nucleotide sequences is introduced to the cell by transduction. Suitably, the nucleotide sequence may be introduced by transduction of a viral vector. For example, a Cas9 ribonucleprotein may be introduced to a cell by electroporation before AAV6 transduction for the delivery of the donor DNA template.

As used herein, the term "introducing" refers to methods for inserting foreign DNA or RNA into a cell. As used herein the term introduced includes both transduction and transfection methods. Transfection is the process of introducing nucleic acids into a cell by non-viral methods. Transduction is the process of introducing foreign DNA or RNA into a cell via a viral vector.

In one embodiment, AAV transduction is used to deliver the donor DNA template.

In one embodiment, AAV6 transduction is used to deliver the donor DNA template.

In one embodiment, the haematopoietic cells, haematopoietic stem cells and/or haematopoietic progenitor cells (e.g. the population of cells in step (a) of the method of gene editing a population of said cells are contacted with the agent about 15 minutes to about 4 hours; about 15 minutes to about 3 hours; or about 15 minutes to about 2 hours before transducing the population of cells with the viral vector. In another embodiment, the cells are contacted with the agent about 1-4 hours; 1-3 hours; or 1-2 hours before transducing the population of cells with the viral vector.

In one embodiment, the haematopoietic cells, haematopoietic stem cells and/or haematopoietic cell progenitor cells (e.g. the population of cells in step (a) of the method of gene editing a population of cells of the invention) are contacted with the agent about 15 minutes, 30 minutes, 1 hour, 1.5 hours, 2 hours, 2.5 hours, 3 hours, 3.5 hours or 4 hours, preferably about 15 minutes, before transducing the population of cells with the viral vector.

Suitably, the agent may be active (e.g. may promote homology directed DNA repair) during gene editing.

In one embodiment, the contacting of step (a) is for about 12-60 h, such as 24-60, 36-60 or 42-54 h, preferably about 42-54 h, before step (b) is started. In one embodiment, the contacting of step (a) is for about 12, 18, 24, 30, 36, 42, 48, 54 or 60 h, preferably about 48 h, before step (b) is started.

In one embodiment, step (b) is carried out about 12-60 h, such as 24-60, 36-60 or 42-54 h, preferably about 42-54 h, after beginning culture of the population of haematopoietic cells, haematopoietic stem cells and/or haematopoietic progenitor cells (e.g. beginning culture after the cells are thawed from a frozen state). In one embodiment, step (b) is carried out about 12, 18, 24, 30, 36, 42, 48, 54 or 60 h, preferably about 48 h, after beginning culture of the population of haematopoietic cells, haematopoietic stem cells and/or haematopoietic progenitor cells.

In one embodiment, step (b) is carried out about 12-60 h, such as 24-60, 36-60 or 42-54 h, preferably about 42-54 h, after thawing the population of haematopoietic cells, hae-matopoietic stem cells and/or haematopoietic progenitor cells (e.g. which had been stored in a frozen state). In one embodiment, step (b) is carried out about 12, 18, 24, 30, 36, 42, 48, 54 or 60 h, preferably about 48 h, after thawing the population of haematopoietic cells, haematopoietic stem cells and/or haematopoietic progenitor cells.

In one embodiment, the agent which promotes homology directed DNA repair is an inhibitor of p53 activation.

In one embodiment, the inhibitor of p53 activation is a p53 dominant negative peptide, an ataxia telangiectasia mutated (ATM) kinase inhibitor, or an ataxia telangiectasia and Rad3-related protein (ATR) inhibitor.

In one embodiment, the inhibitor of p53 activation is pifithrin-α or a derivative thereof, including pifithrin-α cyclic or pifithrin-α p-nitro; KU-55933 or a derivative thereof; GSE56 or a variant thereof; KU-60019, BEZ235, wortmannin, CP-466722, Torin 2, CGK 733, KU-559403, AZD6738 or derivatives thereof; or an siRNA, shRNA, miRNA or antisense DNA/RNA. Preferably, the inhibitor of p53 activation is a dominant negative peptide. Preferably the inhibitor of p53 activation is GSE56 or a variant thereof.

In one embodiment, the inhibitor is added to the haematopoietic cells, haematopoietic stem cells and/or haematopoietic progenitor cells at a concentration of about 1-50 μM.

In one embodiment, the agent comprises a nucleic acid sequence encoding at least one adenoviral protein.

Preferably, the at least one adenoviral protein is E4ORF1, preferably wherein the amino acid sequence of E4ORF1 is set forth in SEQ ID No. 1, or SEQ ID Nos. 57-76. The at least one adenoviral protein may be a variant or fragment of E4ORF1, when the variant or fragment substantially retains the biological activity of the full length E4ORF1, e.g. the ability to increase the survival and/or engraftment of gene edited haematopoietic stem/progenitor cells defined herein.

Preferably, the at least one adenoviral protein is E4ORF6/7, preferably wherein the amino acid sequence of E4ORF6/7 is set forth in SEQ ID No. 2, or SEQ ID Nos. 77-107. The at least one adenoviral protein may be a variant or fragment of E4ORF6/7, when the variant or fragment substantially retains the biological activity of the full length E4ORF6/7, e.g. the ability to increase the survival and/or engraftment of gene edited haematopoietic stem/progenitor cells defined herein.

In one embodiment, the agent comprises adenoviral protein E4ORF1, preferably wherein the amino acid sequence of E4ORF1 is set forth in SEQ ID No. 1, or SEQ ID Nos. 57-76; and adenoviral protein E4ORF6/7, preferably wherein the amino acid sequence of E4ORF6/7 is set forth in SEQ ID No. 2, or SEQ ID Nos. 77-107.

In one embodiment, the agent comprises a nucleic acid sequence encoding adenoviral protein E4ORF1, preferably wherein the amino acid sequence of E4ORF1 is set forth in SEQ ID No. 1, or SEQ ID Nos. 57-76; and a nucleic acid sequence adenoviral protein E4ORF6/7, preferably wherein the amino acid sequence of E4ORF6/7 is set forth in SEQ ID No. 2, or SEQ ID Nos. 77-107.

The adenoviral protein is not limited to a particular Adenovirus serotype. For example, in one embodiment, the at least one adenoviral proteins is from an Adenovirus of serotype 4, Adenovirus of serotype 5, Adenovirus of sero-type 7 and/or Adenovirus of serotype 9. In one embodiment, the at least one adenoviral protein is from an Adenovirus of serotype 5.

In one embodiment, the agent comprises two compounds as defined herein that promote homology directed repair. In one embodiment, the agent comprises the inhibitor of p53 activation and the adenoviral protein, or a nucleotide sequence encoding therefor. Preferably, the inhibitor of p53 activation is GSE56 or a variant thereof.

In one embodiment, the agent comprises:
(a) the inhibitor of p53 activation and adenoviral protein E4ORF1 (or a nucleotide sequence encoding therefor). In one embodiment, the E4ORF1 has the amino acid sequence of E4ORF1 set forth in SEQ ID No. 1, or SEQ ID Nos. 57-76.;
(b) the inhibitor of p53 activation and adenoviral protein E4ORF6/7 (or a nucleotide sequence encoding therefor). In one embodiment, the E4ORF6/7 has the amino acid sequence of E4ORF6/7 set forth in SEQ ID No. 2; or SEQ ID Nos. 77-107.
(c) the inhibitor of p53 activation, adenoviral protein E4ORF1 (or a nucleotide sequence encoding therefor), preferably wherein the amino acid sequence of E4ORF1 is set forth in SEQ ID No. 1, or SEQ ID Nos. 57-76, and adenoviral protein E4ORF6/7 (or a nucleotide sequence encoding therefor), preferably wherein the amino acid sequence of E4ORF6/7 is set forth in SEQ ID No. 2; or SEQ ID Nos. 77-107. Preferably, the inhibitor of p53 activation is GSE56 or a variant thereof.

Preferably, the inhibitor of p53 activation is GSE56 or a variant thereof.

In one embodiment, the agent is a composition comprising the inhibitor of p53 activation and the adenoviral protein, or a nucleotide sequence encoding therefor.

In one embodiment, the inhibitor of p53 activation is administered simultaneously, sequentially or separately in combination with the adenoviral protein, or a nucleotide sequence encoding therefor.

In one embodiment, the adenoviral protein, or a nucleotide sequence encoding therefor, is administered simultaneously, sequentially or separately in combination with the inhibitor of p53 activation.

In one embodiment, the nucleic acid encoding the adenoviral protein is an mRNA.

In one embodiment, the adenoviral protein is expressed transiently in the haematopoietic cell, haematopoietic stem cell and/or haematopoietic progenitor cell.

In one embodiment, the target of the gene editing is selected from the group consisting of CD40L, RAG-1, IL-2RG, CYBA, CYBB, NCF1, NCF2, and NCF4 . . . . Preferably the target of the gene editing is CD40L.

In one embodiment, the population of haematopoietic cells, haematopoietic stem cells and/or haematopoietic progenitor cells is contacted with the agent which promotes homology directed DNA repair concurrently with gene editing.

In one embodiment, the population of haematopoietic stem and/or progenitor cells is obtained from mobilised peripheral blood, bone marrow or umbilical cord blood.

In one embodiment, the method according to the present invention includes a further step of enriching the population for haematopoietic stem and/or progenitor cells.

In another aspect, the present invention provides a method of gene therapy comprising the steps:

a) gene editing a population of haematopoietic cells, haematopoietic stem cells and/or haematopoietic progenitor cells according to the method of the present invention; and b) administering the gene edited haematopoietic cells, haematopoietic stem cells and/or haematopoietic progenitor cells to a subject.

In one embodiment, the gene edited cells are administered to a subject as part of an autologous stem cell transplant procedure or an allogeneic stem cell transplant procedure.

The method of gene therapy may be, for example, a method of treatment of a disease selected from the group consisting of mucopolysaccharidosis type I (MPS-1), chronic granulomatous disorder, Fanconi anaemia (FA), sickle cell disease, metachromatic leukodystrophy (MLD), globoid cell leukodystrophy (GLD), GM$_2$ gangliosidosis, thalassemia and cancer.

The method of gene therapy may be, for example, a method of treatment of diseases caused by Rag-1 mutations, eg SCID, atypical SCID and Omenn syndrome The method of gene therapy may be, for example, a method of treatment of Hyper IgM syndrome (e.g. wherein the target of the gene editing is CD40L).

In one embodiment, the subject is a mammalian subject, preferably a human subject.

In one aspect, the present invention provides a population of gene edited haematopoietic cells, haematopoietic stem cells and/or haematopoietic progenitor cells prepared according to the method according to the present invention.

In another aspect, the present invention provides a pharmaceutical composition comprising the population of gene edited haematopoietic cells, haematopoietic stem cells and/or haematopoietic progenitor cells according to the present invention.

In yet another aspect, the present invention provides a population of gene edited haematopoietic cells, haematopoietic stem cells and/or haematopoietic progenitor cells according to the present invention for use in therapy, preferably for use in gene therapy.

In one aspect, the population of gene edited haematopoietic stem and/or progenitor cells for use according to the present invention is administered as part of an autologous stem cell transplant procedure or an allogeneic stem cell transplant procedure.

In another aspect the invention provides the use of an agent which promotes homology directed DNA repair for the manufacture of a medicament for haematopoietic cell, haematopoietic stem cell and/or haematopoietic progenitor cell gene therapy, where in the haematopoietic cells, haematopoietic stem cells and/or haematopoietic progenitor cells are gene edited.

In another aspect the invention provides the use of agent which promotes homology directed DNA repair for the manufacture of a medicament for increasing survival and/or engraftment of haematopoietic cells, haematopoietic stem cells and/or haematopoietic progenitor cells, where in the haematopoietic stem and/or progenitor cells are gene edited.

In another aspect the present invention provides an AAV vector comprising a barcode sequence.

In another aspect the present invention provides an AAV vector comprising a barcode sequence, for use in gene therapy, preferably haematopoietic gene therapy.

Preferred AAV vectors are those which are able to achieve a high transduction efficiency in human primary cells, such as HSPC cells. The AAV vector may be HDR-proficient. In one embodiment, the vector is an AAV6 vector or a vector derived from an AAV6 vector. Preferably the vector is an AAV6 vector.

A barcode sequence is a random, highly degenerated DNA sequence that acts as a unique identifier. Preferably the barcode sequence is a random DNA sequence. The DNA sequence may comprise or consist of at least 15 bp, or at least 18, 19 or 20 bp, for example, 20-40 bp, 20-30 bp, 20-25 bp, or about 22 bp. Preferably the barcode sequence does not comprise any undesired restriction sites (i.e. restriction sites for cloning restriction enzymes).

The AAV vector may further comprise a nucleotide sequence encoding a gene of interest. The "gene of interest" may be any gene. The gene may be a marker gene and/or a gene involved in human diseases.

The AAV vector may comprise the gene of interest and the barcode sequence such that the barcode sequence is able to report on whether the gene of interest is correctly integrated into a host genome and/or for clonal tracking of cells. In other words, the gene of interest and barcode sequence are flanked by homology sequences, such that during homology directed DNA repair the genome of interest and the barcode sequence are inserted into the host genome together.

The gene of interest may be operably linked to a promoter. The promoter may be any suitable promoter known to those of skill in the art. In some embodiments, the promoter is hPGK promoter.

The gene of interest may be operably linked to a poly-adenylation sequence. The polyadenylation sequence may be any suitable polyadenylation sequence known to those of skill in the art. In some embodiments, the promoter is bGH-pA.

In some embodiments the AAV vector targets a safe harbour locus, preferably the AAVS1 locus, intron 1 of IL2RG, CD40L or RAG-1, most preferably the AAVS1 locus.

The AAV vector may comprise the nucleotide sequence shown below, or a nucleotide sequence having at least 70%, 75%, 80%, 85%, 90%, 95%, 96%, 97%, 98% or 99% identity to the sequence below (barcode sequence underlined):

```
CCACTGAGAACCGGGCAGGTCACGCATCCCCCCCTTCCCTCCCACCCCC

TGCCAAGCTCTCCCTCCCAGGATCCTCTCTGGCTCCATCGTAAGCAAAC

CTTAGAGGTTCTGGCAAGGAGAGAGATGGCTCCAGGAAATGGGGGTGTG

TCACCAGATAAGGAATCTGCCTAACAGGAGGTGGGGGTTAGACCCAATA

TCAGGAGACTAGGAAGGAGGAGGCCTAAGGATGGGGCTTTTCTGTCACC

AATCCTGTCCCTANNYNNNTNTNNNNRTNDNNNHHCCATAGAGCCCACC

GCATCCCCAGCATGCCTGCTATTGTCTTCCCAATCCTCCCCCTTGCTGT

CCTGCCCCACCCCACCCCCCAGAATAGAATGACACCTACTCAGACAATG

CGATGCAATTTCCTCATTTTATTAGGAAAGGACAGTGGGAGTGGCACCT

TCCAGGGTCAAGGAAGGCACGGGGGAGGGGCAAACAACAGATGGCTGGC

AACTAGAAGGCACAGTCGAGGCTGATCAGCGGGTTTAAACGGGCCCTCT

AGACTCGACGCGGCCGCTTTACTTGTACAGCTCGTCCATGCCGAGAGTG

ATCCCGGCGGCGGTCACGAACTCCAGCAGGACCATGTGATCGCGCTTCT

CGTTGGGGTCTTTGCTCAGGGCGGACTGGGTGCTCAGGTAGTGGTTGTC
```

-continued

```
GGGCAGCAGCACGGGGCCGTCGCCGATGGGGGTGTTCTGCTGGTAGTGG

TCGGCGAGCTGCACGCTGCCGTCCTCGATGTTGTGGCGGATCTTGAAGT

TCACCTTGATGCCGTTCTTCTGCTTGTCGGCCATGATATAGACGTTGTG

GCTGTTGTAGTTGTACTCCAGCTTGTGCCCCAGGATGTTGCCGTCCTCC

TTGAAGTCGATGCCCTTCAGCTCGATGCGGTTCACCAGGGTGTCGCCCT

CGAACTTCACCTCGGCGCGGGTCTTGTAGTTGCCGTCGTCCTTGAAGAA

GATGGTGCGCTCCTGGACGTAGCCTTCGGGCATGGCGGACTTGAAGAAG

TCGTGCTGCTTCATGTGGTCGGGGTAGCGGCTGAAGCACTGCACGCCGT

AGGTCAGGGTGGTCACGAGGGTGGGCCAGGGCACGGGCAGCTTGCCGGT

GGTGCAGATGAACTTCAGGGTCAGCTTGCCGTAGGTGGCATCGCCCTCG

CCCTCGCCGGACACGCTGAACTTGTGGCCGTTTACGTCGCCGTCCAGCT

CGACCAGGATGGGCACCACCCCGGTGAACAGCTCCTCGCCCTTGCTCAC

CATGGTGGCGACCGGTGGGGAGAGAGGTCGGTGATTCGGTCAACGAGGG

AGCCGACTGCCGACGTGCGCTCCGGAGGCTTGCAGAATGCGGAACACCG

CGCGGGCAGGAACAGGGCCCACACTACCGCCCCACACCCCGCCTCCCGC

ACCGCCCCTTCCCGGCCGCTGCTCTCGGCGCGCCCTGCTGAGCAGCCGC

TATTGGCCACAGCCCATCGCGGTCGGCGCGCTGCCATTGCTCCCTGGCG

CTGTCCGTCTGCGAGGGTACTAGTGAGACGTGCGGCTTCCGTTTGTCAC

GTCCGGCACGCCGCGAACCGCAAGGAACCTTCCCGACTTAGGGGCGGAG

CAGGAAGCGTCGCCGGGGGGCCCACAAGGGTAGCGGCGAAGATCCGGGT

GACGCTGCGAACGGACGTGAAGAATGTGCGAGACCCAGGGTCGGCGCCG

CTGCGTTTCCCGGAACCACGCCCAGAGCAGCCGCGTCCCTGCGCAAACC

CAGGGCTGCCTTGGAAAAGGCGCAACCCCAACCCCGTGGAAGCTTGCGT

GGGGTGGAGGGGACAGATAAAAGTACCCAGAACCAGAGCCACATTAACC

GGCCCTGGGAATATAAGGTGGTCCCAGCTCGGGGACACAGGATCCCTGG

AGGCAGCAAACATGCTGTCCTGAAGTGGACATAGGGGCCCGGGTTGGAG

GAAGAAGACTAGCTGAGCTCTCGGACCCCTGGAAGATGCCATGACAGGG

GGCTGGAAGAGCTAGCACAGACTAGAGAGGTAAGGGGGGTAGGGGAGCT

GCCCAAATGAAAGGAGTGAGAGGTGACCCGAATCCACAGGAGAACGGGG

TGTCCAGGCAAAGAAAGCAAGAGGATGGAGAGGTGGCTAAAGCCAGGGA

GACGGGGTACTTTGGGGTTGTCCAGAAAAACGGTGATGATGCAGGCCTA

CAAGAAGGGGAGGCGGGACGCAAGGGAGACATCCGTCGGAGAAGGCCAT

CCTAAGAAACGAGAGATGGCACAGGCCCCAGAAGGAGAAGGAAAAGGGA

ACCCAGCGAGTGAAGACGGCATGGGGTTGGGTGAGGGAGGAGAGATGCC

CGGAGAGGACCCAGACACGGGGAGGATCCGCTCAGAGGACATCACGTGG

TGCAGCGCCGAGAAGGAAGTGCTCCGGAAAGAGCATCCTTGGGCAGCAA

CACAGCAGAGAGCAAGGGGAAGAGGGAGTGGAGGAAGACGGAACCTGAA

GGAGGCGGCAGGGAAGGATCTGGGCCAGCCGTAGAGGTGACCCAGGCCA

CAAGCTGCAGACAGAAAGCGGCACAGGCCCAGGGGAGAGAATGCTGGTC

AGAGAAAGCA
```

In another aspect the present invention provides for use of the AAV vector of the present invention for clonal tracking of cells that have been gene-edited using said vector, preferably wherein the cells are haematopoietic cells, haematopoietic stem cells and/or haematopoietic progenitor cells. In one embodiment, the use is in vitro use.

In another aspect the present invention provides a method for clonal tracking of cells using the AAV vector of the present invention, preferably wherein the cells are haematopoietic cells, haematopoietic stem cells and/or haematopoietic progenitor cells.

The method may comprise the following steps:
  (a) providing an isolated population of cells;
  (b) gene editing the isolated population of cells using the AAV vector of the present invention; and
  (c) clonal tracking of the gene-edited cells using the barcode sequence of the AAV vector.

Preferably, the method further comprises: optionally, expanding the isolated population of gene-edited cells; and transplanting the isolated population of gene-edited cells into a subject.

Thus, in a preferred embodiment, the method comprises the steps of:
  (a) providing an isolated population of cells;
  (b) gene editing the isolated population of cells using the AAV vector of the present invention;
  (c) optionally, expanding the isolated population of gene-edited cells;
  (d) transplanting the isolated population of gene-edited cells into a subject; and
  (e) clonal tracking of the gene-edited cells using the barcode sequence of the AAV vector.

More preferably, the method further comprises: harvesting blood and/or tissue samples from the subject; isolating genomic DNA from the blood and/or tissue samples; and quantifying the barcodes in the genomic DNA.

Thus, in a preferred embodiment, the method comprises the steps of:
  (a) providing an isolated population of cells;
  (b) gene editing the isolated population of cells using the AAV vector of the present invention;
  (c) optionally, expanding the isolated population of gene-edited cells;
  (d) transplanting the isolated population of gene-edited cells into a subject;
  (e) harvesting blood and/or tissue samples from the subject;
  (f) isolating genomic DNA from the blood and/or tissue samples; and
  (g) quantifying the barcode sequences from the AAV vector in the genomic DNA.

The cells may be any suitable cells, as described herein. The cells may be haematopoietic cells, haematopoietic stem cells and/or haematopoietic progenitor cells. The cells may be e.g. human or mouse cells. Preferably the cells are human cells and the subject is human. The cells may be CD34+ cells. In some embodiments the cells are HSCs. In some embodiments the cells are HSPCs.

The AAV vector may be transduced into the cells. Preferably the transduction is performed with $1 \times 10^4$ to $5 \times 10^4$ vg/cell.

Blood and/or tissue samples may be harvested after at least 1, 2, 3, 4, 8, 12, 24, 36 or 48 weeks. For example, blood and/or tissue samples may be harvested after about 1-100 weeks, 1-50 weeks, 1-20 weeks, 2-20 weeks, or 5-20 weeks.

Preferably, blood and/or tissue samples are harvested at least about every day, about every week, about every two weeks, or about every month. For example, in some embodiments, blood and/or tissue samples are harvested about every day, about every week, about every two weeks, or about every month.

In preferred embodiments the sample is a blood sample.

Clonal tracking or quantification of the barcode sequences may comprise the steps of:

(i) PCR amplification of the barcode sequences; and (ii) sequencing the PCR-amplified barcode sequences.

Quantification may allow the number and distribution of gene-edited clones to be identified i.e. to allow for clonal tracking.

In another aspect the present invention provides use of a barcode sequence for clonal tracking of cells.

DESCRIPTION OF THE DRAWINGS

FIG. 8: E1B55K and E4orf6 supplementation to gene editing protocol in human CD34+ (A) Percentage of GFP+ cells measured within the indicated subpopulations 4 days after AAVS1 editing of CB-derived CD34+ using AAV6 as donor template with MOI=5×$10^4$ vg/cell, RNP-Cas9 (25 pmol) and supplemented with E1B55K (3 $\mu$g total RNA) and/or E4orf6 (2 $\mu$g total RNA). (B) Percentage of HDR mediated integration measured by ddPCR on the 5' vector-to-genome junction, and GFP+ cells measured by cytofluorimetric analysis within the bulk at 4 days after gene-editing of CB-derived CD34+ using AAV6 as donor template with MOI=5×$10^4$ vg/cell, RNP-Cas9 (25 pmol) and supplemented with E1B55K (3 $\mu$g total RNA) and/or E4orf6 (2 $\mu$g total RNA). (C) Colony forming cell assay. Total number of erythroid (n=3), in red, and myeloid (n=3), in white, colonies measured 15 days after plating. (D) Cell growth curve post-electroporation (n=1).

Figure 9:
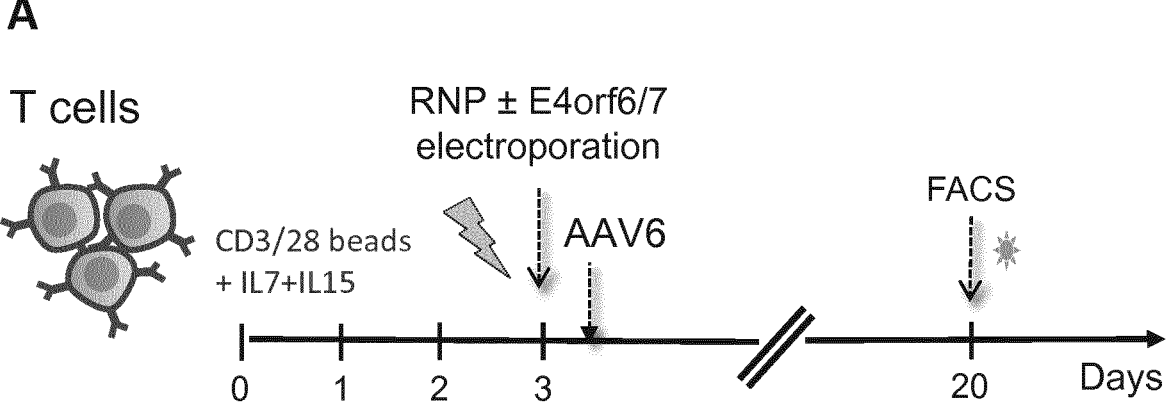
Figure 9:
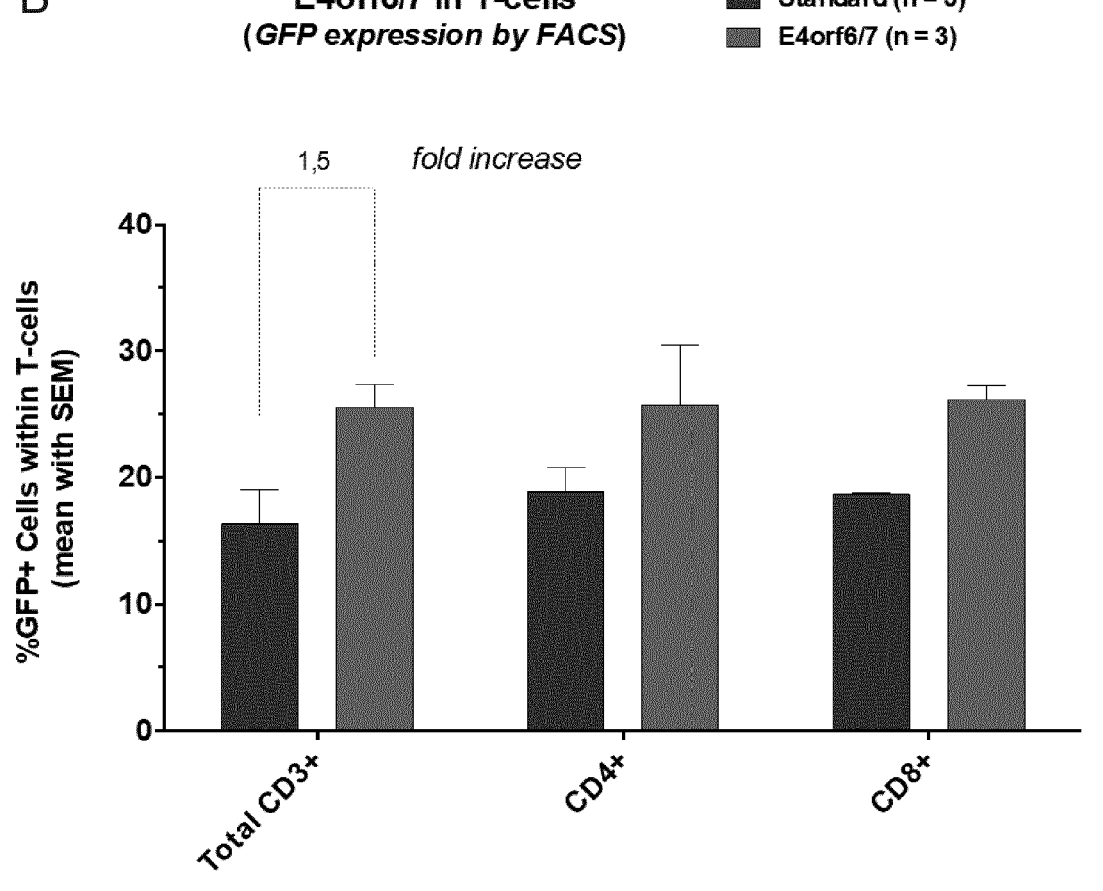

FIG. 9: Gene editing of human T-cells using E4orf6/7. (A) Schematic representation of the T cells gene editing protocol±E4orf6/7 and cell analysis. (B) Percentage of GFP+ cells measured within the indicated subpopulations 20 days after AAVS1 editing of stimulated T-cells (n=3) using AAV6 as donor template with MOI=5×10⁴ vg/cell, RNP-Cas9 (25 pmol) and supplemented with E4orf6/7 (2 µg total RNA).

Figure 10:
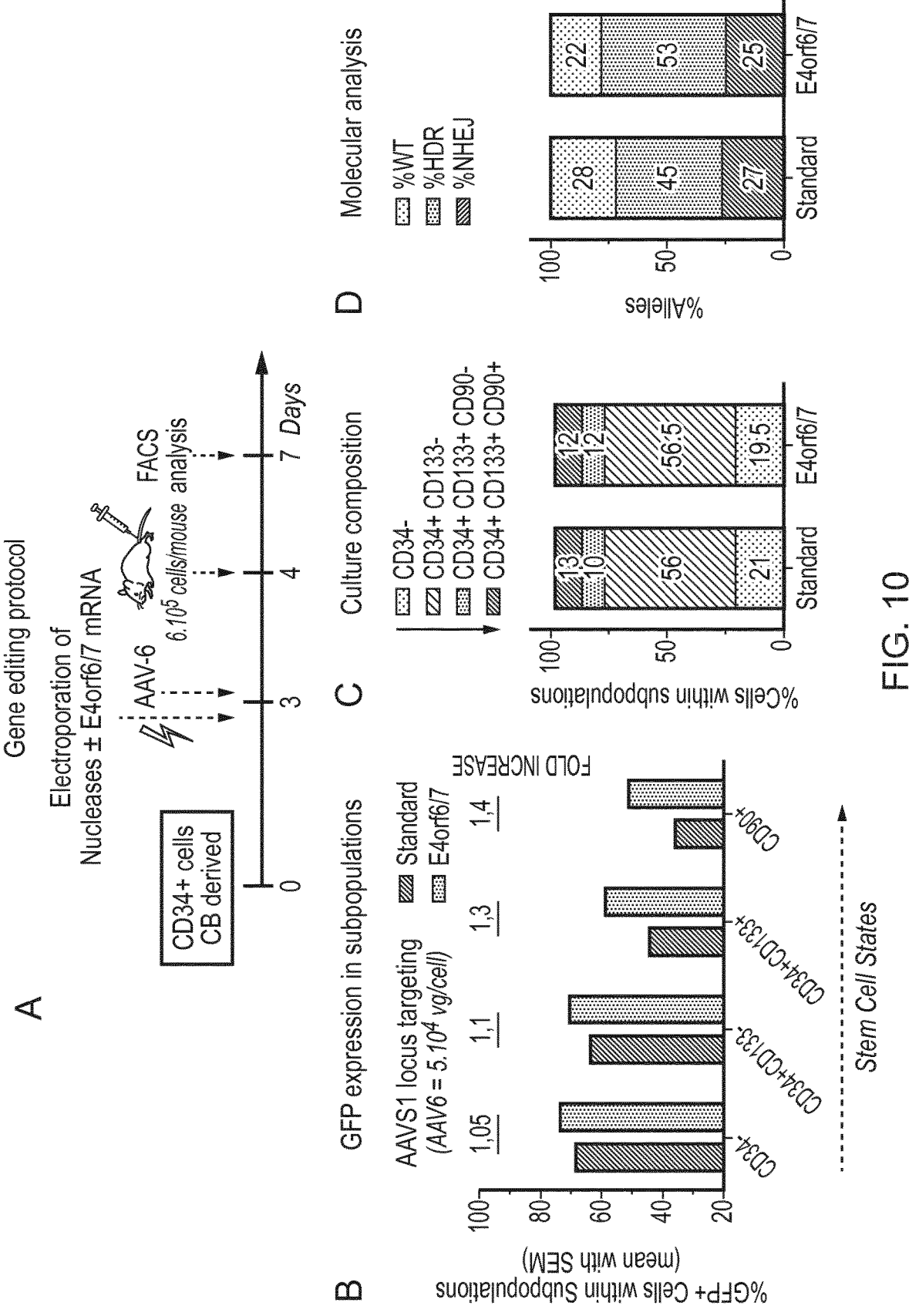

FIG. 10: AAVS1 gene editing of human CB-derived CD34+ using E4orf6/7 followed by NSG mice transplantation. (A) The standard transplantation procedure required 3 days of cells stimulation with cytokines and drugs before electroporation of the complex AAVS1 specific RNP-cas9 (25 pmol) and supplemented with E4orf6/7 (2 µg total RNA). Electroporation procedure is followed by AAV6 transduction at 5×10⁴ viral genome per cell. A total of 6×10⁵ treated cells are transplanted to each mouse (tail intravenous injection); two experimental conditions were tested (standard and supplemented with E4orf6/7). (B) Percentage of GFP+ cells measured within the indicated subpopulations 4 days after AAVS1 editing of CB-derived CD34+ using AAV6 as donor template with MOI=5×10⁴ vg/cell, RNP-Cas9 (25 pmol) and supplemented with E4orf6/7 (2 µg total RNA). (C) Culture composition of treated CD34+ cells from (B). (D) Molecular analysis of the AAVS1 alleles of the cells from (B), represented as percentage of wild-type (WT) or modified alleles by HDR (digital droplet PCR, ddPCR, mediated quantification of the 5' vector-to-genome junction) or by NHEJ (T7 heteroduplex detection assay).

Figure 11:
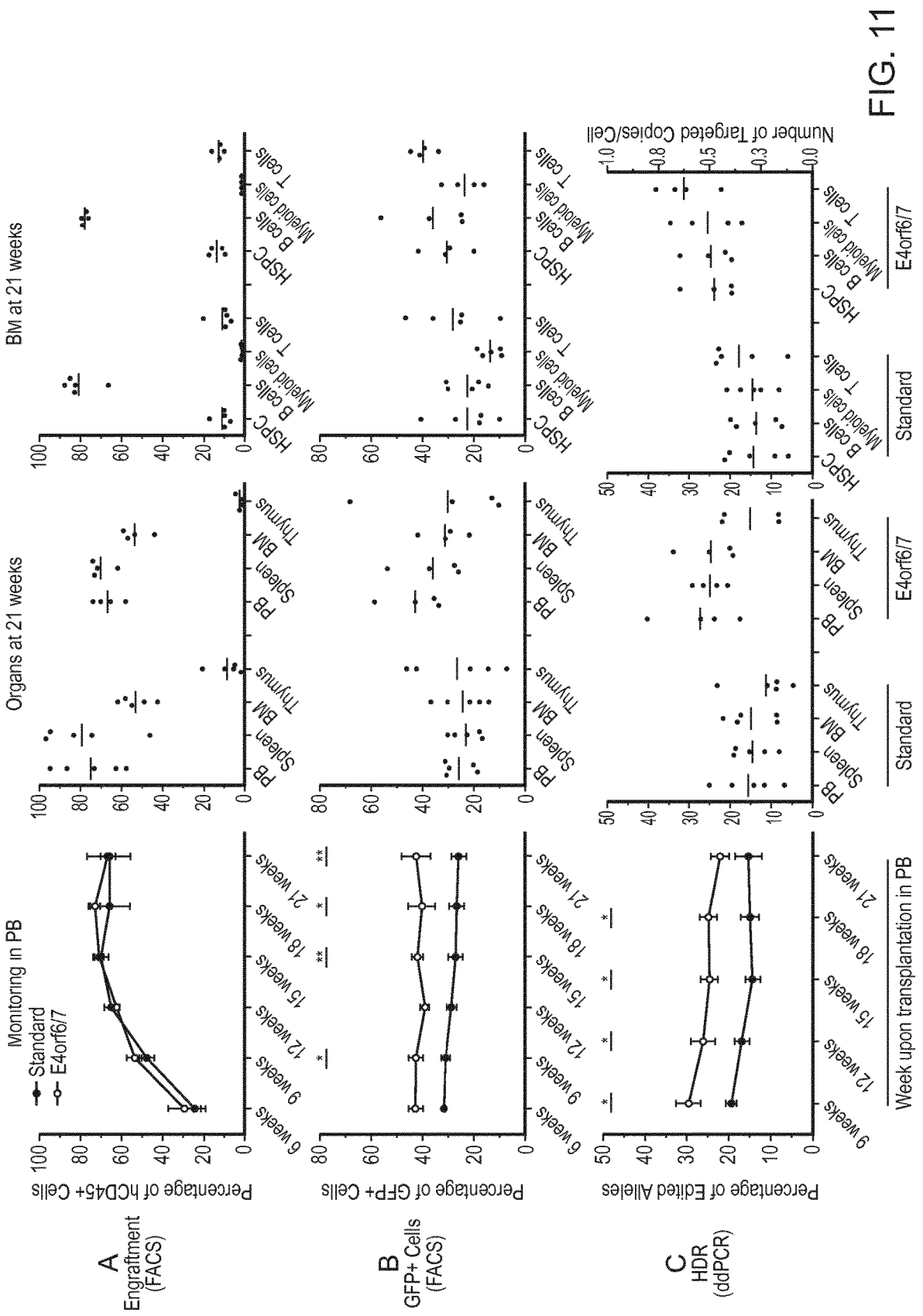

FIG. 11: In-vivo following of AAVS1 targeted human CB-derived CD34+ using E4orf6/7. (A) Human CD45+ engraftment of edited cells in presence (n=4) or not (n=5) with E4orf6 mRNA measured at the indicated times in the peripheral blood (PB) of the transplanted NSG mice and at the end of the experiment in their different organs (spleen, thymus and bone-marrow) and within different blood lineages of the bone marrow (HSPC=CD34+; B cells=CD19+; Myeloid cells=CD33+; T cells=CD3+). (B) Percentage of GFP+ cells measured within the human cells from (A) measured in PB, hematopoietic organs and bone-marrow lineages. (C) Percentage of edited alleles (number of targeted copies per cell) from (A) measured in PB, hematopoietic organs and bone-marrow lineages.

Figure 12:
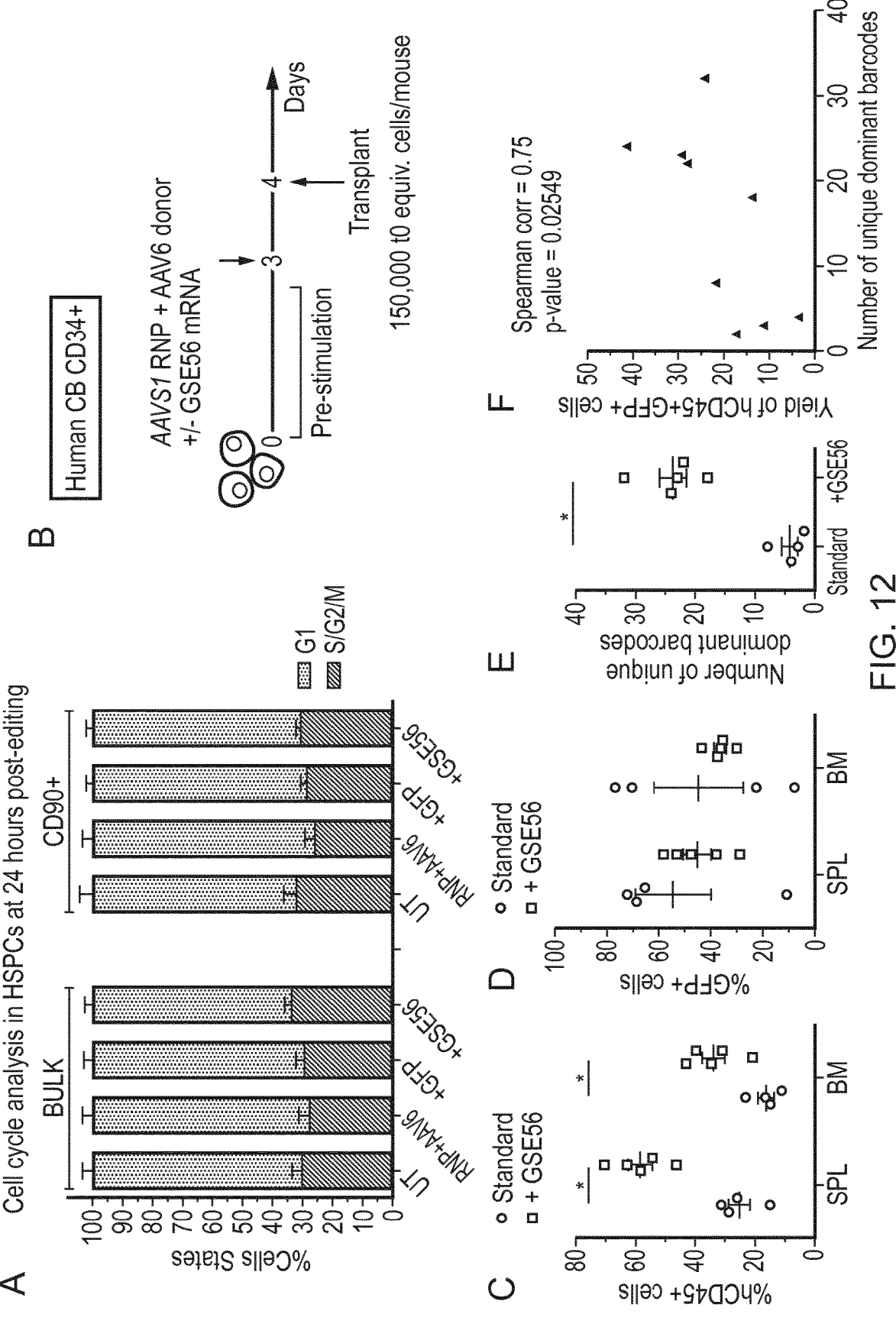

FIG. 12: Transient GSE56 overexpression improves in vivo yield and clonality of AAVS1-edited repopulating HSPCs. (A) Percentage of cell cycle states in bulk culture and CD90+ by Hoechst 33342 staining measured by FACS at 12-24 hours post-editing protocol [Kruskal-Wallis test, relative to standard RNP+AAV6]. (B) Schematic representation of the experimental setting for transplantation into immunodeficient NSG mice of AAVS1 targeted gene editing in human cord blood (CB)-derived CD34+ cells. (C, D) Percentage of human cells (C) and GFP+ (D) within total human cells in spleen (SPL) and bone marrow (BM) at 21 weeks post-xenotransplantation with cells treated (+ GSE56) or not (standard) with the p53 inhibitor [Mann-Withney test]. (E) Number of unique dominant barcodes in the hematopoietic organs of mice transplanted with cells treated (+ GSE56) or not (standard) with the p53 inhibitor [Mann-Withney test]. (F) Correlation between the number of unique dominant barcodes (X axis) and the percentage of CD45+ GFP+ cells (Y axis) (Spearman correlation).

Figure 13:
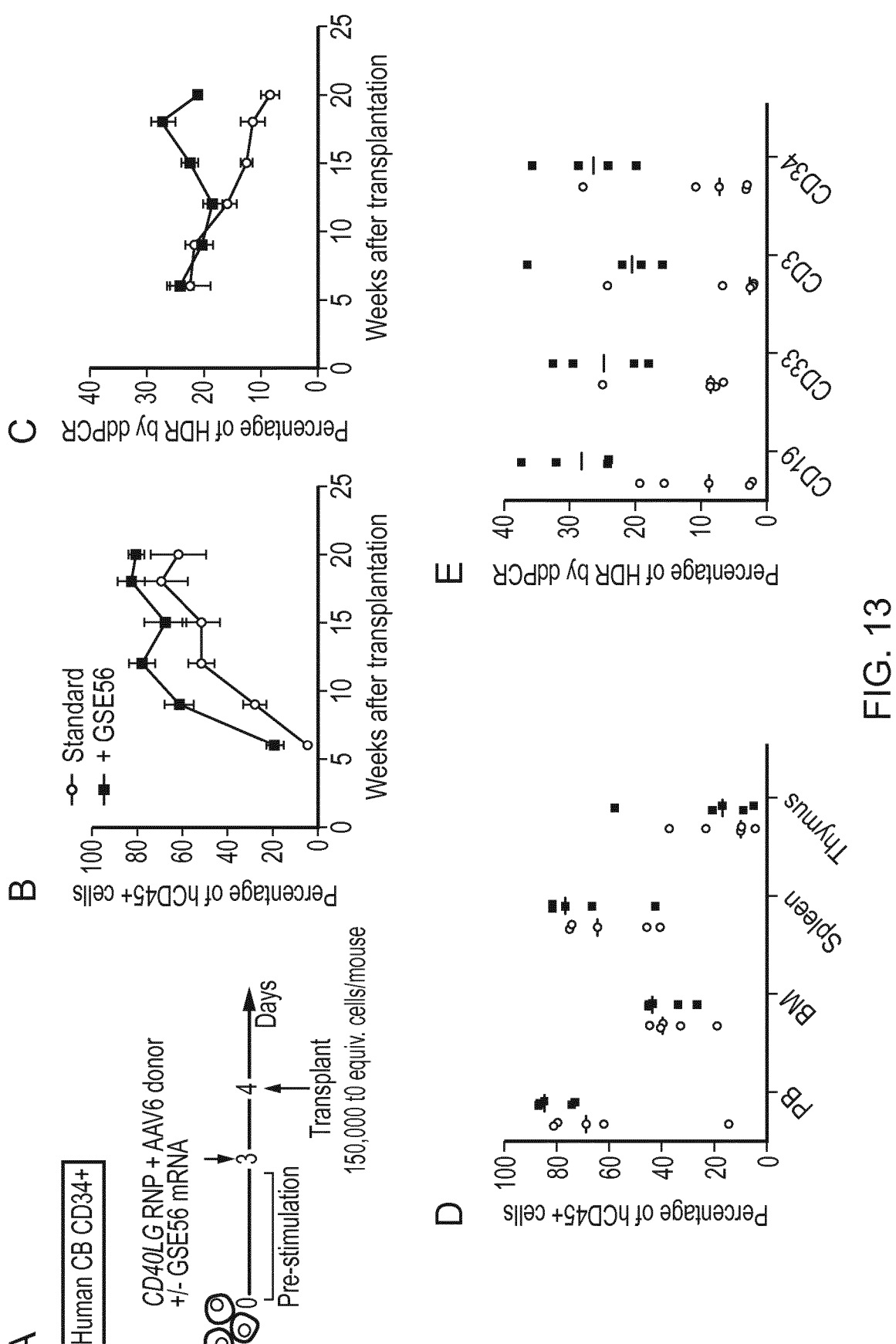

FIG. 13: Transient GSE56 overexpression improves in vivo yield of CD40LG-edited repopulating HSPCs. (A) Schematic representation of the experimental setting for transplantation into immunodeficient NSG mice of CD40LG targeted gene editing in human cord blood (CB)-derived CD34+ cells. (B, C) Percentage of human cells (B) and GFP (C) in peripheral blood of NSG mice transplanted with cells treated (+ GSE56) or not (standard) with the p53 inhibitor. (D) Percentage of human cells in hematopoietic organs of mice from (B). (E) Percentage of targeted integration measured by digital droplet PCR in sorted B cells (CD19+), myeloid (CD33+), T cells (CD3+) and stem cells (CD34+) from mice in (D).

Figure 14:
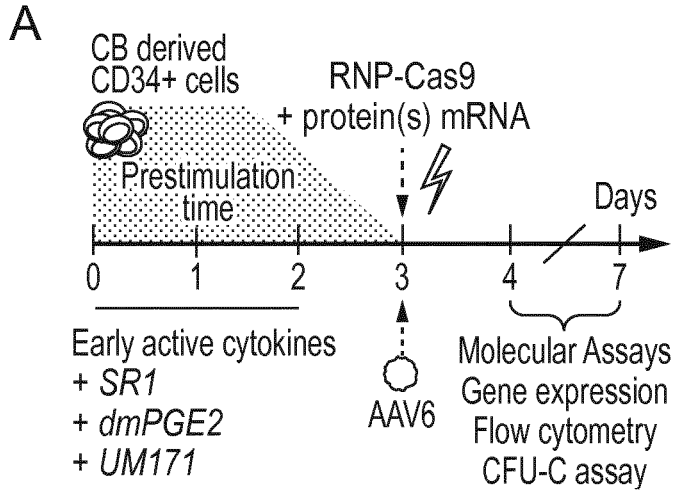
Figure 14:
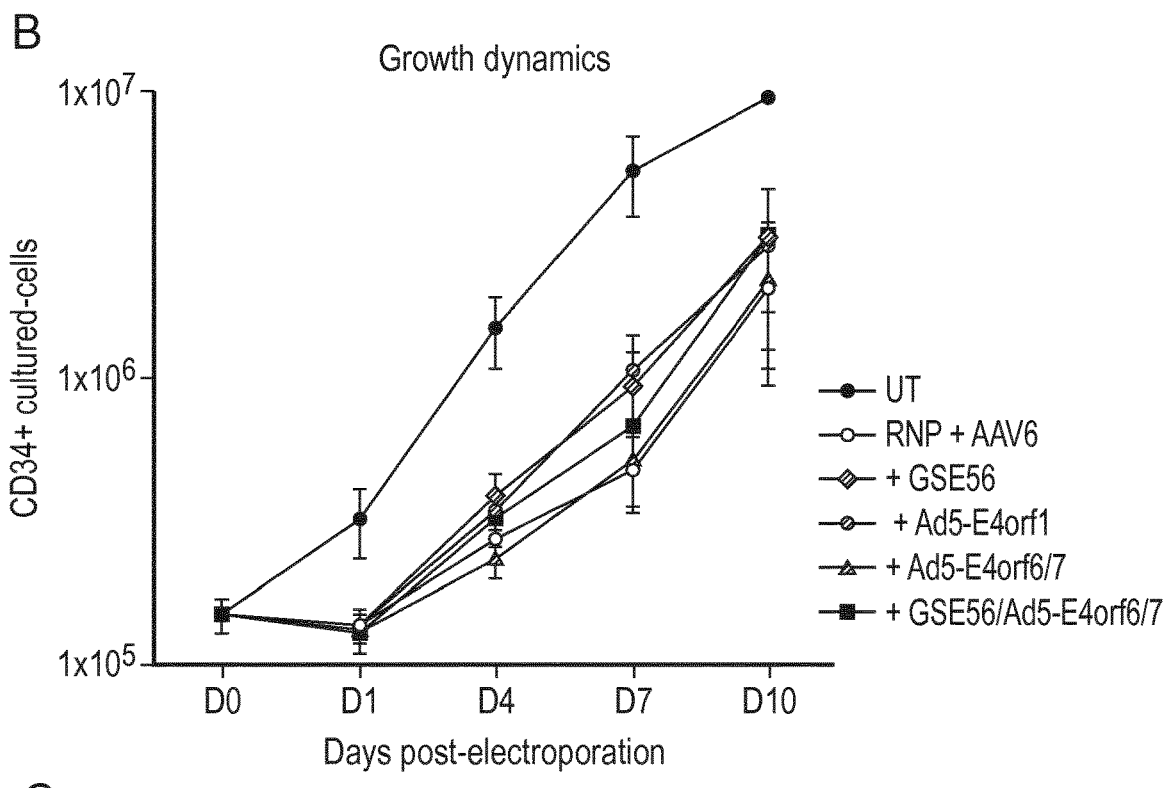
Figure 14:
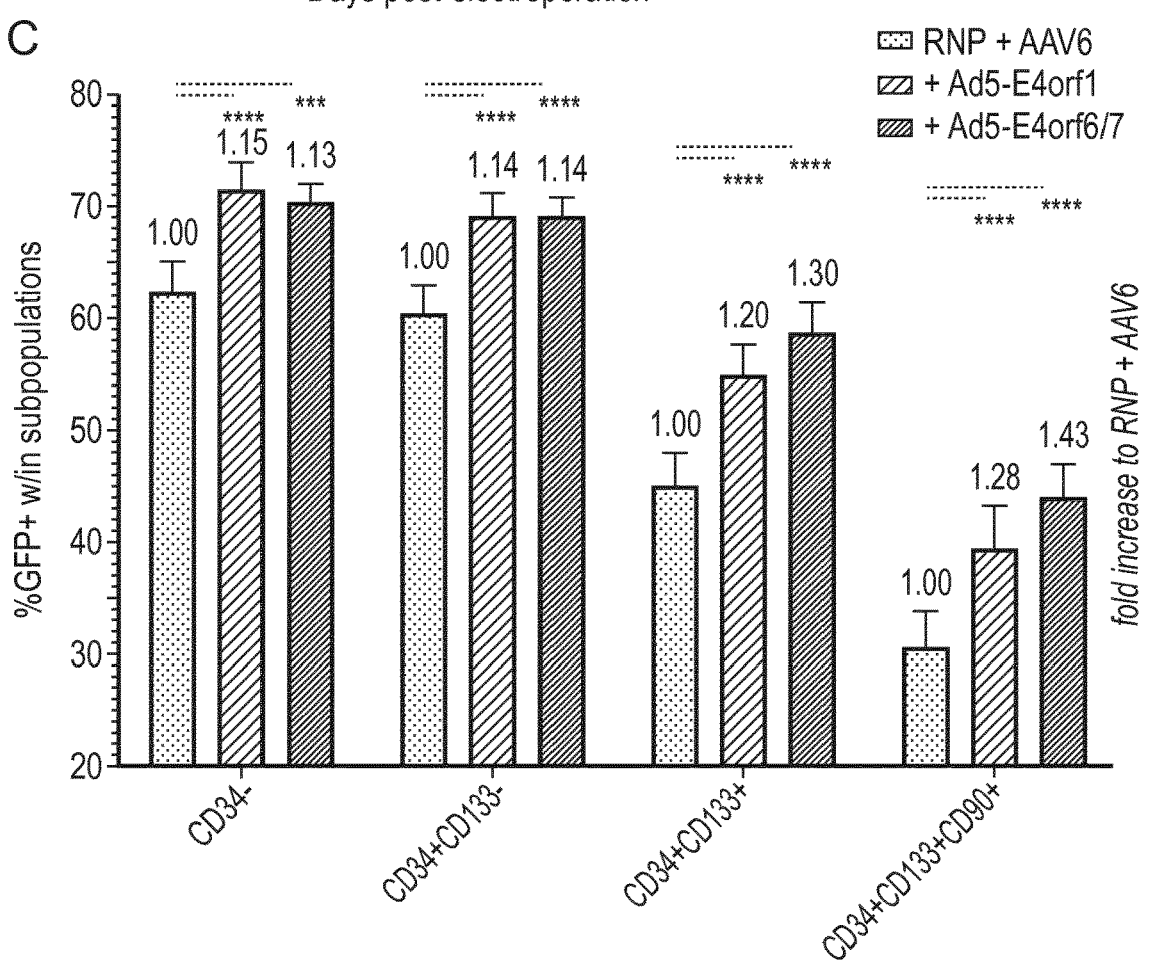
Figure 14:
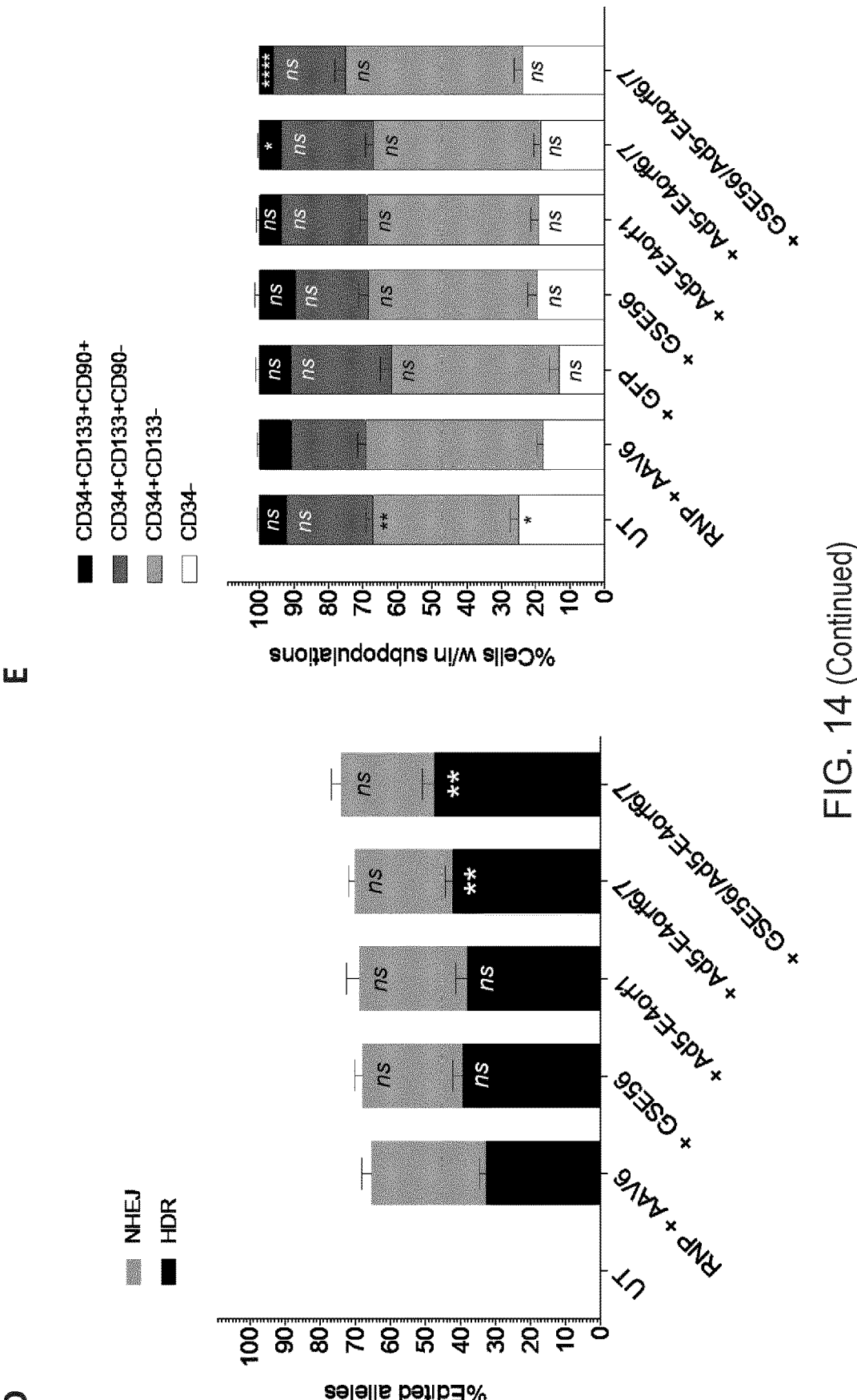
Figure 14:
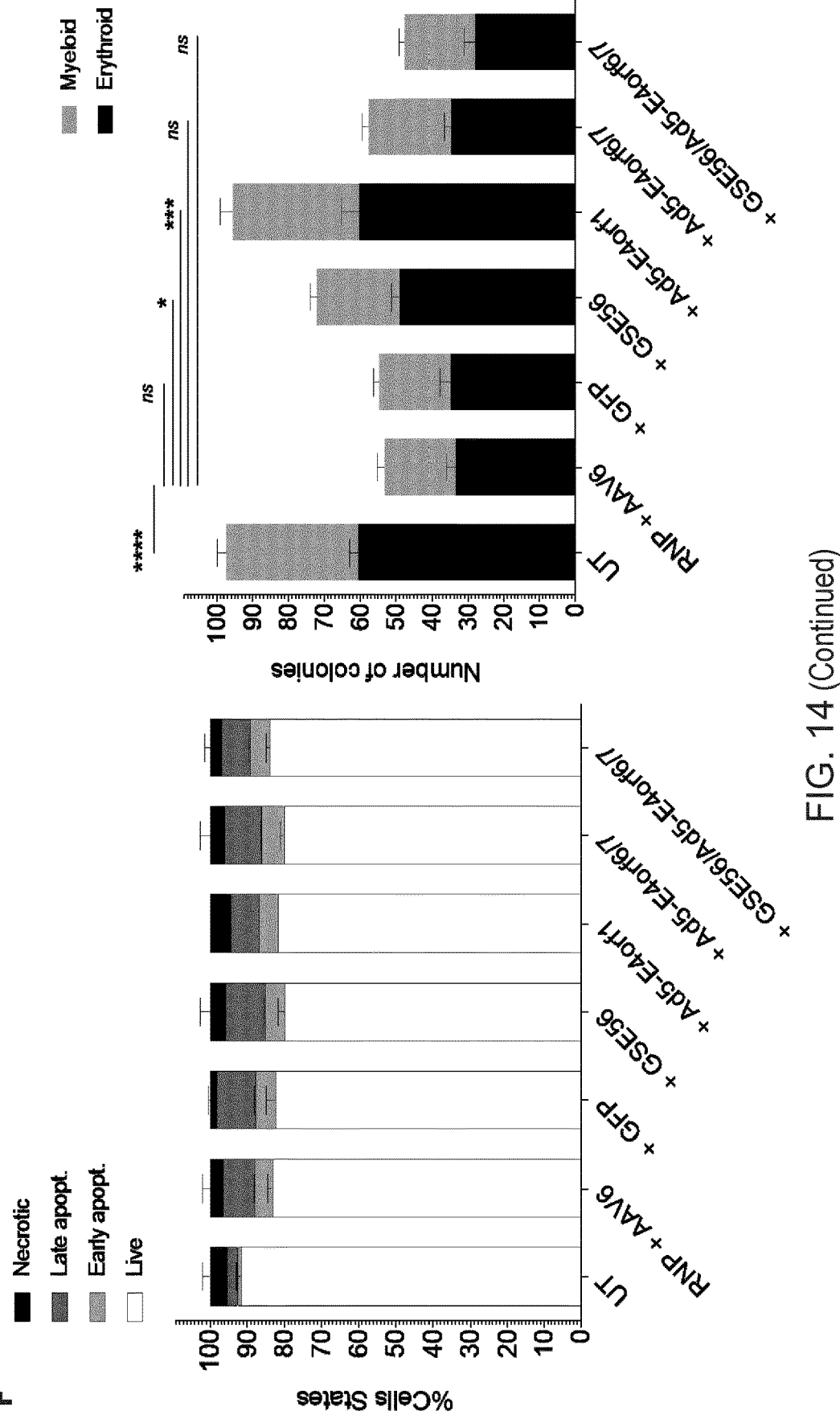
Figure 14:
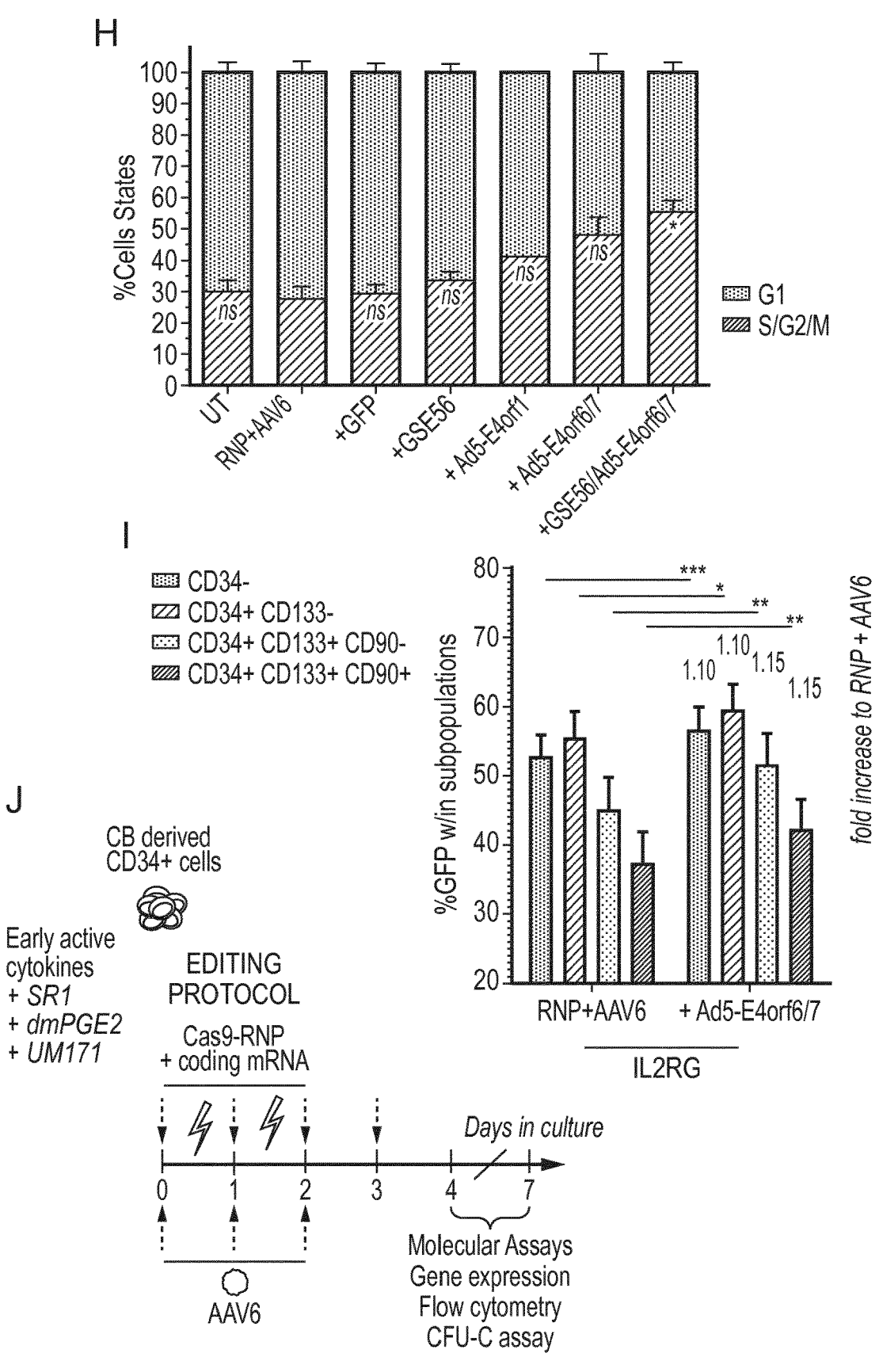
Figure 14:
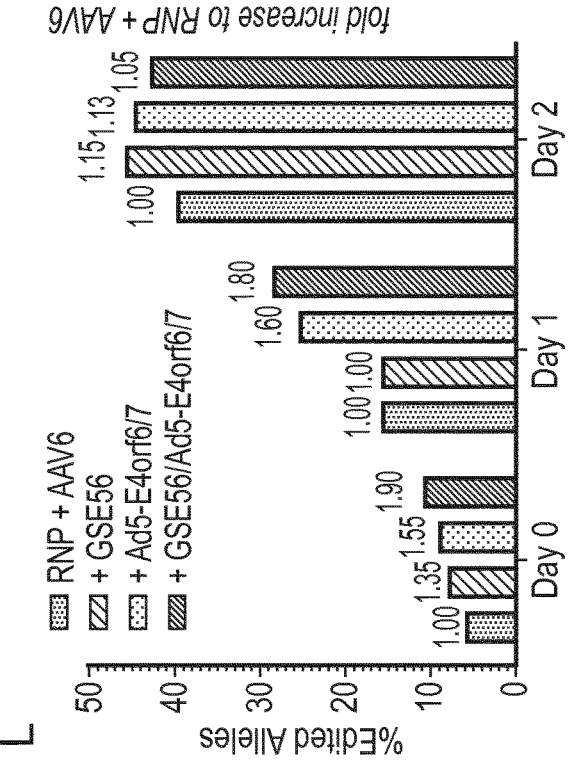
Figure 14:
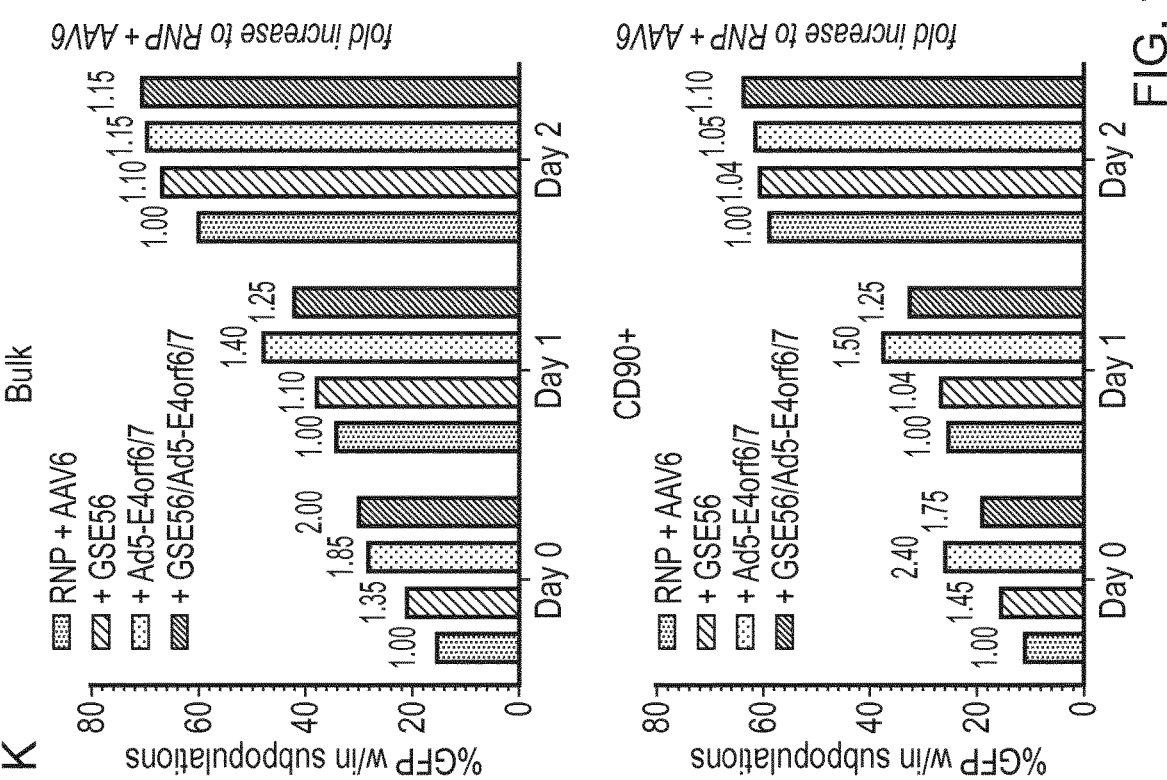

FIG. 14: The adenoviral proteins Ad5-E4orf6/7 and Ad5-E4orf1 both increase the HDR efficiency by targeting the AAVS1 locus in HSPCs. (A) Schematic representation of the targeted gene editing protocol in human cord blood (CB)-derived CD34+ after pre-stimulation with cytokines and drugs and by electroporating at day 3 the RNP-Cas9 (25 µmol) and AAV6 (2.10⁴ vg/ml) as standard editing procedure±GFP, GSE56, Ad5-E4orf1, Ad5-E4orf6/7 or GSE56/Ad5-E4orf6/7 delivered as mRNAs. (B) Monitoring of CD34+ cultured-cells growth over days post-editing. (C left and right panels) Percentage of GFP+ cells measured by FACS within the indicated subpopulations at 96 hours post-editing protocol for standard RNP+AAV6±GSE56, Ad5-E4orf1, Ad5-E4orf6/7 or GSE56/Ad5-E4orf6/7 and associated numeric fold increase [one-way ANOVA]. (D) Percentage of AAVS1 edited alleles by HDR and NHEJ in bulk culture measured by ddPCR on the 5' vector-to-genome junction at 96 hours post-editing protocol [Kruskal-Wallis test, relative to standard RNP+AAV6]. (E) Culture composition from differentiated cells (CD34−) to the most primitive compartment (CD34+CD133+CD90+) at 96 hours post-editing protocol [Kruskal-Wallis test, relative to standard RNP+AAV6]. (F) Percentage of cell states apoptosis in bulk culture by 7-AAD/Annexin staining measured by FACS at 24 hours post-editing protocol. (G) Number of colonies plated from bulk culture at 24 hours post-editing protocol [Kruskal-Wallis test, relative to standard RNP+AAV6]. (H) Percentage of cell cycle states in bulk culture by Hoechst 33342 staining measured by FACS at 12-24 hours post-editing protocol [Kruskal-Wallis test, relative to standard RNP+AAV6]. (I) Percentage of GFP+ cells measured by FACS within the indicated subpopulations at 96 hours post-editing protocol in IL2RG locus, for standard RNP+AAV6±Ad5-E4orf6/7 and associated numeric fold increase [Paired T-test]. (J) Schematic representation of the targeted gene editing protocol in human cord blood (CB)-derived CD34+ by performing electroporation at day 0, 1 and 2 post-thawing with the RNP-Cas9 (25 pmol) and AAV6 (2.10⁴ vg/ml) as standard editing procedure±GSE56, Ad5-E4orf6/7 or GSE56/Ad5-E4orf6/7 delivered as mRNAs. (K) Percentage of GFP+ cells measured by FACS within the indicated subpopulations at 96 hours post-editing protocol (n=1) for standard RNP+AAV6±GSE56, Ad5-E4orf6/7 or GSE56/Ad5-E4orf6/7 and associated numeric fold increase in bulk (left panel) and CD90+ (right panel). (L) Percentage of AAVS1 edited alleles by HDR in bulk culture measured by ddPCR on the 5' vector-to-genome junction at 96 hours post-editing protocol (n=1).

Figure 15:
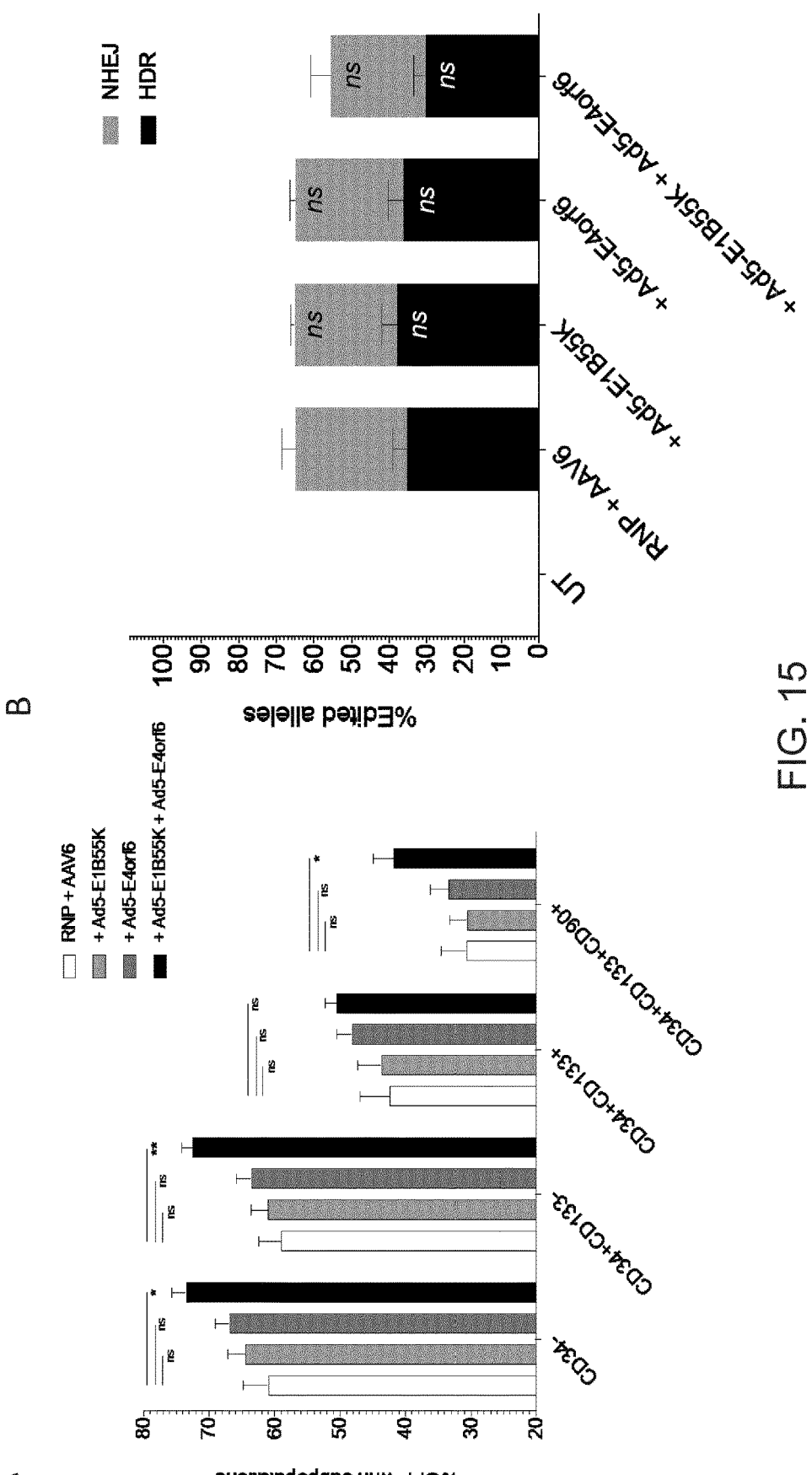
Figure 15:
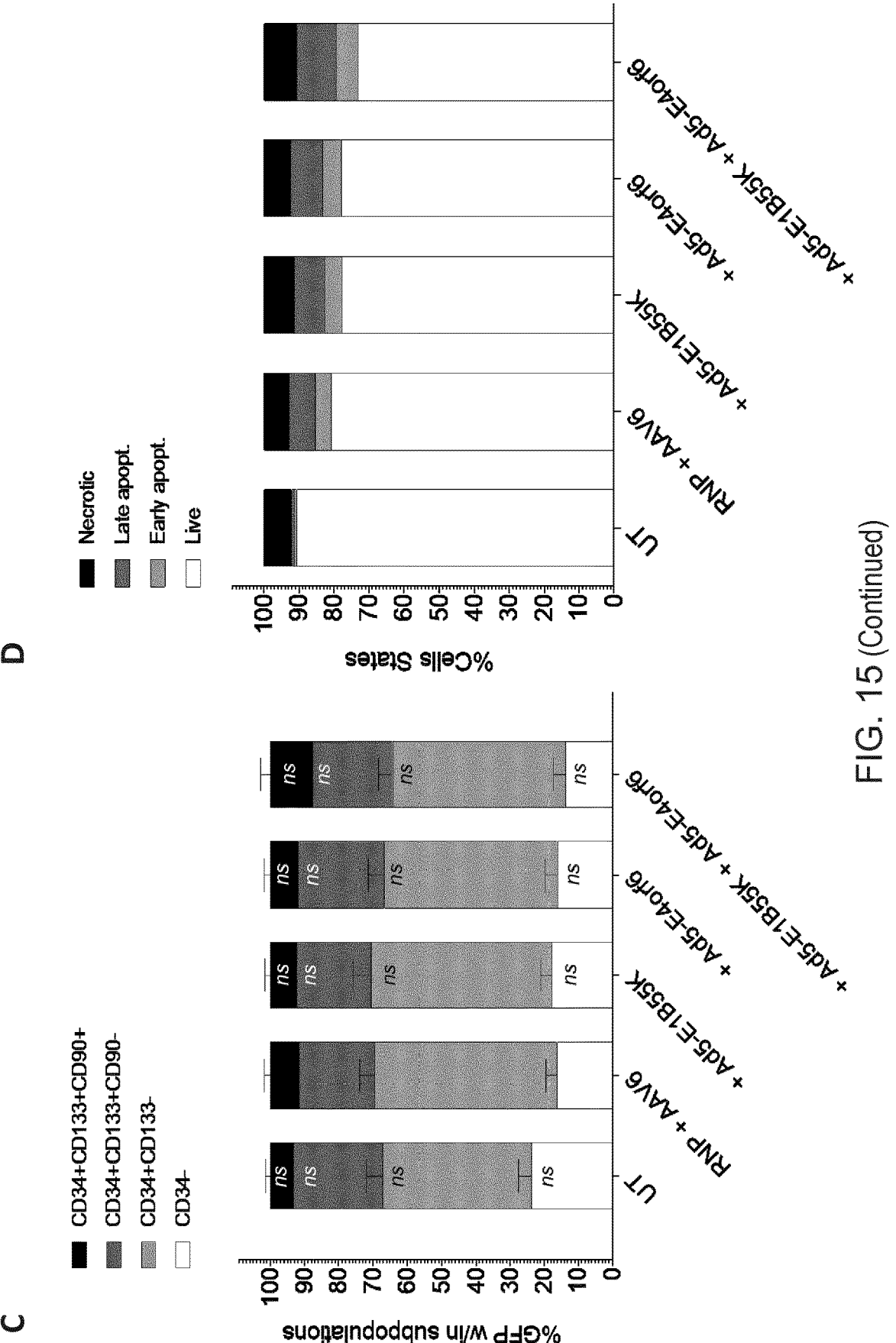
Figure 15:
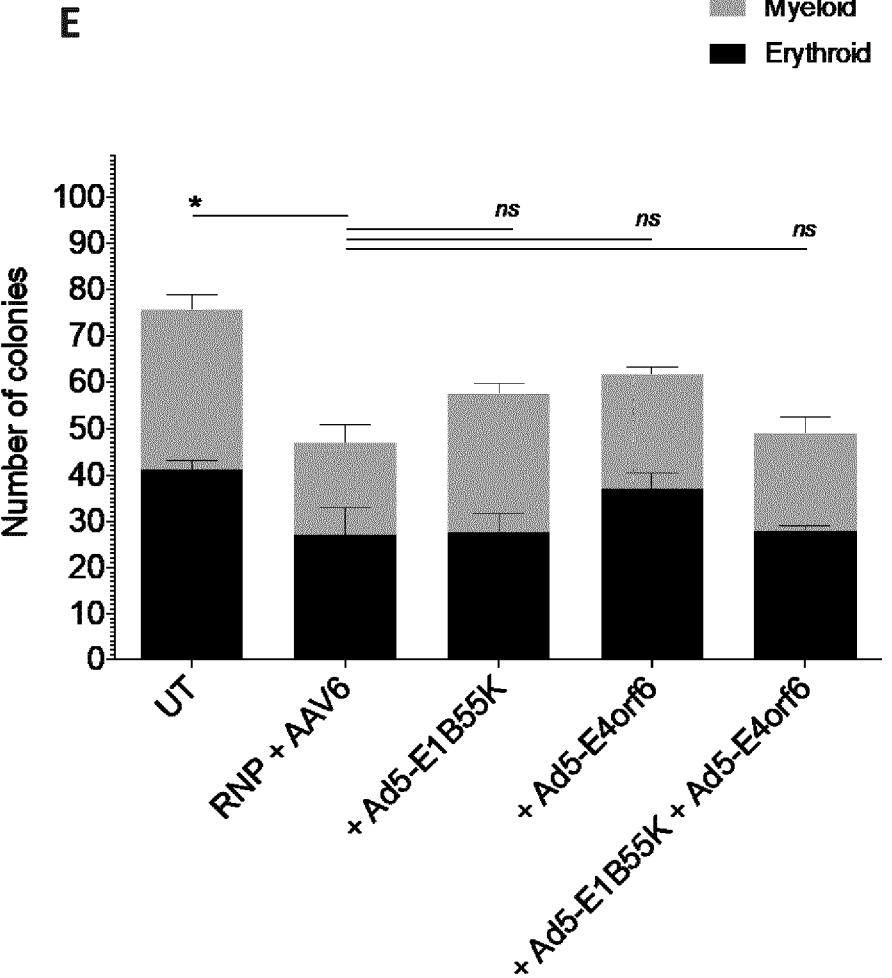

FIG. 15: The combination of adenoviral proteins Ad5-E1B55K and Ad5-E4orf6 increases donor template cassette expression but does not increase HDR efficiency in HSPCs. (A) Percentage of GFP+ cells measured by FACS within the indicated subpopulations at 96 hours post-editing protocol performed in hCB-derived CD34+ by using our standard procedure RNP+AAV6±Ad5-E1B55K and/or Ad5-E4orf6 [one-way ANOVA]. (B) Percentage of AAVS1 edited alleles by HDR and NHEJ in bulk culture measured by ddPCR on the 5' vector-to-genome junction at 96 hours post-editing protocol [Kruskal-Wallis test, relative to standard RNP+AAV6]. (C) Culture composition at 96 hours post-editing protocol. (D) Percentage of cell states apoptosis in bulk culture by 7-AAD/Annexin staining measured by FACS at 24 hours post-editing protocol. (E) Number of colonies plated from bulk culture at 24 hours post-editing protocol [Kruskal-Wallis test, relative to standard RNP+AAV6].

Figure 16:
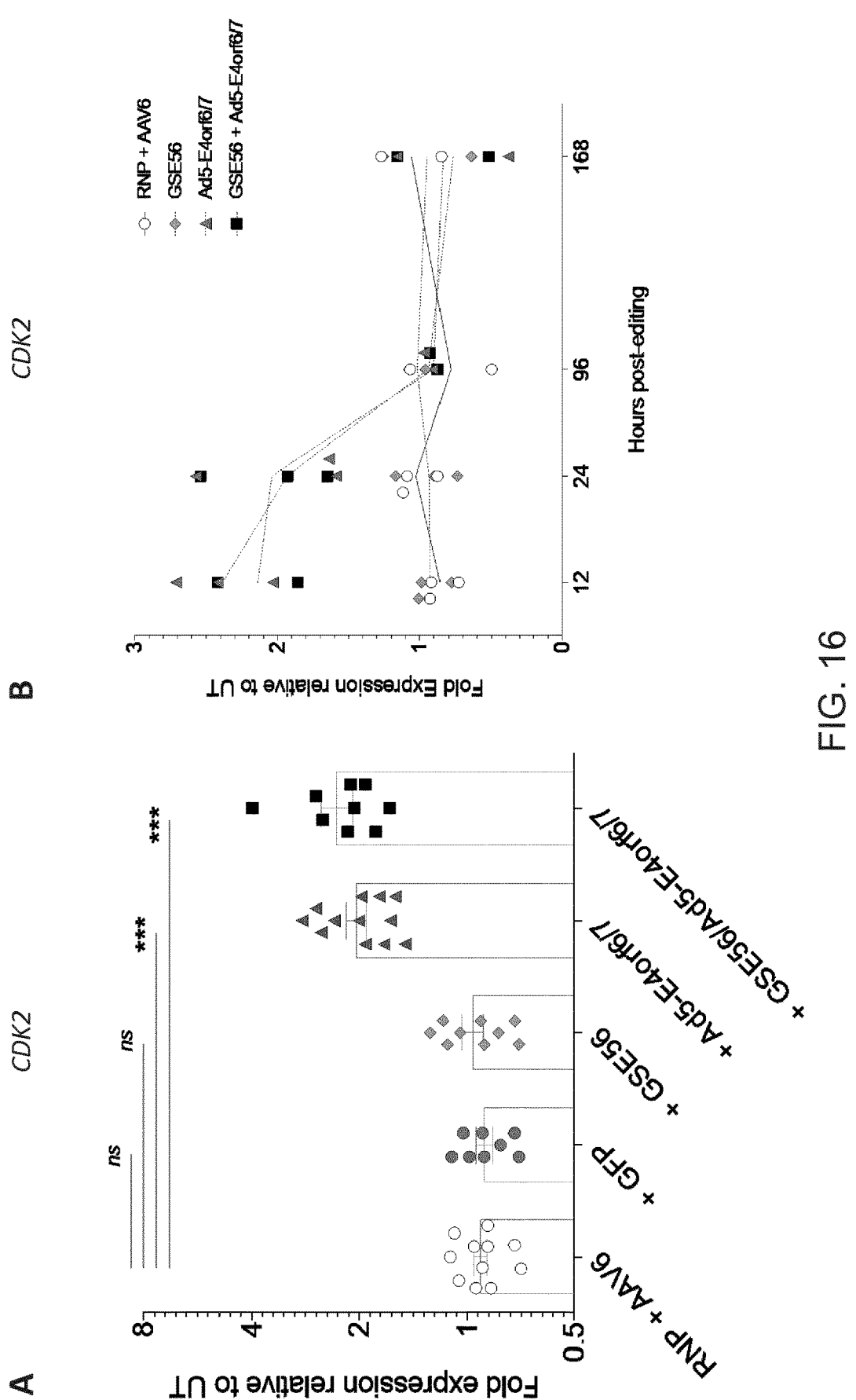
Figure 16:
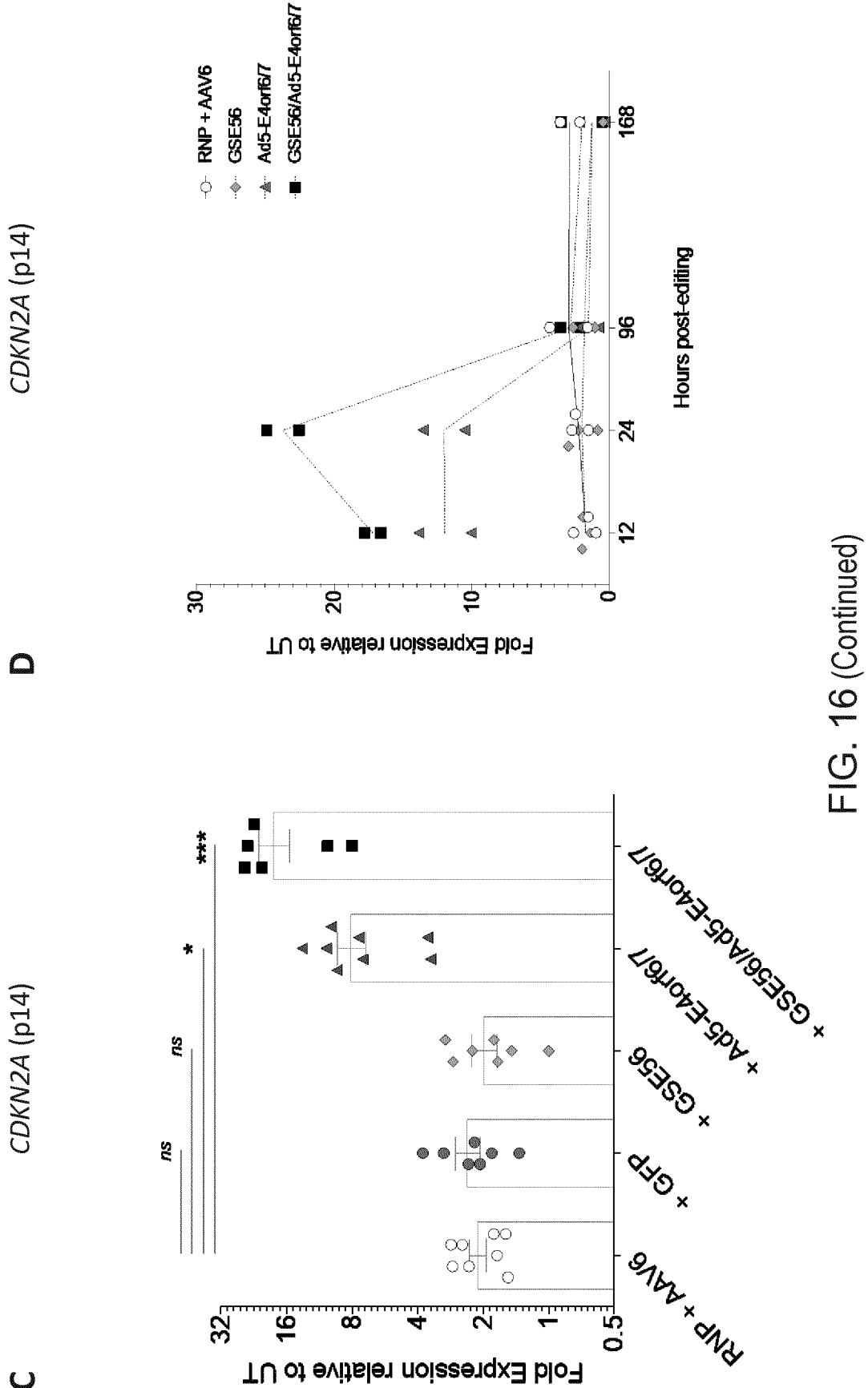
Figure 16:
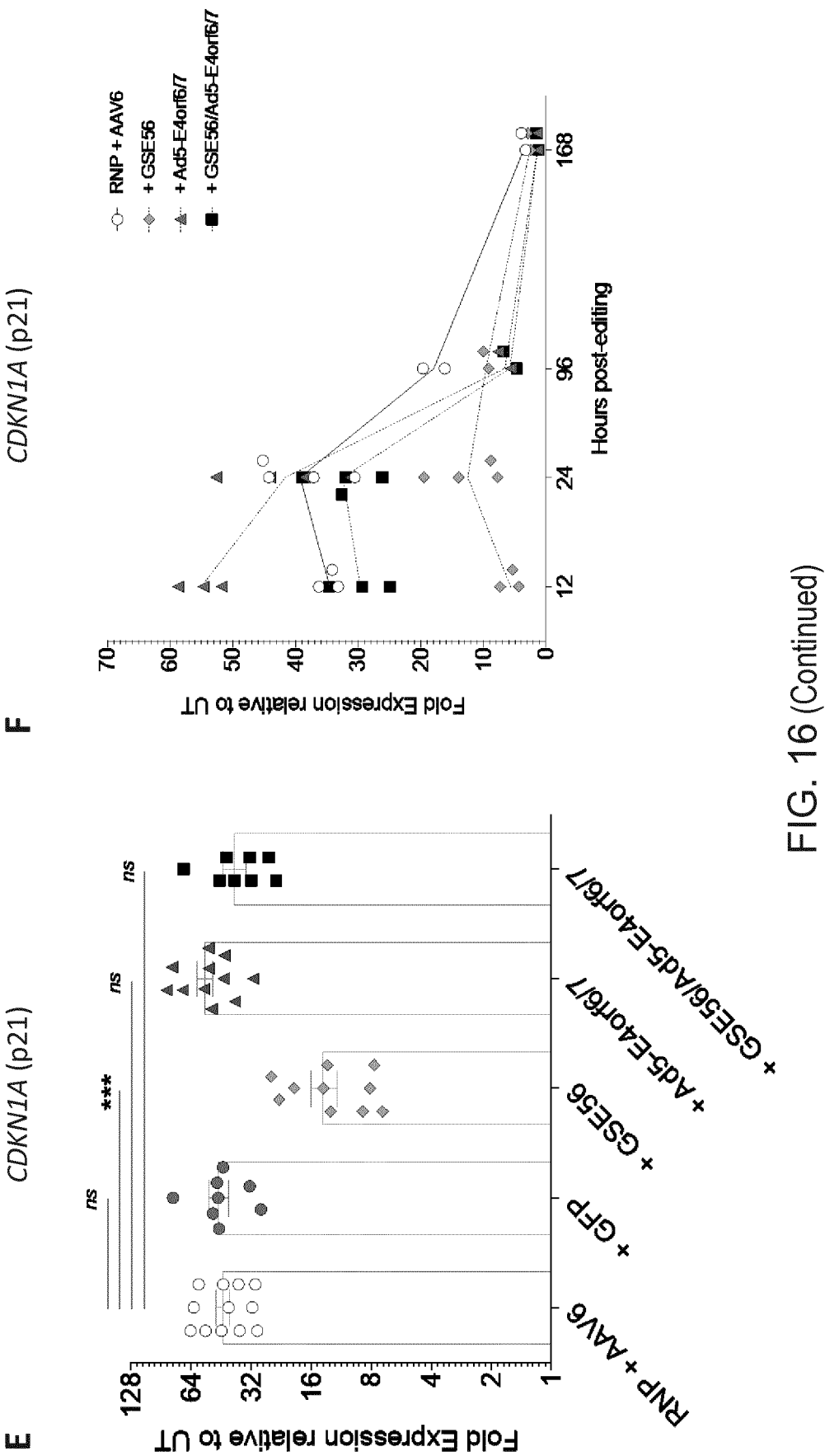
Figure 16:
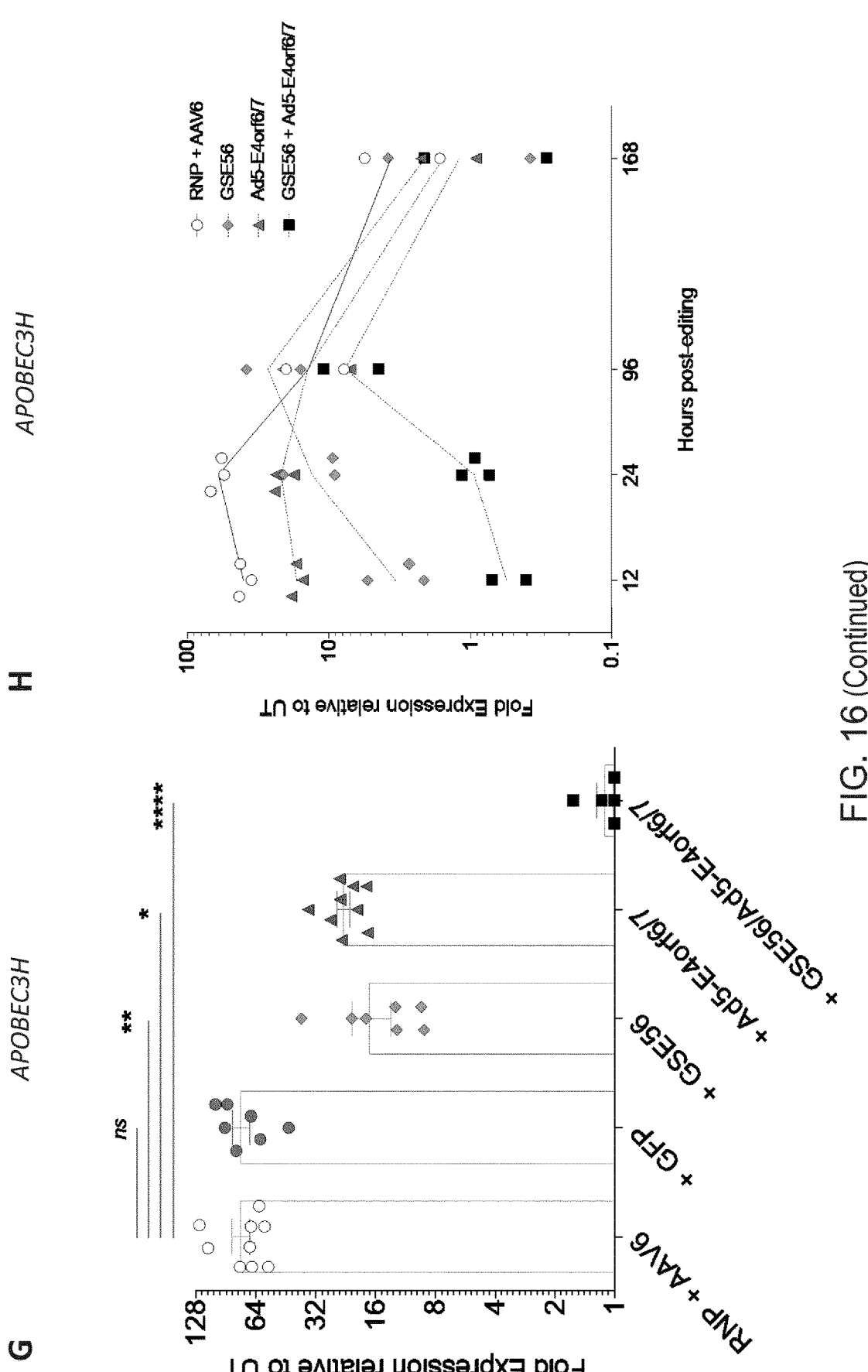
Figure 16:
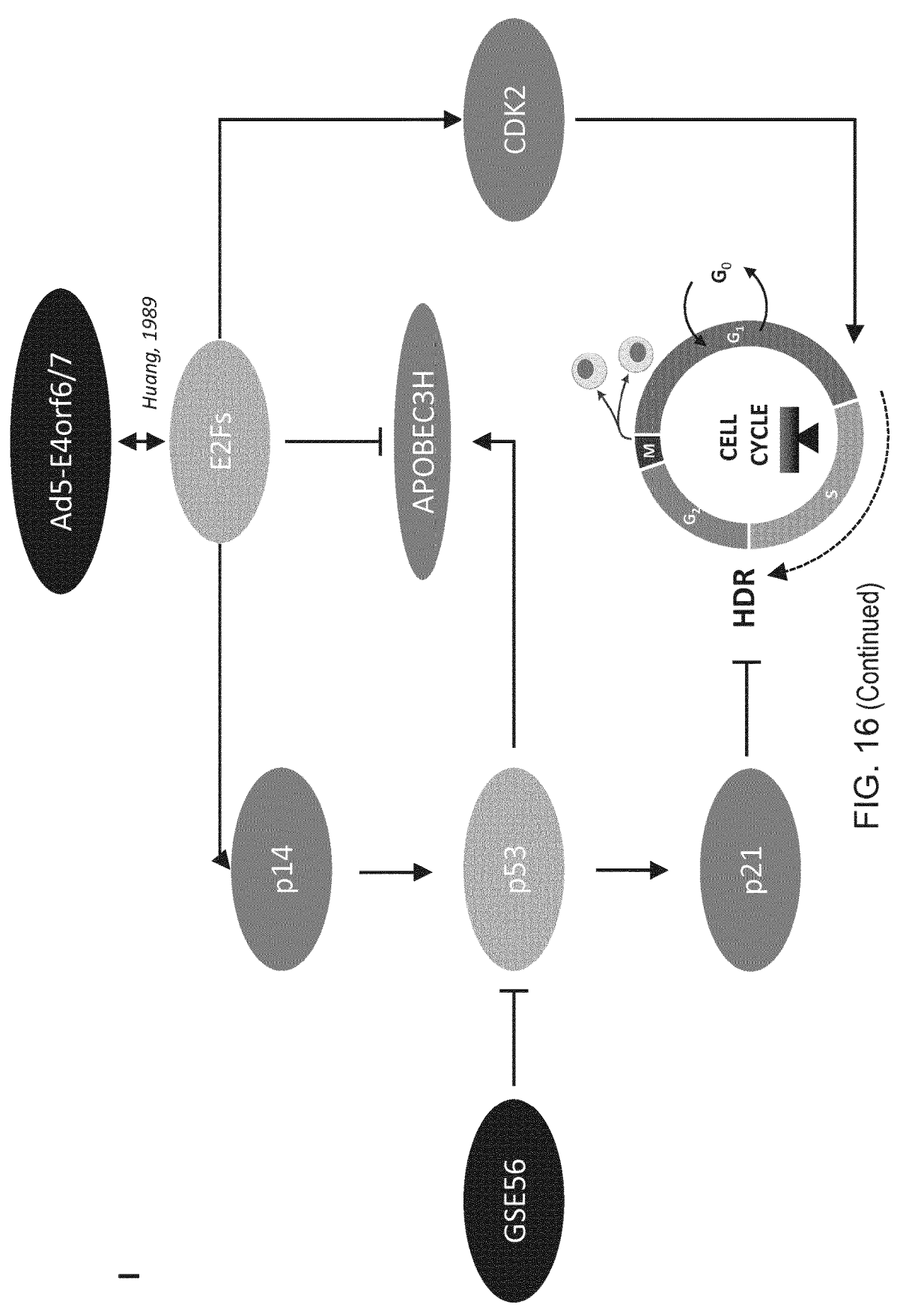

FIG. 16: The adenoviral protein Ad5-E4orf6/7 impacts on E2Fs target genes regulating the cell cycle in HSPCs. (A) TaqMan assay of CDK2 gene fold expression relative to untreated cells (UT) at 24 hours post-editing protocol on standard RNP+AAV6±GFP, GSE56, Ad5-E4orf6/7 or GSE56/Ad5-E4orf6/7 [Kruskal-Wallis test, relative to standard RNP+AAV6]. (B) TaqMan assay of CDK2 gene fold expression relative to UT at 12, 24, 96, and 168 hours post-editing protocol on standard RNP+AAV6±GFP, GSE56, Ad5-E4orf6/7 or GSE56/Ad5-E4orf6/7. (C) TaqMan assay of CDKN2A gene fold expression relative to UT at 24 hours post-editing protocol on standard RNP+AAV6±GFP, GSE56, Ad5-E4orf6/7 or GSE56/Ad5-E4orf6/7 [Kruskal-Wallis test, relative to standard RNP+AAV6]. (D) TaqMan assay of CDKN2A gene fold expression relative to UT at 12, 24, 96, and 168 hours post-editing protocol on standard RNP+AAV6±GFP, GSE56, Ad5-E4orf6/7 or GSE56/Ad5-E4orf6/7. (E) TaqMan assay of CDKN1A gene fold expression relative to UT at 24 hours post-editing protocol on standard RNP+AAV6±GFP, GSE56, Ad5-E4orf6/7 or GSE56/Ad5-E4orf6/7 [Kruskal-Wallis test, relative to standard RNP+AAV6]. (F) TaqMan assay of CDKN1A gene fold expression relative to UT at 12, 24, 96, and 168 hours post-editing protocol on standard RNP+AAV6±GFP, GSE56, Ad5-E4orf6/7 or GSE56/Ad5-E4orf6/7. (G) TaqMan assay of APOBEC3H gene fold expression relative to UT at 24 hours post-editing protocol on standard RNP+AAV6±GFP, GSE56, Ad5-E4orf6/7 or GSE56/Ad5-E4orf6/7 [Kruskal-Wallis test, relative to standard RNP+AAV6]. (H) TaqMan assay of APOBEC3H gene fold expression relative to UT at 12, 24, 96, and 168 hours post-editing protocol on standard RNP+AAV6±GFP, GSE56, Ad5-E4orf6/7 or GSE56/Ad5-E4orf6/7. (I) Schematic representation of cell cycle regulation mechanism in HSPCs after editing-protocol using the adenoviral protein Ad5-E4orf6/7 and/or the p53 inhibitor GSE56.

Figure 17A:
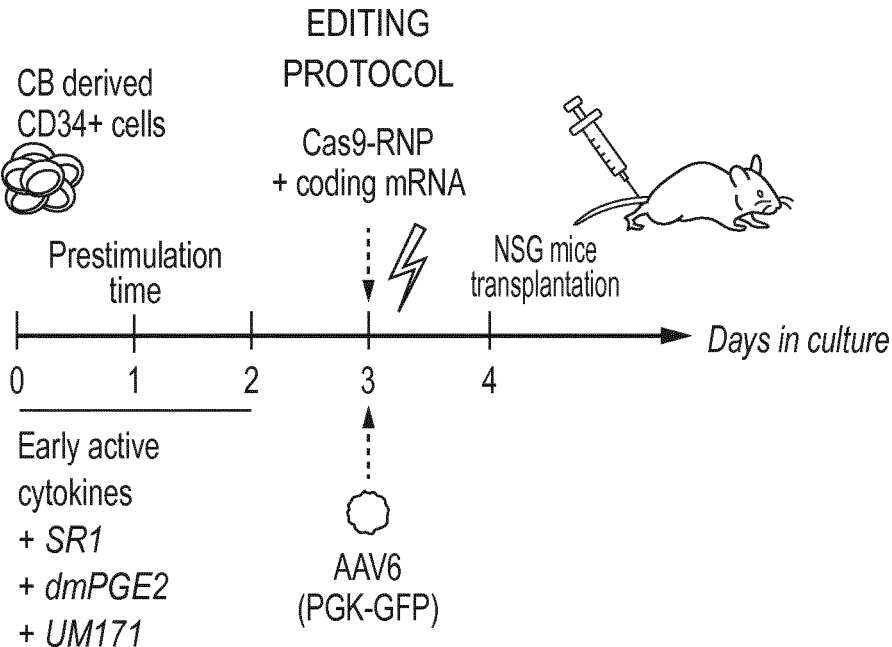
Figure 17:
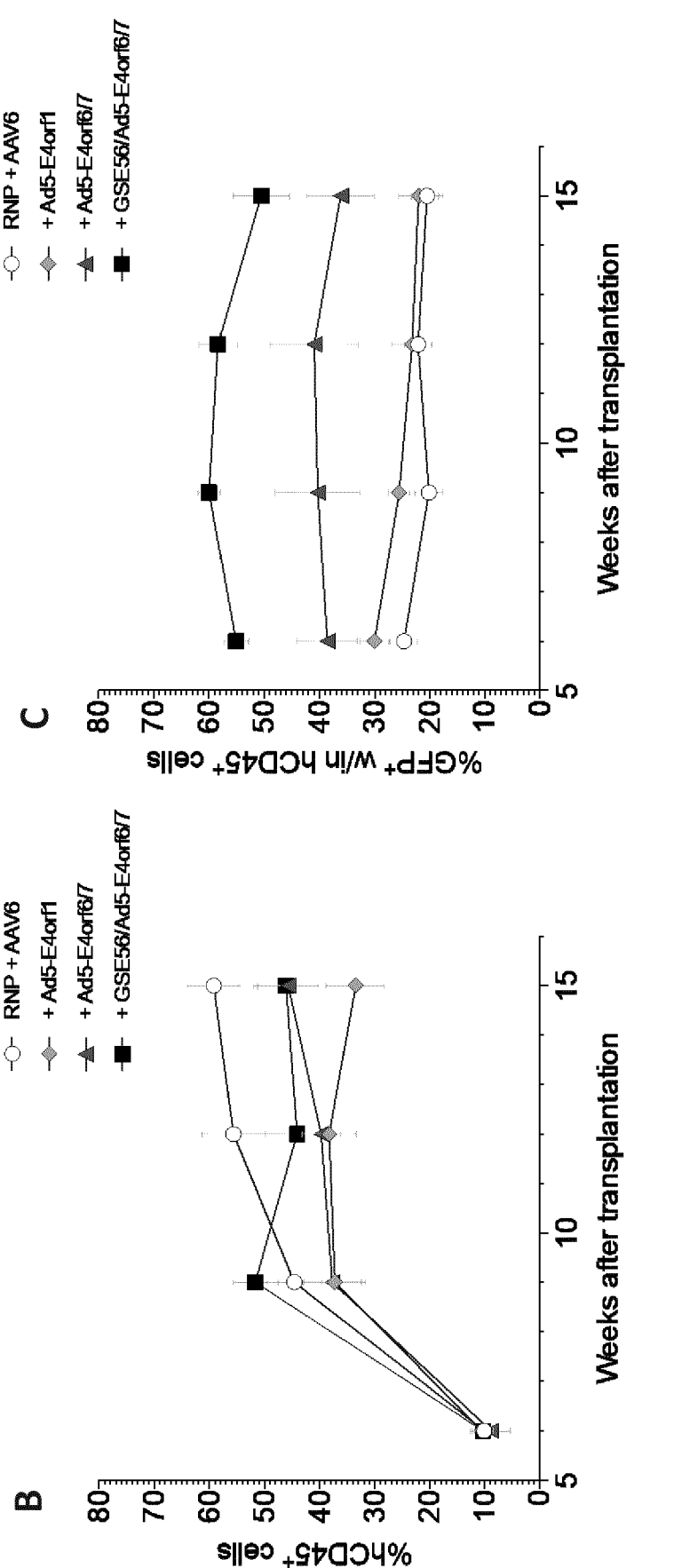
Figure 17:
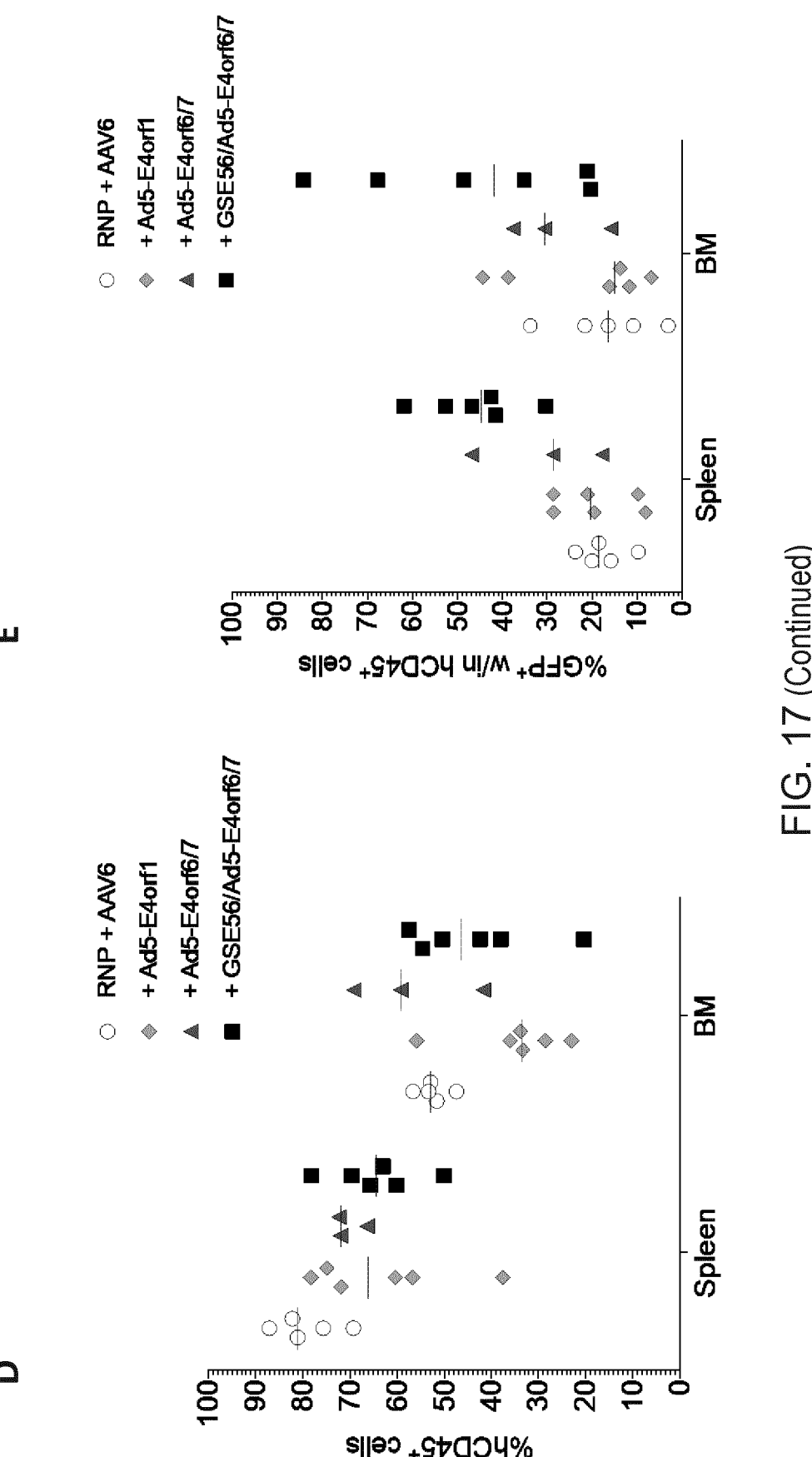
Figure 17:
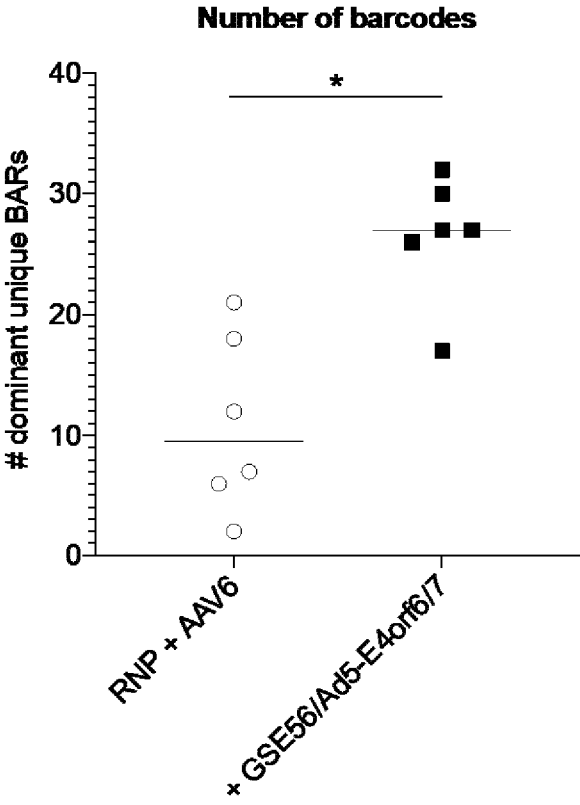

FIG. 17: Primary xenotransplantation follow-up of AAVS1 edited human CB-derived CD34+. (A) Schematic representation of the targeted gene editing protocol in human cord blood (CB)-derived CD34+ and followed by NSG xenotransplantation at 24 hours post-editing protocol. (B) Monitoring of human CD45+ cells engraftment in peripheral blood (PB) over the weeks post-transplantation. (C) Percentage of GFP+ edited cells among engrafted hCD45+ in PB over the weeks post-transplantation. (D, E) Percentage of both hCD45+ engraftment and GFP+ within hCD45+ at long-term in spleen and bone-marrow (BM). (F) Number of unique dominant barcodes in the hematopoietic organs of mice transplanted with cells treated RNP+AAV6±GSE56/Ad5-E4orf6/7 [Mann-Withney test]. Lines indicate median values.

Figure 18:
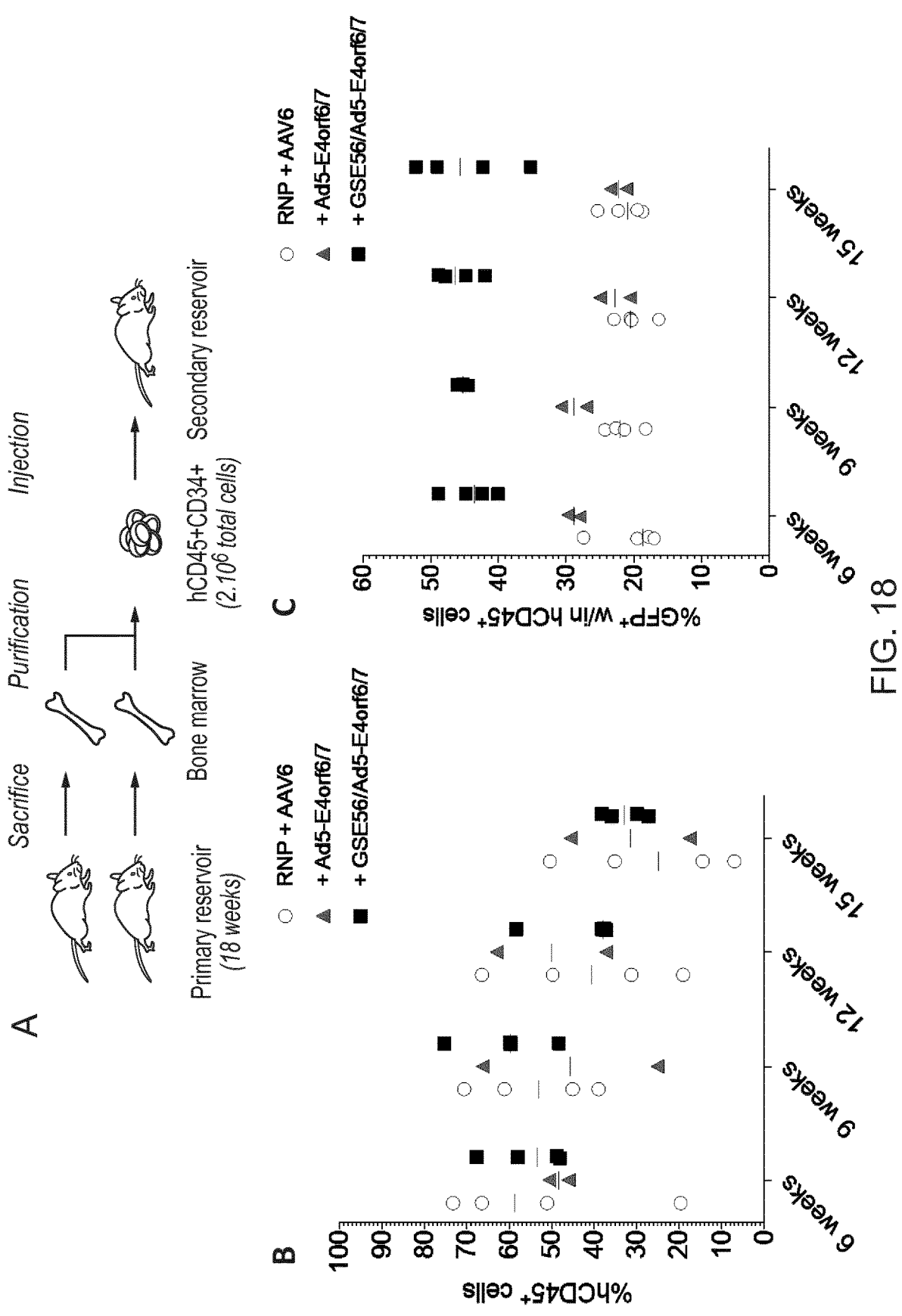
Figure 18:
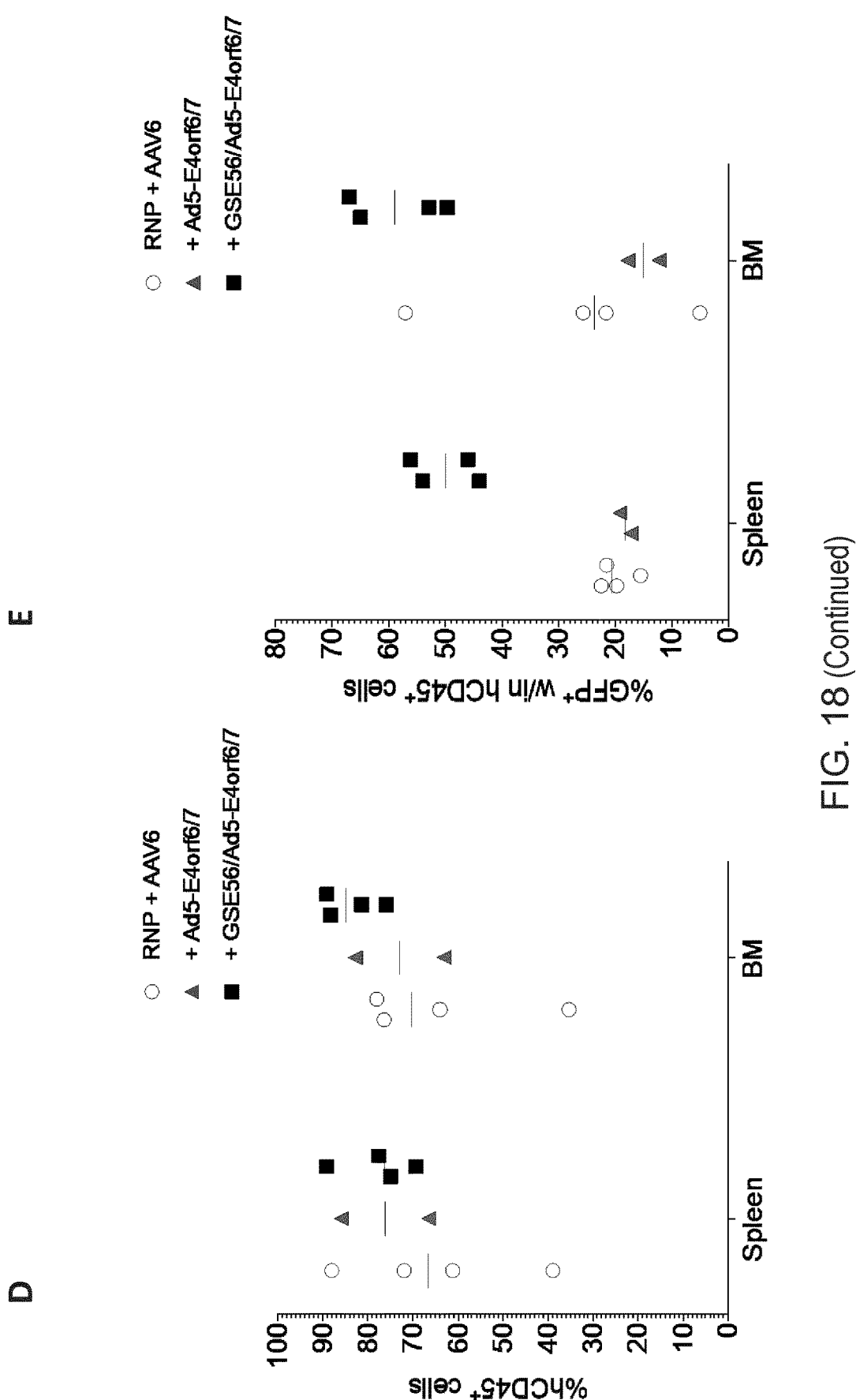
Figure 18:
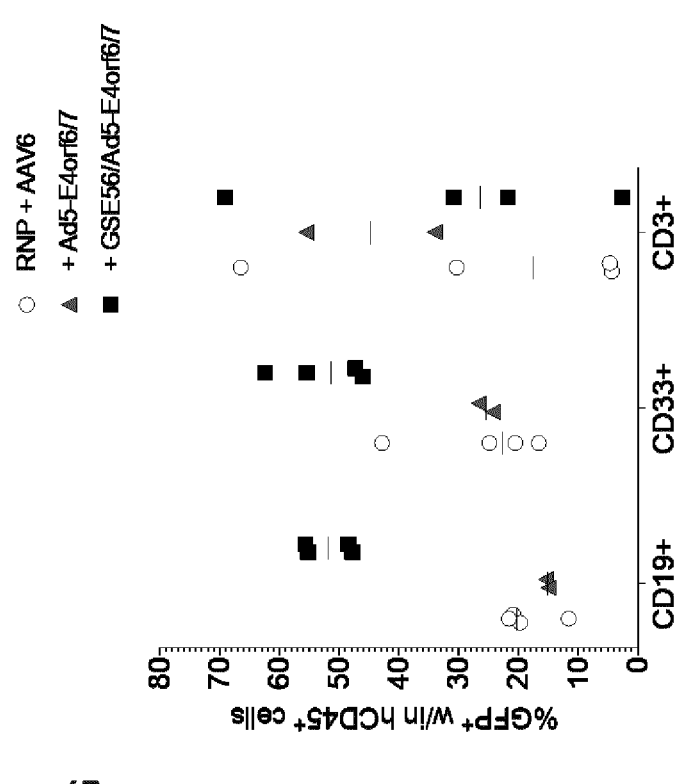
Figure 18:
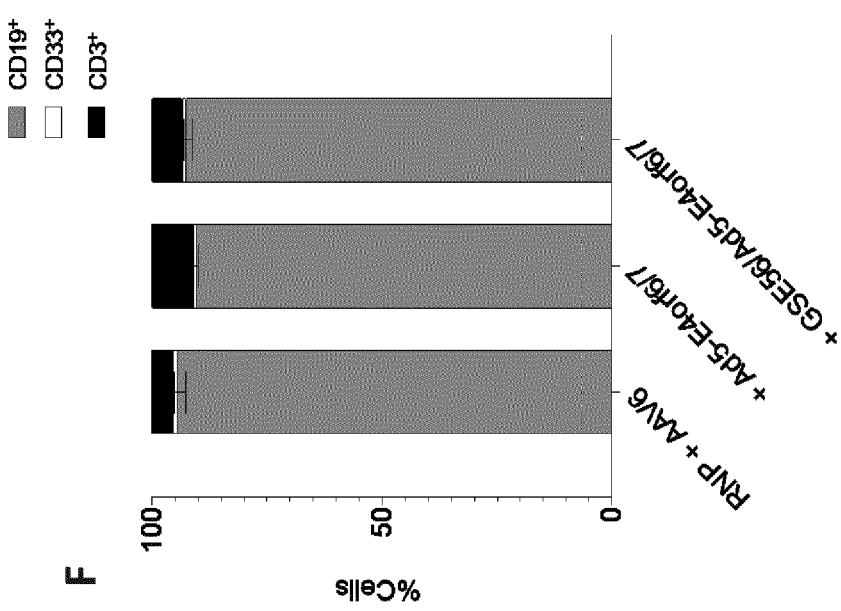

FIG. 18: Secondary xenotransplantation follow-up of AAVS1 edited human CB-derived CD34+. (A) Schematic representation of the secondary transplantation in NSG mice after CD34+ cells selection from BM. (B) Monitoring of human CD45+ cells engraftment in peripheral blood (PB) over the weeks post-transplantation. (C) Percentage of GFP+ edited cells among engrafted hCD45+ in PB over the weeks post-transplantation. (D, E) Percentage of both hCD45+ engraftment and GFP+ within hCD45+ at very long-term in spleen and bone-marrow (BM). (F, G) Blood lineages composition in spleen (CD19+, CD33+ and CD3+) and associated percentages of GFP+ cells. Lines indicate median values.

Figure 19:
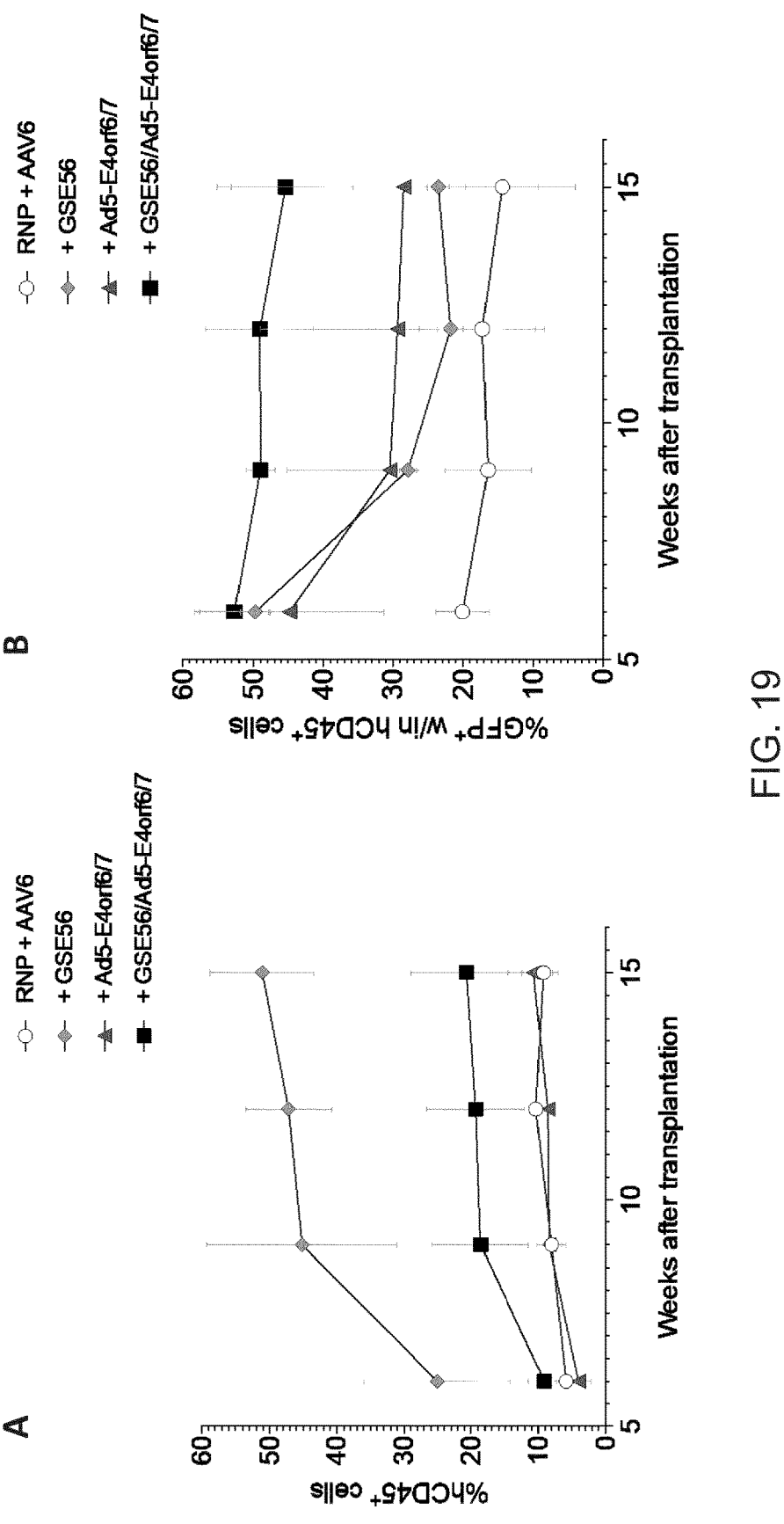

FIG. 19: Primary xenotransplantation follow-up at limiting dose of AAVS1 edited human CB-derived CD34+. (A) Monitoring of human CD45+ cells engraftment in peripheral blood (PB) over the weeks post-transplantation. (B) Percentage of GFP+ edited cells among engrafted hCD45+ in PB over the weeks post-transplantation. Lines indicate median values.

Figure 20:
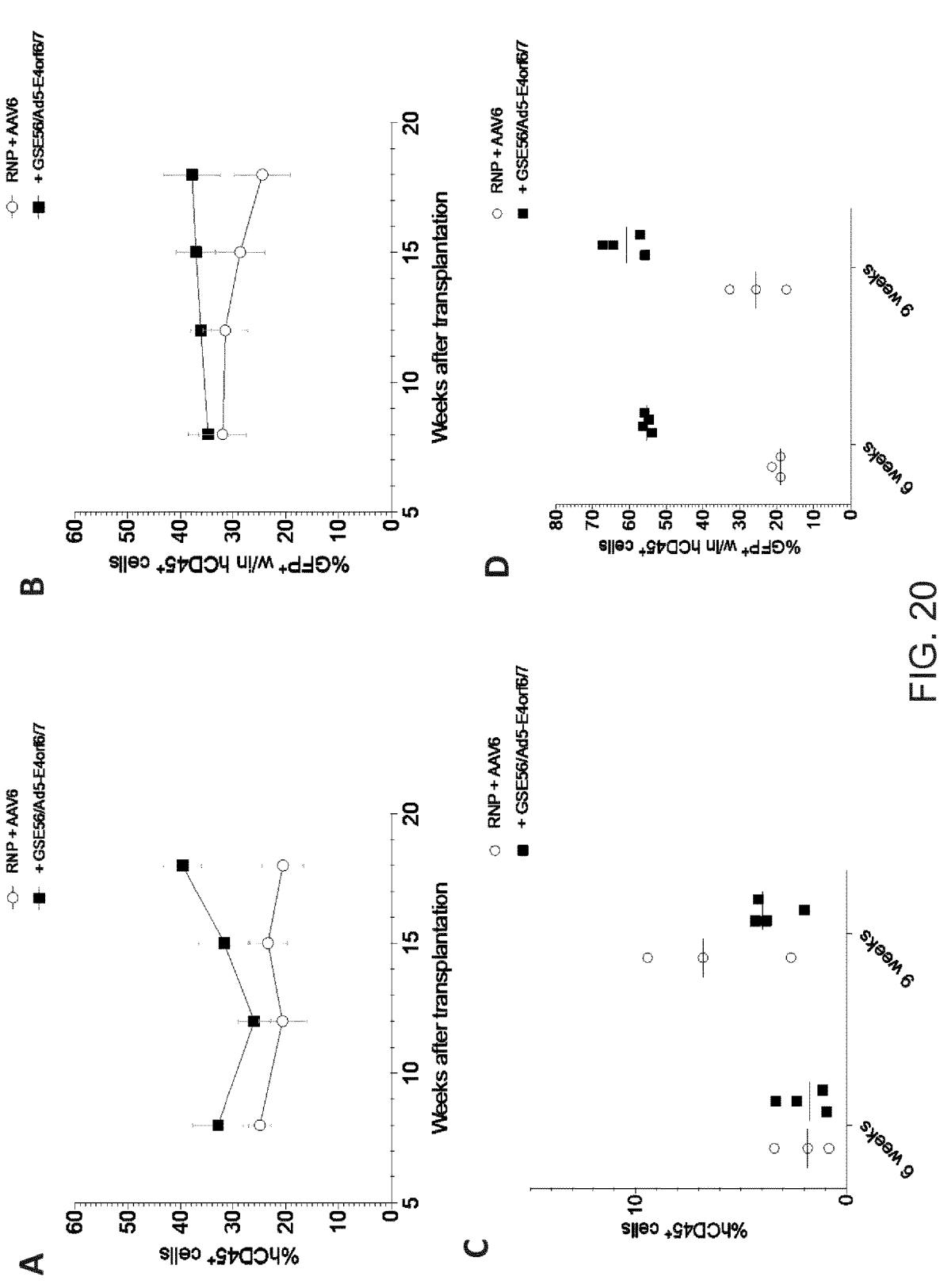
Figure 20:
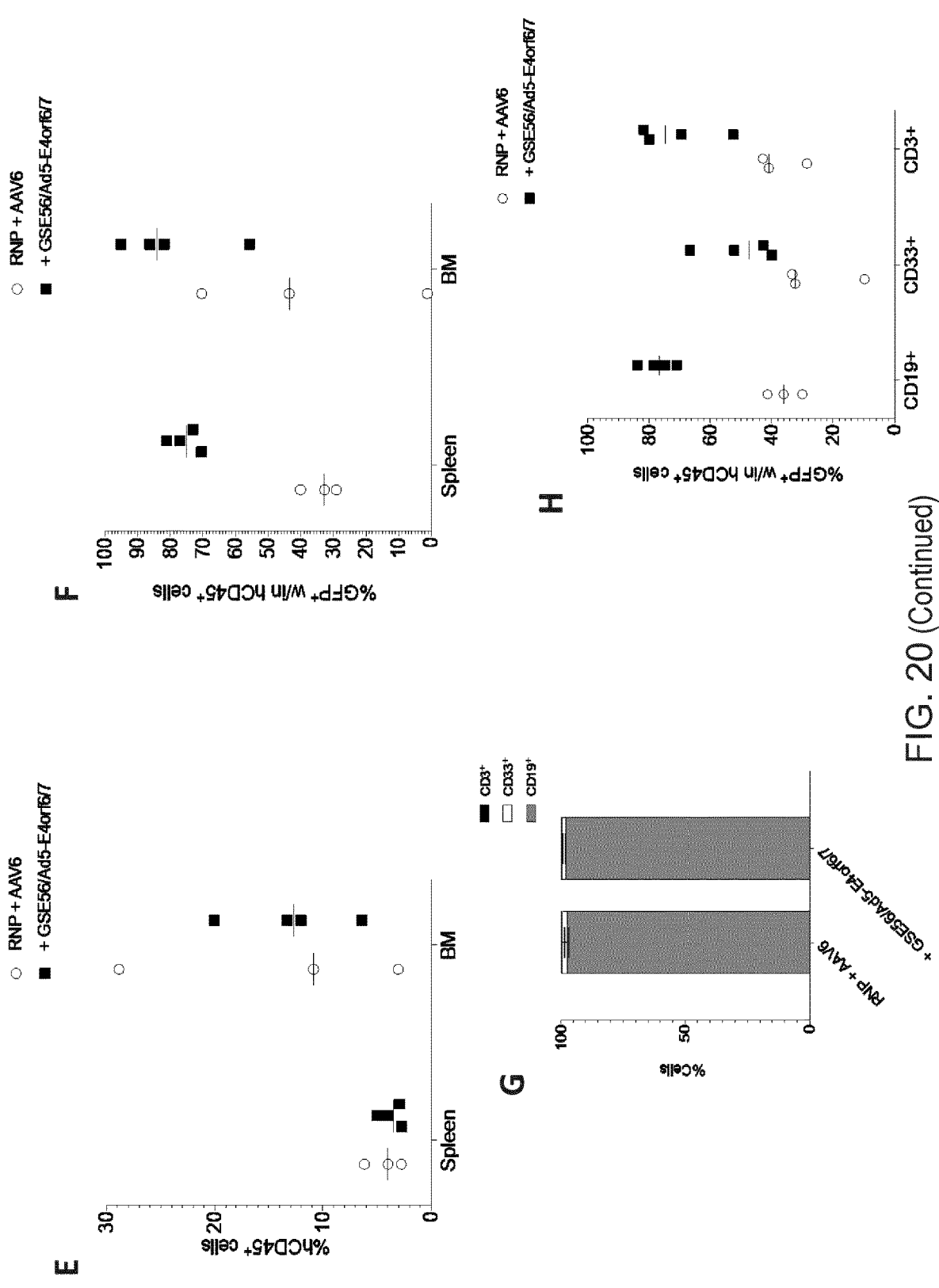
Figure 20:
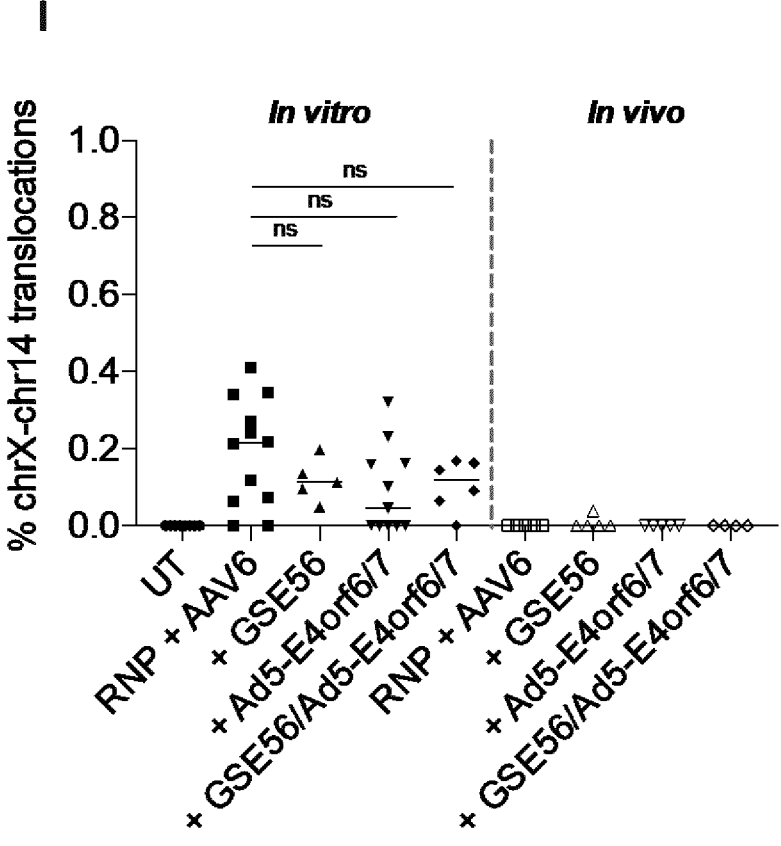

FIG. 20: Primary and secondary xenotransplantation follow-up of IL2RG edited human CB-derived CD34+. (A, B) Monitoring of both human CD45+ cells engraftment and GFP+ edited cells among engrafted hCD45+ in peripheral blood (PB) over the weeks post-primary transplantation. (C, D) Monitoring of both human CD45+ cells engraftment and GFP+ edited cells among engrafted hCD45+ in peripheral blood (PB) over the weeks post-secondary transplantation. (E, F) Percentage of both hCD45+ engraftment and GFP+ within hCD45+ at long-term in spleen and bone-marrow (BM). (G, H) Blood lineages composition in spleen (CD19+, CD33+ and CD3+) and associated percentages of GFP+ cells. Lines indicate median values. (I) Percentage of translocation events between "X" and "14" chromosomes measured by ddPCR, both from in vitro and in vivo samples targeting IL2RG locus [Kruskal-Wallis test, relative to standard RNP+AAV6]. Lines indicate median values.

Figure 21A:
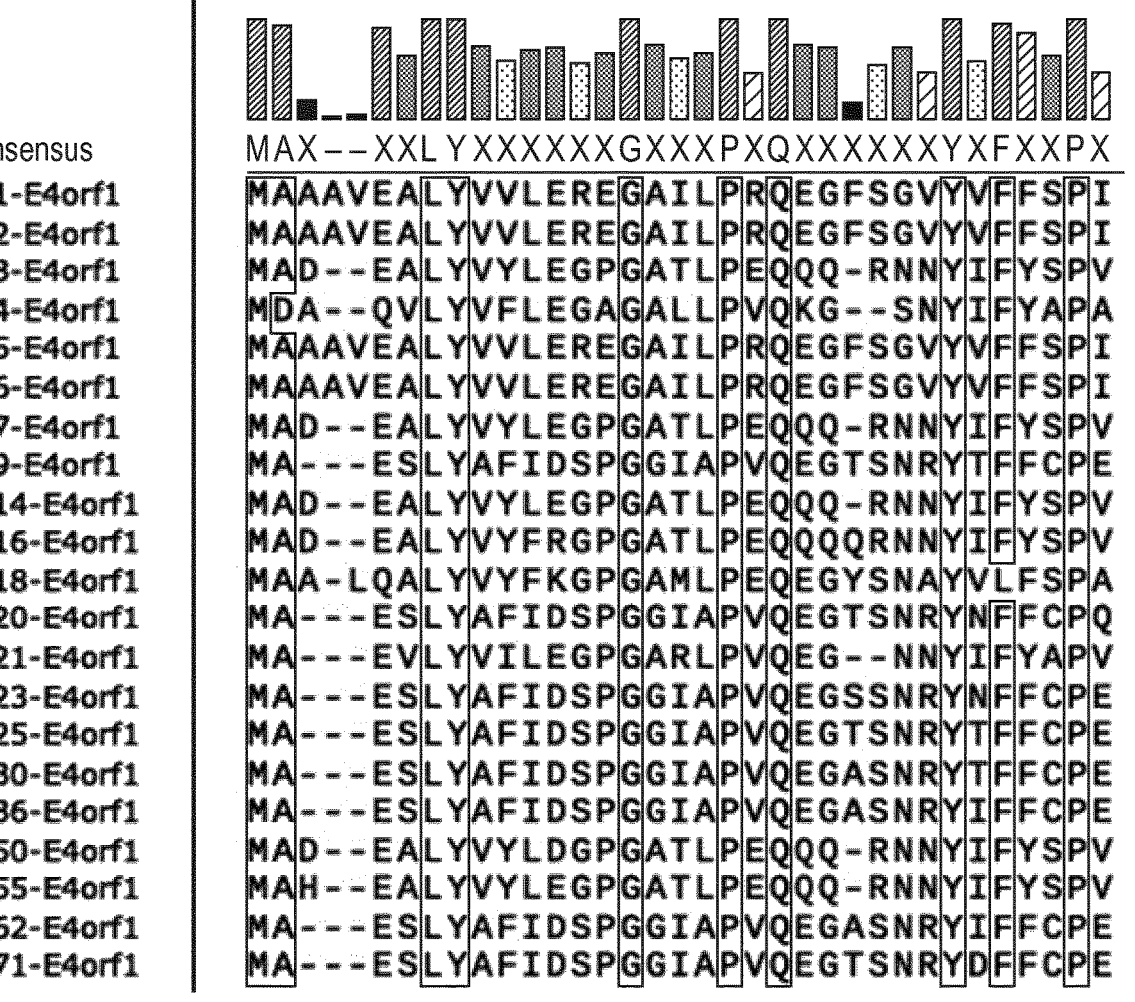
Figure 21A:
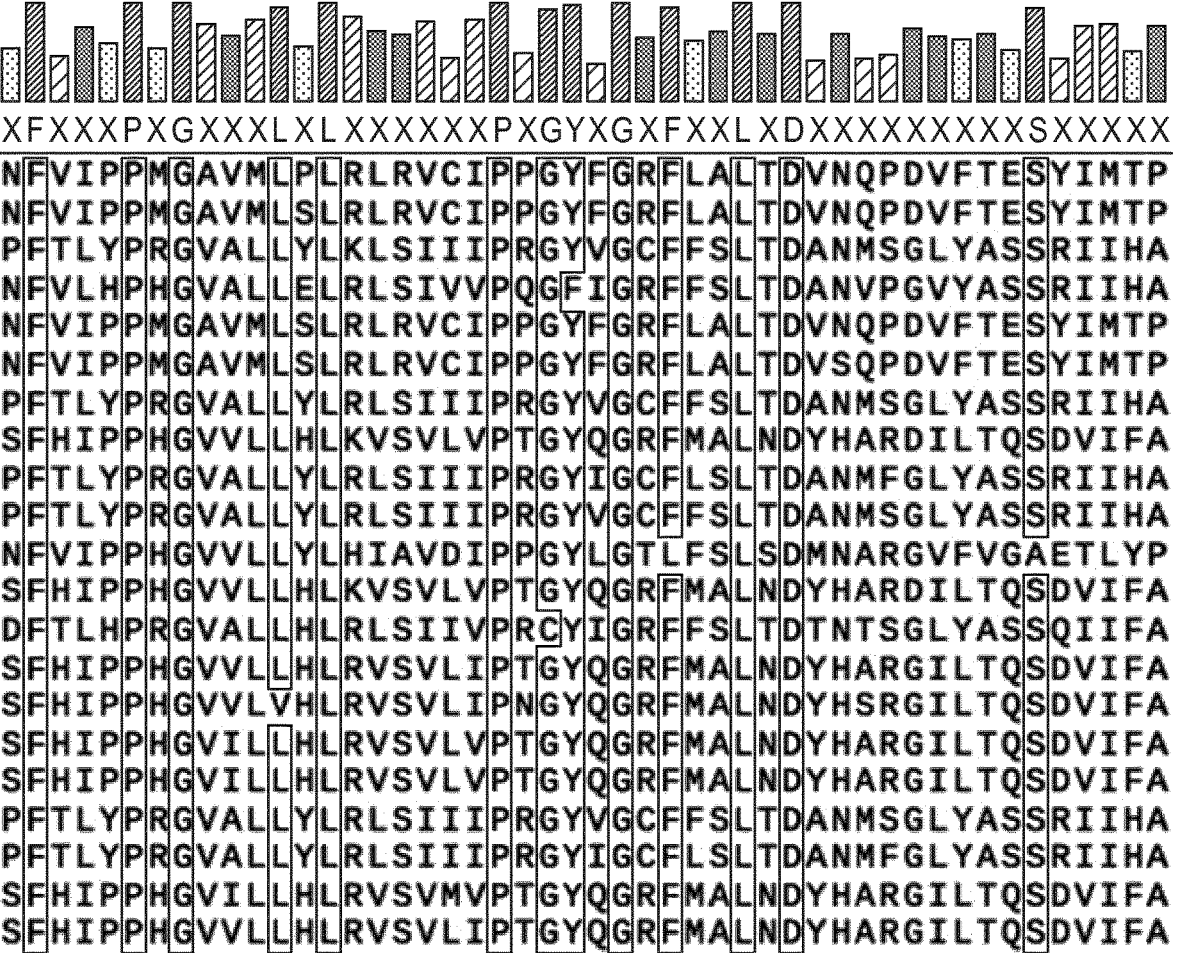
Figure 21B:
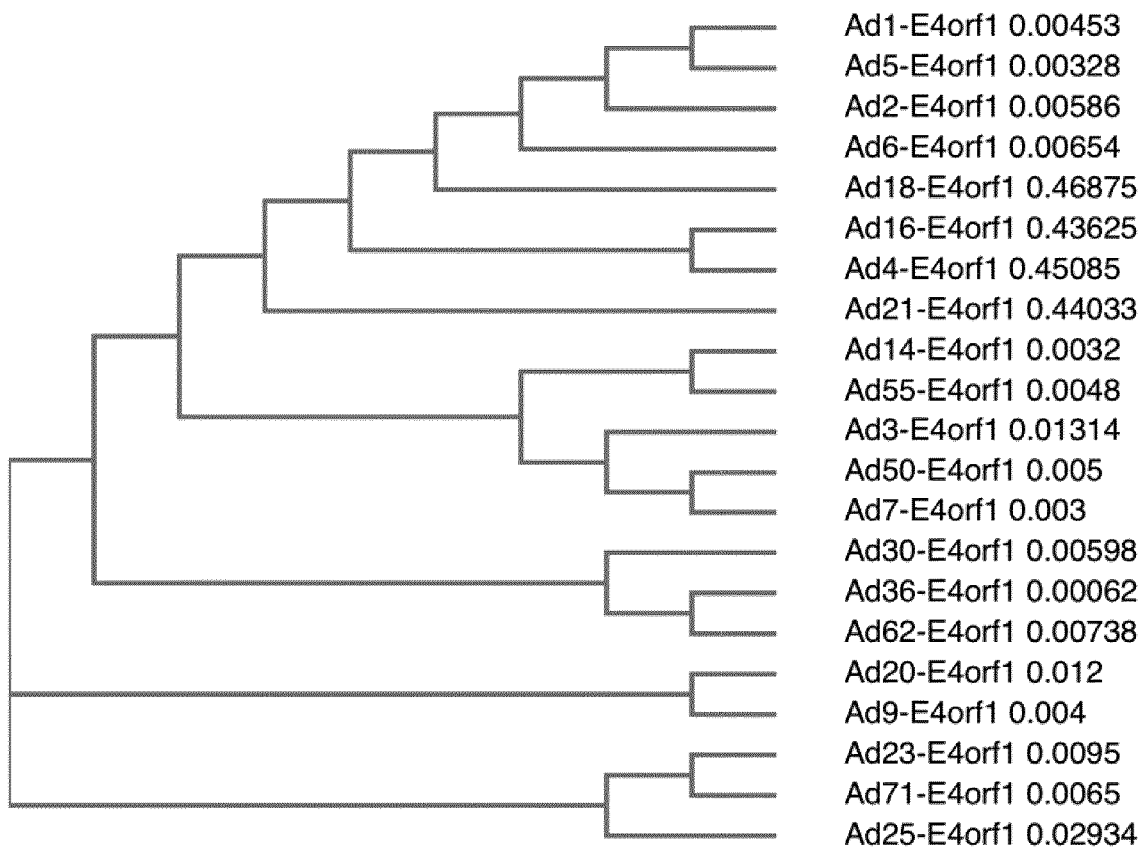
Figure 21:
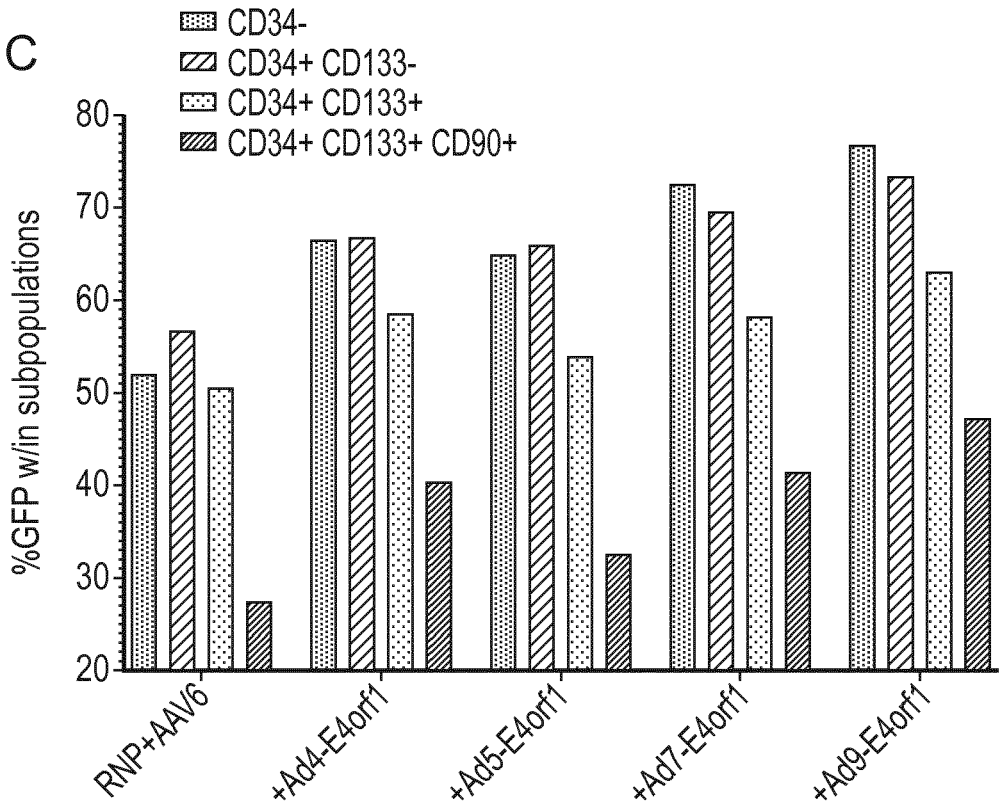
Figure 21:
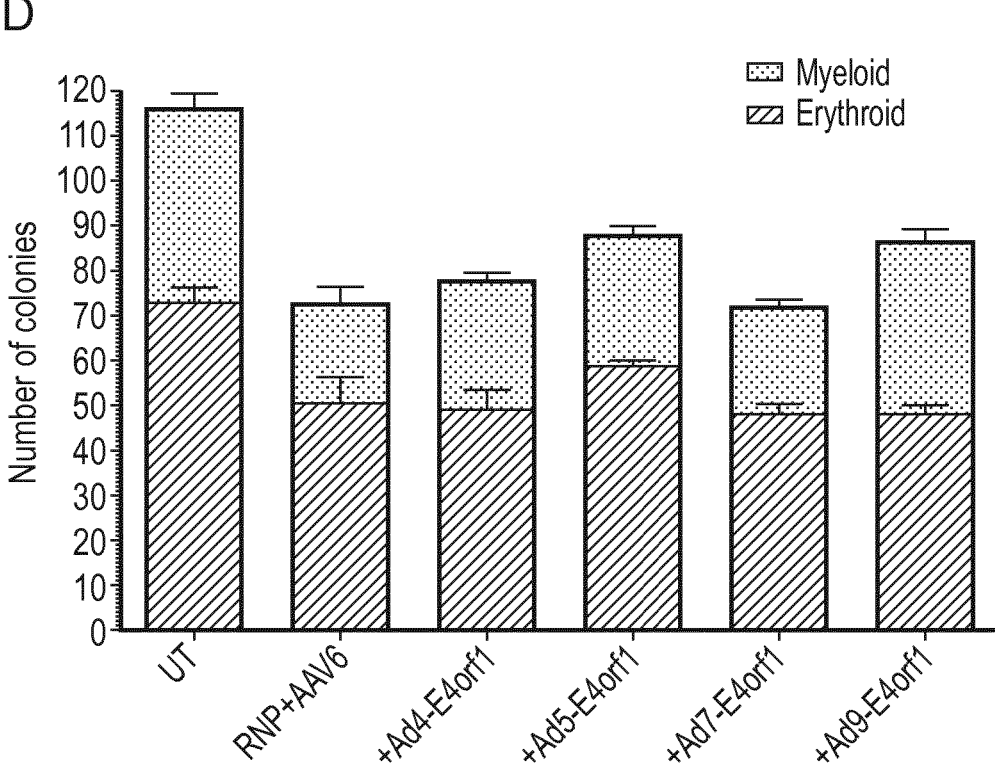
Figure 21:
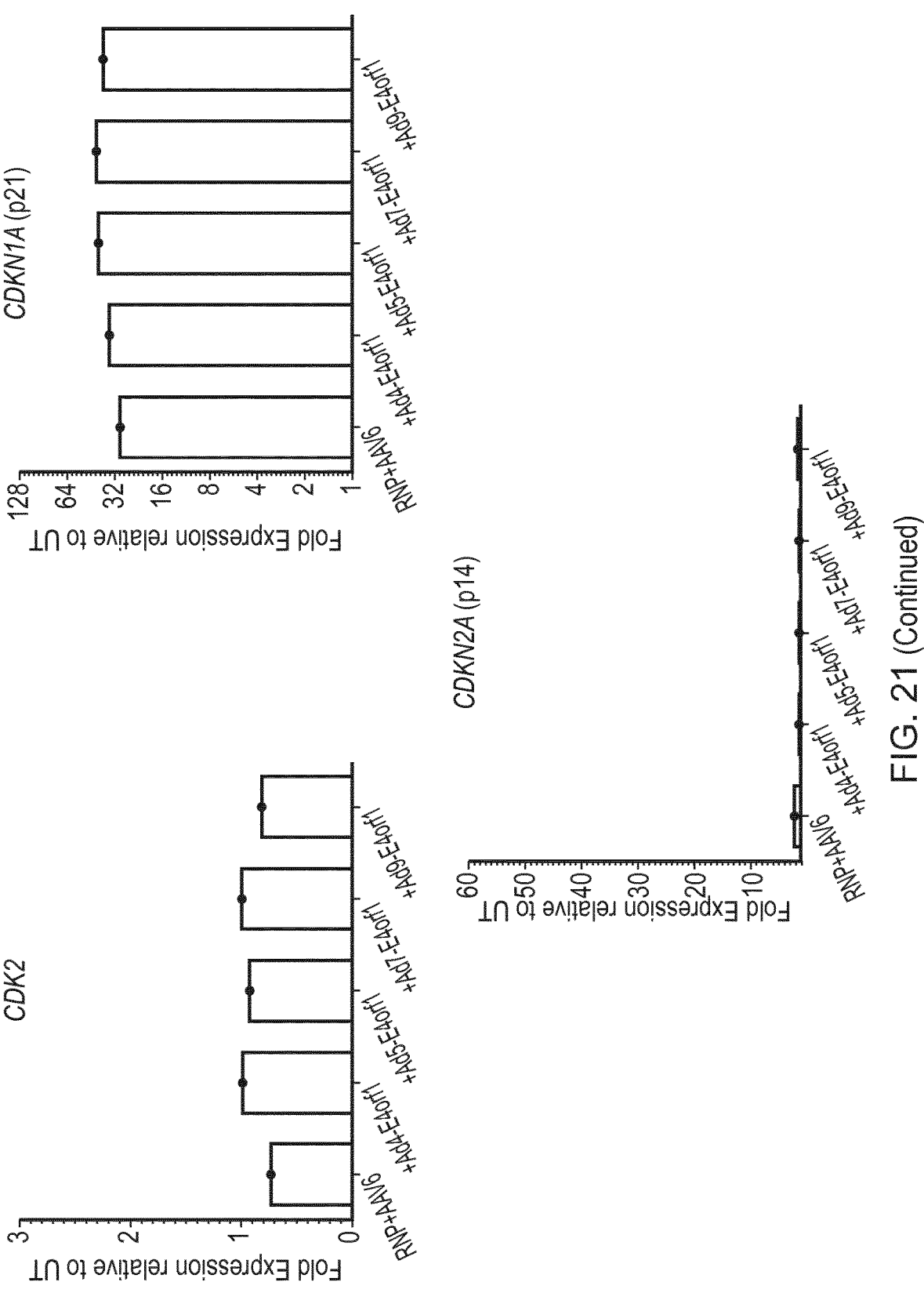

FIG. 21: Exploring adenoviral protein E4orf1 serotype variants. (A) E4orf1 protein sequences alignment (T-Coffee) including highly conserved amino-acids (B) Phylogenetic tree based on T-Coffee analysis and presenting the closest amino-acids composition among adenoviral serotypes. (C) Percentage of GFP+ cells measured by FACS within the indicated subpopulations at 96 hours post-editing protocol performed in hCB-derived CD34+ by using our standard procedure RNP±AAV6±Ad4-E4orf1, Ad5-E4orf1, Ad7-E4orf1, or Ad9-E4orf1 (selected variants). (D) Number of colonies plated from bulk culture at 24 hours post-editing protocol. (E) TaqMan assay of CDK2, CDKN2A and CDKN1A genes fold expression relative to untreated cells (UT) at 24 hours post-editing protocol.

Figure 22A:
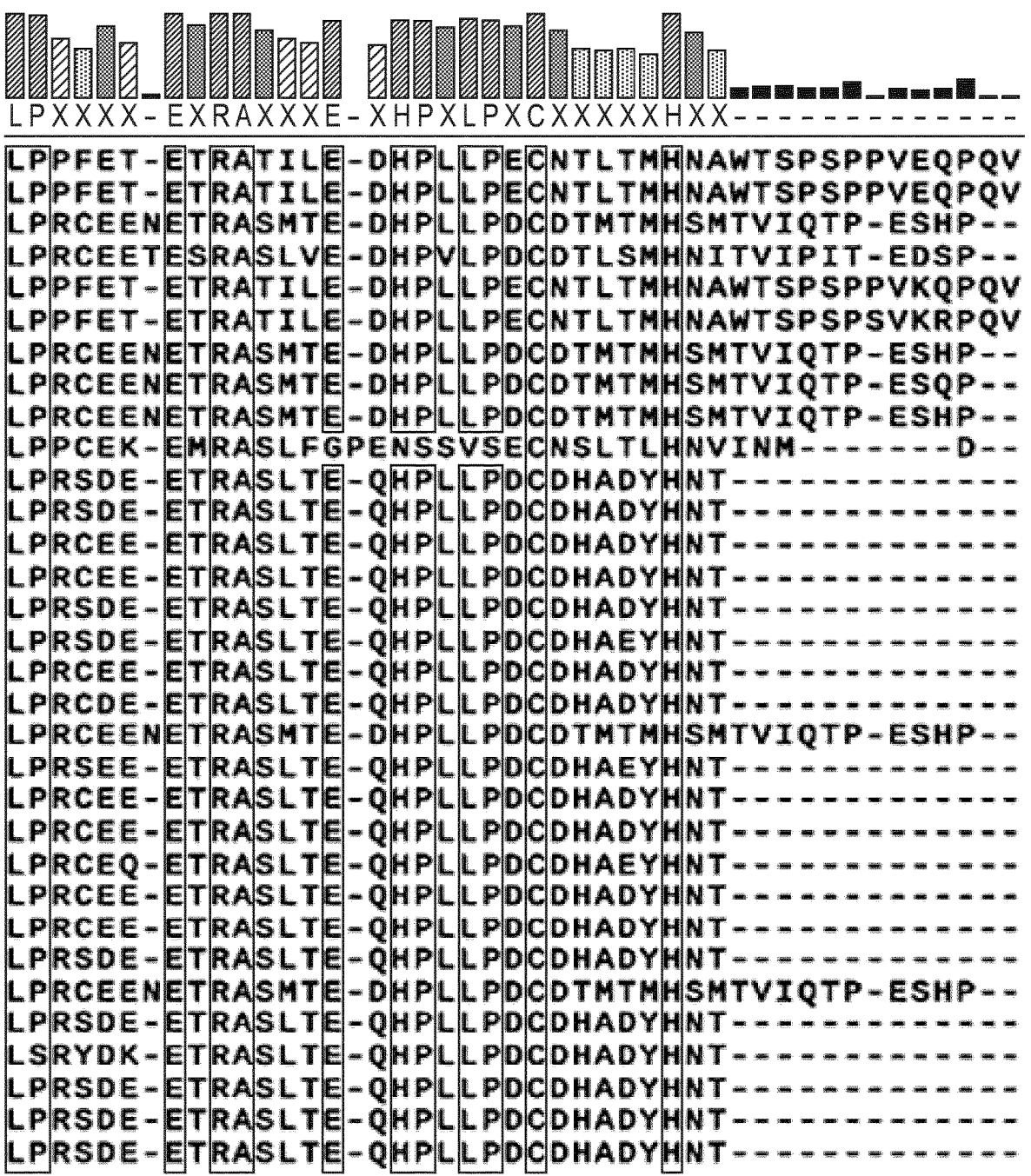
Figure 22A:
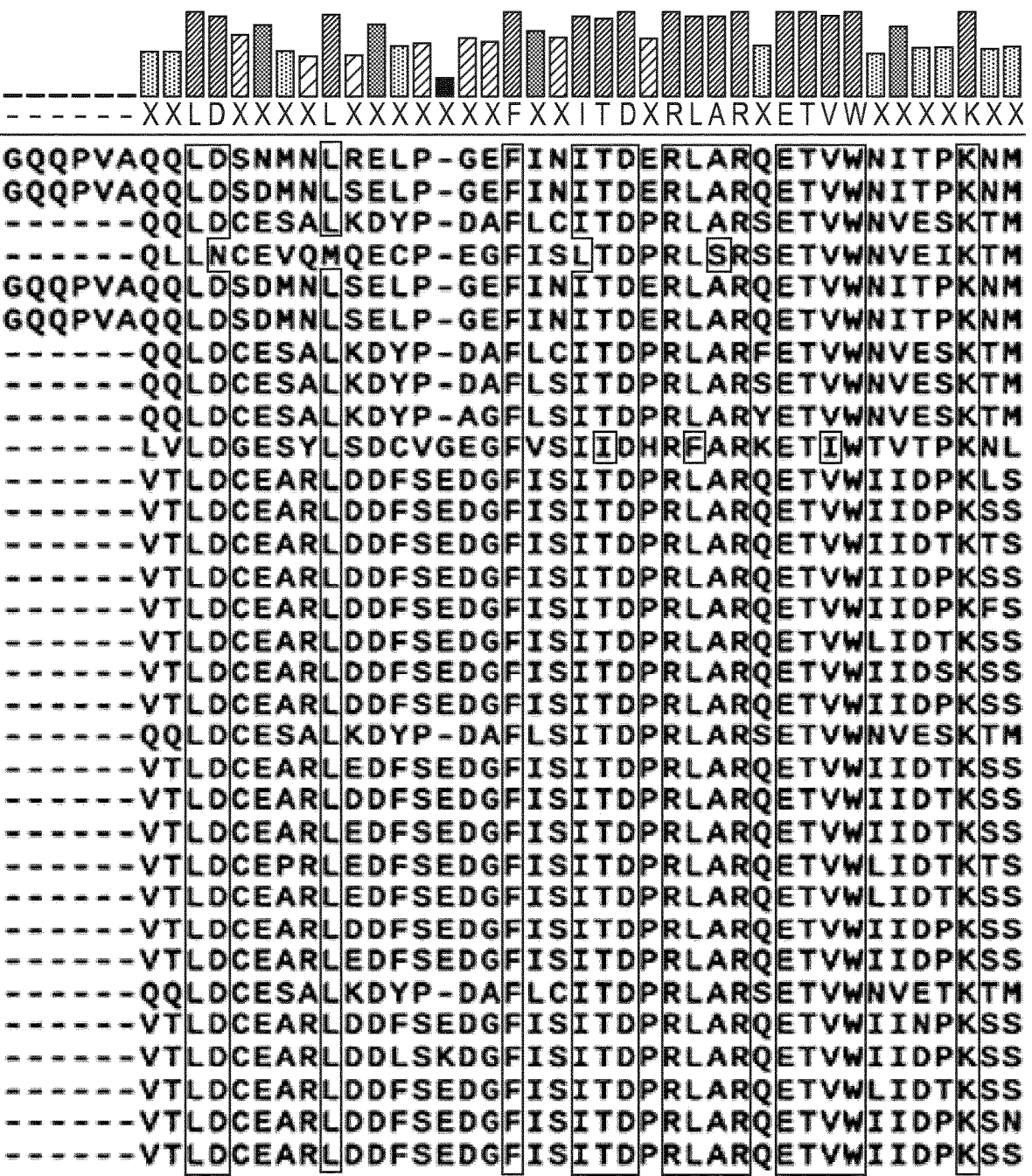
Figure 22A:
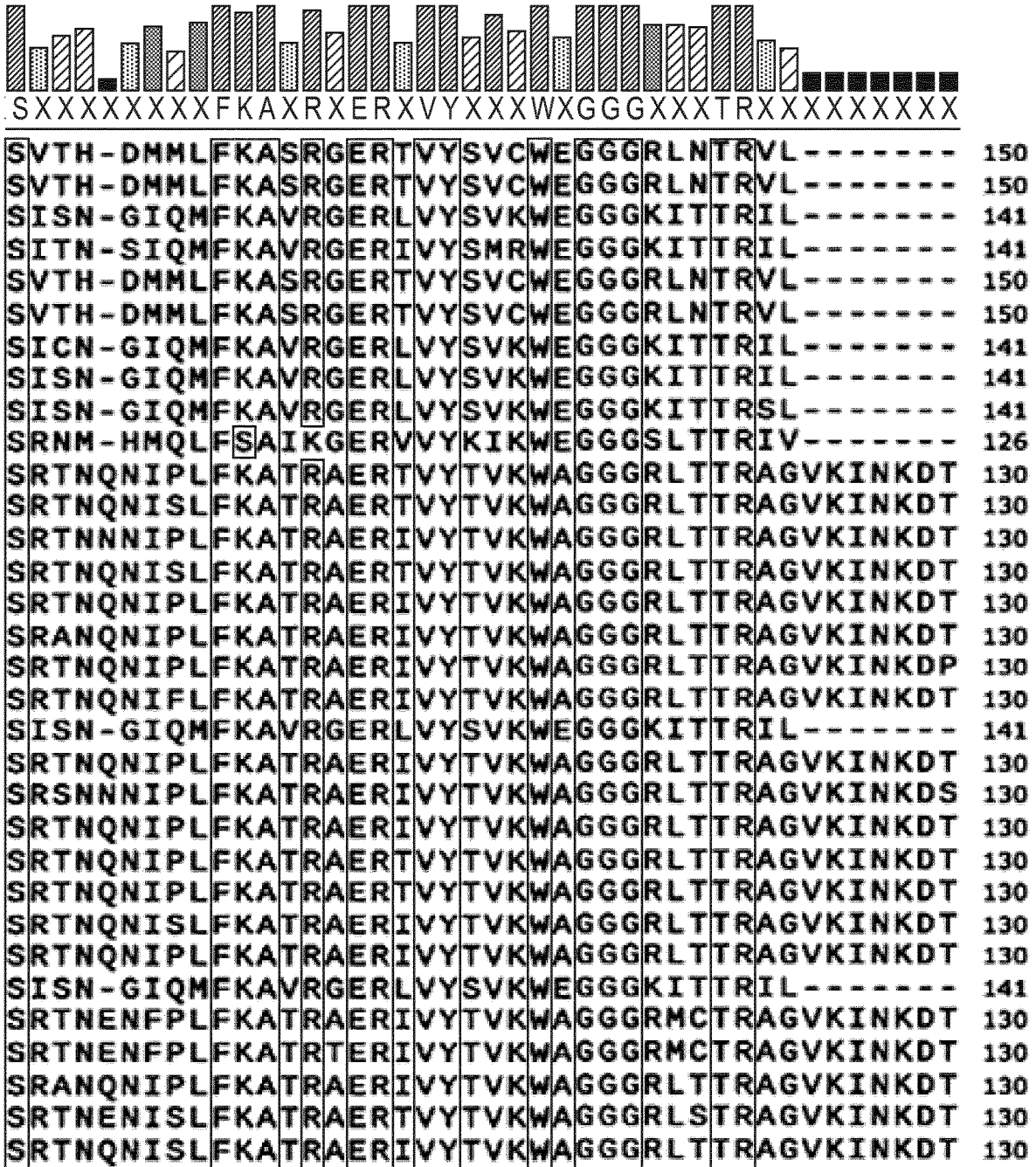
Figure 22B:
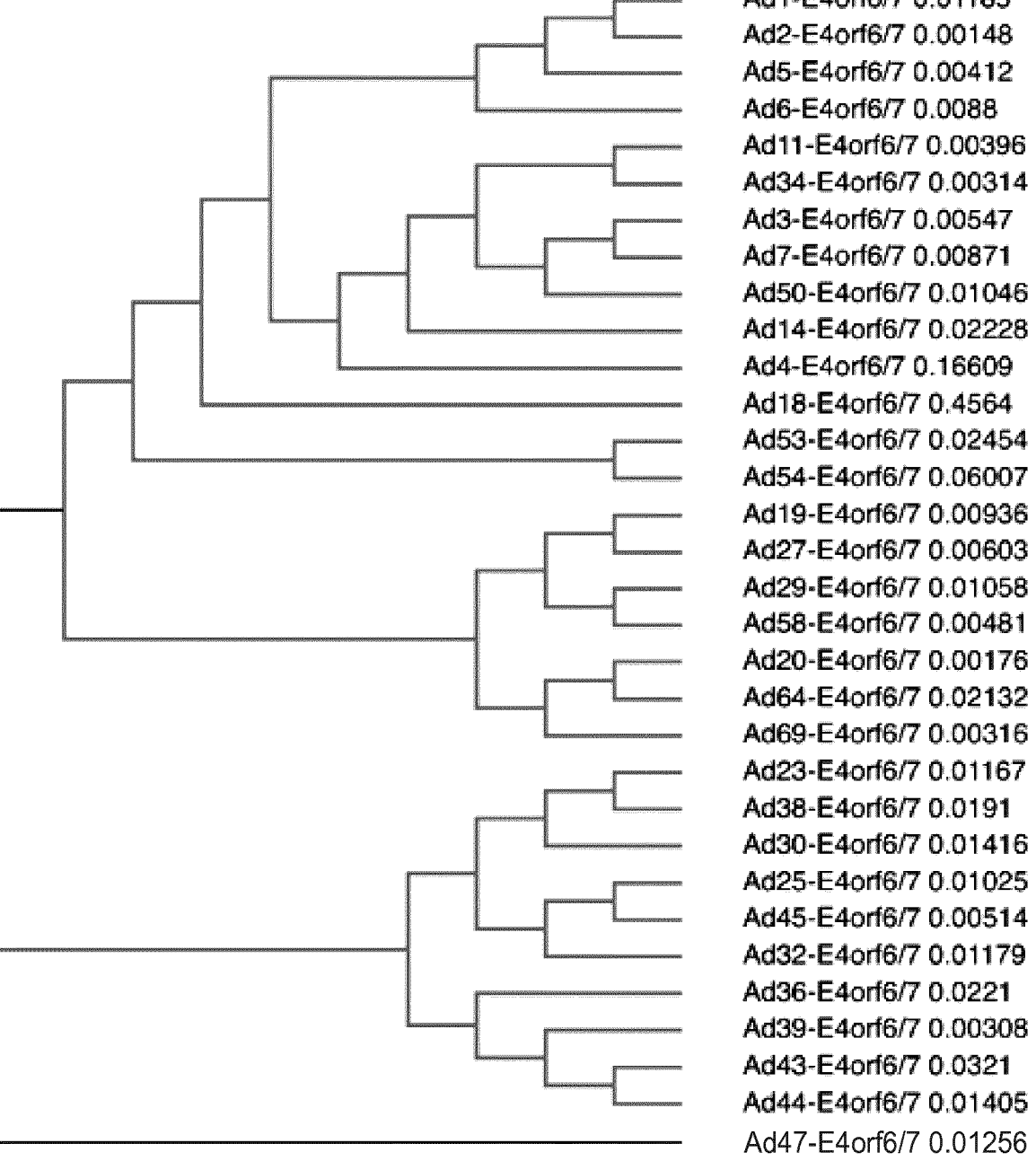
Figure 22:
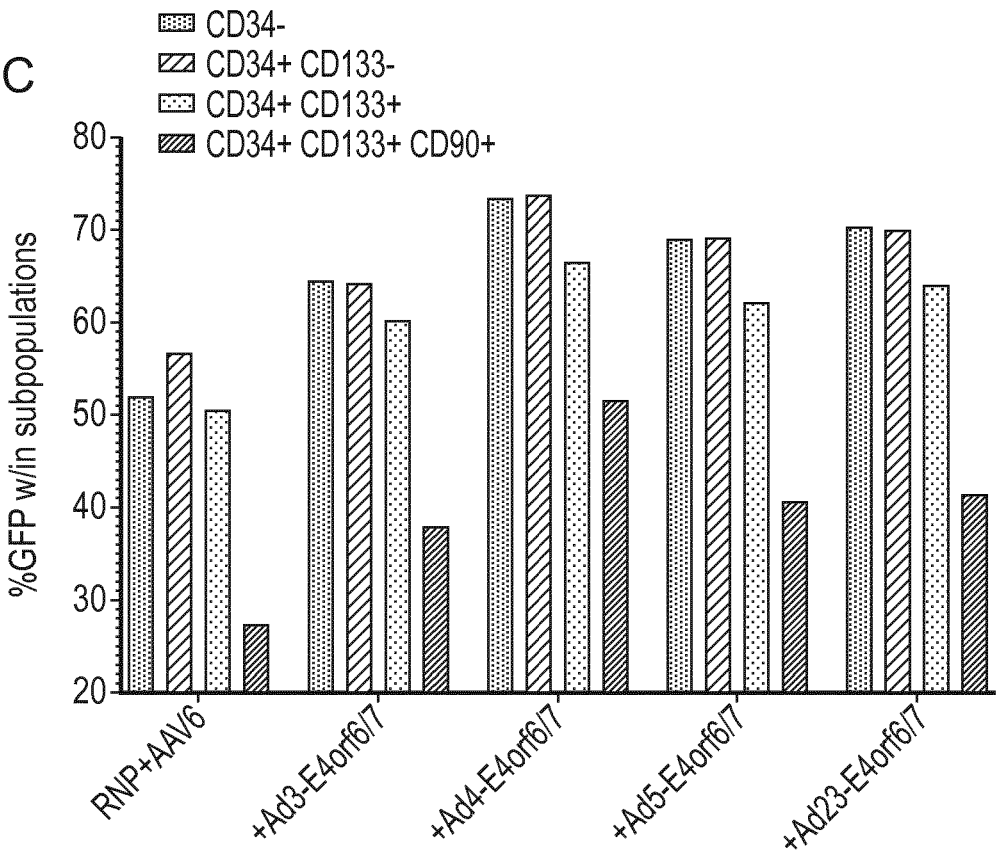
Figure 22:
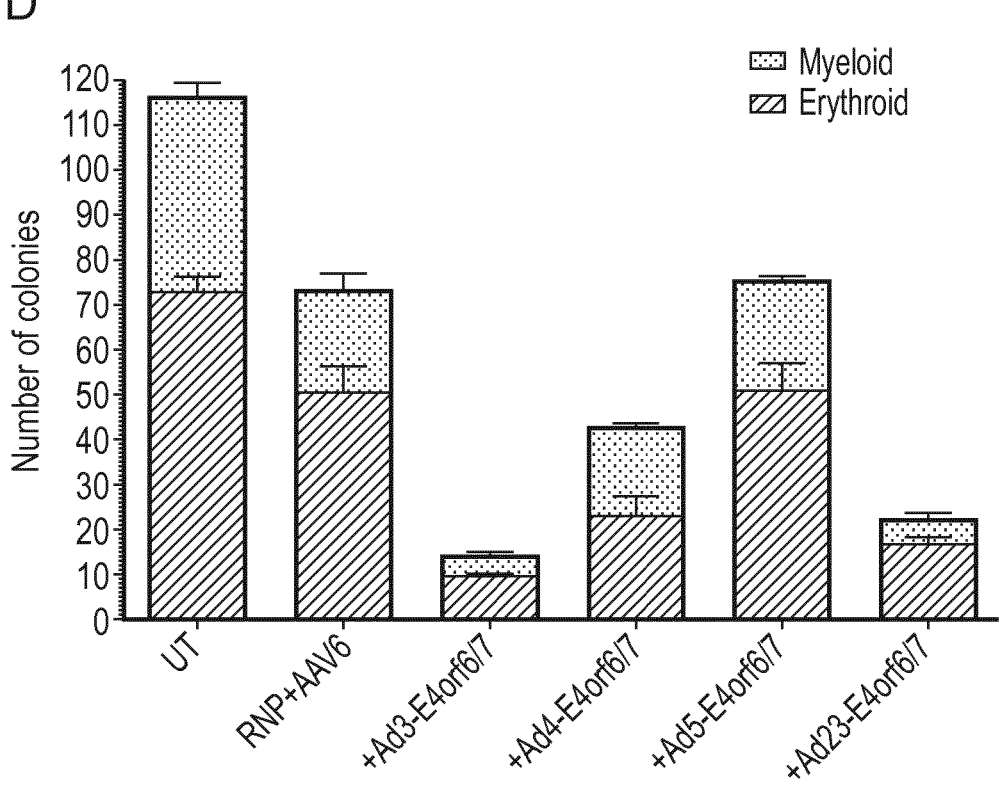
Figure 22:
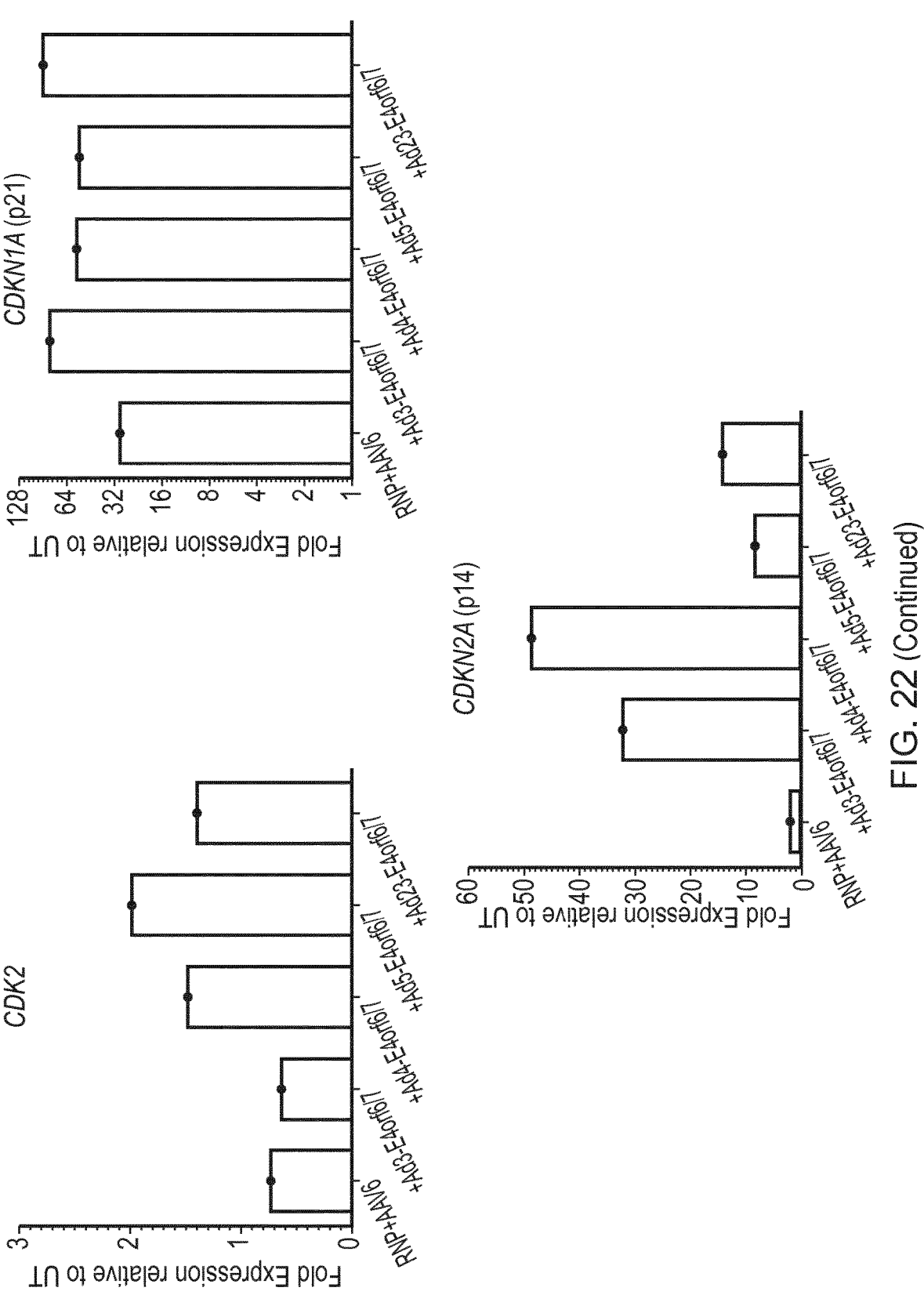

FIG. 22: Exploring adenoviral protein E4orf6/7 serotype variants. (A) E4orf6/7 protein sequences alignment (T-Coffee) including highly conserved amino-acids. (B) Phylogenetic tree based on T-Coffee analysis and presenting the closest amino-acids composition among adenoviral serotypes. (C) Percentage of GFP+ cells measured by FACS within the indicated subpopulations at 96 hours post-editing protocol performed in hCB-derived CD34+ by using our standard procedure RNP+AAV6±Ad3-E4orf6/7, Ad4-E4orf6/7, Ad5-E4orf6/7, or Ad23-E4orf6/7 (selected variants). (D) Number of colonies plated from bulk culture at 24 hours post-editing protocol. (E) TaqMan assay of CDK2, CDKN2A and CDKN1A genes fold expression relative to untreated cells (UT) at 24 hours post-editing protocol.

Figure 23:
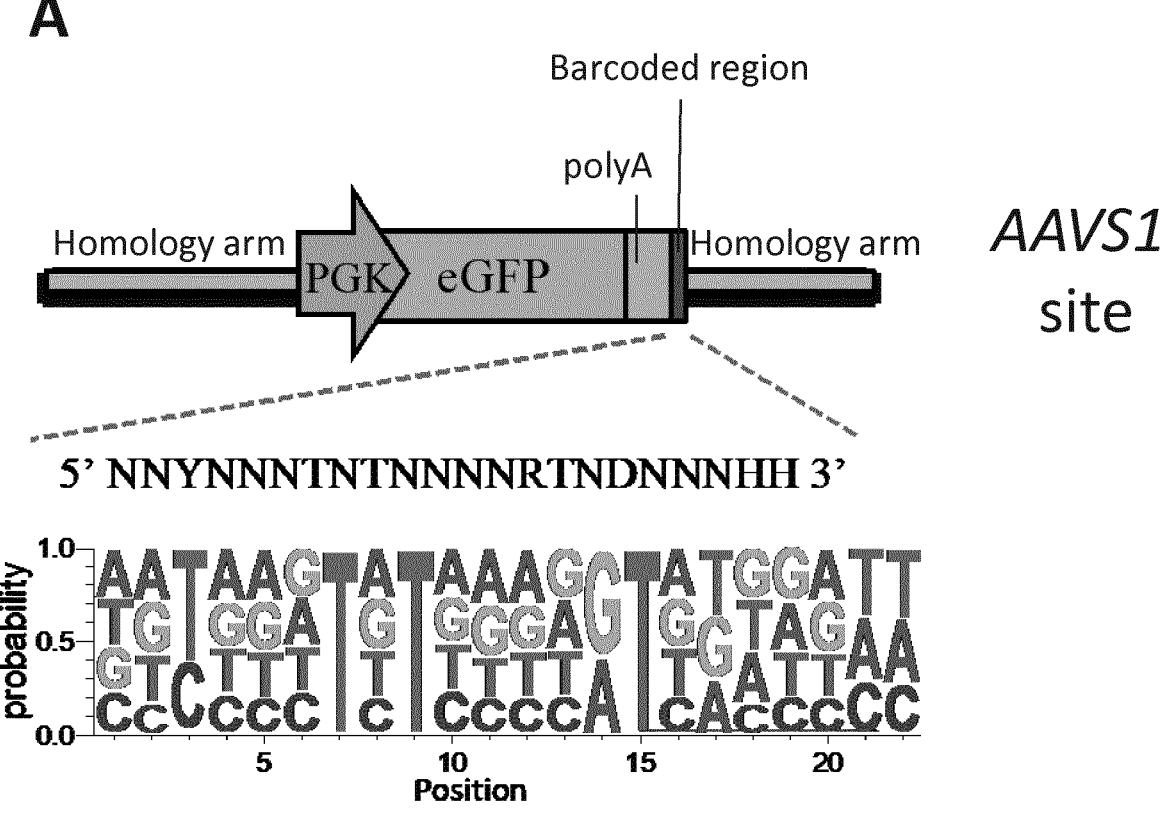

FIG. 23: Vector comprising barcode sequence

Schematic of AAV vector design comprising a barcode sequence.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Cell Survival and Engraftment

The term "survival" refers to the ability of the haematopoietic cells, haematopoietic stem cells and/or haematopoietic progenitor cells to remain alive (e.g. not die or become apoptotic) during in vitro or ex vivo culture. Haematopoietic stem and/or progenitor cells may, for example, undergo increased apoptosis following transduction with a viral vector during cell culture; thus, the surviving cells may have avoided apoptosis and/or cell death.

Cell survival may be readily analysed by the skilled person. For example, the numbers of live, dead and/or apoptotic cells in a cell culture may be quantified at the beginning of culture and/or following culture for a period of time (e.g. about 6 or 12 hours, or 1, 2, 3, 4, 5, 6, 7 or more days; preferably, the period of time begins with the transduction of the cells with a viral vector). The effect of an agent, such as an inhibitor or adenoviral protein of the invention, on cell survival may be assessed by comparing the numbers and/or percentages of live, dead and/or apoptotic cells at the beginning and/or end of the culture period between experiments carried out in the presence and absence of the agent, but under otherwise substantially identical conditions.

Cell numbers and/or percentages in certain states (e.g. live, dead or apoptotic cells) may be quantified using any of a number of methods known in the art, including use of haemocytometers, automated cell counters, flow cytometers and fluorescence activated cell sorting machines. These techniques may enable distinguishing between live, dead and/or apoptotic cells. In addition or in the alternative, apoptotic cells may be detected using readily available apoptosis assays (e.g. assays based on the detection of phosphatidylserine (PS) on the cell membrane surface, such as through use of Annexin V, which binds to exposed PS; apoptotic cells may be quantified through use of fluorescently-labelled Annexin V), which may be used to complement other techniques.

The term "engraftment" refers to the ability of the haematopoietic stem and/or progenitor cells to populate and survive in a subject following their transplantation, i.e. in the short and/or long term after transplantation. For example, engraftment may refer to the number and/or percentages of haematopoietic cells descended from the transplanted haematopoietic stem cells (e.g. graft-derived cells) that are detected about 1 day to 24 weeks, 1 day to 10 weeks, or 1-30 days or 10-30 days after transplantation. In the xenograft model of human haematopoietic stem and/or progenitor cell engraftment and repopulation, engraftment may be evaluated in the peripheral blood as the percentage of cells deriving from the human xenograft (e.g. positive for the CD45 surface marker), for example. In one embodiment, engraftment is assessed at about 1, 2, 3, 4, 5, 6, 7, 8, 9, 10, 15, 20, 25 or 30 days after transplantation. In another embodiment, engraftment is assessed at about 4, 5, 6, 7, 8, 9, 10, 11, 12, 13, 14, 15, 16, 17, 18, 19, 20, 21, 22, 23 or 24 weeks after transplantation. In another embodiment, engraftment is assessed at about 16-24 weeks, preferably 20 weeks, after transplantation.

Engraftment may be readily analysed by the skilled person. For example, the transplanted haematopoietic stem and/or progenitor cells may be engineered to comprise a marker (e.g. a reporter protein, such as a fluorescent protein), which can be used to quantify the graft-derived cells. Samples for analysis may be extracted from relevant tissues and analysed ex vivo (e.g. using flow cytometry).

Suitably, the agent for use according to the present invention may improve engraftment of gene edited haematopoietic stem and/or progenitor cells compared with gene editing without use of the agent. Suitably, engraftment at a given time point may be increased by at least 5%, 10%, 20%, 30%, 40%, 50%, 60%, 70%, 80%, 90% or more when compared with engraftment of untreated gene edited haematopoietic stem and/or progenitor cells.

In a preferred embodiment, an agent for use according to the invention does not adversely affect the growth of gene edited haematopoietic cells, haematopoietic stem cells and/or haematopoietic progenitor cells when compared with untreated gene edited haematopoietic cells, haematopoietic stem cells and/or haematopoietic progenitor cells.

Gene Editing Efficiency

In one aspect, the invention provides the use of an agent which promotes homology directed DNA repair for increasing the efficiency of gene editing of an isolated population of haematopoietic cells, haematopoietic stem cells and/or haematopoietic progenitor cells (e.g. when transduced by a viral vector) and/or increasing survival and or engraftment of gene edited haematopoietic cells, haematopoietic stem cells and/or haematopoietic progenitor cells.

Increasing the efficiency of gene editing refers to an increase in the gene editing of the cells (e.g. haematopoietic cells, haematopoietic stem cells and/or haematopoietic progenitor cells) in the presence of an agent, in comparison to the gene editing achieved in the absence of the agent but under otherwise substantially identical conditions. Where a viral vector is used to introduce gene editing machinery, an increased efficiency may therefore allow the multiplicity of infection (MOI) and/or the time required to achieve effective transduction to be reduced.

In one embodiment, the percentage of cells which have been edited is increased. Methods for determining the percentage of cells which have been edited are known in the art. Suitable methods include flow cytometry, fluorescence-activated cell sorting (FACS) and fluorescence microscopy. The technique employed is preferably one which is amenable to automation and/or high throughput screening.

For example, a population of cells may be edited with a vector which harbours a reporter gene. Suitably, the reporter gene may be expressed when the cell has been edited. Suitable reporter genes include genes encoding fluorescent proteins, for example green, yellow, cherry, cyan or orange fluorescent proteins. Once the population of cells has been edited, both the number of cells expressing and not-expressing the reporter gene may be quantified using a suitable technique, such as FACS. The percentage of cells which have been edited may then be calculated.

Alternatively, quantitative PCR (qPCR) may be used to determine the percentage of cells which have been gene edited without the use of a reporter gene. For example, single colonies of cells (e.g. CD34+ cells) may be picked from a semi-solid culture and qPCR may be performed on each colony separately to determine the percentage of gene-edited-positive colonies among those analysed.

Methods for determining vector copy number are also known in the art. The technique employed is preferably one which is amenable to automation and/or high throughput screening. Suitable techniques include quantitative PCR (qPCR) and Southern blot-based approaches.

Increasing the efficiency of gene editing may refer to an increase in the number of cells (e.g. haematopoietic cells, haematopoietic stem cells or haematopoietic progenitor cells) in which a target gene or site has been edited (e.g. disrupted, replaced, deleted or had a nucleic acid sequence inserted within or at it) in the intended manner following transduction of a population of cells with a viral vector in the presence of an agent (e.g. inhibitor of p53 activation or adenoviral protein), in comparison to that achieved in the absence of the agent but under otherwise substantially identical conditions. An increased efficiency of gene editing may therefore allow the multiplicity of infection (MOI) and/or the transduction time required to achieve effective gene editing to be reduced. Methods for determining whether a target gene or site has been edited are known in the art.

In the context of gene editing, for example using a CRISPR/Cas system, preferably the vector used to transduce the population of cells is a non-integrating vector (e.g. an integration-defective lentiviral vector, IDLV).

In one embodiment, the agent for use according to the present invention improves gene editing efficiency compared with gene editing without use of the agent (i.e. standard gene editing). Suitably, gene editing efficiency may be improved by at least 1.1 fold, 1.2 fold, 1.3 fold, 1.4 fold, 1.5 fold, 1.6 fold, 1.7 fold, 1.8 fold, 1.9 fold, 1.8 fold, 1.9 fold, 2.0 fold, 2.1 fold, 2.2 fold, 2.3 fold, 2.4 fold, 2.5 fold, 3 fold or more.

Suitably, the gene editing efficiency may be improved in a particular cell compartment. Suitably, gene editing is improved in a primitive HSPC cell compartment. Suitably, gene editing may be improved in CD34+ CD133-cells. Suitably, gene editing may be improved in CD34+ CD133+ cells. Suitably, gene editing may be improved in CD34+ CD133+ CD90+ cells.

Preferably gene editing efficiency of CD34+ CD133+ CD90+ cells may be improved by at least 1.1 fold, 1.2 fold, 1.3 fold, 1.4 fold, 1.5 fold, 1.6 fold, 1.7 fold, 1.8 fold, 1.9 fold, 1.8 fold, 1.9 fold, 2.0 fold, 2.1 fold, 2.2 fold, 2.3 fold, 2.4 fold, 2.5 fold, 3 fold or more.

An Agent which Promotes Homology Directed DNA Repair

The present inventors have determined that improving the efficiency of HDR in HSC increases cell survival and engraftment of gene edited HSCs.

Gene editing in primary cells and the HSPC in particular may be hampered by gene transfer efficiency and limited HDR, likely due to low levels of expression of the HDR machinery and high activity of NHEJ pathway.

As used herein "an agent which promotes homology directed DNA repair" refers to an agent which enhances and/or improves the efficiency of HDR relative to the level of HDR in a cell which has not been treated with the agent.

Suitably, HDR may be increased by 5%, 10%, 20%, 30%, 40%, 50%, 60%, 70%, 80%, 90% or more. Suitably, HDR may be increased by 1.1, 1.2, 1.3, 1.4, 1.5, 1.6, 1.7, 1.8, 1.9, 2.0, 2.5, 3.0 fold or more.

Figure 2:
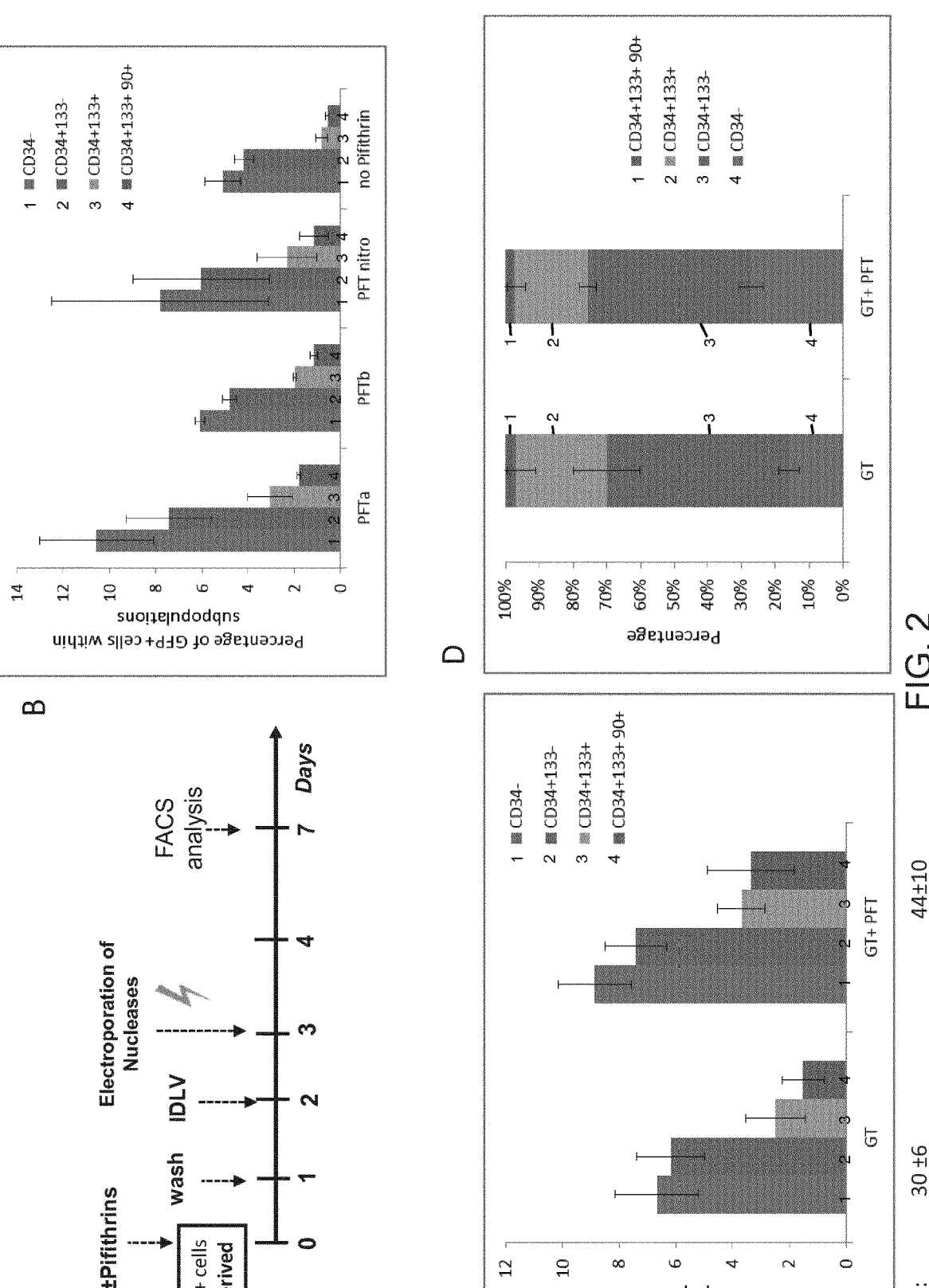
FIG. 2. Transient p53 inhibition by pifithrins. (A) Schematic representation of the gene editing protocol and the timing of phithrins addition. (B) Percentage of GFP+ cells measured within the indicated subpopulations 3 days after gene editing in presence or not of different phfithin-$\alpha$ derivatives (n=2). (C) Percentage of GFP+ cells measured within the indicated subpopulations and of NHEJ measured on the bulk cells 3 days after gene editing in presence or not of phfithin-$\alpha$ ciclic (n=5) (D) Subpopulation composition of treated CD34+ cells from (C) (n=5).

HDR efficiency may be measured using any method in the art. Suitably, HDR efficiency may be determined by FACS measuring the presence of a marker in donor template vector which is introduced to the cell by HDR-mediated integration at the targeted locus. For example, an AAV6 donor template may comprise a PGK.GFP reporter cassette. FIG. 2B demonstrates that an increase in HDR efficiency was obtained via transient p53 inhibition, as measured by determining the percentage of GFP+ cells.

Targeting integration ("on target" HDR) can be determined by digital PCR by using primers and probes which were designed on the junction between the vector sequence and the targeted locus and on control sequences used for normalization (human TTC5 genes).

The percentage of insertions and deletion (indels) introduced by the Non Homologous End Joining (NHEJ) repair pathway on the nucleases target site was measured by a mismatch-sensitive endonuclease assay (PCR-based amplification of the targeted locus followed by digestion with T7 Endonuclease I; digested DNA fragments were resolved and quantified by capillary electrophoresis on LabChip GX Touch HT, Perkin Elmer) The levels of NHEJ-induced mutations were used as surrogate readout for scoring nucleases activity.

Preferably, the agent has low cellular toxicity.

Preferably, the agent does not significantly change the composition of the gene edited cells.

Preferably, the agent does not significantly induce differentiation of the gene edited haematopoietic stem and/or progenitor cells. Therefore, the gene edited haematopoietic stem and/or progenitor cells according to the present invention retain their long-term re-population capacity.

Suitably, the change in composition or differentiation of the gene edited cells is less than 5%, less than 4%, less than 3% less than 2% or less than 1% when compared with an untreated control.

Figure 3:
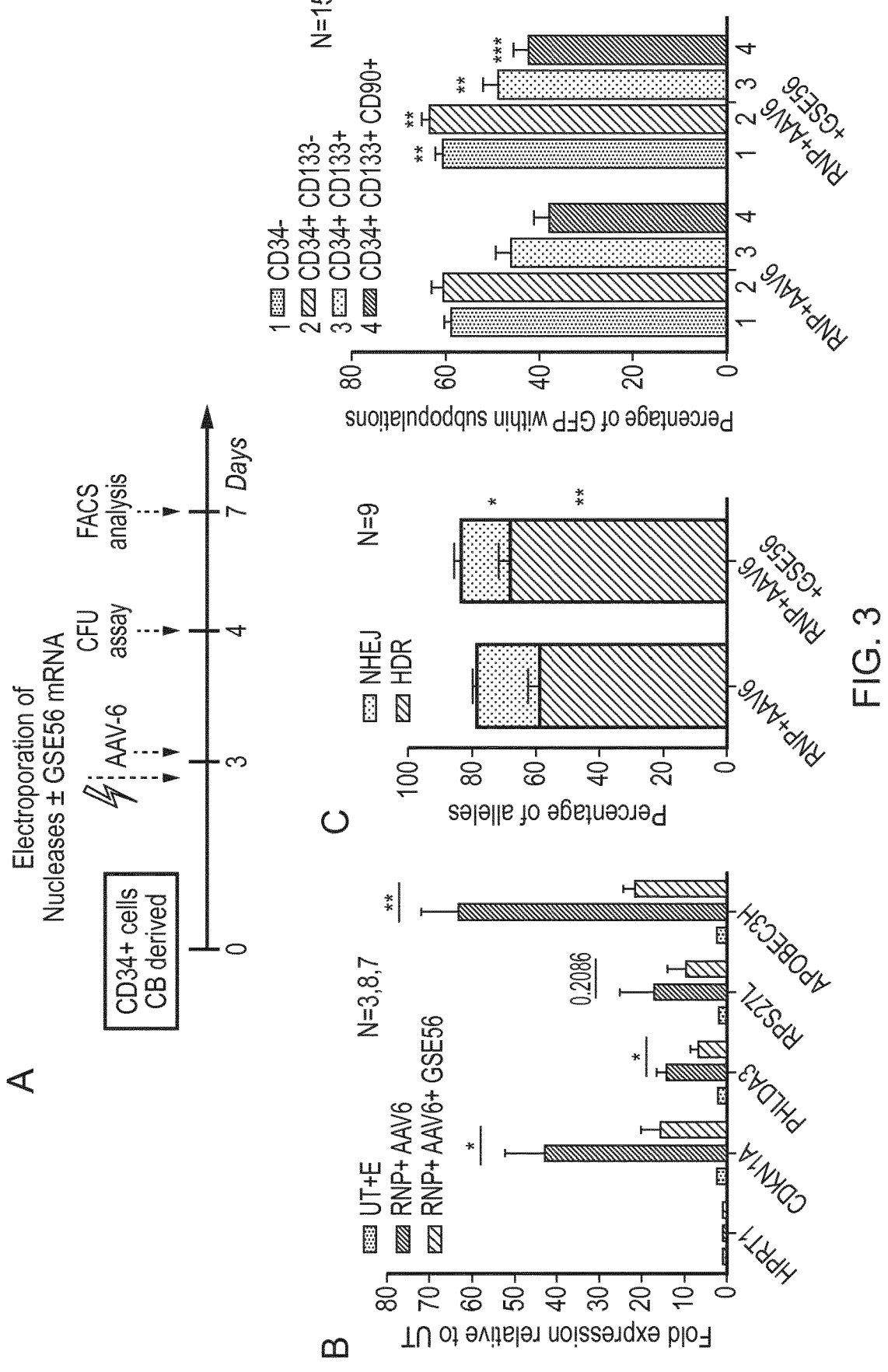
FIG. 3. Transient p53 inhibition by GSE56 mRNA. (A) Schematic representation of the gene editing protocol±GSE56 and cell analyses. (B) Fold expression of the indicated p53-target genes (CDKN1A, PHLDA3, RPS27L, APOBEC3H) relative to untreated control (UT) measured 24 hrs after electroporation of CD34+ cells treated as indicated (UT, RNP+AAV6, RNP+AAV6+GSE56 n=8; mock electro n=3) *P<0.05, ** P<0.01; Mann-Whitney Test. (C) (Left) Percentage of HDR (measured by ddPCR) or NHEJ (measured by heteroduplex assay) 3 days after AAVS1 or IL2RG gene editing in presence or not GSE56 mRNA (n=9)*P<0.05,  P<0.01; Wilcoxon matched-pairs signed-rank test. (Right) Percentage of GFP+ cells measured within the indicated subpopulations 3 days after AAVS1 or IL2RG gene editing in presence or not GSE56 mRNA (n=15)  P<0.01; Wilcoxon matched-pairs signed-rank test. (D) Growth curve of AAVS1 edited cells in presence or not GSE56 mRNA (n=2) (E) Subpopulation composition of treated CD34+ cells from (B). (F) Number of erythroid or myeloid single colonies counted upon plating in CFU-C assay edited cells sorted for CD133+ CD90+ or CD133+ 90− (n=11) ns: P>0.05, *P<0.05; Mann-Whitney Test.
Figure 3:
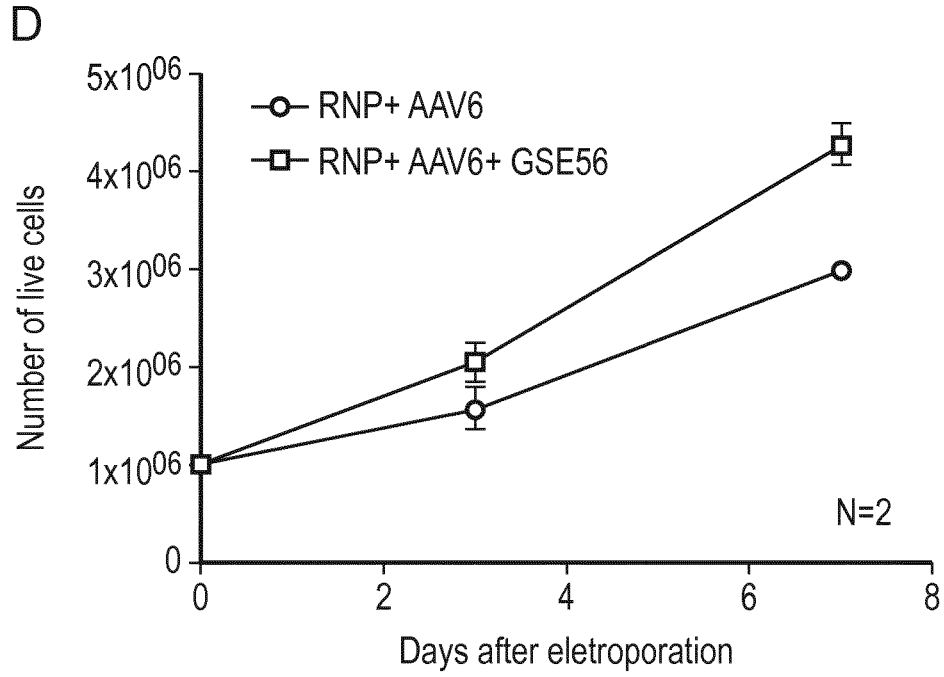
Figure 3:
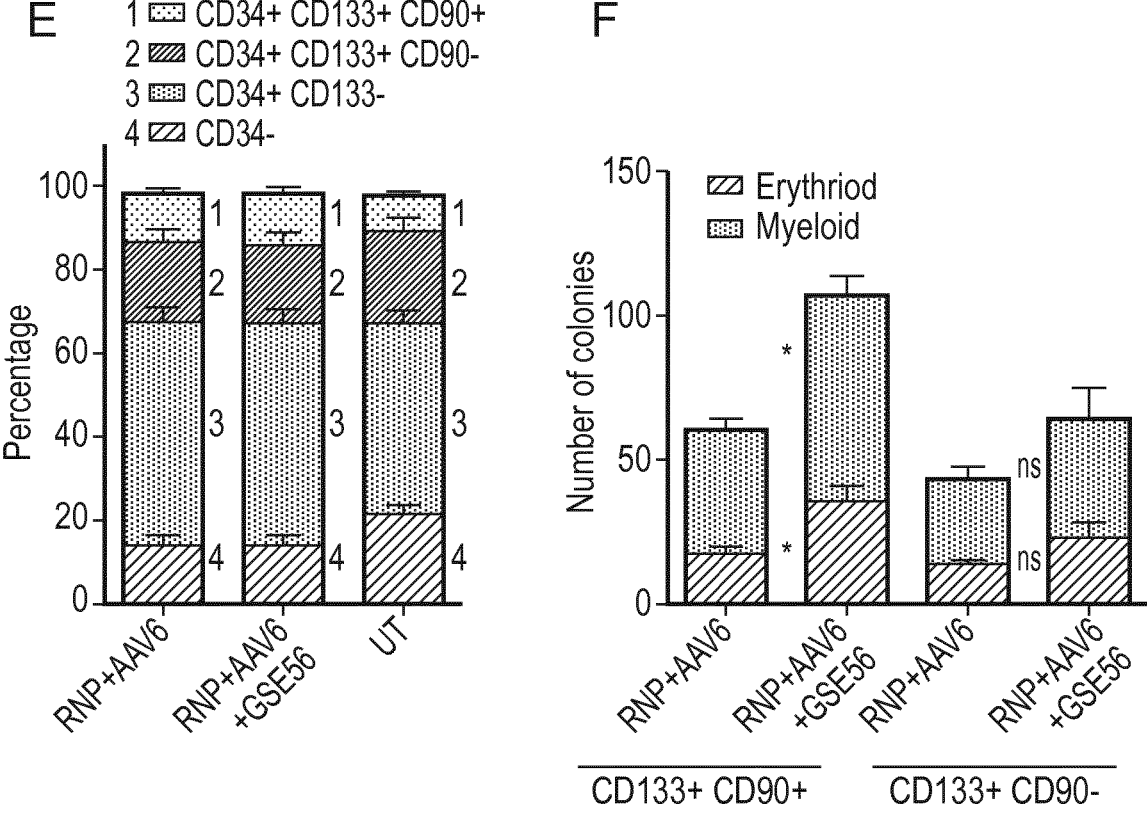

For example, FIG. 3E shows that there was no change in relative composition of the haematopoietic populations measured at 3 days post editing in gene edited cells compared with untreated controls.

p53 Activation

The term "p53 activation" refers to an increase in the activity of p53, for example through a post-translational modification of the p53 protein. Example post-translational modifications include phosphorylation, acetylation and methylation, and are described in Kruse, J. P. et al. (2008) SnapShot: p53 Posttranslational Modifications Cell 133: 930-931. In the context of the invention, the p53 activation preferably results from phosphorylation of p53, particularly preferably at amino acid Serine 15.

Methods for analysing such post-translational modifications are known in the art (example methods for analysing kinase activity are disclosed herein, further methods include, for example, mass spectrometry- and antibody recognition-based methods).

An example amino acid sequence of p53, which may be used to provide an amino acid numbering convention, is:

```
                   (SEQ ID NO: 3; NCBI Accession NO. 000537.3)
MEEPQSDPSVEPPLSQETFSDLWKLLPENNVLSPLPSQAMDDLMLSPDD

IEQWFTEDPGPDEAPRMPEAAPPVAPAPAAPTPAAPAPAPSWPLSSSVP

SQKTYQGSYGFRLGFLHSGTAKSVTCTYSPALNKMFCQLAKTCPVQLWV

DSTPPPGTRVRAMAIYKQSQHMTEVVRRCPHHERCSDSDGLAPPQHLIR

VEGNLRVEYLDDRNTFRHSVVVPYEPPEVGSDCTTIHYNYMCNSSCMGG

MNRRPILTIITLEDSSGNLLGRNSFEVRVCACPGRDRRTEEENLRKKGE

PHHELPPGSTKRALPNNTSSSPQPKKKPLDGEYFTLQIRGRERFEMFRE

LNEALELKDAQAGKEPGGSRAHSSHLKSKKGQSTSRHKKLMEKTEGPDS

D
```

Ataxia Telangiectasia Mutated (ATM) Kinase

Ataxia telangiectasia mutated (ATM) kinase (also known as "ataxia telangiectasia mutated") is a serine/threonine kinase which is recruited to and activated by double-strand DNA breaks. ATM kinase is known to phosphorylate a number of proteins (including p53, CHK2, BRCA1, NBS1 and H2AX) that initiate activation of the DNA damage checkpoint, leading to cell cycle arrest, DNA repair or apoptosis.

In one embodiment, the ATM kinase is human ATM kinase.

In one embodiment, the amino acid sequence of ATM kinase is the sequence deposited under NCBI Accession No. NP_000042.3.

An example amino acid sequence of the ATM kinase is:

(SEQ ID NO: 4)
MSLVLNDLLICCRQLEHDRATERKKEVEKFKRLIRDPETIKHLDRHSDS

KQGKYLNWDAVFRFLQKYIQKETECLRIAKPNVSASTQASRQKKMQEIS

SLVKYFIKCANRRAPRLKCQELLNYIMDTVKDSSNGAIYGADCSNILLK

DILSVRKYWCEISQQQWLELFSVYFRLYLKPSQDVHRVLVARIIHAVTK

GCCSQTDGLNSKFLDFFSKAIQCARQEKSSSGLNHILAALTIFLKTLAV

NFRIRVCELGDEILPTLLYIWTQHRLNDSLKEVIIELFQLQIYIHHPKG

AKTQEKGAYESTKWRSILYNLYDLLVNEISHIGSRGKYSSGFRNIAVKE

NLIELMADICHQVFNEDTRSLEISQSYTTTQRESSDYSVPCKRKKIELG

WEVIKDHLQKSQNDFDLVPWLQIATQLISKYPASLPNCELSPLLMILSQ

LLPQQRHGERTPYVLRCLTEVALCQDKRSNLESSQKSDLLKLWNKIWCI

TFRGISSEQIQAENFGLLGAIIQGSLVEVDREFWKLFTGSACRPSCPAV

CCLTLALTTSIVPGTVKMGIEQNMCEVNRSFSLKESIMKWLLFYQLEGD

LENSTEVPPILHSNFPHLVLEKILVSLTMKNCKAAMNFFQSVPECEHHQ

KDKEELSFSEVEELFLQTTFDKMDFLTIVRECGIEKHQSSIGFSVHQNL

KESLDRCLLGLSEQLLNNYSSEITNSETLVRCSRLLVGVLGCYCYMGVI

AEEEAYKSELFQKAKSLMQCAGESITLFKNKTNEEFRIGSLRNMMQLCT

RCLSNCTKKSPNKIASGFFLRLLTSKLMNDIADICKSLASFIKKPFDRG

EVESMEDDINGNLMEVEDQSSMNLENDYPDSSVSDANEPGESQSTIGAI

NPLAEEYLSKQDLLFLDMLKFLCLCVTTAQTNTVSFRAADIRRKLLMLI

DSSTLEPTKSLHLHMYLMLLKELPGEEYPLPMEDVLELLKPLSNVCSLY

RRDQDVCKTILNHVLHVVKNLGQSNMDSENTRDAQGQFLTVIGAFWHLT

KERKYIFSVRMALVNCLKTLLEADPYSKWAILNVMGKDFPVNEVFTQFL

ADNHHQVRMLAAESINRLFQDTKGDSSRLLKALPLKLQQTAFENAYLKA

QEGMREMSHSAENPETLDEIYNRKSVLLTLIAVVLSCSPICEKQALFAL

CKSVKENGLEPHLVKKVLEKVSETFGYRRLEDFMASHLDYLVLEWLNLQ

DTEYNLSSFPILLNYTNIEDFYRSCYKVLIPHLVIRSHFDEVKSIANQ

IQEDWKSLLTDCFPKILVNILPYFAYEGTRDSGMAQQRETATKVYDMLK

SENLLGKQIDHLFISNLPEIVVELLMTLHEPANSSASQSTDLCDFSGDL

DPAPNPPHFPSHVIKATFAYISNCHKTKLKSILEILSKSPDSYQKILLA

ICEQAAETNNVYKKHRILKIYHLFVSLLLKDIKSGLGGAWAFVLRDVIY

TLIHYINQRPSCIMDVSLRSFSLCCDLLSQVCQTAVTYCKDALENHLHV

IVGTLIPLVYEQVEVQKQVLDLLKYLVIDNKDNENLYITIKLLDPFPDH

VVFKDLRITQQKIKYSRGPFSLLEEINHFLSVSVYDALPLTRLEGLKDL

-continued
RRQLELHKDQMVDIMRASQDNPQDGIMVKLVVNLLQLSKMAINHTGEKE

VLEAVGSCLGEVGPIDFSTIAIQHSKDASYTKALKLFEDKELQWTFIML

TYLNNTLVEDCVKVRSAAVTCLKNILATKTGHSFWEIYKMTTDPMLAYL

QPFRTSRKKFLEVPREDKENPFEGLDDINLWIPLSENHDIWIKTLTCAF

LDSGGTKCEILQLLKPMCEVKTDFCQTVLPYLIHDILLQDTNESWRNLL

STHVQGFFTSCLRHFSQTSRSTTPANLDSESEHFFRCCLDKKSQRTMLA

VVDYMRRQKRPSSGTIFNDAFWLDLNYLEVAKVAQSCAAHFTALLYAEI

YADKKSMDDQEKRSLAFEEGSQSTTISSLSEKSKEETGISLQDLLLEIY

RSIGEPDSLYGCGGGKMLQPITRLRTYEHEAMWGKALVTYDLETAIPSS

TRQAGIIQALQNLGLCHILSVYLKGLDYENKDWCPELEELHYQAAWRNM

QWDHCTSVSKEVEGTSYHESLYNALQSLRDREFSTFYESLKYARVKEVE

EMCKRSLESVYSLYPTLSRLQAIGELESIGELFSRSVTHRQLSEVYIKW

QKHSQLLKDSDFSFQEPIMALRTVILEILMEKEMDNSQRECIKDILTKH

LVELSILARTFKNTQLPERAIFQIKQYNSVSCGVSEWQLEEAQVFWAKK

EQSLALSILKQMIKKLDASCAANNPSLKLTYTECLRVCGNWLAETCLEN

PAVIMQTYLEKAVEVAGNYDGESSDELRNGKMKAFLSLARFSDTQYQRI

ENYMKSSEFENKQALLKRAKEEVGLLREHKIQTNRYTVKVQRELELDEL

ALRALKEDRKRFLCKAVENYINCLLSGEEHDMWVFRLCSLWLENSGVSE

VNGMMKRDGMKIPTYKFLPLMYQLAARMGTKMMGGLGFHEVLNNLISRI

SMDHPHHTLFIILALANANRDEFLTKPEVARRSRITKNVPKQSSQLDED

RTEAANRIICTIRSRRPQMVRSVEALCDAYIILANLDATQWKTQRKGIN

IPADQPITKLKNLEDVVVPTMEIKVDHTGEYGNLVTIQSFKAEFRLAGG

VNLPKIIDCVGSDGKERRQLVKGRDDLRQDAVMQQVFQMCNTLLQRNTE

TRKRKLTICTYKVVPLSQRSGVLEWCTGTVPIGEFLVNNEDGAHKRYRP

NDFSAFQCQKKMMEVQKKSFEEKYEVFMDVCQNFQPVFRYFCMEKFLDP

AIWFEKRLAYTRSVATSSIVGYILGLGDRHVQNILINEQSAELVHIDLG

VAFEQGKILPTPETVPFRLTRDIVDGMGITGVEGVFRRCCEKTMEVMRN

SQETLLTIVEVLLYDPLFDWTMNPLKALYLQQRPEDETELHPTLNADDQ

ECKRNLSDIDQSENKVAERVLMRLQEKLKGVEEGTVLSVGGQVNLLIQQ

AIDPKNLSRLFPGWKAWV

An example nucleic acid sequence encoding the ATM kinase is:

(SEQ ID NO: 5; NCBI Accession NO. NM_000051.3)
ATGAGTCTAGTACTTAATGATCTGCTTATCTGCTGCCGTCAACTAGAAC

ATGATAGAGCTACAGAACGAAAGAAAGAAGTTGAGAAATTTAAGCGCCT

GATTCGAGATCCTGAAACAATTAAACATCTAGATCGGCATTCAGATTCC

AAACAAGGAAAATATTTGAATTGGGATGCTGTTTTTAGATTTTTACAGA

AATATATTCAGAAAGAAACAGAATGTCTGAGAATAGCAAAACCAAATGT

ATCAGCCTCAACACAAGCCTCCAGGCAGAAAAAGATGCAGGAAATCAGT

AGTTTGGTCAAATACTTCATCAAATGTGCAAACAGAAGAGCACCTAGGC

-continued

```
TAAAATGTCAAGAACTCTTAAATTATATCATGGATACAGTGAAAGATTC

ATCTAATGGTGCTATTTACGGAGCTGATTGTAGCAACATACTACTCAAA

GACATTCTTTCTGTGAGAAAATACTGGTGTGAAATATCTCAGCAACAGT

GGTTAGAATTGTTCTCTGTGTACTTCAGGCTCTATCTGAAACCTTCACA

AGATGTTCATAGAGTTTTAGTGGCTAGAATAATTCATGCTGTTACCAAA

GGATGCTGTTCTCAGACTGACGGATTAAATTCCAAATTTTTGGACTTTT

TTTCCAAGGCTATTCAGTGTGCGAGACAAGAAAGAGCTCTTCAGGTCT

AAATCATATCTTAGCAGCTCTTACTATCTTCCTCAAGACTTTGGCTGTC

AACTTTCGAATTCGAGTGTGTGAATTAGGAGATGAAATTCTTCCCACTT

TGCTTTATATTTGGACTCAACATAGGCTTAATGATTCTTTAAAAGAAGT

CATTATTGAATTATTTCAACTGCAAATTTATATCCATCATCCGAAAGGA

GCCAAAACCCAAGAAAAAGGTGCTTATGAATCAACAAAATGGAGAAGTA

TTTTATACAACTTATATGATCTGCTAGTGAATGAGATAAGTCATATAGG

AAGTAGAGGAAAGTATTCTTCAGGATTTCGTAATATTGCCGTCAAAGAA

AATTTGATTGAATTGATGGCAGATATCTGTCACCAGGTTTTTAATGAAG

ATACCAGATCCTTGGAGATTTCTCAATCTTACACTACTACACAAAGAGA

ATCTAGTGATTACAGTGTCCCTTGCAAAAGGAAGAAAATAGAACTAGGC

TGGGAAGTAATAAAAGATCACCTTCAGAAGTCACAGAATGATTTTGATC

TTGTGCCTTGGCTACAGATTGCAACCCAATTAATATCAAAGTATCCTGC

AAGTTTACCTAACTGTGAGCTGTCTCCATTACTGATGATACTATCTCAG

CTTCTACCCCAACAGCGACATGGGGAACGTACACCATATGTGTTACGAT

GCCTTACGGAAGTTGCATTGTGTCAAGACAAGAGGTCAAACCTAGAAAG

CTCACAAAAGTCAGATTTATTAAAACTCTGGAATAAAATTTGGTGTATT

ACCTTTCGTGGTATAAGTTCTGAGCAAATACAAGCTGAAAACTTTGGCT

TACTTGGAGCCATAATTCAGGGTAGTTTAGTTGAGGTTGACAGAGAATT

CTGGAAGTTATTTACTGGGTCAGCCTGCAGACCTTCATGTCCTGCAGTA

TGCTGTTTGACTTTGGCACTGACCACCAGTATAGTTCCAGGAACGGTAA

AAATGGGAATAGAGCAAAATATGTGTGAAGTAAATAGAAGCTTTTCTTT

AAAGGAATCAATAATGAAATGGCTCTTATTCTATCAGTTAGAGGGTGAC

TTAGAAAATAGCACAGAAGTGCCTCCAATTCTTCACAGTAATTTTCCTC

ATCTTGTACTGGAGAAAATTCTTGTGAGTCTCACTATGAAAAACTGTAA

AGCTGCAATGAATTTTTTCCAAAGCGTGCCAGAATGTGAACACCACCAA

AAAGATAAAGAAGAACTTTCATTCTCAGAAGTAGAAGAACTATTTCTTC

AGACAACTTTTGACAAGATGGACTTTTTAACCATTGTGAGAGAATGTGG

TATAGAAAGCACCAGTCCAGTATTGGCTTCTCTGTCCACCAGAATCTC

AAGGAATCACTGGATCGCTGTCTTCTGGGATTATCAGAACAGCTTCTGA

ATAATTACTCATCTGAGATTACAAATTCAGAAACTCTTGTCCGGTGTTC

ACGTCTTTTGGTGGGTGTCCTTGGCTGCTACTGTTACATGGGTGTAATA

GCTGAAGAGGAAGCATATAAGTCAGAATTATTCCAGAAAGCCAAGTCTC

TAATGCAATGTGCAGGAGAAAGTATCACTCTGTTTAAAAATAAGACAAA

TGAGGAATTCAGAATTGGTTCCTTGAGAAATATGATGCAGCTATGTACA
```

-continued

```
CGTTGCTTGAGCAACTGTACCAAGAAGAGTCCAAATAAGATTGCATCTG

GCTTTTTCCTGCGATTGTTAACATCAAAGCTAATGAATGACATTGCAGA

TATTTGTAAAAGTTTAGCATCCTTCATCAAAAAGCCATTTGACCGTGGA

GAAGTAGAATCAATGGAAGATGATACTAATGGAAATCTAATGGAGGTGG

AGGATCAGTCATCCATGAATCTATTTAACGATTACCCTGATAGTAGTGT

TAGTGATGCAAACGAACCTGGAGAGAGCCAAAGTACCATAGGTGCCATT

AATCCTTTAGCTGAAGAATATCTGTCAAAGCAAGATCTACTTTTCTTAG

ACATGCTCAAGTTCTTGTGTTTGTGTGTAACTACTGCTCAGACCAATAC

TGTGTCCTTTAGGGCAGCTGATATTCGGAGGAAATTGTTAATGTTAATT

GATTCTAGCACGCTAGAACCTACCAAATCCCTCCACCTGCATATGTATC

TAATGCTTTTAAAGGAGCTTCCTGGAGAAGAGTACCCCTTGCCAATGGA

AGATGTTCTTGAACTTCTGAAACCACTATCCAATGTGTGTTCTTTGTAT

CGTCGTGACCAAGATGTTTGTAAAACTATTTTAAACCATGTCCTTCATG

TAGTGAAAAACCTAGGTCAAAGCAATATGGACTCTGAGAACACAAGGGA

TGCTCAAGGACAGTTTCTTACAGTAATTGGAGCATTTTGGCATCTAACA

AAGGAGAGGAAATATATATTCTCTGTAAGAATGGCCCTAGTAAATTGCC

TTAAAACTTTGCTTGAGGCTGATCCTTATTCAAAATGGGCCATTCTTAA

TGTAATGGGAAAAGACTTTCCTGTAAATGAAGTATTTACACAATTTCTT

GCTGACAATCATCACCAAGTTCGCATGTTGGCTGCAGAGTCAATCAATA

GATTGTTCCAGGACACGAAGGGAGATTCTTCCAGGTTACTGAAAGCACT

TCCTTTGAAGCTTCAGCAAACAGCTTTTGAAAATGCATACTTGAAAGCT

CAGGAAGGAATGAGAGAAATGTCCCATAGTGCTGAGAACCCTGAAACTT

TGGATGAAATTTATAATAGAAATCTGTTTTACTGACGTTGATAGCTGT

GGTTTTATCCTGTAGCCCTATCTGCGAAAAACAGGCTTTGTTTGCCCTG

TGTAAATCTGTGAAAGAGAATGGATTAGAACCTCACCTTGTGAAAAAGG

TTTTAGAGAAAGTTTCTGAAACTTTTGGATATAGACGTTTAGAAGACTT

TATGGCATCTCATTTGATTATCTGGTTTTGGAATGGCTAAATCTTCAA

GATACTGAATACAACTTATCTTCTTTTCCTTTTATTTTATTAAACTACA

CAAATATTGAGGATTTCTATAGATCTTGTTATAAGGTTTTGATTCCACA

TCTGGTGATTAGAAGTCATTTTGATGAGGTGAAGTCCATTGCTAATCAG

ATTCAAGAGGACTGGAAAAGTCTTCTAACAGACTGCTTTCCAAAGATTC

TTGTAAATATTCTTCCTTATTTTGCCTATGAGGGTACCAGAGACAGTGG

GATGGCACAGCAAAGAGAGACTGCTACCAAGGTCTATGATATGCTTAAA

AGTGAAAACTTATTGGGAAAACAGATTGATCACTTATTCATTAGTAATT

TACCAGAGATTGTGGTGGAGTTATTGATGACGTTACATGAGCCAGCAAA

TTCTAGTGCCAGTCAGAGCACTGACCTCTGTGACTTTTCAGGGGATTTG

GATCCTGCTCCTAATCCACCTCATTTTCCATCGCATGTGATTAAAGCAA

CATTTGCCTATATCAGCAATTGTCATAAAACCAAGTTAAAAAGCATTTT

AGAAATTCTTTCCAAAAGCCCTGATTCCTATCAGAAAATTCTTCTTGCC

ATATGTGAGCAAGCAGCTGAAACAAATAATGTTTATAAGAAGCACAGAA
```

Line numbers in the center column: 5, 10, 15, 20, 25, 30, 35, 40, 45, 50, 55, 60, 65

-continued

TTCTTAAAATATATCACCTGTTTGTTAGTTTATTACTGAAAGATATAAA

AAGTGGCTTAGGAGGAGCTTGGGCCTTTGTTCTTCGAGACGTTATTTAT

ACTTTGATTCACTATATCAACCAAAGGCCTTCTTGTATCATGGATGTGT

CATTACGTAGCTTCTCCCTTTGTTGTGACTTATTAAGTCAGGTTTGCCA

GACAGCCGTGACTTACTGTAAGGATGCTCTAGAAAACCATCTTCATGTT

ATTGTTGGTACACTTATACCCCTTGTGTATGAGCAGGTGGAGGTTCAGA

AACAGGTATTGGACTTGTTGAAATACTTAGTGATAGATAACAAGGATAA

TGAAAACCTCTATATCACGATTAAGCTTTTAGATCCTTTTCCTGACCAT

GTTGTTTTTAAGGATTTGCGTATTACTCAGCAAAAAATCAAATACAGTA

GAGGACCCTTTTCACTCTTGGAGGAAATTAACCATTTTCTCTCAGTAAG

TGTTTATGATGCACTTCCATTGACAAGACTTGAAGGACTAAAGGATCTT

CGAAGACAACTGGAACTACATAAAGATCAGATGGTGGACATTATGAGAG

CTTCTCAGGATAATCCGCAAGATGGGATTATGGTGAAACTAGTTGTCAA

TTTGTTGCAGTTATCCAAGATGGCAATAAACCACACTGGTGAAAAAGAA

GTTCTAGAGGCTGTTGGAAGCTGCTTGGGAGAAGTGGGTCCTATAGATT

TCTCTACCATAGCTATACAACATAGTAAAGATGCATCTTATACCAAGGC

CCTTAAGTTATTTGAAGATAAAGAACTTCAGTGGACCTTCATAATGCTG

ACCTACCTGAATAACACACTGGTAGAAGATTGTGTCAAAGTTCGATCAG

CAGCTGTTACCTGTTTGAAAAACATTTTAGCCACAAAGACTGGACATAG

TTTCTGGGAGATTTATAAGATGACAACAGATCCAATGCTGGCCTATCTA

CAGCCTTTTAGAACATCAAGAAAAAAGTTTTTAGAAGTACCCAGATTTG

ACAAAGAAAACCCTTTTGAAGGCCTGGATGATATAAATCTGTGGATTCC

TCTAAGTGAAAATCATGACATTTGGATAAAGACACTGACTTGTGCTTTT

TTGGACAGTGGAGGCACAAAATGTGAAATTCTTCAATTATTAAAGCCAA

TGTGTGAAGTGAAAACTGACTTTTGTCAGACTGTACTICCATACTTGAT

TCATGATATTTTACTCCAAGATACAAATGAATCATGGAGAAATCTGCTT

TCTACACATGTTCAGGGATTTTTCACCAGCTGTCTTCGACACTTCTCGC

AAACGAGCCGATCCACAACCCCTGCAAACTTGGATTCAGAGTCAGAGCA

CTTTTTCCGATGCTGTTTGGATAAAAAATCACAAAGAACAATGCTTGCT

GTTGTGGACTACATGAGAAGACAAAAGAGACCTTCTTCAGGAACAATTT

TTAATGATGCTTTCTGGCTGGATTTAAATTATCTAGAAGTTGCCAAGGT

AGCTCAGTCTTGTGCTGCTCACTTTACAGCTTTACTCTATGCAGAAATC

TATGCAGATAAGAAAAGTATGGATGATCAAGAGAAAAGAAGTCTTGCAT

TTGAAGAAGGAAGCCAGAGTACAACTATTTCTAGCTTGAGTGAAAAAAG

TAAAGAAGAAACTGGAATAAGTTTACAGGATCTTCTCTTAGAAATCTAC

AGAAGTATAGGGGAGCCAGATAGTTTGTATGGCTGTGGTGGAGGGAAGA

TGTTACAACCCATTACTAGACTACGAACATATGAACACGAAGCAATGTG

GGGCAAAGCCCTAGTAACATATGACCTCGAAACAGCAATCCCCTCATCA

ACACGCCAGGCAGGAATCATTCAGGCCTTGCAGAATTTGGGACTCTGCC

ATATTCTTTCCGTCTATTTAAAAGGATTGGATTATGAAAATAAAGACTG

GTGTCCTGAACTAGAAGAACTTCATTACCAAGCAGCATGGAGGAATATG

-continued

CAGTGGGACCATTGCACTTCCGTCAGCAAAGAAGTAGAAGGAACCAGTT

ACCATGAATCATTGTACAATGCTCTACAATCTCTAAGAGACAGAGAATT

CTCTACATTTTATGAAAGTCTCAAATATGCCAGAGTAAAAGAAGTGGAA

GAGATGTGTAAGCGCAGCCTTGAGTCTGTGTATTCGCTCTATCCCACAC

TTAGCAGGTTGCAGGCCATTGGAGAGCTGGAAAGCATTGGGGAGCTTTT

CTCAAGATCAGTCACACATAGACAACTCTCTGAAGTATATATTAAGTGG

CAGAAACACTCCCAGCTTCTCAAGGACAGTGATTTTAGTTTTCAGGAGC

CTATCATGGCTCTACGCACAGTCATTTTGGAGATCCTGATGGAAAAGGA

AATGGACAACTCACAAAGAGAATGTATTAAGGACATTCTCACCAAACAC

CTTGTAGAACTCTCTATACTGGCCAGAACTTTCAAGAACACTCAGCTCC

CTGAAAGGGCAATATTTCAAATTAAACAGTACAATTCAGTTAGCTGTGG

AGTCTCTGAGTGGCAGCTGGAAGAAGCACAAGTATTCTGGGCAAAAAAG

GAGCAGAGTCTTGCCCTGAGTATTCTCAAGCAAATGATCAAGAAGTTGG

ATGCCAGCTGTGCAGCGAACAATCCCAGCCTAAAACTTACATACACAGA

ATGTCTGAGGGTTTGTGGCAACTGGTTAGCAGAAACGTGCTTAGAAAAT

CCTGCGGTCATCATGCAGACCTATCTAGAAAAGGCAGTAGAAGTTGCTG

GAAATTATGATGGAGAAAGTAGTGATGAGCTAAGAAATGGAAAAATGAA

GGCATTTCTCTCATTAGCCCGGTTTTCAGATACTCAATACCAAAGAATT

GAAAACTACATGAAATCATCGGAATTTGAAAACAAGCAAGCTCTCCTGA

AAAGAGCCAAAGAGGAAGTAGGTCTCCTTAGGGAACATAAAATTCAGAC

AAACAGATACACAGTAAAGGTTCAGCGAGAGCTGGAGTTGGATGAATTA

GCCCTGCGTGCACTGAAAGAGGATCGTAAACGCTTCTTATGTAAAGCAG

TTGAAAATTATATCAACTGCTTATTAAGTGGAGAAGAACATGATATGTG

GGTATTCCGACTTTGTTCCCTCTGGCTTGAAAATTCTGGAGTTTCTGAA

GTCAATGGCATGATGAAGAGAGACGGAATGAAGATTCCAACATATAAAT

TTTTGCCTCTTATGTACCAATTGGCTGCTAGAATGGGGACCAAGATGAT

GGGAGGCCTAGGATTTCATGAAGTCCTCAATAATCTAATCTCTAGAATT

TCAATGGATCACCCCCATCACACTTTGTTTATTATACTGGCCTTAGCAA

ATGCAAACAGAGATGAATTCTGACTAAACCAGAGGTAGCCAGAAGAAG

CAGAATAACTAAAAATGTGCCTAAACAAAGCTCTCAGCTTGATGAGGAT

CGAACAGAGGCTGCAAATAGAATAATATGTACTATCAGAAGTAGGAGAC

CTCAGATGGTCAGAAGTGTTGAGGCACTTTGTGATGCTTATATTATATT

AGCAAACTTAGATGCCACTCAGTGGAAGACTCAGAGAAAAGGCATAAAT

ATTCCAGCAGACCAGCCAATTACTAAACTTAAGAATTTAGAAGATGTTG

TTGTCCCTACTATGGAAATTAAGGTGGACCACACAGGAGAATATGGAAA

TCTGGTGACTATACAGTCATTTAAAGCAGAATTTCGCTTAGCAGGAGGT

GTAAATTTACCAAAAAATAATAGATTGTGTAGGTTCCGATGGCAAGGAGA

GGAGACAGCTTGTTAAGGGCCGTGATGACCTGAGACAAGATGCTGTCAT

GCAACAGGTCTTCCAGATGTGTAATACATTACTGCAGAGAAACACGGAA

ACTAGGAAGAGGAAATTAACTATCTGTACTTATAAGGTGGTTCCCCTCT

-continued

-continued

```
CTCAGCGAAGTGGTGTTCTTGAATGGTGCACAGGAACTGTCCCCATTGG

TGAATTTCTTGTTAACAATGAAGATGGTGCTCATAAAAGATACAGGCCA

AATGATTTCAGTGCCTTTCAGTGCCAAAAGAAAATGATGGAGGTGCAAA

AAAAGTCTTTTGAAGAGAAATATGAAGTCTTCATGGATGTTTGCCAAAA

TTTTCAACCAGTTTTCCGTTACTTCTGCATGGAAAAATTCTTGGATCCA

GCTATTTGGTTTGAGAAGCGATTGGCTTATACGCGCAGTGTAGCTACTT

CTTCTATTGTTGGTTACATACTTGGACTTGGTGATAGACATGTACAGAA

TATCTTGATAAATGAGCAGTCAGCAGAACTTGTACATATAGATCTAGGT

GTTGCTTTTGAACAGGGCAAAATCCTTCCTACTCCTGAGACAGTTCCTT

TTAGACTCACCAGAGATATTGTGGATGGCATGGGCATTACGGGTGTTGA

AGGTGTCTTCAGAAGATGCTGTGAGAAAACCATGGAAGTGATGAGAAAC

TCTCAGGAAACTCTGTTAACCATTGTAGAGGTCCTTCTATATGATCCAC

TCTTTGACTGGACCATGAATCCTTTGAAAGCTTTGTATTTACAGCAGAG

GCCGGAAGATGAAACTGAGCTTCACCCTACTCTGAATGCAGATGACCAA

GAATGCAAACGAAATCTCAGTGATATTGACCAGAGTTTCAACAAAGTAG

CTGAACGTGTCTTAATGAGACTACAAGAGAAACTGAAAGGAGTGGAAGA

AGGCACTGTGCTCAGTGTTGGTGGACAAGTGAATTTGCTCATACAGCAG

GCCATAGACCCCAAAAATCTCAGCCGACTTTTCCCAGGATGGAAAGCTT

GGGTGTGA
```

Ataxia Telangiectasia and Rad3-Related Protein (ATR)

Ataxia telangiectasia and Rad3-related protein (ATR), also known as serine/threonine-protein kinase ATR or FRAP-related protein 1 (FRP1), is a serine/threonine-specific kinase involved in DNA damage sensing. It may be involved in activating the DNA damage checkpoint, which leads to cell cycle arrest In one embodiment, the ATR is human ATR.

In one embodiment, the amino acid sequence of ATR is the sequence deposited under NCBI Accession No. NP_001175.2.

An example amino acid sequence of the ATR is:

```
                                        (SEQ ID NO: 6)
MGEHGLELASMIPALRELGSATPEEYNTVVQKPRQILCQFIDRILTDVN

VVAVELVKKTDSQPTSVMLLDFIQHIMKSSPLMFVNVSGSHEAKGSCIE

FSNWIITRLLRIAATPSCHLLHKKICEVICSLLFLFKSKSPAIFGVLTK

ELLQLFEDLVYLHRRNVMGHAVEWPVVMSRFLSQLDEHMGYLQSAPLQL

MSMQNLEFIEVTLLMVLTRIIAIVFFRRQELLLWQIGCVLLEYGSPKIK

SLAISFLTELFQLGGLPAQPASTFFSSFLELLKHLVEMDTDQLKLYEEP

LSKLIKTLFPFEAEAYRNIEPVYLNMLLEKLCVMFEDGVLMRLKSDLLK

AALCHLLQYFLKFVPAGYESALQVRKVYVRNICKALLDVLGIEVDAEYL

LGPLYAALKMESMEIIEEIQCQTQQENLSSNSDGISPKRRRLSSSLNPS

KRAPKQTEEIKHVDMNQKSILWSALKQKAESLQISLEYSGLKNPVIEML

EGIAVVLQLTALCTVHCSHQNMNCRTFKDCQHKSKKKPSVVITWMSLDF

YTKVLKSCRSLLESVQKLDLEATIDKVVKIYDALIYMQVNSSFEDHILE

DLCGMLSLPWIYSHSDDGCLKLTTFAANLLTLSCRISDSYSPQAQSRCV
```

```
FLLTLFPRRIFLEWRTAVYNWALQSSHEVIRASCVSGFFILLQQQNSCN

RVPKILIDKVKDDSDIVKKEFASILGQLVCTLHGMFYLTSSLTEPFSEH

GHVDLFCRNLKATSQHECSSSQLKASVCKPFLFLLKKKIPSPVKLAFID

NLHHLCKHLDFREDETDVKAVLGTLLNLMEDPDKDVRVAFSGNIKHILE

SLDSEDGFIKELFVLRMKEAYTHAQISRNNELKDTLILTTGDIGRAAKG

DLVPFALLHLLHCLLSKSASVSGAAYTEIRALVAAKSVKLQSFFSQYKK

PICQFLVESLHSSQMTALPNTPCQNADVRKQDVAHQREMALNTLSEIAN

VFDFPDLNRFLTRTLQVLLPDLAAKASPAASALIRTLGKQLNVNRREIL

INNFKYIFSHLVCSCSKDELERALHYLKNETEIELGSLLRQDFQGLHNE

LLLRIGEHYQQVENGLSILASFASSDDPYQGPRDIISPELMADYLQPKL

LGILAFFNMQLLSSSVGIEDKKMALNSLMSLMKLMGPKHVSSVRVKMMT

TLRTGLRFKDDFPELCCRAWDCFVRCLDHACLGSLLSHVIVALLPLIHI

QPKETAAIFHYLIIENRDAVQDFLHEIYFLPDHPELKKIKAVLQEYRKE

TSESTDLQTTLQLSMKAIQHENVDVRIHALTSLKETLYKNQEKLIKYAT

DSETVEPIISQLVTVLLKGCQDANSQARLLCGECLGELGAIDPGRLDFS

TTETQGKDFTFVTGVEDSSFAYGLLMELTRAYLAYADNSRAQDSAAYAI

QELLSIYDCREMETNGPGHQLWRRFPEHVREILEPHLNTRYKSSQKSTD

WSGVKKPIYLSKLGSNFAEWSASWAGYLITKVRHDLASKIFTCCSIMMK

HDFKVTIYLLPHILVYVLLGCNQEDQQEVYAEIMAVLKHDDQHTINTQD

IASDLCQLSTQTVFSMLDHLTQWARHKFQALKAEKCPHSKSNRNKVDSM

VSTVDYEDYQSVTRFLDLIPQDTLAVASFRSKAYTRAVMHFESFITEKK

QNIQEHLGFLQKLYAAMHEPDGVAGVSAIRKAEPSLKEQILEHESLGLL

RDATACYDRAIQLEPDQIIHYHGVVKSMLGLGQLSTVITQVNGVHANRS

EWTDELNTYRVEAAWKLSQWDLVENYLAADGKSTTWSVRLGQLLLSAKK

RDITAFYDSLKLVRAEQIVPLSAASFERGSYQRGYEYIVRLHMLCELEH

SIKPLFQHSPGDSSQEDSLNWVARLEMTQNSYRAKEPILALRRALLSLN

KRPDYNEMVGECWLQSARVARKAGHHQTAYNALLNAGESRLAELYVERA

KWLWSKGDVHQALIVLQKGVELCFPENETPPEGKNMLIHGRAMLLVGRF

MEETANFESNAIMKKYKDVTACLPEWEDGHFYLAKYYDKLMPMVTDNKM

EKQGDLIRYIVLHFGRSLQYGNQFIYQSMPRMLTLWLDYGTKAYEWEKA

GRSDRVQMRNDLGKINKVITEHTNYLAPYQFLTAFSQLISRICHSHDEV

FVVLMEIIAKVFLAYPQQAMWMMTAVSKSSYPMRVNRCKEILNKAIHMK

KSLEKFVGDATRLTDKLLELCNKPVDGSSSTLSMSTHFKMLKKLVEEAT

FSEILIPLQSVMIPTLPSILGTHANHASHEPFPGHWAYIAGFDDMVEIL

ASLQKPKKISLKGSDGKFYIMMCKPKDDLRKDCRLMEFNSLINKCLRKD

AESRRRELHIRTYAVIPLNDECGIIEWVNNTAGLRPILTKLYKEKGVYM

TGKELRQCMLPKSAALSEKLKVFREFLLPRHPPIFHEWFLRTFPDPTSW

YSSRSAYCRSTAVMSMVGYILGLGDRHGENILFDSLTGECVHVDENCLE

NKGETFEVPEIVPFRLTHNMVNGMGPMGTEGLFRRACEVTMRLMRDQRE
```

-continued

PLMSVLKTFLHDPLVEWSKPVKGHSKAPLNETGEVVNEKAKTHVLDIEQ

RLQGVIKTRNRVTGLPLSIEGHVHYLIQEATDENLLCQMYLGWTPYM

An example nucleic acid sequence encoding the ATR is:

(SEQ ID NO: 7; NCBI Accession NO. NM_001184.3)
ATGGGGGAACATGGCCTGGAGCTGGCTTCCATGATCCCCGCCCTGCGGG

AGCTGGGCAGTGCCACACCAGAGGAATATAATACAGTTGTACAGAAGCC

AAGACAAATTCTGTGTCAATTCATTGACCGGATACTTACAGATGTAAAT

GTTGTTGCTGTAGAACTTGTAAAGAAAACTGACTCTCAGCCAACCTCCG

TGATGTTGCTTGATTTCATCCAGCATATCATGAAATCCTCCCCACTTAT

GTTTGTAAATGTGAGTGGAAGCCATGAGGCCAAAGGCAGTTGTATTGAA

TTCAGTAATTGGATCATAACGAGACTTCTGCGGATTGCAGCAACTCCCT

CCTGTCATTTGTTACACAAGAAAATCTGTGAAGTCATCTGTTCATTATT

ATTTCTTTTTAAAAGCAAGAGTCCTGCTATTTTTGGGGTACTCACAAAA

GAATTATTACAACTTTTTGAAGACTTGGTTTACCTCCATAGAAGAAATG

TGATGGGTCATGCTGTGGAATGGCCAGTGGTCATGAGCCGATTTTTAAG

TCAATTAGATGAACACATGGGATATTTACAATCAGCTCCTTTGCAGTTG

ATGAGTATGCAAAATTTAGAATTTATTGAAGTCACTTTATTAATGGTTC

TTACTCGTATTATTGCAATTGTGTTTTTTAGAAGGCAAGAACTCTTACT

TTGGCAGATAGGTTGTGTTCTGCTAGAGTATGGTAGTCCAAAAATTAAA

TCCCTAGCAATTAGCTTTTTAACAGAACTTTTTCAGCTTGGAGGACTAC

CAGCACAACCAGCTAGCACTTTTTTCAGCTCATTTTTGGAATTATTAAA

ACACCTTGTAGAAATGGATACTGACCAATTGAAACTCTATGAAGAGCCA

TTATCAAAGCTGATAAAGACACTATTTCCCTTTGAAGCAGAAGCTTATA

GAAATATTGAACCTGTCTATTTAAATATGCTGCTGGAAAAACTCTGTGT

CATGTTTGAAGACGGTGTGCTCATGCGGCTTAAGTCTGATTTGCTAAAA

GCAGCTTTGTGCCATTTACTGCAGTATTTCCTTAAATTTGTGCCAGCTG

GGTATGAATCTGCTTTACAAGTCAGGAAGGTCTATGTGAGAAATATTTG

TAAAGCTCTTTTGGATGTGCTTGGAATTGAGGTAGATGCAGAGTACTTG

TTGGGCCCACTTTATGCAGCTTTGAAAATGGAAAGTATGGAAATCATTG

AGGAGATTCAATGCCAAACTCAACAGGAAAACCTCAGCAGTAATAGTGA

TGGAATATCACCCAAAAGGCGTCGTCTCAGCTCGTCTCTAAACCCTTCT

AAAAGAGCACCAAAACAGACTGAGGAAATTAAACATGTGGACATGAACC

AAAAGAGCATATTATGGAGTGCACTGAAACAGAAAGCTGAATCCCTTCA

GATTTCCCTTGAATACAGTGGCCTAAAGAATCCTGTTATTGAGATGTTA

GAAGGAATTGCTGTTGTCTTACAACTGACTGCTCTGTGTACTGTTCATT

GTTCTCATCAAAACATGAACTGCCGTACTTTCAAGGACTGTCAACATAA

ATCCAAGAAGAAACCTTCTGTAGTGATAACTTGGATGTCATTGGATTTT

TACACAAAAGTGCTTAAGAGCTGTAGAAGTTTGTTAGAATCTGTTCAGA

AACTGGACCTGGAGGCAACCATTGATAAGGTGGTGAAAATTTATGATGC

TTTGATTTATATGCAAGTAAACAGTTCATTTGAAGATCATATCCTGGAA

-continued

GATTTATGTGGTATGCTCTCACTTCCATGGATTTATTCCCATTCTGATG

ATGGCTGTTTAAAGTTGACCACATTTGCCGCTAATCTTCTAACATTAAG

CTGTAGGATTTCAGATAGCTATTCACCACAGGCACAATCACGATGTGTG

TTTCTTCTGACTCTGTTTCCAAGAAGAATATTCCTTGAGTGGAGAACAG

CAGTTTACAACTGGGCCCTGCAGAGCTCCCATGAAGTAATCCGGGCTAG

TTGTGTTAGTGGATTTTTTATCTTATTGCAGCAGCAGAATTCTTGTAAC

AGAGTTCCCAAGATTCTTATAGATAAAGTCAAAGATGATTCTGACATTG

TCAAGAAAGAATTTGCTTCTATACTTGGTCAACTTGTCTGTACTCTTCA

CGGCATGTTTTATCTGACAAGTTCTTTAACAGAACCTTTCTCTGAACAC

GGACATGTGGACCTCTTCTGTAGGAACTTGAAAGCCACTTCTCAACATG

AATGTTCATCTTCTCAACTAAAAGCTTCTGTCTGCAAGCCATTCCTTTT

CCTACTGAAAAAAAAAATACCTAGTCCAGTAAAACTTGCTTTCATAGAT

AATCTACATCATCTTTGTAAGCATCTTGATTTTAGAGAAGATGAAACAG

ATGTAAAAGCAGTTCTTGGAACTTTATTAAATTTAATGGAAGATCCAGA

CAAAGATGTTAGAGTGGCTTTTAGTGGAAATATCAAGCACATATTGGAA

TCCTTGGACTCTGAAGATGGATTTATAAAGGAGCTTTTTGTCTTAAGAA

TGAAGGAAGCATATACACATGCCCAAATATCAAGAAATAATGAGCTGAA

GGATACCTTGATTCTTACAACAGGGGATATTGGAAGGGCCGCAAAAGGA

GATTTGGTACCATTTGCACTCTTACACTTATTGCATTGTTTGTTATCCA

AGTCAGCATCTGTCTCTGGAGCAGCATACACAGAAATTAGAGCTCTGGT

TGCAGCTAAAAGTGTTAAACTGCAAAGTTTTTTCAGCCAGTATAAGAAA

CCCATCTGTCAGTTTTTGGTAGAATCCCTTCACTCTAGTCAGATGACAG

CACTTCCGAATACTCCATGCCAGAATGCTGACGTGCGAAAACAAGATGT

GGCTCACCAGAGAGAAATGGCTTTAAATACGTTGTCTGAAATTGCCAAC

GTTTTCGACTTTCCTGATCTTAATCGTTTTCTTACTAGGACATTACAAG

TTCTACTACCTGATCTTGCTGCCAAAGCAAGCCCTGCAGCTTCTGCTCT

CATTCGAACTTTAGGAAAACAATTAAATGTCAATCGTAGAGAGATTTTA

ATAAACAACTTCAAATATATTTTTTCTCATTTGGTCTGTTCTTGTTCCA

AAGATGAATTAGAACGTGCCCTTCATTATCTGAAGAATGAAACAGAAAT

TGAACTGGGGAGCCTGTTGAGACAAGATTTCCAAGGATTGCATAATGAA

TTATTGCTGCGTATTGGAGAACACTATCAACAGGTTTTTAATGGTTTGT

CAATACTTGCCTCATTTGCATCCAGTGATGATCCATATCAGGGCCCGAG

AGATATCATATCACCTGAACTGATGGCTGATTATTTACAACCCAAATTG

TTGGGCATTTTGGCTTTTTTTAACATGCAGTTACTGAGCTCTAGTGTTG

GCATTGAAGATAAGAAAATGGCCTTGAACAGTTTGATGTCTTTGATGAA

GTTAATGGGACCCAAACATGTCAGTTCTGTGAGGGTGAAGATGATGACC

ACACTGAGAACTGGCCTTCGATTCAAGGATGATTTTCCTGAATTGTGTT

GCAGAGCTTGGGACTGCTTTGTTCGCTGCCTGGATCATGCTTGTCTGGG

CTCCCTTCTCAGTCATGTAATAGTAGCTTTGTTACCTCTTATACACATC

CAGCCTAAAGAAACTGCAGCTATCTTCCACTACCTCATAATTGAAAACA

-continued

GGGATGCTGTGCAAGATTTTCTTCATGAAATATATTTTTTACCTGATCA

TCCAGAATTAAAAAAGATAAAAGCCGTTCTCCAGGAATACAGAAAGGAG

ACCTCTGAGAGCACTGATCTTCAGACAACTCTTCAGCTCTCTATGAAGG

CCATTCAACATGAAAATGTCGATGTTCGTATTCATGCTCTTACAAGCTT

GAAGGAAACCTTGTATAAAAATCAGGAAAAACTGATAAAGTATGCAACA

GACAGTGAAACAGTAGAACCTATTATCTCACAGTTGGTGACAGTGCTTT

TGAAAGGTTGCCAAGATGCAAACTCTCAAGCTCGGTTGCTCTGTGGGA

ATGTTTAGGGGAATTGGGGGCGATAGATCCAGGTCGATTAGATTTCTCA

ACAACTGAAACTCAAGGAAAAGATTTTACATTTGTGACTGGAGTAGAAG

ATTCAAGCTTTGCCTATGGATTATTGATGGAGCTAACAAGAGCTTACCT

TGCGTATGCTGATAATAGCCGAGCTCAAGATTCAGCTGCCTATGCCATT

CAGGAGTTGCTTTCTATTTATGACTGTAGAGAGATGGGAGACCAACGGCC

CAGGTCACCAATTGTGGAGGAGATTTCCTGAGCATGTTCGGGAAATACT

AGAACCTCATCTAAATACCAGATACAAGAGTTCTCAGAAGTCAACCGAT

TGGTCTGGAGTAAAGAAGCCAATTTACTTAAGTAAATTGGGTAGTAACT

TTGCAGAATGGTCAGCATCTTGGGCAGGTTATCTTATTACAAAGGTTCG

ACATGATCTTGCCAGTAAAATTTTCACCTGCTGTAGCATTATGATGAAG

CATGATTTCAAAGTGACCATCTATCTTCTTCCACATATTCTGGTGTATG

TCTTACTGGGTTGTAATCAAGAAGATCAGCAGGAGGTTTATGCAGAAAT

TATGGCAGTTCTAAAGCATGACGATCAGCATACCATAAATACCCAAGAC

ATTGCATCTGATCTGTGTCAACTCAGTACACAGACTGTGTTCTCCATGC

TTGACCATCTCACACAGTGGGCAAGGCACAAATTTCAGGCACTGAAAGC

TGAGAAATGTCCACACAGCAAATCAAACAGAAATAAGGTAGACTCAATG

GTATCTACTGTGGATTATGAAGACTATCAGAGTGTAACCCGTTTTCTAG

ACCTCATACCCCAGGATACTCTGGCAGTAGCTTCCTTTCGCTCCAAAGC

ATACACACGAGCTGTAATGCACTTTGAATCATTTATTACAGAAAAGAAG

CAAAATATTCAGGAACATCTTGGATTTTTACAGAAATTGTATGCTGCTA

TGCATGAACCTGATGGAGTGGCCGGAGTCAGTGCAATTAGAAAGGCAGA

ACCATCTCTAAAAGAACAGATCCTTGAACATGAAAGCCTTGGCTTGCTG

AGGGATGCCACTGCTTGTTATGACAGGGCTATTCAGCTAGAACCAGACC

AGATCATTCATTATCATGGTGTAGTAAAGTCCATGTTAGGTCTTGGTCA

GCTGTCTACTGTTATCACTCAGGTGAATGGAGTGCATGCTAACAGGTCC

GAGTGGACAGATGAATTAAACACGTACAGAGTGGAAGCAGCTTGGAAAT

TGTCACAGTGGGATTTGGTGGAAAACTATTTGGCAGCAGATGGAAAATC

TACAACATGGAGTGTCAGACTGGGACAGCTATTATTATCAGCCAAAAAA

AGAGATATCACAGCTTTTTATGACTCACTGAAACTAGTGAGAGCAGAAC

AAATTGTACCTCTTTCAGCTGCAAGCTTTGAAAGAGGCTCCTACCAACG

AGGATATGAATATATTGTGAGATTGCACATGTTATGTGAGTTGGAGCAT

AGCATCAAACCACTTTTCCAGCATTCTCCAGGTGACAGTTCTCAAGAAG

ATTCTCTAAACTGGGTAGCTCGACTAGAAATGACCCAGAATTCCTACAG

AGCCAAGGAGCCTATCCTGGCTCTCCGGAGGGCTTTACTAAGCCTCAAC

-continued

AAAAGACCAGATTACAATGAAATGGTTGGAGAATGCTGGCTGCAGAGTG

CCAGGGTAGCTAGAAAGGCTGGTCACCACCAGACAGCCTACAATGCTCT

CCTTAATGCAGGGGAATCACGACTCGCTGAACTGTACGTGGAAAGGGCA

AAGTGGCTCTGGTCCAAGGGTGATGTTCACCAGGCACTAATTGTTCTTC

AAAAAGGTGTTGAATTATGTTTTCCTGAAAATGAAACCCCACCTGAGGG

TAAGAACATGTTAATCCATGGTCGAGCTATGCTACTAGTGGGCCGATTT

ATGGAAGAAACAGCTAACTTTGAAAGCAATGCAATTATGAAAAAATATA

AGGATGTGACCGCGTGCCTGCCAGAATGGGAGGATGGGCATTTTTACCT

TGCCAAGTACTATGACAAATTGATGCCCATGGTCACAGACAACAAAATG

GAAAAGCAAGGTGATCTCATCCGGTATATAGTTCTTCATTTTGGCAGAT

CTCTACAATATGGAAATCAGTTCATATATCAGTCAATGCCACGAATGTT

AACTCTATGGCTTGATTATGGTACAAAGGCATATGAATGGGAAAAAGCT

GGCCGCTCCGATCGTGTACAAATGAGGAATGATTTGGGTAAAATAAACA

AGGTTATCACAGAGCATACAAACTATTTAGCTCCATATCAATTTTTGAC

TGCTTTTTCACAATTGATCTCTCGAATTTGTCATTCTCACGATGAAGTT

TTTGTTGTCTTGATGGAAATAATAGCCAAAGTATTTCTAGCCTATCCTC

AACAAGCAATGTGGATGATGACAGCTGTGTCAAAGTCATCTTATCCCAT

GCGTGTGAACAGATGCAAGGAAATCCTCAATAAAGCTATTCATATGAAA

AAATCCTTAGAGAAGTTTGTTGGAGATGCAACTCGCCTAACAGATAAGC

TTCTAGAATTGTGCAATAAACCGGTTGATGGAAGTAGTTCCACATTAAG

CATGAGCACTCATTTTAAAATGCTTAAAAAGCTGGTAGAAGAAGCAACA

TTTAGTGAAATCCTCATTCCTCTACAATCAGTCATGATACCTACACTTC

CATCAATTCTGGGTACCCATGCTAACCATGCTAGCCATGAACCATTTCC

TGGACATTGGGCCTATATTGCAGGGTTTGATGATATGGTGGAAATTCTT

GCTTCTCTTCAGAAACCAAAGAAGATTTCTTTAAAAGGCTCAGATGGAA

AGTTCTACATCATGATGTGTAAGCCAAAAGATGACCTGAGAAAGGATTG

TAGACTAATGGAATTCAATTCCTTGATTAATAAGTGCTTAAGAAAAGAT

GCAGAGTCTCGTAGAAGAGAACTTCATATTCGAACATATGCAGTTATTC

CACTAAATGATGAATGTGGGATTATTGAATGGGTGAACAACACTGCTGG

TTTGAGACCTATTCTGACCAAACTATATAAAGAAAAGGGAGTGTATATG

ACAGGAAAAGAACTTCGCCAGTGTATGCTACCAAAGTCAGCAGCTTTAT

CTGAAAAACTCAAAGTATTCCGAGAATTTCTCCTGCCCAGGCATCCTCC

TATTTTTCATGAGTGGTTTCTGAGAACATTCCCTGATCCTACATCATGG

TACAGTAGTAGATCAGCTTACTGCCGTTCCACTGCAGTAATGTCAATGG

TTGGTTATATTCTGGGGCTTGGAGACCGTCATGGTGAAAATATTCTCTT

TGATTCTTTGACTGGTGAATGCGTACATGTAGATTTCAATTGTCTTTTC

AATAAGGGAGAAACCTTTGAAGTTCCAGAAATTGTGCCATTTCGCCTGA

CTCATAATATGGTTAATGGAATGGGTCCTATGGGAACAGAGGGTCTTTT

TCGAAGAGCATGTGAAGTTACAATGAGGCTGATGCGTGATCAGCGAGAG

CCTTTAATGAGTGTCTTAAAGACTTTTCTACATGATCCTCTTGTGGAAT

-continued

```
GGAGTAAACCAGTGAAAGGGCATTCCAAAGCGCCACTGAATGAAACTGG

AGAAGTIGTCAATGAAAAGGCCAAGACCCATGTTCTTGACATTGAGCAG

CGACTACAAGGTGTAATCAAGACTCGAAATAGAGTGACAGGACTGCCGT

TATCTATTGAAGGACATGTGCATTACCTTATACAGGAAGCTACTGATGA

AAACTTACTATGCCAGATGTATCTTGGTTGGACTCCATATATGTGA
```

Kinase Inhibitors

In one aspect the invention provides an ataxia telangiectasia mutated (ATM) kinase inhibitor or an ataxia telangiectasia and Rad3-related protein (ATR) inhibitor for use in haematopoietic cell, haematopoietic stem cell and/or haematopoietic progenitor cell gene therapy.

The invention also provides methods for identifying agents that are capable of acting as ATM kinase or ATR inhibitors and agents that are identified by such methods.

The activity of ATM kinase and ATR may be analysed directly, for example by analysing the enzymatic activity of the ATM kinase or ATR in vitro.

The ability of a candidate agent to inhibit (e.g. reduce the activity) ATM kinase or ATR may be expressed in terms of an IC50 value, which is the concentration of an agent that is required to give rise to a 50% reduction in the activity of the kinase. Preferably, the inhibitors of the invention have an IC50 value for inhibition (e.g. of ATM kinase or ATR) of less than 100 μM, more preferably less than 10 μM, for example less than 1 μM, less than 100 nM or less than 10 nM (e.g. KU-55933 has an IC50 value of about 13 nM for ATM kinase).

A number of techniques are known in the art for measuring kinase activity. Preferably, the kinase activity assays are carried out on a kinase (e.g. ATM kinase or ATR) that has been isolated from a cell. The kinase may have been expressed using recombinant techniques, and preferably has been purified. For example, kinase activity may be determined by monitoring the incorporation of radiolabelled phosphate from $[\gamma\text{-}^{32}P]$-labelled ATP into a substrate. Such assay techniques are described in, for example, Hastie et al. (Hastie, C. J. et al. (2006) Nat. Protocols 1: 968-971).

Preferably, the inhibitors are of low toxicity for mammals, such as humans, and in particular are of low toxicity for haematopoietic stem and/or progenitor cells.

A candidate inhibitor may be further analysed for its ability to increase cell survival and/or engraftment using a method as disclosed herein.

Preferably, the inhibitor is a transient inhibitor (e.g. has an inhibitory action lasting less than about 1, 2, 3, 4, 5, 6, 7 or 14 days).

Preferably, the inhibitor is a pharmacological inhibitor. KU-55933

In a preferred embodiment, the inhibitor is KU-55933 or a derivative thereof.

KU-55933 (CAS No. 587871-26-9) is a selective, competitive ATM kinase inhibitor having the following structure:

Solutions of KU-55933 for use in the invention may be prepared using routine methods known in the art, for example KU-55933 is known to be soluble in DMSO and ethanol.

The concentration at which KU-55933 or a derivative thereof is applied to a population of haematopoietic stem and/or progenitor cells may be adjusted for different vector systems to optimise cell survival (e.g. during in vitro or ex vivo culture) and/or engraftment.

The invention encompasses the use of KU-55933 and derivatives of KU-55933. The KU-55933 derivatives of the invention are those which increase the survival (e.g. during in vitro or ex vivo culture) and/or engraftment of haematopoietic cells, haematopoietic stem cells and/or haematopoietic progenitor cells, in particular cells transduced by a viral vector.

KU-55933 derivatives of the invention may have been developed, for example, for increased solubility, increased stability and/or reduced toxicity.

KU-55933 derivatives of the invention are preferably of low toxicity for mammals, in particular humans. Preferably, KU-55933 derivatives of the invention are of low toxicity for haematopoietic cells, haematopoietic stem cells and/or haematopoietic progenitor cells.

Suitable KU-55933 derivatives may be identified using methods known in the art for determining cell survival in culture and/or engraftment. Examples of such methods have been described above. The method employed is preferably one which is amenable to automation and/or high throughput screening of candidate KU-55933 derivatives. The candidate KU-55933 derivatives may form part of a library of KU-55933 derivatives.

Additional Inhibitors

Further kinase inhibitors that may be used in the invention include:

KU-60019, which is an improved analogue of KU-55933 and has an IC50 of 6.3 nM for ATM kinase in cell-free assays. KU-60019 has the structure:

BEZ235 (NVP-BEZ235, Dactolisib), which is a dual ATP-competitive PI3K and mTOR inhibitor for p110α/γ/δ/β and mTOR(p70S6K) and inhibits ATR with an IC50 of about 21 nM in 3T3TopBP1-ER cells. BEZ235 has the structure:

Wortmannin, which has the structure:

CP-466722, which is a potent and reversible ATM kinase inhibitor, but does not affect ATR. CP-466722 has the structure:

Torin 2, which ATM kinase and ATR with EC50 values of 28 nM and 35 nM, respectively. Torin 2 has the structure:

CGK 733 (CAS No. 905973-89-9), which is a potent and selective inhibitor of ATM kinase and ATR with IC50 values of about 200 nM. CGK 733 has the structure:

KU-559403 (Weber et al. (2015) Pharmacology & Therapeutics 149: 124-138). KU-559403 has the structure:

AZD6738, which has the structure:

Derivatives of these inhibitors, possessing characteristics as described for the KU-55933 derivatives, may also be used in the invention, and may be identified using analogous methods to those described for the KU-55933 derivatives.

In a preferred embodiment, the p53 inhibitor may be pifithrin-α, pifithrin-α cyclic and pifithrin-α p-nitro or a derivative thereof. Pifithrin-α has the structure:

siRNAs, shRNAs, miRNAs and antisense DNAs/RNAs

Inhibition (e.g. of the kinase) may be achieved using post-transcriptional gene silencing (PTGS). Post-transcriptional gene silencing mediated by double-stranded RNA (dsRNA) is a conserved cellular defence mechanism for controlling the expression of foreign genes. It is thought that the random integration of elements such as transposons or viruses causes the expression of dsRNA which activates sequence-specific degradation of homologous single-stranded mRNA or viral genomic RNA. The silencing effect is known as RNA interference (RNAi) (Ralph et al. (2005) Nat. Medicine 11: 429-433). The mechanism of RNAi involves the processing of long dsRNAs into duplexes of about 21-25 nucleotide (nt) RNAs. These products are called small interfering or silencing RNAs (siRNAs) which are the sequence-specific mediators of mRNA degradation. In differentiated mammalian cells, dsRNA>30 bp has been found to activate the interferon response leading to shut-down of protein synthesis and non-specific mRNA degradation (Stark et al. (1998) Ann. Rev. Biochem. 67:227-64). However, this response can be bypassed by using 21 nt siRNA duplexes (Elbashir et al. (2001) EMBO J. 20: 6877-88; Hutvagner et al. (2001) Science 293: 834-8) allowing gene function to be analysed in cultured mammalian cells.

shRNAs consist of short inverted RNA repeats separated by a small loop sequence. These are rapidly processed by the cellular machinery into 19-22 nt siRNAs, thereby suppressing the target gene expression.

Micro-RNAs (miRNAs) are small (22-25 nucleotides in length) noncoding RNAs that can effectively reduce the translation of target mRNAs by binding to their 3' untranslated region (UTR). Micro-RNAs are a very large group of small RNAs produced naturally in organisms, at least some of which regulate the expression of target genes. Founding members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors which are processed to their mature forms by Dicer enzyme.

The antisense concept is to selectively bind short, possibly modified, DNA or RNA molecules to messenger RNA in cells and prevent the synthesis of the encoded protein.

Methods for the design of siRNAs, shRNAs, miRNAs and antisense DNAs/RNAs to modulate the expression of a target protein, and methods for the delivery of these agents to a cell of interest are well known in the art.

Dominant Negative Peptides

In a preferred embodiment, the inhibitor of p53 activation is a mutant p53 peptide.

In a preferred embodiment, the inhibitor of p53 activation is a dominant negative peptide (e.g. a dominant negative p53 peptide).

Suitably, a dominant negative peptide may comprise mutations in the homo-oligomerisation domain. Suitably, dominant negative peptides comprising mutations in the homo-oligomerisation domain may dimerise with wild-type p53 and prevent wild-type p53 from activating transcription.

In a preferred embodiment the dominant negative peptide is GSE56 or a variant thereof.

In one embodiment the nucleotide sequence for mRNA translation of GSE56 is set forth in SEQ ID No. 8.

(SEQ ID NO. 8)
ATGGATGGATGGTGTCCTGGGAGAGACCGTCGGACAGAGGAAGAAATT

TCCGCAAAAAAGAAGAGCATTGCCCGGAGCTGCCCCCAGGGAGTGCAAA

GAGAGCACTGCCCACCAGCACAAGCTCCTCTCCCCAGCAAAAGAAAAAA

CCACTCGATGGAGAATATTTCACCCTTAAGATCCGTGGGCGTGAGCGCT

TCGAGATGTTCCGAGAGCTGAATGAGGCCTTGGAATTAAAGGATGCCCG

TGCTGCCGAGGAGTCAGGAGACAGCAGGGCTCACTCCAGCTACCCGAAG

ATAGTTAGTTAG

In one embodiment, the amino acid sequence of GSE56 is set forth in SEQ ID No. 9.

(SEQ ID NO. 9)
MDGWCPGRDRRTEEENFRKKEEHCPELPPGSAKRALPTSTSSSPQQKKK

PLDGEYFTLKIRGRERFEMFRELNEALELKDARAAEESGDSRAHSSYPK

IVS

Suitably, the inhibitor of 53 activation may be a nucleotide sequence which encodes GSE56. Suitably, the inhibitor of p53 activation may be an amino acid sequence encoding GSE56. Suitably, the inhibitor of p53 activation may be GSE56 mRNA.

Adenoviral Proteins

Adenoviruses are natural co-helpers of AAV infection and provide a set of genes: E1a, E1b, E2a and E4 which optimize AAV infection.

The present inventors have demonstrated that delivery of adenoviral proteins during gene editing improves the efficiency of HDR in HSC (and enhances the long-term repopulating activity of HSC. Without wishing to be bound by theory, the adenoviral proteins may provide helper functions to the AAV infection during gene editing. The adenoviral proteins may act directly or indirectly on the p53 pathway.

In one embodiment, the agent which promotes homology directed DNA repair comprises a nucleic acid sequence encoding at least one adenoviral protein. The adenoviral protein is not limited to a particular Adenovirus serotype. For example, in one embodiment, the at least one adenoviral proteins is from an Adenovirus of serotype 4, Adenovirus of serotype 5, Adenovirus of serotype 7 and/or Adenovirus of serotype 9.

In one embodiment, the at least one adenoviral protein is selected from the group comprising E1a, E1b, E2a and E4.

In a preferred embodiment, the at least one adenoviral protein is an open reading frame of the E4 gene.

In a preferred embodiment, the at least one adenoviral protein is E4orf1 or a variant thereof.

An example of a nucleotide sequence encoding Ad5-E4orf1 is set forth in SEQ ID No. 10. Suitably, the at least one adenoviral protein may comprise a nucleotide sequence for mRNA translation as set forth in SEQ ID No. 10 or a variant thereof.

(SEQ ID NO. 10)
ATGGCCGCTGCTGTGGAAGCCCTGTACGTGGTGCTTGAAAGAGAGGGCG

CCATCCTGCCTAGACAAGAGGGCTTTTCTGGCGTGTACGTGTTCTTCAG

CCCCATCAACTTCGTGATCCCTCCAATGGGCGCCGTGATGCTGAGCCTG

AGACTGAGAGTGTGTATCCCTCCTGGCTACTTCGGCCGGTTTCTGGCCC

TGACCGATGTGAACCAGCCTGACGTGTTCACCGAGAGCTACATCATGAC

CCCTGACATGACCGAGGAACTGAGCGTGGTGCTGTTCAACCACGGCGAC

CAGTTCTTTTATGGCCACGCCGGAATGGCCGTCGTGCGGCTGATGCTGA

TCAGAGTGGTGTTTCCCGTCGTCCGGCAGGCCAGCAATGTTTGA

An example of an amino acid sequence of Ad5-E4orf1 is set forth in SEQ ID No. 1. Suitably, the at least one adenoviral protein may comprise an amino acid sequence as set forth in SEQ ID No. 1 or a variant thereof.
MAAAVEALYVVLEREGAILPRQEGFSGVYVFF-
SPINFVIPPMGAVMLSLRLRVCIPPGYFGRFLA-
LTDVNQPDVF TESYIMTPDM-
TEELSVVLFNHGDQFFYGHAGMAVVRLMLIRVVFP
VVROASNV (SEQ ID No. 1)

Other examples of an amino acid sequence of E4orf1 are set forth in SEQ ID No. 57 to SEQ ID No. 76. Suitably, the at least one adenoviral protein may comprise an amino acid sequence as set forth in SEQ ID No. 57 to SEQ ID No. 76 or a variant thereof.

| | | |
|---|---|---|
| SEQ ID NO. 57 | Ad1-E4orf1 | MAAAVEALYVVLEREGAILPRQEGFSGVYVFFSPINF VIPPMGAVMLPLRLRVCIPPGYFGRFLALTDVNQPDV FTESYIMTPDMTEELSVVLFNHGDQFFYGHAGMAVV RLMLIRVVFPVVRQASNV |
| SEQ ID NO. 58 | Ad2-E4orf1 | MAAAVEALYVVLEREGAILPRQEGFSGVYVFFSPINF VIPPMGAVMLSLRLRVCIPPGYFGRFLALTDVNQPDV FTESYIMTPDMIEELSVVLFNHGDQFFYGHAGMAVVR LMLIRVVFPVVRQASNV |
| SEQ ID NO. 59 | Ad3-E4orf1 | MADEALYVYLEGPGATLPEQQQRNNYIFYSPVPFTLY PRGVALLYLKLSIIIPRGYVGCFFSLTDANMSGLYAS SRIIHAGHREELSVLLFNHNDRFYEGRAGDPVACLVM ERLIFPPVRQATMI |
| SEQ ID NO. 60 | Ad4-E4orf1 | MDAQVLYVFLEGAGALLPVQKGSNYIFYAPANFVLHP HGVALLELRLSIVVPQGFIGRFFSLTDANVPGVYASS RIIHAGHREGLSVMLFNHNVSFYNGRAGDPVACLVLE RVIYPPVRQASMV |
| SEQ ID NO. 61 | Ad6-E4orf1 | MAAAVEALYVVLEREGAILPRQEGFSGVYVFFSPINF VIPPMGAVMLSLRLRVCIPPGYFGRFLALTDVSQPDV FTESYIMTPDMTEELSVVLFNHGDQFFYGHAGMAVVR LMLIRVVFPVVRQASNV |
| SEQ ID NO. 62 | Ad7-E4orf1 | MADEALYVYLEGPGATLPEQQQRNNYIFYSPVPFTLY PRGVALLYLRLSIIIPRGYVGCFFSLTDANMSGLYAS SRIIHAGHREELSVLLFNHDDRFYEGRAGDPVACLVM ERLIYPPVRQATMI |
| SEQ ID NO. 63 | Ad9-E4orf1 | MAESLYAFIDSPGGIAPVQEGTSNRYTFFCPESFHIP PHGVVLLHLKVSVLVPTGYQGRFMALNDYHARDILTQ SDVIFAGRRQELTVLLFNHTDRFLYVRKGHPVGTLLL ERVIFPSVKIATLV |
| SEQ ID NO. 64 | Ad14-E4orf1 | MADEALYVYLEGPGATLPEQQQRNNYIFYSPVPFTLY PRGVALLYLRLSIIIPRGYIGCFLSLTDANMFGLYAS SRIIHAGHREELSVLLFNHDDRFYEGRAGDPVACLVM ERLIYPPVRQATLI |
| SEQ ID NO. 65 | Ad16-E4orf1 | MADEALYVYFRGPGATLPEQQQQRNNYIFYSPVPFTL YPRGVALLYLRLSIIIPRGYVGCFFSLTDANMSGLYA SSRIIHAGHREELSVLLFNHDDRFYEGRAGDPVACLV MERLIYPPVRQATMI |
| SEQ ID NO. 66 | Ad18-E4orf1 | MAALQALYVYFKGPGAMLPEQEGYSNAYVLFSPANF VIPPHGVVLLYLHIAVDIPPGYLGTLFSLSDMNARG VFVGAETLYPGSRMELSVLLFNHSDVFCDVRAKQPV ARLLLSRVIFPPVRQASLL |
| SEQ ID NO. 67 | Ad20-E4orf1 | MAESLYAFIDSPGGIAPVQEGTSNRYNFFCPQSFHIP PHGVVLLHLKVSVLVPTGYQGRFMALNDYHARDILTQ SDVIFAGRRQELTVLLFNHTDRFLYVRKGHPVGTLLL ERVIFPSVKIATLV |
| SEQ ID NO. 68 | Ad21-E4orf1 | MAEVLYVILEGPGARLPVQEGNNYIFYAPVDFTLHPR GVALLHLRLSIIVPRCYIGRFFSLTDTNTSGLYASSQ IIFAAHQQPLSVMLFNHTDRFYEGRVGDPVACLVLER VIYPSVRQASMM |
| SEQ ID NO. 69 | Ad23-E4orf1 | MAESLYAFIDSPGGIAPVQEGSSNRYNFFCPESFHIP PHGVVLLHLRVSVLIPTGYQGRFMALNDYHARGILTQ SDVIFAGRRHELTVLLFNHTDRFLYVREGHPVGTLLL ERVIFPSVRLATLV |
| SEQ ID NO. 70 | Ad25-E4orf1 | MAESLYAFIDSPGGIAPVQEGTSNRYTFFCPESFHIP PHGVVLVHLRVSVLIPNGYQGRFMALNDYHSRGILTQ SDVIFAGRRQELTVLLFNHTDRFLYVREGHPVGTLLL ERVIFPSVRLATLV |
| SEQ ID NO. 71 | Ad30-E4orf1 | MAESLYAFIDSPGGIAPVQEGASNRYTFFCPESFHIP PHGVILLHLRVSVLVPTGYQGRFMALNDYHARGILTQ SDVIFAGRRHDLSVLLFNHTDRFLYVREGHPVGTLLL ERVIFPSVRLATLV |

-continued

| SEQ ID<br>NO. 72 | Ad36-E4orf1 | MAESLYAFIDSPGGIAPVQEGASNRYIFFCPESFHIP<br>PHGVILLHLRVSVLVPTGYQGRFMALNDYHARGILTQ<br>SDVIFAGRRHDLSVLLFNHTDRFLYVREGHPVGTLLL<br>ERVIFPSVRIATLV |
| SEQ ID<br>NO. 73 | Ad50-E4orf1 | MADEALYVYLDGPGATLPEQQQRNNYIFYSPVPFTLY<br>PRGVALLYLRLSIIIPRGYVGCFFSLTDANMSGLYAS<br>SRIIHAGHREELSVLLFNHDDRFYEGRAGDPVACLVM<br>ERLIYPPVRQATMI |
| SEQ ID<br>NO. 74 | Ad55-E4orf1 | MAHEALYVYLEGPGATLPEQQQRNNYIFYSPVPFTLY<br>PRGVALLYLRLSIIIPRGYIGCFLSLTDANMFGLYAS<br>SRIIHAGHREELSVLLFNHDDRFYEGRAGDPVACLVM<br>ERLIYPPVRQATLI |
| SEQ ID<br>NO. 75 | Ad62-E4orf1 | MAESLYAFIDSPGGIAPVQEGASNRYIFFCPESFHIP<br>PHGVILLHLRVSVMVPTGYQGRFMALNDYHARGILTQ<br>SDVIFAGRRHDLSVLLFNHTDRFLYVREGHPVGTLLL<br>ERVIFPSVRIATLV |
| SEQ ID<br>NO. 76 | Ad71-E4orf1 | MAESLYAFIDSPGGIAPVQEGTSNRYDFFCPESFHIP<br>PHGVVLLHLRVSVLIPTGYQGRFMALNDYHARGILTQ<br>SDVIFAGRRHELTVLLFNHTDRFLYVREGHPVGTLLL<br>ERVIFPSVRLATLV |

In a preferred embodiment, the at least one adenoviral protein is E4orf6/7 or a variant thereof.

An example of a nucleotide sequence encoding Ad5-E4orf6/7 is set forth in SEQ ID No. 11. Suitably, the at least one adenoviral protein may comprise a nucleotide sequence for mRNA translation as set forth in SEQ ID No. 11 or a variant thereof.

(SEQ ID NO. 11)
ATGACCACCAGCGGCGTGCCCTTCGGCATGACACTCAGACCTACCAGAA

GCCGGCTGAGCAGAAGAACCCCTTACAGCAGAGACAGGCTGCCTCCATT

CGAGACAGAGACACGGGCCACCATCCTGGAAGATCACCCTCTGCTGCCC

GAGTGTAACACCCTGACCATGCACAACGCCTGGACAAGCCCATCTCCTC

CAGTGAAACAGCCCCAAGTGGGACAGCAGCCTGTTGCTCAGCAGCTGGA

CAGCGACATGAACCTGTCTGAACTGCCCGGCGAGTTCATCAACATCACC

GACGAGAGACTGGCCCGGCAAGAGACAGTGTGGAACATCACCCCTAAGA

ACATGAGCGTGACCCACGACATGATGCTGTTCAAGGCCAGCAGAGGCGA

-continued
GCGGACAGTGTACAGCGTTTGTTGGGAAGGCGGCGGACGGCTGAATACC

AGAGTGCTG
TAA

An example of an amino acid sequence of Ad5-E4orf6/7 is set forth in SEQ ID No. 2. Suitably, the at least one adenoviral protein may comprise an amino acid sequence as set forth in SEQ ID No. 2 or a variant thereof.

(SEQ ID NO. 2)
MTTSGVPFGMTLRPTRSRLSRRTPYSRDRLPPFETETRATILEDHPLLP

ECNTLTMHNAWTSPSPPVKQPQVGQQPVAQQLDSDMNLSELPGEFINIT

DERLARQETVWNITPKNMSVTHDMMLFKASRGERTVYSVCWEGGGRLNT

RVL

Other examples of an amino acid sequence of E4orf6/7 are set forth in SEQ ID No. 77 to SEQ ID No. 107. Suitably, the at least one adenoviral protein may comprise an amino acid sequence as set forth in SEQ ID No. 77 to SEQ ID No. 107 or a variant thereof.

| SEQ ID<br>NO. 77 | Ad1-E4orf6/7 | MTTSGVPFGMTLRPTRSRLSRRTPYSRDRLPPFETE<br>TRATILEDHPLLPECNTLTMHNAWTSPSPPVEQPQVG<br>QQPVAQQLDSNMNLRELPGEFINITDERLARQETVW<br>NITPKNMSVTHDMMLFKASRGERTVYSVCWEGGGR<br>LNTRVL* |
| SEQ ID<br>NO. 78 | Ad2-E4orf6/7 | MTTSGVPFGMTLRPTRSRLSRRTPYSRDRLPPFETE<br>TRATILEDHPLLPECNTLTMHNAWTSPSPPVEQPQVG<br>QQPVAQQLDSDMNLSELPGEFINITDERLARQETVW<br>NITPKNMSVTHDMMLFKASRGERTVYSVCWEGGGR<br>LNTRVL* |
| SEQ ID<br>NO. 79 | Ad3-E4orf6/7 | MSGSNSIMTRLRARSTSCARHHPYTRAQLPRCEENE<br>TRASMTEDHPLLPDCDTMTMHSMTVIQTPESHPQQL<br>DCESALKDYPDAFLCITDPRLARSETVWNVESKTMSI<br>SNGIQMFKAVRGERLVYSVKWEGGGKITTRIL* |
| SEQ ID<br>NO. 80 | Ad4-E4orf6/7 | MSGNSSIMTRSRTRLALSRHHPYQPPATLPRCEETES<br>RASLVEDHPVLPDCDTLSMHNITVIPITEDSPQLLNCE |

```
                             VQMQECPEGFISLTDPRLSRSETVWNVEIKTMSITNSI
                             QMFKAVRGERIVYSMRWEGGGKITTRIL*

SEQ ID    Ad6-E4orf6/7       MTTSGVPFGMTLRPTRSRLSRRTPYSRDRLPPFETE
NO. 81                       TRATILEDHPLLPECNTLTMHNAWTSPSPSVKRPQVG
                             QQPVAQQLDSDMNLSELPGEFINITDERLARQETVW
                             NITPKNMSVTHDMMLFKASRGERTVYSVCWEGGGR
                             LNTRVL*

SEQ ID    Ad7-E4orf6/7       MSGSNSIMTRLRARSTSCARHHPYTRAQLPRCEENE
NO. 82                       TRASMTEDHPLLPDCDTMTMHSMTVIQTPESHPQQL
                             DCESALKDYPDAFLCITDPRLARFETVWNVESKTMSI
                             CNGIQMFKAVRGERLVYSVKWEGGGKITTRIL*

SEQ ID    Ad11-E4orf6/7      MSGSNSIMTRLRARSTSCARHHPYTRAQLPRCEENE
NO. 83                       TRASMTEDHPLLPDCDTMTMHSMTVIQTPESQPQQL
                             DCESALKDYPDAFLSITDPRLARSETVWNVESKTMSI
                             SNGIQMFKAVRGERLVYSVKWEGGGKITTRIL*

SEQ ID    Ad14-E4orf6/7      MSGSNSIMTRLCARSTSCARHHPYTRAQLPRCEENE
NO. 84                       TRASMTEDHPLLPDCDTMTMHSMTVIQTPESHPQQL
                             DCESALKDYPAGFLSITDPRLARYETVWNVESKTMSI
                             SNGIQMFKAVRGERLVYSVKWEGGGKITTRSL*

SEQ ID    Ad18-E4orf6/7      MQRNRRYPYRLAPYGKYPLPPCEKEMRASLFGPENS
NO. 85                       SVSECNSLTLHNVINMDLVLDGESYLSDCVGEGFVSII
                             DHRFARKETIWTVTPKNLSRNMHMQLFSAIKGERVVY
                             KIKWEGGGSLTTRIV*

SEQ ID    Ad19-E4orf6/7      MQTEDQSSLLRHHPYRRARLPRSDEETRASLTEQHP
NO. 86                       LLPDCDHADYHNTVTLDCEARLDDFSEDGFISITDPRL
                             ARQETVWIIDPKLSSRTNQNIPLFKATRAERTVYTVKW
                             AGGGRLTTRAGVKINKDT*

SEQ ID    Ad20-E4orf6/7      MQTEIQSSSLRHHPYRRARLPRSDEETRASLTEQHPL
NO. 87                       LPDCDHADYHNTVTLDCEARLDDFSEDGFISITDPRLA
                             RQETVWIIDPKSSSRTNQNISLFKATRAERTVYTVKW
                             AGGGRLTTRAGVKINKDT*

SEQ ID    Ad23-E4orf6/7      MSTEEQSSSLRHHPYRRARLPRCEEETRASLTEQHP
NO. 88                       LLPDCDHADYHNTVTLDCEARLDDFSEDGFISITDPRL
                             ARQETVWIIDTKTSSRTNNNIPLFKATRAERIVYTVKW
                             AGGGRLTTRAGVKINKDT*

SEQ ID    Ad25-E4orf6/7      MSTEEQSSSLRHHPYRRARLPRCEEETRASLTEQHP
NO. 89                       LLPDCDHADYHNTVTLDCEARLDDFSEDGFISITDPRL
                             ARQETVWIIDPKSSSRTNQNISLFKATRAERTVYTVK
                             WAGGGRLTTRAGVKINKDT*

SEQ ID    Ad27-E4orf6/7      MQTEDQSSLRHHPYRRARLPRSDEETRASLTEQHP
NO. 90                       LLPDCDHADYHNTVTLDCEARLDDFSEDGFISITDPRL
                             ARQETVWIIDPKFSSRTNQNIPLFKATRAERIVYTVKW
                             AGGGRLTTRAGVKINKDT*

SEQ ID    Ad29-E4orf6/7      MQTEDQSSLLRHHPYRRARLPRSDEETRASLTEQHP
NO. 91                       LLPDCDHAEYHNTVTLDCEARLDDFSEDGFISITDPRL
                             ARQETVWLIDTKSSSRANQNIPLFKATRAERIVYTVK
                             WAGGGRLTTRAGVKINKDT*

SEQ ID    Ad30-E4orf6/7      MSTEEQSSSLRHHPYRRARLPRCEEETRASLTEQHP
NO. 92                       LLPDCDHADYHNTVTLDCEARLDDFSEDGFISITDPRL
                             ARQETVWIIDSKSSSRTNQNIPLFKATRAERIVYTVKW
                             AGGGRLTTRAGVKINKDP*

SEQ ID    Ad32-E4orf6/7      MSTEEQSSSLRHHPYRRARLPRCDEETRASLTEQHP
NO. 93                       LLPDCDHADYHNTVTLDCEARLDDFSEDGFISITDPRL
                             ARQETVWIIDPKSSSRTNQNIFLFKATRAERIVYTVKW
                             AGGGRLTTRAGVKINKDT*

SEQ ID    Ad34-E4orf6/7      MSGSNSIMTRLRARSTSCARHHPYTRAQLPRCEENE
NO. 94                       TRASMTEDHPLLPDCDTMTMHSMTVIQTPESHPQQL
                             DCESALKDYPDAFLSITDPRLARSETVWNVESKTMSI
                             SNGIQMFKAVRGERLVYSVKWEGGGKITTRIL*

SEQ ID    Ad36-E4orf6/7      MSTEEQSTSLRHHPYRRARLPRSEEETRASLTEQHP
NO. 95                       LLPDCDHAEYHNTVTLDCEARLEDFSEDGFISITDPRL
                             ARQETVWIIDTKSSSRTNQNIPLFKATRAERIVYTVKW
                             AGGGRLTTRAGVKINKDT*
```

-continued

```
SEQ ID    Ad38-E4orf6/7   MSTEEQSSLLRHHPYRRARLPRCEEETRASLTEQHP
NO. 96                    LLPDCDHADYHNTVTLDCEARLDDFSEDGFISITDPRL
                         ARQETVWIIDTKSSSRSNNNIPLFKATRAERIVYTVKW
                         AGGGRLTTRAGVKINKDS*

SEQ ID    Ad39-E4orf6/7   MSTEEQSSLLRHHPYRRARLPRCEEETRASLTEQHP
NO. 97                    LLPDCDHADYHNTVTLDCEARLEDFSEDGFISITDPRL
                         ARQETVWIIDTKSSSRTNQNIPLFKATRAERIVYTVKW
                         AGGGRLTTRAGVKINKDT*

SEQ ID    Ad43-E4orf6/7   MSTEEQSSLLRHHPYRRARLPRCEQETRASLTEQHP
NO. 98                    LLPDCDHAEYHNTVTLDCEPRLEDFSEDGFISITDPRL
                         ARQETVWLIDTKTSSRTNQNIPLFKATRAERTVYTVK
                         WAGGGRLTTRAGVKINKDT*

SEQ ID    Ad44-E4orf6/7   MQTEDQSSLLRHHPYRRARLPRCEEETRASLTEQHP
NO. 99                    LLPDCDHADYHNTVTLDCEARLEDFSEDGFISITDPRL
                         ARQETVWLIDTKSSSRTNQNIPLFKATRAERTVYTVK
                         WAGGGRLTTRAGVKINKDT*

SEQ ID    Ad45-E4orf6/7   MSTEEQSSLLRHHPYRRARLPRCEEETRASLTEQHP
NO. 100                   LLPDCDHADYHNTVTLDCEARLDDFSEDGFISITDPRL
                         ARQETVWIIDPKSSSRTNQNISLFKATRAERIVYTVKW
                         AGGGRLTTRAGVKINKDT*

SEQ ID    Ad47-E4orf6/7   MSTEEQSSLLRHHPYRRARLPRSDEETRASLTEQHP
NO. 101                   LLPDCDHADYHNTVTLDCEARLEDFSEDGFISITDPRL
                         ARQETVWIIDPKSSSRTNQNIPLFKATRAERIVYTVKW
                         AGGGRLTTRAGVKINKDT*

SEQ ID    Ad50-E4orf6/7   MSGNNSIMTRLRARSTSCARHHPYTRAQLPRCEENE
NO. 102                   TRASMTEDHPLLPDCDTMTMHSMTVIQTPESHPQQL
                         DCESALKDYPDAFLCITDPRLARSETVWNVETKTMSI
                         SNGIQMFKAVRGERLVYSVKWEGGGKITTRIL*

SEQ ID    Ad53-E4orf6/7   MQTEIQSSSLRHHPYRRARLPRSDEETRASLTEQHPL
NO. 103                   LPDCDHADYHNTVTLDCEARLDDFSEDGFISITDPRLA
                         RQETVWIINPKSSSRTNENFPLFKATRAERIVYTVKWA
                         GGGRMCTRAGVKINKDT*

SEQ ID    Ad54-E4orf6/7   MSTEEQSTLLRHHPYRRARLSRYDKETRASLTEQHP
NO. 104                   LLPDCDHADYHNTVTLDCEARLDDLSKDGFISITDPRL
                         ARQETVWIIDPKSSSRTNENFPLFKATRTERIVYTVKW
                         AGGGRMCTRAGVKINKDT*

SEQ ID    Ad58-E4orf6/7   MQTEIQSSLLRHHPYRRARLPRSDEETRASLTEQHPL
NO. 105                   LPDCDHADYHNTVTLDCEARLDDFSEDGFISITDPRLA
                         RQETVWLIDTKSSSRANQNIPLFKATRAERIVYTVKW
                         AGGGRLTTRAGVKINKDT*

SEQ ID    Ad64-E4orf6/7   MQTEIQSSSLRHHPYRRARLPRSDEETRASLTEQHPL
NO. 106                   LPDCDHADYHNTVTLDCEARLDDFSEDGFISITDPRLA
                         RQETVWIIDPKSNSRTNENISLFKATRAERTVYTVKW
                         AGGGRLSTRAGVKINKDT*

SEQ ID    Ad69-E4orf6/7   MQTEIQSSSLRHHPYRRARLPRSDEETRASLTEQHPL
NO. 107                   LPDCDHADYHNTVTLDCEARLDDFSEDGFISITDPRLA
                         RQETVWIIDPKSSSRTNQNISLFKATRAERIVYTVKWA
                         GGGRLTTRAGVKINKDT*
```

Variant sequences of SEQ ID NOs recited herein may have at least 80%, 85%, 90%, 95%, 98% or 99% sequence identity to the reference sequence SEQ ID NOs. Preferably, the variant sequence retains one or more functions of the reference sequence (i.e. is a functional variant).

Variant sequences may comprise one or more conservative substitutions. Conservative amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) variants i.e. like-for-like substitution such as basic for basic, acidic for acidic, polar for polar etc.

Unless otherwise explicitly stated herein by way of reference to a specific, individual amino acid, amino acids may be substituted using conservative substitutions as recited below.

An aliphatic, non-polar amino acid may be a glycine, alanine, proline, isoleucine, leucine or valine residue.

An aliphatic, polar uncharged amino may be a cysteine, serine, threonine, methionine, asparagine or glutamine residue.

An aliphatic, polar charged amino acid may be an aspartic acid, glutamic acid, lysine or arginine residue.

An aromatic amino acid may be a histidine, phenylalanine, tryptophan or tyrosine residue.

Suitably, a conservative substitution may be made between amino acids in the same line in the Table above.

An example of a nucleotide sequence encoding E4orf6 is set forth in SEQ ID No. 12.

```
                                      (SEQ ID NO. 12)
ATGACAACCAGCGGCGTGCCCTTCGGCATGACACTGAGGCCTACAAGAA

GCCGGCTGAGCAGAAGAACCCCTTACAGCAGAGACAGACTGCCTCCATT

CGAGACAGAGACACGGGCCACCATCCTGGAAGATCACCCTCTGCTGCCC

GAGTGCAACACCCTGACAATGCACAACGTGTCCTACGTGCGGGGCCTGC

CTTGTAGCGTTGGCTTCACACTGATCCAAGAGTGGGTCGTGCCCTGGGA

CATGGTGCTGACCAGAGAGGAACTGGTCATCCTGCGGAAGTGTATGCAC

GTGTGCCTGTGCTGCGCCAACATCGACATCATGACCAGCATGATGATCC

ACGGCTACGAGAGCTGGGCCCTGCACTGTCACTGTTCTAGCCCTGGCAG

CCTGCAGTGTATTGCTGGTGGACAGGTTCTGGCCAGCTGGTTCAGAATG

GTGGTGGACGGCGCCATGTTCAACCAGAGATTCATCTGGTACAGAGAGG

TGGTCAACTACAACATGCCCAAAGAAGTGATGTTCATGAGCAGCGTTTT

CATGCGGGGCAGACACCTGATCTACCTGCGGCTTTGGTACGATGGCCAC

GTGGGATCTGTGGTGCCTGCCATGAGCTTTGGCTACAGCGCCCTGCATT

GCGGCATCCTGAACAACATCGTGGTGCTGTGCTGCAGCTACTGCGCCGA

TCTGAGCGAGATCAGAGTGCGGTGTTGTGCCAGACGGACCAGACGGCTG

ATGCTGAGAGCCGTGCGGATCATTGCCGAAGAGACAACCGCCATGCTGT

ACTCTTGCCGGACCGAGAGAAGAAGGCAGCAGTTCATCAGAGCCCTGCT

CCAGCACCACCGGCCTATCCTGATGCACGACTACGACAGCACCCCTATG

TAG
```

An example of an amino acid sequence of E4orf6 is set forth in SEQ ID No. 13.

```
                                      (SEQ ID NO. 13)
MTTSGVPFGMTLRPTRSRLSRRTPYSRDRLPPFETETRATILEDHPLLP

ECNTLTMHNVSYVRGLPCSVGFTLIQEWVVPWDMVLTREELVILRKCMH

VCLCCANIDIMTSMMIHGYESWALHCHCSSPGSLQCIAGGQVLASWFRM

VVDGAMFNQRFIWYREVVNYNMPKEVMFMSSVFMRGRHLIYLRLWYDGH
```

-continued
```
VGSVVPAMSFGYSALHCGILNNIVVLCCSYCADLSEIRVRCCARRTRRL

MLRAVRIIAEETTAMLYSCRTERRRQQFIRALLQHHRPILMHDYDSTPM
```

An example of a nucleotide sequence encoding E1B55K is set forth in SEQ ID No. 14.

```
                                      (SEQ ID NO. 14)
ATGGAAAGACGGAACCCCAGCGAGAGAGGCGTGCCAGCTGGATTTTCTG

GACACGCCAGCGTGGAAAGCGGCTGCGAGACACAAGAAAGCCCTGCCAC

CGTGGTGTTCAGACCACCTGGCGATAATACCGATGGCGGAGCTGCTGCT

GCAGCTGGTGGATCTCAGGCAGCAGCTGCAGGCGCTGAACCTATGGAAC

CTGAGAGCAGACCTGGACCTAGCGGCATGAATGTGGTGCAGGTCGCCGA

GCTGTATCCCGAGCTGAGAAGAATCCTGACCATCACCGAGGATGGCCAG

GGACTGAAGGGCGTGAAGAGAGAAAGAGGCGCCTGCGAGGCCACAGAGG

AAGCCAGAAATCTGGCCTTCAGCCTGATGACCAGACACAGACCCGAGTG

CATCACCTTCCAGCAGATCAAGGACAACTGCGCCAACGAGCTGGACCTG

CTGGCCCAGAAGTACAGCATCGAGCAGCTGACCACCTACTGGCTGCAAC

CCGGCGACGATTTCGAAGAGGCCATCAGAGTGTACGCCAAGGTGGCCCT

CAGACCTGACTGCAAGTACAAGATCAGCAAGCTGGTCAACATCCGGAAC

TGCTGCTACATCAGCGGCAATGGCGCCGAGGTGGAAATCGACACAGAGG

ACAGAGTGGCCTTCCGGTGCAGCATGATCAACATGTGGCCTGGCGTGCT

CGGCATGGATGGCGTGGTCATTATGAACGTGCGGTTCACAGGCCCCAAC

TTCAGCGGCACAGTGTTTCTGGCCAACACCAACCTGATCCTGCACGGCG

TGTCCTTCTACGGCTTCAACAATACCTGCGTGGAAGCCTGGACCGACGT

TCGCGTTAGAGGCTGCGCCTTCTACTGCTGTTGGAAGGGCGTCGTGTGC

AGACCCAAGAGCAGAGCCAGCATCAAGAAGTGCCTGTTCGAGAGATGCA

CCCTGGGCATCCTGAGCGAGGGCAACAGCAGAGTCAGACACAACGTGGC

CAGCGACTGCGGCTGCTTCATGCTGGTTAAGAGCGTGGCCGTGATCAAG

CACAACATGGTCTGCGGCAACTGCGAGGATAGAGCCAGCCAGATGCTGA

CCTGCAGCGACGGCAATTGTCATCTGCTGAAAACCATCCACGTGGCCTC

TCACAGCAGAAAGGCCTGGCCTGTGTTCGAGCACAATATCCTGACACGG

TGCTCCCTGCACCTGGGCAATAGACGGGGAGTGTTCCTGCCTTACCAGT

GCAACCTGAGCCACACCAAGATCCTGCTGGAACCCGAGTCCATGAGCAA

AGTGAACCTGAATGGCGTGTTCGACATGACCATGAAGATCTGGAAAGTG

CTGCGCTACGACGAGACACGGACCAGATGTAGACCTTGCGAGTGTGGCG

GCAAGCACATCAGAAACCAGCCTGTGATGCTGGACGTGACCGAGGAACT

GAGGCCTGATCATCTGGTGCTGGCCTGTACCAGAGCCGAGTTTGGCAGC

TCCGACGAGGATACCGAT
```

An example of an amino acid sequence of E1B55K is set forth in SEQ ID No. 15.

```
                                      (SEQ ID NO. 15)
MERRNPSERGVPAGFSFGHASVESGETQESPATVVFRPPGDNTDGGAAA
```

```
-continued
AAGGSQAAAAGAEPMEPESRPGPSGMNVVQVAELYPELRRILTITEDGQ

GLKGVKRERGACEATEEARNLAFSLMTRHRPECITFQQIKDNCANELDL

LAQKYSIEQLTTYWLQPGDDFEEAIRVYAKVALRPDCKYKISKLVNIRN

CCYISGNGAEVEIDTEDRVAFRCSMINMWPGVLGMDGVVIMNVRFTGPN

FSGTVFLANTNLILHGVSFYGFNNTCVEAWTDVRVRGCAFYCCWKGVVC

RPKSRASIKKCLFERCTLGILSEGNSRVRHNVASDCGCFMLVKSVAVIK

HNMVCGNCEDRASQMLTCSDGNCHLLKTIHVASHSRKAWPVFEHNILTR

CSLHLGNRRGVFLPYQCNLSHTKILLEPESMSKVNLNGVFDMTMKIWKV

LRYDETRTRCRPCECGGKHIRNQPVMLDVTEELRPDHLVLACTRAEFGS

SDEDTD
```

In one embodiment, the at least one adenoviral protein is not E4orf6. In one embodiment, the at least one adenoviral protein is not E1B55K. In one embodiment, the at least one adenoviral proteins does not comprise E4orf6 or E1B55K.

Haematopoietic Stem and Progenitor Cells

A stem cell is able to differentiate into many cell types. A cell that is able to differentiate into all cell types is known as totipotent. In mammals, only the zygote and early embryonic cells are totipotent. Stem cells are found in most, if not all, multicellular organisms. They are characterised by the ability to renew themselves through mitotic cell division and differentiate into a diverse range of specialised cell types. The two broad types of mammalian stem cells are embryonic stem cells that are isolated from the inner cell mass of blastocysts, and adult stem cells that are found in adult tissues. In a developing embryo, stem cells can differentiate into all of the specialised embryonic tissues. In adult organisms, stem cells and progenitor cells act as a repair system for the body, replenishing specialised cells, but also maintaining the normal turnover of regenerative organs, such as blood, skin or intestinal tissues.

Haematopoietic stem cells (HSCs) are multipotent stem cells that may be found, for example, in peripheral blood, bone marrow and umbilical cord blood. HSCs are capable of self-renewal and differentiation into any blood cell lineage. They are capable of recolonising the entire immune system, and the erythroid and myeloid lineages in all the haematopoietic tissues (such as bone marrow, spleen and thymus). They provide for life-long production of all lineages of haematopoietic cells.

Haematopoietic progenitor cells have the capacity to differentiate into a specific type of cell. In contrast to stem cells however, they are already far more specific: they are pushed to differentiate into their "target" cell. A difference between stem cells and progenitor cells is that stem cells can replicate indefinitely, whereas progenitor cells can only divide a limited number of times. Haematopoietic progenitor cells can be rigorously distinguished from HSCs only by functional in vivo assay (i.e. transplantation and demonstration of whether they can give rise to all blood lineages over prolonged time periods).

The haematopoietic stem and progenitor cells of the invention comprise the CD34 cell surface marker (denoted as CD34+).

In one embodiment, the cells for use in the present invention are HSPCs.

In one embodiment, the cells for use in the present invention are primitive HSPCs. In one embodiment, a primitive subset of HSPCs refers to a population of HSCs which is CD90+. In one embodiment, a primitive subset of HSPCs refers to a population of cells which is CD34+ CD133+ and CD90+.

In one embodiment, the cells for use in the present invention are HSCs.

Haematopoietic Stem and Progenitor Cell (HSPC) Sources

A population of haematopoietic stem and/or progenitor cells may be obtained from a tissue sample.

For example, a population of haematopoietic stem and/or progenitor cells may be obtained from peripheral blood (e.g. adult and foetal peripheral blood), umbilical cord blood, bone marrow, liver or spleen. Preferably, these cells are obtained from peripheral blood or bone marrow. They may be obtained after mobilisation of the cells in vivo by means of growth factor treatment.

Mobilisation may be carried out using, for example, G-CSF, plerixaphor or combinations thereof. Other agents, such as NSAIDs and dipeptidyl peptidase inhibitors, may also be useful as mobilising agents.

With the availability of the stem cell growth factors GM-CSF and G-CSF, most haematopoietic stem cell transplantation procedures are now performed using stem cells collected from the peripheral blood, rather than from the bone marrow. Collecting peripheral blood stem cells provides a bigger graft, does not require that the donor be subjected to general anaesthesia to collect the graft, results in a shorter time to engraftment and may provide for a lower long-term relapse rate.

Bone marrow may be collected by standard aspiration methods (either steady-state or after mobilisation), or by using next-generation harvesting tools (e.g. Marrow Miner).

In addition, haematopoietic stem and progenitor cells may also be derived from induced pluripotent stem cells.

HSC Characteristics

HSCs are typically of low forward scatter and side scatter profile by flow cytometric procedures. Some are metabolically quiescent, as demonstrated by Rhodamine labelling which allows determination of mitochondrial activity. HSCs may comprise certain cell surface markers such as CD34, CD45, CD133, CD90 and CD49f. They may also be defined as cells lacking the expression of the CD38 and CD45RA cell surface markers. However, expression of some of these markers is dependent upon the developmental stage and tissue-specific context of the HSC. Some HSCs called "side population cells" exclude the Hoechst 33342 dye as detected by flow cytometry. Thus, HSCs have descriptive characteristics that allow for their identification and isolation.

Negative Markers

CD38 is the most established and useful single negative marker for human HSCs.

Human HSCs may also be negative for lineage markers such as CD2, CD3, CD14, CD16, CD19, CD20, CD24, CD36, CD56, CD66b, CD271 and CD45RA. However, these markers may need to be used in combination for HSC enrichment.

By "negative marker" it is to be understood that human HSCs lack the expression of these markers.

Positive Markers

CD34 and CD133 are the most useful positive markers for HSCs.

Some HSCs are also positive for lineage markers such as CD90, CD49f and CD93. However, these markers may need to be used in combination for HSC enrichment.

By "positive marker" it is to be understood that human HSCs express these markers.

In one embodiment, the haematopoietic stem and progenitor cells are CD34+CD38-cells.

Differentiated Cells

A differentiated cell is a cell which has become more specialised in comparison to a stem cell or progenitor cell. Differentiation occurs during the development of a multicellular organism as the organism changes from a single zygote to a complex system of tissues and cell types. Differentiation is also a common process in adults: adult stem cells divide and create fully-differentiated daughter cells during tissue repair and normal cell turnover. Differentiation dramatically changes a cell's size, shape, membrane potential, metabolic activity and responsiveness to signals. These changes are largely due to highly-controlled modifications in gene expression. In other words, a differentiated cell is a cell which has specific structures and performs certain functions due to a developmental process which involves the activation and deactivation of specific genes. Here, a differentiated cell includes differentiated cells of the haematopoietic lineage such as monocytes, macrophages, neutrophils, basophils, eosinophils, erythrocytes, megakaryocytes/platelets, dendritic cells, T cells, B-cells and NK-cells. For example, differentiated cells of the haematopoietic lineage can be distinguished from stem cells and progenitor cells by detection of cell surface molecules which are not expressed or are expressed to a lesser degree on undifferentiated cells. Examples of suitable human lineage markers include CD33, CD13, CD14, CD15 (myeloid), CD19, CD20, CD22, CD79a (B), CD36, CD71, CD235a (erythroid), CD2, CD3, CD4, CD8 (T) and CD56 (NK).

In one embodiment, the haematopoietic cells referred to herein is a T-cell.

Isolation and Enrichment of Populations of Cells

The term "isolated population" of cells as used herein may refer to the population of cells having been previously removed from the body. An isolated population of cells may be cultured and manipulated ex vivo or in vitro using standard techniques known in the art. An isolated population of cells may later be reintroduced into a subject. Said subject may be the same subject from which the cells were originally isolated or a different subject.

A population of cells may be purified selectively for cells that exhibit a specific phenotype or characteristic, and from other cells which do not exhibit that phenotype or characteristic, or exhibit it to a lesser degree. For example, a population of cells that expresses a specific marker (such as CD34) may be purified from a starting population of cells. Alternatively, or in addition, a population of cells that does not express another marker (such as CD38) may be purified.

By "enriching" a population of cells for a certain type of cells it is to be understood that the concentration of that type of cells is increased within the population. The concentration of other types of cells may be concomitantly reduced.

Purification or enrichment may result in the population of cells being substantially pure of other types of cell.

Purifying or enriching for a population of cells expressing a specific marker (e.g. CD34 or CD38) may be achieved by using an agent that binds to that marker, preferably substantially specifically to that marker.

An agent that binds to a cellular marker may be an antibody, for example an anti-CD34 or anti-CD38 antibody.

The term "antibody" refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

The agents that bind to specific markers may be labelled so as to be identifiable using any of a number of techniques known in the art. The agent may be inherently labelled, or may be modified by conjugating a label thereto. By "conjugating" it is to be understood that the agent and label are operably linked. This means that the agent and label are linked together in a manner which enables both to carry out their function (e.g. binding to a marker, allowing fluorescent identification or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the agent may be labelled with a magnetic bead or an affinity tag, such as avidin), detected or both. Detectable markers suitable for use as a label include fluorophores (e.g. green, cherry, cyan and orange fluorescent proteins) and peptide tags (e.g. His tags, Myc tags, FLAG tags and HA tags).

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such biotin columns to separate avidin-labelled agents) and microscopy-based techniques.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

It is also envisaged that dye exclusion properties (e.g. side population or rhodamine labelling) or enzymatic activity (e.g. ALDH activity) may be used to enrich for haematopoietic stem cells.

Suitably, the agent does not reduce the fraction CD34+ CD133+ CD90+ cells in population of gene edited cells compared with a population of untreated gene edited cells.

Gene Editing

The term "gene editing" refers to a type of genetic engineering in which a nucleic acid is inserted, deleted or replaced in a cell. Gene editing may be achieved using engineered nucleases, which may be targeted to a desired site in a polynucleotide (e.g. a genome). Such nucleases may create site-specific double-strand breaks at desired locations, which may then be repaired through non-homologous end-joining (NHEJ) or homologous recombination (HR), resulting in targeted mutations.

Such nucleases may be delivered to a target cell using viral vectors. The present invention provides methods of increasing the efficiency of the gene editing process.

Examples of suitable nucleases known in the art include zinc finger nucleases (ZFNs), transcription activator like effector nucleases (TALENs), and the clustered regularly interspaced short palindromic repeats (CRISPR)/Cas system (Gaj, T. et al. (2013) Trends Biotechnol. 31:397-405; Sander, J. D. et al. (2014) Nat. Biotechnol. 32:347-55).

Meganucleases (Silve, G. et al. (2011) Cur. Gene Ther. 11:11-27) may also be employed as suitable nucleases for gene editing.

The CRISPR/Cas system is an RNA-guided DNA binding system (van der Oost et al. (2014) Nat. Rev. Microbiol. 12:479-92), wherein the guide RNA (gRNA) may be selected to enable a Cas9 domain to be targeted to a specific sequence. Methods for the design of gRNAs are known in the art. Furthermore, fully orthogonal Cas9 proteins, as well as Cas9/gRNA ribonucleoprotein complexes and modifications of the gRNA structure/composition to bind different proteins, have been recently developed to simultaneously and directionally target different effector domains to desired genomic sites of the cells (Esvelt et al. (2013) Nat. Methods 10:1116-21; Zetsche, B. et al. (2015) Cell pii: S0092-8674 (15) 01200-3; Dahlman, J. E. et al. (2015) Nat. Biotechnol. 2015 Oct. 5. doi: 10.1038/nbt.3390. [Epub ahead of print]; Zalatan, J. G. et al. (2015) Cell 160:339-50; Paix, A. et al. (2015) Genetics 201: 47-54), and are suitable for use in the invention.

Vectors

A vector is a tool that allows or facilitates the transfer of an entity from one environment to another. The vectors used to transduce haematopoietic stem and/or progenitor cells in the invention are viral vectors.

Preferably, the viral vector is in the form of a viral vector particle.

The viral vector may be, for example, an adeno-associated viral (AAV), adenoviral, a retroviral or lentiviral vector. Preferably, the viral vector is an AAV vector or a retroviral or lentiviral vector, more preferably an AAV vector. Preferably, the retroviral vector is not a γ-retroviral vector.

By "vector derived from" a certain type of virus, it is to be understood that the vector comprises at least one component part derivable from that type of virus.

Adeno-Associated Viral (AAV) Vectors

Adeno-associated virus (AAV) is an attractive vector system for use in the invention as it has a high frequency of integration and it can infect non-dividing cells. This makes it useful for delivery of genes into mammalian cells in tissue culture.

AAV has a broad host range for infectivity. Details concerning the generation and use of AAV vectors are described in U.S. Pat. Nos. 5,139,941 and 4,797,368.

Recombinant AAV vectors have been used successfully for in vitro and in vivo transduction of marker genes and genes involved in human diseases.

Preferred vectors are those which are able to achieve a high transduction efficiency in human primary cells, such as HSPC cells.

In one embodiment, the vector is an AAV6 vector or a vector derived from an AAV6 vector. Preferably the vector is an AAV6 vector.

Adenoviral Vectors

The adenovirus is a double-stranded, linear DNA virus that does not go through an RNA intermediate. There are over 50 different human serotypes of adenovirus divided into 6 subgroups based on the genetic sequence homology. The natural targets of adenovirus are the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses have been used as vectors for gene therapy and for expression of heterologous genes. The large (36 kb) genome can accommodate up to 8 kb of foreign insert DNA and is able to replicate efficiently in complementing cell lines to produce very high titres of up to 1012. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, they function episomally (independently from the host genome) as a linear genome in the host nucleus. Hence the use of recombinant adenovirus alleviates the problems associated with random integration into the host genome.

Retroviral and Lentiviral Vectors

A retroviral vector may be derived from or may be derivable from any suitable retrovirus. A large number of different retroviruses have been identified. Examples include murine leukaemia virus (MLV), human T-cell leukaemia virus (HTLV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), avian myelocytomatosis virus-29 (MC29) and avian erythroblastosis virus (AEV). A detailed list of retroviruses may be found in Coffin, J. M. et al. (1997) Retroviruses, Cold Spring Harbour Laboratory Press, 758-63.

Retroviruses may be broadly divided into two categories, "simple" and "complex". Retroviruses may be even further divided into seven groups. Five of these groups represent retroviruses with oncogenic potential. The remaining two groups are the lentiviruses and the spumaviruses. A review of these retroviruses is presented in Coffin, J. M. et al. (1997) Retroviruses, Cold Spring Harbour Laboratory Press, 758-63.

The basic structure of retrovirus and lentivirus genomes share many common features such as a 5' LTR and a 3' LTR. Between or within these are located a packaging signal to enable the genome to be packaged, a primer binding site, integration sites to enable integration into a host cell genome, and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration and transcription. LTRs also serve as enhancer-promoter sequences and can control the expression of the viral genes.

The LTRs themselves are identical sequences that can be divided into three elements: U3, R and U5. U3 is derived from the sequence unique to the 3' end of the RNA. R is derived from a sequence repeated at both ends of the RNA. U5 is derived from the sequence unique to the 5' end of the RNA. The sizes of the three elements can vary considerably among different retroviruses.

In a defective retroviral vector genome gag, pol and env may be absent or not functional.

In a typical retroviral vector, at least part of one or more protein coding regions essential for replication may be removed from the virus. This makes the viral vector replication-defective. Portions of the viral genome may also be replaced by a library encoding candidate modulating moieties operably linked to a regulatory control region and a reporter moiety in the vector genome in order to generate a vector comprising candidate modulating moieties which is capable of transducing a target host cell and/or integrating its genome into a host genome.

Lentivirus vectors are part of the larger group of retroviral vectors. A detailed list of lentiviruses may be found in Coffin, J. M. et al. (1997) Retroviruses, Cold Spring Harbour Laboratory Press, 758-63. In brief, lentiviruses can be divided into primate and non-primate groups. Examples of primate lentiviruses include but are not limited to human immunodeficiency virus (HIV), the causative agent of human acquired immunodeficiency syndrome (AIDS); and simian immunodeficiency virus (SIV). Examples of non-primate lentiviruses include the prototype "slow virus" visna/maedi virus (VMV), as well as the related caprine arthritis-encephalitis virus (CAEV), equine infectious anaemia virus (EIAV), and the more recently described feline immunodeficiency virus (FIV) and bovine immunodeficiency virus (BIV).

The lentivirus family differs from retroviruses in that lentiviruses have the capability to infect both dividing and non-dividing cells (Lewis, P et al. (1992) EMBO J. 11:3053-8; Lewis, P. F. et al. (1994) J. Virol. 68:510-6). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "primate" vector. The lentiviral vector may be a "non-primate" vector (i.e. derived from a virus which does not primarily infect primates, especially humans). Examples of non-primate lentiviruses may be any member of the family of lentiviridae which does not naturally infect a primate.

As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat.

Most HIV-2-based vectors are structurally very similar to HIV-1 vectors. Similar to HIV-1-based vectors, HIV-2 vectors also require RRE for efficient transport of the full-length or singly spliced viral RNAs.

In one system, the vector and helper constructs are from two different viruses, and the reduced nucleotide homology may decrease the probability of recombination. In addition to vectors based on the primate lentiviruses, vectors based on FIV have also been developed as an alternative to vectors derived from the pathogenic HIV-1 genome. The structures of these vectors are also similar to the HIV-1 based vectors.

Preferably, the viral vector used in the present invention has a minimal viral genome.

By "minimal viral genome" it is to be understood that the viral vector has been manipulated so as to remove the non-essential elements and to retain the essential elements in order to provide the required functionality to infect, transduce and deliver a nucleotide sequence of interest to a target host cell. Further details of this strategy can be found in WO 1998/017815.

Preferably, the plasmid vector used to produce the viral genome within a host cell/packaging cell will have sufficient lentiviral genetic information to allow packaging of an RNA genome, in the presence of packaging components, into a viral particle which is capable of infecting a target cell, but is incapable of independent replication to produce infectious viral particles within the final target cell. Preferably, the vector lacks a functional gag-pol and/or env gene and/or other genes essential for replication.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed viral sequence (i.e. the 5' U3 region), or they may be a heterologous promoter, such as another viral promoter (e.g. the CMV promoter).

The vectors may be self-inactivating (SIN) vectors in which the viral enhancer and promoter sequences have been deleted. SIN vectors can be generated and transduce non-dividing cells in vivo with an efficacy similar to that of wild-type vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

The vectors may be integration-defective. Integration defective lentiviral vectors (IDLVs) can be produced, for example, either by packaging the vector with catalytically inactive integrase (such as an HIV integrase bearing the D64V mutation in the catalytic site; Naldini, L. et al. (1996) Science 272:263-7; Naldini, L. et al. (1996) Proc. Natl. Acad. Sci. USA 93:11382-8; Leavitt, A. D. et al. (1996) J. Virol. 70:721-8) or by modifying or deleting essential att sequences from the vector LTR (Nightingale, S. J. et al. (2006) Mol. Ther. 13:1121-32), or by a combination of the above.

In one embodiment, the gene editing targets a haematopoietic stem cell and/or progenitor locus. In one embodiment, the donor template targets a haematopoietic stem cell and/or progenitor locus.

In one embodiment, the gene editing targets the adeno-associated virus integration site 1 (AAVS1) locus. In one embodiment, the donor template targets the adeno-associated virus integration site 1 (AAVS1) locus.

An example of an AAV donor cassette for AAVS1 may comprise the following nucleotide sequences:

```
3'-ITR
                                        (SEQ ID NO. 16)
cctgcaggcagctgcgcgctcgctcgctcactgaggccgcccgggcaaa gcccgggcgtcgggcgacctttggtcgcccggcctcagtgagcgagcga gcgcgcagagagggagtggccaactccatcact Homologous arm-left
```

-continued (SEQ ID NO. 17)
tgctttctctgaccagcattctctccctgggcctgtgccgctttctgt ctgcagcttgtggcctgggtcacctctacggctggcccagatccttccc tgccgcctccttcaggttccgtcttcctccactccctcttccccttgct ctctgctgtgttgctgcccaaggatgctctttccggagcacttccttct cggcgctgcaccacgtgatgtcctctgagcggatcctccccgtgtctgg gtcctctccgggcatctctcctccctcacccaaccccatgccgtcttca ctcgctgggttcccttttccttctccttctggggcctgtgccatctctc gtttcttaggatggccttctccgacggatgtctcccttgcgtcccgcct cccccttcttgtaggcctgcatcatcaccgtttttctggacaaccccaaa gtaccccgtctccctggctttagccacctctccatcctcttgctttctt tgcctggacaccccgttctcctgtggattcgggtcacctctcactcctt tcatttgggcagctcccctaccccccttacctctctagtctgtgctagc tcttccagcccctgtcatggcatcttccaggggtccgagagctcagct agtcttcttcctccaacccgggcccctatgtccacttcaggacagcatg tttgctgcctccagggatcctgtgtccccgagctgggaccaccttatat tcccagggccggttaatgtggctctggttctgggtacttttatctgtcc cctccaccccac hPGK promoter (without SA)

(SEQ ID NO. 18)
ccacggggtggggttgcgccttttccaaggcagccctgggtttgcgca gggacgcggctgctctgggcgtggttccgggaaacgcagcggcgccgac cctgggtctcgcacattcttcacgtccgttcgcagcgtcacccggatct tcgccgctaccttgtgggcccccggcgacgcttcctgctccgccct aagtcgggaaggttccttgcggttcgcggcgtgccggacgtgacaaacg gaagccgcacgtctcactagtaccctcgcagacggacagcgccagggag caatggcagcgcgccgaccgcgatgggctgtggccaatagcggctgctc agcagggcgcgccgagagcagcggccgggaaggggcggtgcgggaggcg gggtgtggggcggtagtgtgggccctgttcctgcccgcgcggtgttccg cattctgcaagcctccggagcgcacgtcggcagtcggctccctcgttga ccgaatcaccgacctctctcccca eGFP (SEQ ID NO. 19)
atggtgagcaagggcgaggagctgttcaccggggtggtgcccatcctgg tcgagctggacggcgacgtaaacggccacaagttcagcgtgtccggcga gggcgagggcgatgccacctacggcaagctgaccctgaagttcatctgc accaccggcaagctgcccgtgccctggcccaccctcgtgaccaccctga cctacggcgtgcagtgcttcagccgctaccccgaccacatgaagcagca cgacttcttcaagtccgccatgcccgaaggctacgtccaggagcgcacc atcttcttcaaggacgacggcaactacaagacccgcgccgaggtgaagt tcgagggcgacaccctggtgaaccgcatcgagctgaagggcatcgactt caaggaggacggcaacatcctggggcacaagctggagtacaactacaac agccacaacgtctatatcatggccgacaagcagaagaacggcatcaagg -continued tgaacttcaagatccgccacaacatcgaggacggcagcgtgcagctcgc cgaccactaccagcagaacacccccatcggcgacgggcccgtgctgctg cccgacaaccactacctgagcacccagtccgccctgagcaaagacccca acgagaagcgcgatcacatggtcctgctggagttcgtgaccgccgccgg gatcactctcggcatggacgagctgtacaagtaa bGH-pA (SEQ ID NO. 20)
actgtgccttctagttgccagccatctgttgtttgcccctcccccgtgc cttccttgaccctggaaggtgccactcccactgtcctttcctaataaaa tgaggaaattgcatcgcattgtctgagtaggtgtcattctattctgggg ggtggggtggggcaggacagcaagggggaggattgggaagacaatagca ggcatgctggggatgcggtgggctctatgg Homologous arm-right (SEQ ID NO. 21)
tagggacaggattggtgacagaaaagccccatccttaggcctcctcctt cctagtctcctgatattgggtctaacccccacctcctgttaggcagatt ccttatctggtgacacaccccatttcctggagccatctctctccttgc cagaacctctaaggtttgcttacgatggagccagagaggatcctgggag ggagagcttggcagggggggagggaaggggggatgcgtgacctgccc ggttctcagtgg

5'-ITR (SEQ ID NO. 22)
agtgatggagttggccactccctctctgcgcgctcgctcgctcactgag gccgggcgaccaaaggtcgcccgacgcccgggcggcctcagtgagcgag cgagcgcgcagctgcctgcagg In another embodiment, the gene editing targets Interleukin 2 Receptor Subunit Gamma (IL2RG), preferably targeting intron 1 of IL2RG. In another embodiment, the donor template targets Interleukin 2 Receptor Subunit Gamma (IL2RG), preferably targeting intron 1 of IL2RG.

An example of an AAV donor cassette for IL2RG may comprise the following nucleotide sequences:

3'-ITR (SEQ ID NO. 23)
cctgcaggcagctgcgcgctcgctcgctcactgaggccgcccgggcaaa gcccgggcgtcgggcgacctttggtcgcccggcctcagtgagcgagcga gcgcgcagagagggagtggccaactccatcact Homologous arm-left (SEQ ID NO. 24)
agaggaaacgtgtgggtggggaggggtagtgggtgagggacccaggttc ctgacacagacagactacacccagggaatgaagagcaagcgccatgttg aagccatcattaccattcacatccctcttattcctgcagctgccctgc tgggagtggggctgaacacgacaattctgacgcccaatgggaatgaaga caccacagctggtgggaaatctgggactggagggggctggtgagaaggg tggctgtgggaaggggccgtacagagatctggtgcctgccactgg Exon2

(SEQ ID NO. 25)
atttctttctgaccaccatgcccaccgacagcctgagcgtgagcaccct gcccctgcccgaggtgcagtgcttcgtgttcaacgtggagtacatgaac -continued tgcacctggaacagcagcagcgagccccagcccaccaatctgaccctgc actactg Exon3

(SEQ ID NO. 26)

gtacaagaacagcgacaacgacaaggtgcagaagtgcagccactacctg ttcagcgaggaaatcaccagcggctgccagctgcagaagaaagagatcc acctgtaccagaccttcgtggtgcagctgcaggaccccgggagccccg caggcaggccacccagatgctgaagctgcagaacctgg Exon4

(SEQ ID NO. 27)

tgatcccctgggcccctgagaacctgacactgcacaagctgtccgagag ccagctggaactgaactggaacaaccgcttcctgaaccactgcctggaa cacctggtgcagtaccggaccgactgggaccacagctggacc Exon5

(SEQ ID NO. 28)

gagcagagcgtggactaccggcacaagttcagcctgcccagcgtggacg gccagaagcggtacaccttcagagtgcggagccggttcaacccctgtg cggcagcgcccagcactggtccgagtggagccaccccatccactgggc agcaacaccagcaaag Exon6

(SEQ ID NO. 29)

agaacccttcctgttcgccctggaagccgtggtgatcagcgtgggcag catgggcctgatcatctccctgctgtgcgtgtacttctggctggaacg Exon7

(SEQ ID NO. 30)

gaccatgcccagaatccccaccctgaagaacctggaagatctggtgacc gagtaccacggcaacttcagc

Exon8

(SEQ ID NO. 31)

gcctggtccggcgtgagcaagggcctggccgagagcctgcagcccgact acagcgagcggctgtgcctggtgtccgagatcccccccaaaggcggagc cctgggcgaaggccctggcgccagcccctgcaaccagcacagcccctac tgggcccctccttgctacaccctgaagcccgagacctga

3'-UTR (SEQ ID NO. 32)

tgaaccccaatcctctgacagaagaacccagggtcctgtagccctaag tggtactaactttccttcattcaacccactgcgtctcatactcacctca ccccactgtggctgatttggaattttgtgcccccatgtaagcacccctt catttggcattccccacttgagaattacccttttgccccgaacatgttt ttcttctccctcagtctggcccttccttttcgcaggattcttcctcccc ccctctttccctcccttcctcttttccatctaccctccgattgttcctga accgatgagaaataaagtttctgttgataatcatcg bGH-pA (SEQ ID NO. 33)

actgtgccttctagttgccagccatctgttgtttgcccctcccccgtgc cttccttgaccctggaaggtgccactcccactgcccctttcctaataaaa tgaggaaattgcatcgcattgtctgagtaggtgtcattctattctgggg ggtggggtgggcaggacagcaaggggggaggattgggaagacaatagca ggcatgctggggatgcggtgggctctatg -continued g hPGK promoter (SEQ ID NO. 34)

ccacggggttggggttgcgcctttttccaaggcagccctgggtttgcgca gggacgcggctgctctgggcgtggttccgggaaacgcagcggcgccgac cctgggtctcgcacattcttcacgtccgttcgcagcgtcacccggatct tcgccgctaccccttgtgggcccccggcgacgcttcctgctccgcccct aagtcgggaaggttccttgcggttcgcggcgtgccggacgtgacaaacg gaagccgcacgtctcactagtaccctcgcagacggacagcgccagggag caatggcagcgcgccgaccgcgatgggctgtggccaatagcggctgctc agcagggcgcgccgagagcagcggccgggaaggggcggtgcgggagggg ggtgtggggcggtagtgtgggccctgttcctgcccgcgcggtgttccgc attctgcaagcctccggagcgcacgtcggcagtcggctccctcgttgac cgaatcaccgacctctctccccagg eGFP (SEQ ID NO. 35)

atggtgagcaagggcgaggagctgttcaccggggtggtgcccatcctgg tcgagctggacggcgacgtaaacggccacaagttcagcgtgtccggcga gggcgaggcgatgccacctacggcaagctgaccctgaagttcatctgc accaccggcaagctgcccgtgccctggcccaccctcgtgaccaccctga cctacggcgtgcagtgcttcagccgctacccccgaccacatgaagcagca cgacttcttcaagtccgccatgcccgaaggctacgtccaggagcgcacc atcttcttcaaggacgacggcaactacaagacccgcgccgaggtgaagt tcgagggcgacaccctggtgaaccgcatcgagctgaagggcatcgactt caaggaggacggcaacatcctggggcacaagctggagtacaactacaac agccacaacgtctatatcatggccgacaagcagaagaacggcatcaagg tgaacttcaagatccgccacaacatcgaggacggcagcgtgcagctcgc cgaccactaccagcagaacacccccatcggcgacggccccgtgctgctg cccgacaaccactacctgagcacccagtccgccctgagcaaagacccca acgagaagcgcgatcacatggtcctgctggagttcgtgaccgccgccgg gatcactctcggcatggacgagctgtacaagtaa SV40-pA (SEQ ID NO. 36)

tgagatccagacatgataagatacattgatgagtttggacaaaccaaaa ctagaatgcagtgaaaaaaatgccttatttgtgaaatttgtgatgctat tgccttatttgtaaccattataagctgcaataaacaagttaacaacaac aattgcattcattttatgtttcaggttcaggggggaggtgtgggaggttt tttaaagcaagtaaaacctctacaaatgtggtatggctgattatgatc Homologous arm-right (SEQ ID NO. 37)

tacaatcatgtgggcagaattgaaaagtggagtgggaagggcaagggggg agggttccctgcctcacgctacttcttctttctttcttgtttgtttgtt tctttctttcttttgaggcagggtctcactatgttgcctaggctggtct caaactcctggcctctagtgatcctcctgcctcagcctttcaaagcacc aggattacagacatgagccaccgtgcttggcctcctccttctgaccatc

65

-continued

```
atttctctttccctccctgcct

5'-ITR
                                    (SEQ ID NO. 38)
agtgatggagttggccactccctctctgcgcgctcgctcgctcactgag gccgggcgaccaaaggtcgcccgacgcccgggcggcctcagtgagcgag cgagcgcgcagctgcctgcagg
```

In another embodiment, the gene editing targets CD40L. In another embodiment, the donor template targets CD40L.

In another embodiment, the gene editing targets RAG-1. In another embodiment, the donor template targets RAG-1.

Nucleotide of Interest

The vector used in the present invention preferably comprises one or more nucleotides of interest.

Preferably the nucleotide of interest gives rise to a therapeutic effect.

Suitably, the one or more NOIs for use in the present invention may be selected from: a guide RNA, a nucleotide encoding a Cas9 ribonucleoprotein, nucleotide sequences encoding one or more adenoviral proteins, nucleotide sequences encoding an agent which promotes homology directed DNA repair (such as an inhibitor of p53 activation or nucleotide sequences encoding one or more adenoviral proteins).

Suitable NOIs include, but are not limited to sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, guide RNA (gRNA, e.g. used in connection with a CRISPR/Cas system), ribozymes, miRNA target sequences, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group). The NOIs may also encode pro-drug activating enzymes. Preferably, the NOI is a guide RNA (gRNA).

Pharmaceutical Composition

In one embodiment, the cells of the present invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy product is preferably performed in compliance with FACT-JACIE International Standards for cellular therapy.

Haematopoietic Cell, Haematopoietic Stem and/or Haematopoietic Progenitor Cell Transplantation The present invention provides a population of haematopoietic cells, haematopoietic stem cells and/or haematopoietic progenitor cells, prepared according to a method of the invention for use in therapy, for example for use in gene therapy.

The use may be as part of a cell transplantation procedure, for example a haematopoietic stem cell transplantation procedure.

Haematopoietic stem cell transplantation (HSCT) is the transplantation of blood stem cells derived from the bone marrow (in this case known as bone marrow transplantation) or blood. Stem cell transplantation is a medical procedure in the fields of haematology and oncology, most often performed for people with diseases of the blood or bone marrow, or certain types of cancer.

Many recipients of HSCTs are multiple myeloma or leukaemia patients who would not benefit from prolonged treatment with, or are already resistant to, chemotherapy. Candidates for HSCTs include paediatric cases where the patient has an inborn defect such as severe combined immunodeficiency or congenital neutropenia with defective stem cells, and also children or adults with aplastic anaemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumour and Hodgkin's disease. More recently non-myeloablative, or so-called "mini transplant", procedures have been developed that require smaller doses of preparative chemotherapy and radiation. This has allowed HSCT to be conducted in the elderly and other patients who would otherwise be considered too weak to withstand a conventional treatment regimen.

In one embodiment, a population of haematopoietic stem cells prepared according to a method of the invention is administered as part of an autologous stem cell transplant procedure.

In another embodiment, a population of haematopoietic stem cells prepared according to a method of the invention is administered as part of an allogeneic stem cell transplant procedure.

The term "autologous stem cell transplant procedure" as used herein refers to a procedure in which the starting population of cells (which are then transduced according to a method of the invention) is obtained from the same subject as that to which the transduced cell population is administered. Autologous transplant procedures are advantageous as they avoid problems associated with immunological incompatibility and are available to subjects irrespective of the availability of a genetically matched donor.

The term "allogeneic stem cell transplant procedure" as used herein refers to a procedure in which the starting population of cells (which are then transduced according to a method of the invention) is obtained from a different subject as that to which the transduced cell population is administered. Preferably, the donor will be genetically matched to the subject to which the cells are administered to minimise the risk of immunological incompatibility.

Suitable doses of transduced cell populations are such as to be therapeutically and/or prophylactically effective. The dose to be administered may depend on the subject and condition to be treated, and may be readily determined by a skilled person.

Haematopoietic progenitor cells provide short term engraftment. Accordingly, gene therapy by administering transduced haematopoietic progenitor cells would provide a non-permanent effect in the subject. For example, the effect may be limited to 1-6 months following administration of the transduced haematopoietic progenitor cells.

Such haematopoietic progenitor cell gene therapy may be suited to treatment of acquired disorders, for example cancer, where time-limited expression of a (potentially toxic) anti-cancer nucleotide of interest may be sufficient to eradicate the disease.

The present invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated of receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimoorchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

In addition, or in the alternative, the invention may be useful in the treatment of β-thalassemia, chronic granulomatous disease, metachromatic leukodystrophy, mucopolysaccharidoses disorders and other lysosomal storage disorders.

Kit

In one aspect, the invention provides a kit comprising an agent which promotes homology directed DNA repair and/or cell populations of the invention.

In another aspect, the present invention provides a kit comprising an agent which promotes homology directed DNA repair, one or more nucleotide sequences encoding gene editing machinery and means for selecting haematopoietic stem cells.

The agent which promotes homology directed DNA repair, and/or cell populations may be provided in suitable containers.

Suitably, the kit may comprise an inhibitor of p53 activation.

Suitably, the kit may comprise a nucleic acid sequence encoding at least one adenoviral protein The kit may also include instructions for use.

Method of Treatment

It is to be appreciated that all references herein to treatment include curative, palliative and prophylactic treatment; although in the context of the invention references to preventing are more commonly associated with prophylactic treatment. In one embodiment, the treatment of mammals, particularly humans, is preferred. Both human and veterinary treatments are within the scope of the invention.

The skilled person will understand that they can combine all features of the invention disclosed herein without departing from the scope of the invention as disclosed.

Administration

Although the agents for use in the invention (in particular, the populations of cells produced by a method of the invention) can be administered alone, they will generally be administered in admixture with a pharmaceutical carrier, excipient or diluent, particularly for human therapy.

Dosage

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

Subject

A "subject" refers to either a human or non-human animal.

Examples of non-human animals include vertebrates, for example mammals, such as non-human primates (particularly higher primates), dogs, rodents (e.g. mice, rats or guinea pigs), pigs and cats. The non-human animal may be a companion animal.

Preferably, the subject is a human.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1—Inhibitors of p53 Activation

Materials and Methods

Vectors and Nucleases

AAV6 donor templates for HDR were generated from a construct containing AAV2 inverted terminal repeats, produced by triple-transfection method and purified by ultracentrifugation on a cesium chloride gradient as previously described (J. Wang et al. 2015 *Nat Biotechnol* 33, 1256-1263). Design of AAV6 donor templates with homologies for AAVS1 locus (encoding for a PGK.GFP reporter cassette) or targeting the intron 1 of IL2RG (encoding for IL2RG corrective cDNA followed by a PGK.GFP reporter cassette was previously reported G. Schiroli et al. 2017 *Sci Transl Med* 9).

Sequences of the gRNAs were designed using an online CRISPR design tool (P. D. Hsu et al. 2013 DNA targeting specificity of RNA-guided Cas9 nucleases. *Nat Biotechnol* 31, 827-832) and selected for predicted specificity score and on target activity. Genomic sequences recognized by the gRNAs are indicated in the Table below. Ribonucleoproteins (RNPs) were assembled by incubating at 1:1.5 molar ratio s.p.Cas9 protein (Aldevron) with synthetic cr:tracrRNA (Integrated DNA Technologies) for 10 minutes at 25° C. Electroporation enhancer (Integrated DNA Technologies) was added prior to electroporation according to manufacturer's instructions.

Sequences of the gRNA are reported below.

| Guide ID | Genomic sequence (5'-3') |
| --- | --- |
| AAVS1 gRNA | GTCACCAATCCTGTCCCTAGTGG (SEQ ID NO. 39) |
| IL2RG gRNA | ACTGGCCATTACAATCATGTGGG (SEQ ID NO. 40) |

GSE56.WPRE construct was cloned from a lentivirus expressing GSE56.WPRE in a pVax plasmid for mRNA in vitro transcription containing a T7 promoter, β-globin 3'UTR and 64 bp-polyA.

Gene Editing of Human CD34$^+$ Cells

CD34+ cells were either freshly purified from human CB after obtaining informed consent and upon approval by the Ospedale San Raffaele Bioethical Committee, or purchased frozen from Lonza. CD34+ cells were edited according to a previously optimized protocol (Schiroli et al. 2017 supra).

Briefly, $5\times10^5$ CD34+ cells/ml were stimulated in serum-free StemSpan medium (StemCell Technologies) supplemented with penicillin, streptomycin, glutamine, 1 μM SR-1 (Biovision), 50 μM UM171 (STEMCell Technologies), 10 μM PGE2 added only at the beginning of the culture (Cayman), and human early-acting cytokines (SCF 100 ng/ml, Flt3-L 100 ng/ml, TPO 20 ng/ml, and IL-6 20 ng/ml; all purchased from Peprotech). After 3 days of prestimulation, cells were washed with PBS and electroporated using P3 Primary Cell 4D-Nucleofector X Kit and program EO-100 (Lonza). Cells were electroporated with 2.5-1.25 μM of RNPs.

Transduction with AAV6 was performed at a dose of $1\text{-}2\times10^4$ vg/cell 15' after electroporation. GSE56 mRNA was utilized where indicated at a dose of 150 μg/ml. Gene editing efficiency was measured from cultured cells in vitro 3 days after electroporation by flow cytometry measuring the percentage of cells expressing the GFP marker or by digital droplet PCR analysis designing primers and probe on the junction between the vector sequence and the targeted locus and on control sequences utilized as normalizer as previously described (Schiroli et al. 2017 supra).

CD34+ HSPC Xenotransplantation Studies in NSG Mice

NOD-SCID-IL2Rg$^{-/-}$ (NSG) mice were purchased from The Jackson Laboratory and were maintained in specific-pathogen-free (SPF) conditions. The procedures involving animals were designed and performed with the approval of the Animal Care and Use Committee of the San Raffaele Hospital (IACUC #749) and communicated to the Ministry of Health and local authorities according to Italian law.

For transplantation, $3\times10^5$ CD34+ cells treated for editing at day 5 of culture were injected intravenously into NSG mice after sub-lethal irradiation (150-180 cGy). Sample size was determined by the total number of available treated and quantified by capillary electrophoresis on LabChip GX Touch HT (Perkin Elmer) according to the manufacturer's instructions.

For digital droplet PCR analysis, 5-50 ng of genomic DNA were analyzed in duplicate using the QX200 Droplet Digital PCR System (Biorad) according to the manufacturer's instructions.

For HDR ddPCR, primers and probes were designed on the junction between the vector sequence and the targeted locus and on control sequences used for normalization (human TTC5 genes). Thermal conditions for annealing and extension were adjusted for each specific application as follows: AAVS1/Intron 1 IL2RG HDR 3' integration junction ddPCR: 55° C. for 30 sec, 72° C. for 2 min. Primers and probes for PCR and ddPCR amplifications are shown below.

| Description | Orientation | Sequence (5'-3') |
|---|---|---|
| NHEJ AAVS1 | FW | CTTCAGGACAGCATGTTTGC (SEQ ID NO. 41) |
| | RV | ACAGGAGGTGGGGGTTAGAC (SEQ ID NO. 42) |
| NHEJ Intron 1 | FW | CACCCTCTGTAAAGCCCTGG (SEQ ID NO. 43) |
| IL2RG | RV | AAGAAATCTAGATTGGGGAG (SEQ ID NO. 44) |
| Intron 1 IL2RG 3' | FW | CTAGATTGGGGAGAAAATGA (SEQ ID NO. 45) |
| integration junction | RV | GTGGGAAGGGGCCGTACAG (SEQ ID NO. 46) |
| ddPCR | Probe (FAM) | GTAGCTCCTATGCTAGGCGTAGCC (SEQ ID NO. 47) |
| AAVS1 3' | FW | GATTGGGAAGACAATAGCAG (SEQ ID NO. 48) |
| integration junction | RV | TCTTGGGAAGTGTAAGGAAG (SEQ ID NO. 49) |
| ddPCR | Probe (FAM) | CCAGATAAGGAATCTGCCTA (SEQ ID NO. 50) |
| Human TTC5 ddPCR | (HEX) | PrimePCR ddPCR Copy Number Assay: TTC5, Human (Biorad) |
| CDKN1A | Probe (FAM) | Hs00355782_m1 (Life Technologies) |
| HPRT1 | Probe (FAM) | Hs99999909_m1 (Life Technologies) |
| | Probe (FAM) | Hs02800695_m1 (Life Technologies) |
| RPS27L | Probe (FAM) | Hs00955038_g1 (Life Technologies) |
| APOBEC3H | Probe (FAM) | Hs00419665_m1 (Life Technologies) |
| PHLDA3 | Probe (FAM) | Hs00385313_m1 (Life Technologies) | cells. Mice were attributed to each experimental group randomly. Human CD45+ cell engraftment and the presence of gene-edited cells were monitored by serial collection of blood from the mouse tail and, at the end of the experiment (>20 weeks after transplantation), BM and spleen were harvested and analyzed.

Molecular Analyses

For molecular analyses, genomic DNA was isolated with DNeasy Blood & Tissue Kit or QIAamp DNA Micro Kit (QIAGEN) according to the number of cells available. Nuclease activity (IL2RG intron 1, AAVS1) was measured by mismatch-sensitive endonuclease assay by PCR-based amplification of the targeted locus followed by digestion with T7 Endonuclease I (NEB) according to the manufacturer's instructions. Digested DNA fragments were resolved For gene expression analyses, total RNA was extracted using the RNeasy Plus Micro Kit (QIAGEN). cDNA was synthetized with SuperScript VILO IV cDNA Synthesis Kit (Invitrogen) and used for Q-PCR in a Viia7 Real-time PCR thermal cycler using TaqMan Gene Expression Assays (Applied Biosystems) mapping to CDKN1A, RPS27L, PHLDA3, APOBEC3H, and HPRT as normalizer. The relative expression of each gene was first normalized to HPRT expression and then represented as fold change relative to the mock-treated sample.

Flow Cytometry

For immunophenotypic analyses (performed on FACSCanto II; BD Pharmingen), we used the antibodies listed below. Single stained and Fluorescence Minus One stained cells were used as controls. LIVE/DEAD Fixable Dead Cell Stain Kit (Thermo Fisher), 7-aminoactinomycin (Sigma Aldrich), were included in the sample preparation for flow cytometry according to the manufacturer's instructions to exclude dead cells from the analysis. Cell sorting was performed using MoFlo XDP Cell Sorter (Beckman Coulter) or FACSAria Fusion (BD Biosciences).

| Anti-Human Antibody | Fluorochrome | Clone | Company |
|---|---|---|---|
| Annexin V | PB | | Biolegend |
| CD16/32 | none | | Miltenyi Biotec |
| CD133/2 | PE | 293C3 | Miltenyi Biotec |
| CD34 | PB | AC136 | Miltenyi Biotec |
| CD34 | PECy7 | 8G12 | BD |
| CD90 | APC | 5E10 | BD |
| CD132 | APC | TUGm2 | Biolegend |
| CD45 | PB | HI30 | Biolegend |
| CD45 | APCH7 | HI30 | eBioscience |
| CD19 | PE | HIB19 | BD |
| CD19 | Pecy7 | HIB19 | Biolegend |
| CD3 | Pecy7 | HIT3a | Biolegend |
| CD3 | PE | SK7 | BD |
| CD13 | APC | WM15 | BD |
| CD33 | PeCy7 | P67.6 | BD |
| CD38 | APC | HB7 | BD |
| CD38 | Percp5.5 | HB7 | Biolegend |
| CD4 | PB | RPA-T4 | BD |
| CD8 | APCH7 | SK1 | BD |
| CD235a | PE | JC159 | Dako |

Single-Cell RNA-Sequencing and Analyses

Droplet-based digital 3' end scRNA-Seq was performed on a Chromium Single-Cell Controller (10× Genomics) using the Chromium Single Cell 3' Reagent Kit v2 according to the manufacturer's instructions. 24 hrs after the editing treatment, CD34+ cells were sorted according to surface expression of CD34+ CD133+ CD90+ and CD34+ CD133+ CD90−; viable cells were counted with Trypan Blue solution 0.4% (Gibco) and 5200 viable cells (2700 from each population) were utilized for the subsequent procedure (estimated recovery: 3000 cells/sample). Briefly, single cells were partitioned in Gel Beads in Emulsion (GEMs) and lysed, followed by RNA barcoding, reverse transcription and PCR amplification (12-14 cycles, according to the available cDNA quantity). scRNA-Seq libraries were prepared according to the manufacturer's instructions, checked and quantified on LabChip GX Touch HT (Perkin Elmer) and Qubit 3.0 (Invitrogen) instruments. Sequencing was performed on a NextSeq 500 machine (Illumina) using the NextSeq 500/550 High Output v2 kit (75 cycles).

Fastq files were processed with Cell Ranger (v. 1.3, https://support.10×genomics.com/single-cell-gene expression/software/pipelines/latest/what-is-cell-ranger) using default parameters. Reads were aligned to reference genome hg19.

Reads processing: Gene counts were processed with Seurat (v 2.3.1, http://satijalab.org/seurat/). Cells expressing less than 200 unique genes and genes expressed in less than 3 cells/sample were discarded. Counts were normalized using Seurat function NormalizeData with default parameters. Genes with a mean expression lower than 0.01 were excluded. Cells with a ratio of mitochondrial versus endogenous genes expression exceeding 0.15 were also excluded. Expression data were than scaled using ScaleData function, regressing on difference between S and G2M scores. Cell cycle scores were calculated using CellCycleScoring function. Multi-Set Canonical Correlation Analysis (mCCA) A. Butler et al. 2018 *Nat Biotechnol* 36, 411-420 was then performed for all the samples. For mCCA computation, a list of genes differentially expressed between cultured CD34+

CB-derived primitive and committed cellsI. Fares et al. 2017 *Blood* 129, 3344-3351 was used as input, and the first 20 dimensions were aligned.

Differential expression analysis: Genes differentially expressed across different conditions were identified using FindMarkers function, using MAST test G. Finak et al. 2015 *Genome Biol* 16, 278 with Bonferroni correction. avglogFC was computed adding to averaged pseudocount expression values of 0.001 and only genes expressed in at least 1% of cells in at least one sample were considered. Gene Ontology enrichment analysis was then performed on these sets of genes using EnrichR (http://amp.pharm.mssm.edu/Enrichr/).

Results

Figure 1:
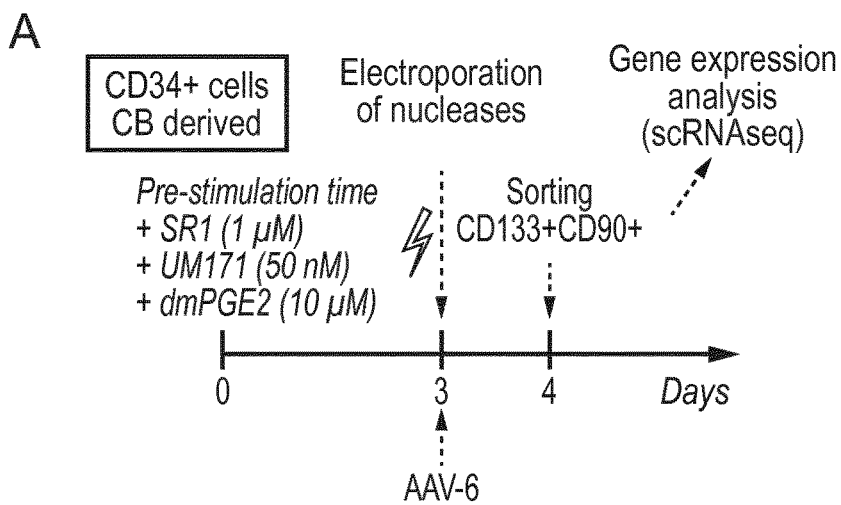
FIG. 1. Single cell transcriptional impact of gene editing in HSPC. (A) Schematic representation of the gene editing protocol and scRNA-Seq analyses. Briefly, ~3000 cells for each experimental condition were FACS-enriched for CD133+ and CD90+ surface markers and subsequently collected for Drop-seq analysis at 24 hrs after electroporation. (B) Reactome analysis on the top 100 genes (ranked by log 2-fold change (2FC)) up-regulated in scRNA-Seq data comparing edited vs. mock treated CD34+ cells. (C) Heatmap showing the expression level of a list of p53-activated genes retrived from *M. Fischer* 2017 *Oncogene* 36, 3943-3956 in single cells edited with RNP+AAV6 or Mock-treated. (D) Fold expression of CDKN1A relative to mock control measured 24 hrs after electroporation of CD34+ cells treated as indicated (RNP+ssODN n=3, other conditions n=5).
Figure 1:
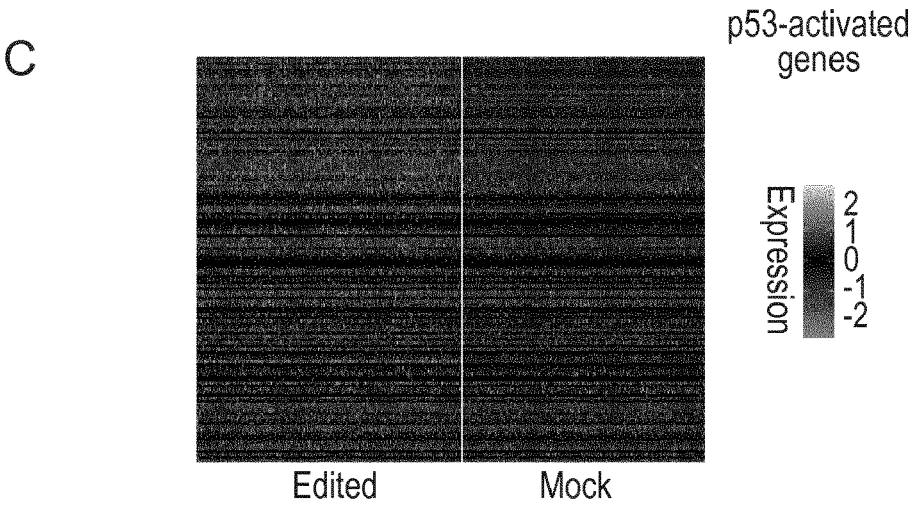
Figure 1:
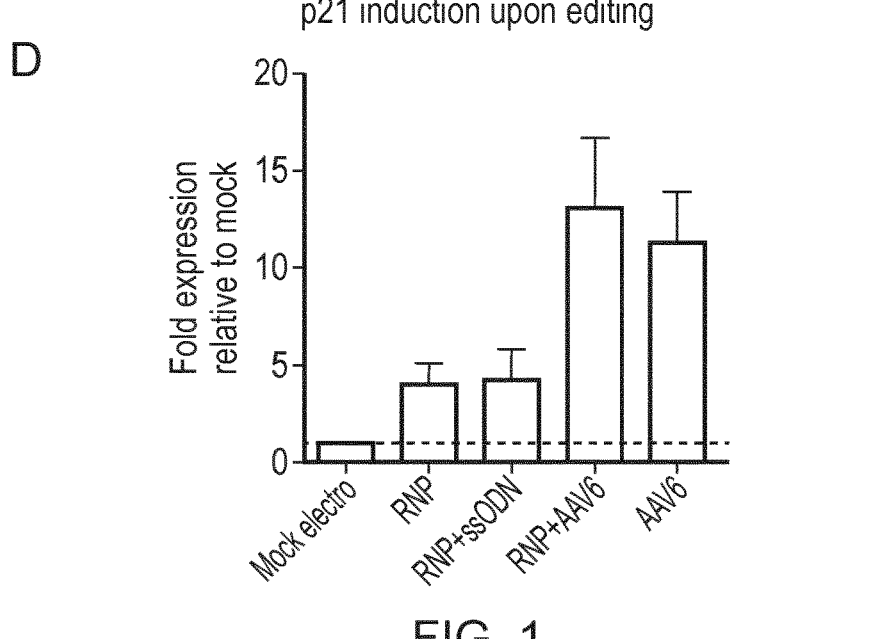

Gene Editing of HSPCs Causes Deregulation of the p53-Related Transcriptional Response To dissect the impact of gene editing procedure on human HSPC in an unbiased manner, we performed single-cell (sc) RNA-Seq on primitive HSPCs populations enriched for CD133 and CD90 surface markers at 24 hrs time point after the editing procedure (FIG. 1A).

Using a droplet-based approach (G. X. Zhenget al. 2017 *Nat Commun* 8, 14049) we generated scRNA-Seq data from cells treated with RNP specific for IL2RG and AAV6 as DNA template for HDR or mock treated as negative control. By performing pathway analysis of the genes found differentially expressed between edited and control cells, the top enriched pathways are related to p53 transcriptional activity (FIG. 1B-C). This p53-related transcriptional response was mildly triggered after the DNA DSB induced by the nucleases, and mostly related to the transduction with AAV6 vector, which are reported to broadly interact with the host cell DDR machinery (M Fragkos et al. 2009 *Mol Cell Biol* 29, 2828-2840), as measured by the induction of p21 expression shortly after the editing procedure (FIG. 1D).

Transient p53 Inhibition by Pifithrin-α or Derivatives Thereof Improve HDR Efficiency and Increases Gene Editing in Primitive Cell Compartment Since we showed that the most deregulated genes in edited HSPC converge significantly into the DDR and in particular into the p53 signaling pathway, we further investigated the functional consequences of this response on HSPC self-renewal, survival, and DNA repair choice in gene edited cells.

We thus tested transient p53 inhibition by the addition of pifithrin-α or derivatives (pifithrin-α cyclic and pifithrin-α p-nitro), molecules which are reported to inhibit p53-mediated apoptosis and p53-dependent gene transcription (P. G. Komarov et al. 1999 *Science* 285, 1733-1737 and K. I. Lenova et al. 2010 *Cell Cycle* 9, 1434-1443) (FIG. 2A). By adding the molecules one day before viral transduction in the gene editing protocol, we were able to measure an increase in HDR efficiency with all the three compounds (FIG. 2B). For further experiments we selected the pifithrin-α cyclic compound, which had the lowest cellular toxicity, and showed a two-fold in increase in gene editing in the most primitive CD34+ CD133+ CD90+ cell compartment, which are basally endowed with the highest p53 transcriptional activity (V. Pant et al. 2012 *Blood* 120, 5118-5127) and in DNA repair by NHEJ, possibly due to higher survival of edited cells (FIG. 2C).

Transient p53 Inhibition by a Dominant Negative Peptide Promotes the HDR Response and, Causes Expansion of the Primitive Subset without Impacting on Cell Differentiation We transiently inhibited p53 transcriptional activity by mRNA overexpression of a dominant negative peptide (GSE56) (M. Milyavsky et al. 2010 *Cell stem cell* 7, 186-197) during the electroporation procedure (FIG. 3A).

By addition of GSE56 we were able to reduce the amplitude of the p53-dependent transcriptional response, as measured by expression level of some downstream target genes found highly upregulated by the gene editing procedure (FIG. 3B). This treatment did not negatively impact overall efficiency of DNA repair and promoted HDR-mediated integration at the targeted locus (FIG. 3C, left panel) especially in the most primitive cell compartment (mean 42% in the CD34+ 133+ 90+ fraction; FIG. 3D, right panel), consistently with p53-mediated control of DNA repair choice (23). HSPC treated with GSE56 showed higher expansion (FIG. 3D), compatibly with the reduced induction of cell cycle inhibitors, and there was no change in relative composition of the hematopoietic populations measured at 3 days post editing in edited cells compared to untreated controls (FIG. 3E), suggesting effective proliferation of primitive cells without overt induction of differentiation. Upon seeding sorted populations in CFU-C assay, erythroid and myeloid clonogenic output was increased particularly in CD90+ fraction (FIG. 3F), indicating increased expansion potential of the most primitive subset, without impacting on cell differentiation of the treated cells.

Figure 4:
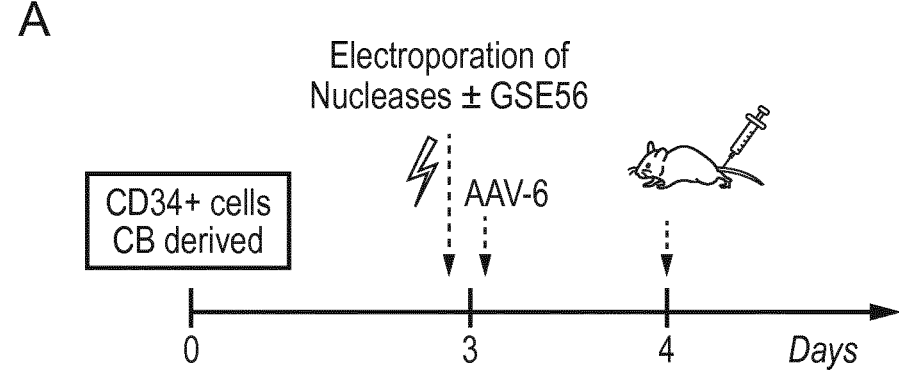
FIG. 4. Dampening the transcriptional signature induced by gene editing increases HSPC long-term repopulation capacity. (A) Schematic representation of the gene editing protocol±GSE56 and transplantation in NSG mice. (B) Human CD45+ engraftment of IL2RG edited cells in presence (n=6) or not GSE56 mRNA (n=5) measured at the indicated times in the PB of transplanted NSG mice. (C) Percentage of human lymphoid (CD19+ and CD3+) and myeloid (CD13+) populations measured in the PB of mice from (B). (D) Percentage of GFP+ cells measured in the indicated human PB populations in mice from (B).
Figure 4:
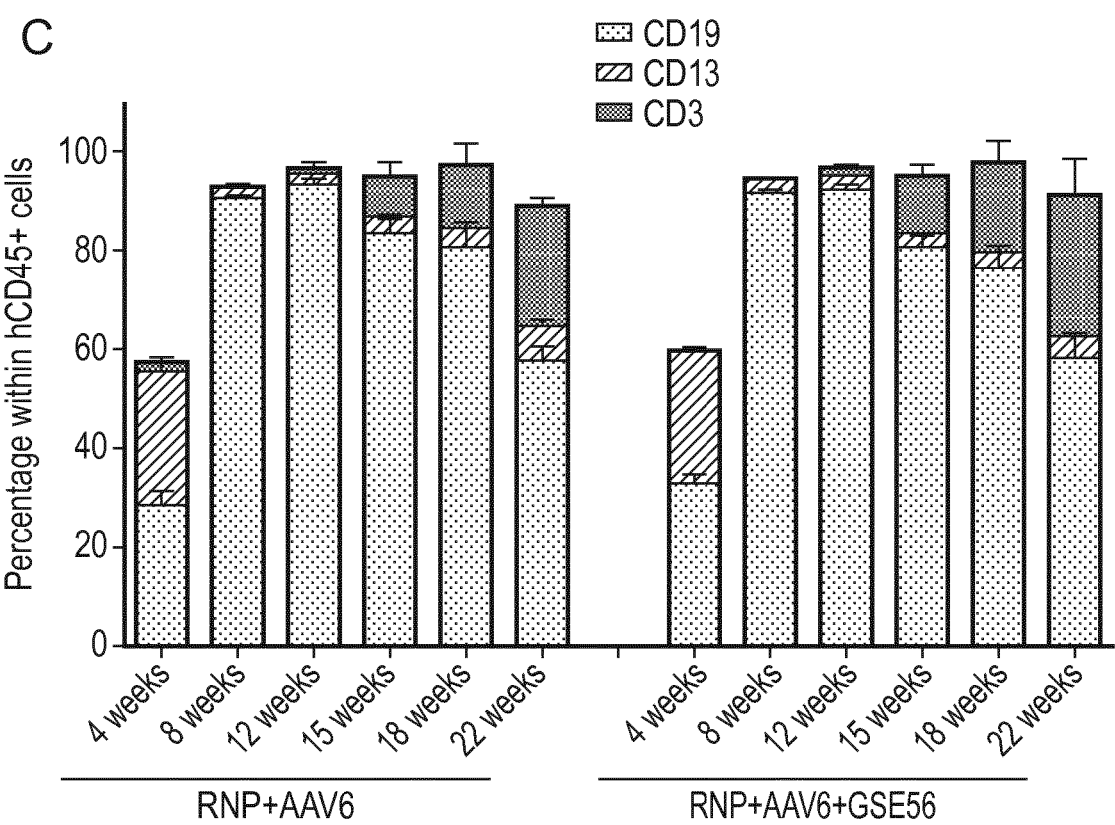
Figure 4:
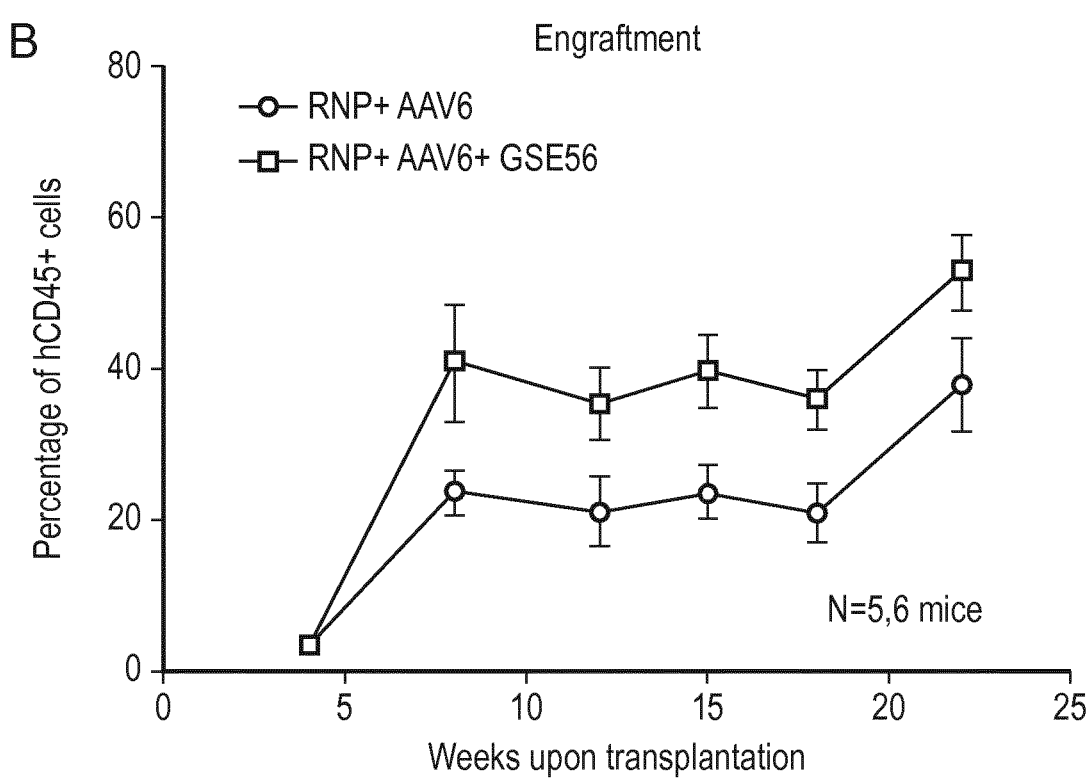
Figure 4:
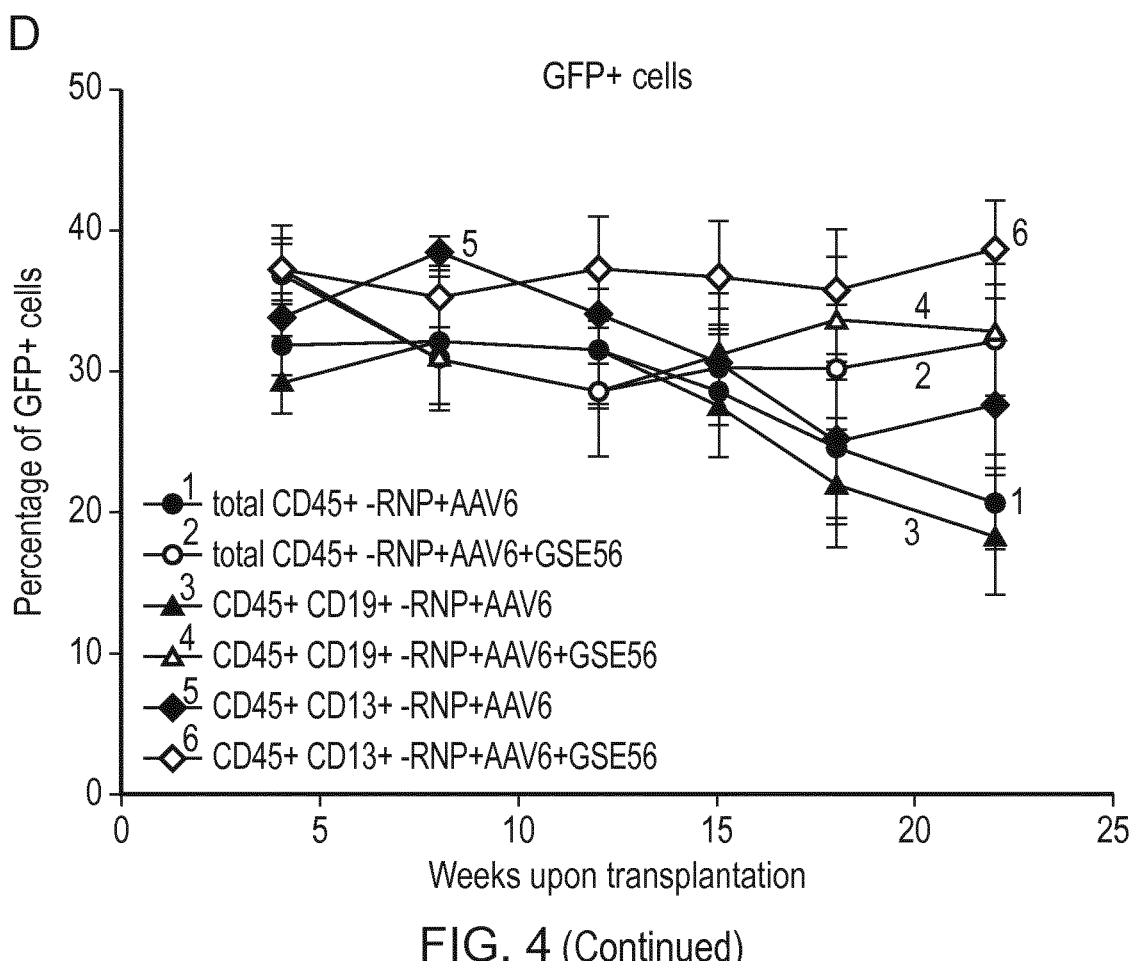

Edited Cells Treated with GSE56 Show Increased Engraftment without Skewing Differentiation in Immunodeficient NSG Mice We then performed transplantation of the edited cells into immunodeficient NSG mice, which represent a surrogate assay for long-term repopulating HSC (FIG. 4A). Edited cells treated with GSE56 showed increased engraftment (FIG. 4B), without any skewing in the differentiation output (FIG. 4C). Interestingly, while the fraction of HDR-edited cells slightly decreased over time in mice transplanted with cells edited with conventional protocol, as previously reported (Schiroli et al. 2017 supra and S. S. De Ravin 2017 *Science translational medicine* 9), by transient p53 inhibition it remained stable at long-term, reaching an average of 32% in the PB at 22 weeks post transplantation (FIG. 4D).

Overall, these results indicate that p53-dependent transcriptional response contributes to reduce the repopulation capacity of gene edited cells, and its transient reduction could help to better preserve the long-term function of the most primitive HSPC compartments.

Example 2—Adenoviral Proteins

Materials and Methods

Vector

AAV stocks were produced by triple transfection of the plasmids carrying the cassette of interest framed by deleted AAV-ITRs, the Rep2 and Cap6 protein coding sequences and the adenoviral helper genes in HEK293-T cell line. Transfected cells are collected 48 hours later and purified over cesium chloride gradients (Wang, J. et al. (2015) Nat Biotechnol 33: 1256-1263). Titers of the viral stocks were determined by qPCR of AAV genomes (vg/ml). The design of AAV-6 donor templates including homology sequences for AAVS1 locus (encoding for the PGK-GFP reporter cassette) or intron 1 within IL2RG locus (encoding for the IL2RG corrective cDNA followed by the PGK-GFP reporter cassette), were previously reported (Schiroli, G. et al. (2017) Sci Transl Med 9) and Schiroli, G. 2019 Celle stem cell The barcoded AAV6 donor template targeting the AAVS1 locus was obtained by subcloning the degenerated sequence into the previously reported AAVS1 AAV6 transfer vector plasmid downstream of the polyadenylation sequence. Briefly, a ssODN embedding the random sequence flanked by the unique cloning restriction sites (Bsu36l and Sphl) was obtained from Sigma Aldrich. The degenerated region was designed to avoid any undesired cutting by cloning restriction enzymes. To generate the complementary strand, 50 pmol of the ssODN were amplified with 10 cycles of PCR with Easy-A High-Fidelity enzyme (Agilent Technologies) using the appropriate forward and reverse primers according to the manufacturer's instructions. The amplified product was purified with MinElute PCR Purification kit (QIAGEN), digested with the restriction enzymes and checked by capillary electrophoresis. 2 μg of the Bsu36l/Sphl-digested AAVS1 HDR donor template were ligated with the digested insert (molar ratio 1:7) using T4 DNA Ligase (NEB) by scaling up the manufacturer's protocol. Finally, XL-10 Gold Ultracompetent Cells (Agilent Technologies) were transformed with the ligation product, plated and incubated for 12 hours of incubation at 30° C. to minimise the risk of recombination. Colonies were scraped, mixed, grown in LB medium for an additional 6 hours and processed with NucleoBond Xtra MaxiPrep according to the manufacturer's instructions. Ultimately, the plasmid prep was screened with restriction enzymes for ITR and plasmid integrity.

Nuclease

Sequences of the gRNAs were designed using an online CRISPR design tool (Hsu, P. D. et al. (2013) Nat Biotechnol 31:827-832) and selected for predicted specificity score and on target activity. Genomic sequences recognised by the gRNAs are indicated in the table below. Ribonucleoproteins (RNPs) were assembled by incubating at 1:1.5 molar ratio SpCas9 protein (Aldevron) with synthetic cr:tracrRNA (Integrated DNA Technologies) for at least 10 min at 25° C. Electroporation enhancer (Integrated DNA Technologies) was added prior to electroporation according to the manufacturer's instructions.

| Guide ID | Genomic sequence (5'-3') |
|---|---|
| AAVS1 gRNA | GTCACCAATCCTGTCCCTAGTGG (SEQ ID NO: 51) |
| IL2RG gRNA | ACTGGCCATTACAATCATGTGGG |

Proteins

E4orf1, E4orf6/7, GSE56/Ad5-E4orf6/7, E4orf6 and E1B55K adenoviral protein sequences derived from wild-type serotype 5 were collected from RCSB PDB and UniProt online databanks. Moreover, a multiple-sequence alignment was performed among various Adenovirus serotypes for each adenoviral protein family E4orf1 and E4orf6/7 using the T-Coffee algorithm (Notredame, C. et al. (2000) J. Mol. Biol. doi: 10.1006/jmbi.2000.4042) to select some variants. All sequences were synthesised with codon optimisation for *Homo sapiens* (GeneArt™). Each construct was cloned in a "pVax" plasmid for mRNA in vitro transcription containing a T7 promoter, WPRE or 3'UTR and 64 bp-polyA. pVax was linearised with the restriction enzyme (Spel) and purified using phenol-chloroform. RNA was in vitro transcribed using the commercial 5×MEGAscript T7 kit (Invitrogen) with slight modifications from the manufacturer's protocol as by adding ARCA (BioLabs). Synthetic RNA was purified using the RNeasy Plus Mini Kit (Qiagen)

followed by HPLC column purification to remove RNA contaminants and reagents. RNA was finally concentrated using a tube Amicon Ultra-15 (30K) (Millipore).

Gene Editing Protocol in Human HSPCs

CD34$^+$ cells were purchased frozen from Lonza. CD34$^+$ cells were edited according to a previously optimised protocol (Schiroli, G. et al (2017) Sci Transl Med 9). Briefly, 1-5×10$^5$ CD34$^+$ cells/ml were stimulated in serum-free StemSpan medium (StemCell Technologies) supplemented with penicillin, streptomycin, glutamine, 1 µM of the aryl-hydrocarbon receptor antagonist SR-1 (Biovision), 50 µM of the pyrimidoindole-derivative UM171 (STEMCell Technologies), 10 µM of the 15-hydroxy PGDH competitive inhibitor dmPGE-2 added only at the beginning of the culture (Cayman), and human early-acting cytokines (SCF 100 ng/ml, Flt3-L 100 ng/ml, TPO 20 ng/ml, and IL-6 20 ng/ml; all purchased from Peprotech). After 3 days of pre-stimulation, cells were washed with PBS and electroporated using P3 Primary Cell 4D-Nucleofector X Kit and program EO-100 (Lonza). Cells were electroporated with 1-1.2 µM of RNPs. Where specified, electroporation mixture was supplemented with Ad5-E4orf1, Ad5-E4orf6/7 and GSE56/Ad5-E4orf6/7 mRNAs, which were respectively utilized at doses of 120, 80 and 200 µg/ml, or Ad5-E1B55K and Ad5-E4orf6 mRNAs were used at 120 and 80 µg/ml. All other adenoviral protein variants were used at standard dose 120 µg/ml. Transduction with AAV-6 was performed 15 min post-electroporation at dose of 1-5×10$^4$ vg/cell. Where specified, CD34+ cells were stimulated for shorter time in culture (0, 24 or 48 hours) and edited as described above. Gene editing efficiency was measured from cultured cells in vitro at 4 days post-editing by flow cytometry measuring the percentage of cells expressing the GFP reporter gene or by digital droplet PCR analysis designing primers and probe on the junction between the vector sequence and the targeted locus and on control sequence utilised as normaliser as previously described (Schiroli, G. et al (2017) Sci Transl Med 9) and Schiroli et al., Cell Stem Cell 2019.

CD34$^+$ Xenotransplantation in NSG Mice

NOD-SCID-IL2Rg$^{-/-}$ (NSG) mice were purchased from The Jackson Laboratory and were maintained in specific-pathogen-free (SPF) conditions. The procedures involving animals were designed and performed with the approval of the Animal Care and Use Committee of the San Raffaele Hospital (IACUC #749) and communicated to the Ministry of Health and local authorities according to Italian law. For transplantation, 1.5-3×10$^5$ (for primary) or 2×10$^6$ (for secondary) CD34$^+$ treated cells at 24 hours post-editing protocol were injected intravenously into NSG mice after sub-lethal irradiation (180 cGy). Sample size was determined by the total number of available treated cells. Mice were attributed to each experimental group randomly. Human CD45$^+$ cell engraftment and the percentage of edited GFP$^+$ cells were monitored by serial collection of blood from the mouse tail over the weeks post-transplantation and at the end of the experiment (18-20 weeks post-transplantation) both spleen and bone-marrow were harvested and analysed.

Molecular Analyses

For molecular analyses, genomic DNA was isolated with DNeasy Blood & Tissue Kit or QIAamp DNA Micro Kit (QIAGEN) according to the number of cells available. Nuclease activity (AAVS1) was measured by mismatch-sensitive endonuclease assay by PCR-based amplification of the targeted locus followed by digestion with T7 Endonuclease I (NEB) according to the manufacturer's instructions. Digested DNA fragments were resolved and quantified by capillary electrophoresis on LabChip GX Touch HT (Perkin Elmer) according to the manufacturer's instructions.

For digital droplet PCR analysis, 5-50 ng of genomic DNA were analysed in duplicate using the QX200 Droplet Digital PCR System (Biorad) according to the manufacturer's instructions.

For HDR ddPCR as for translocations ddPCR, primers and probes were designed on the junction between the vector sequence and the targeted locus and on control sequences used for normalisation (human TTC5 genes). Thermal conditions for annealing and extension were adjusted for each specific application as follows: AAVS1 HDR 3' integration junction ddPCR: 55° C. for 30 sec, 72° C. for 2 min. Primers and probes for PCR and ddPCR amplifications are shown below.

| Description | Orientation | Sequence (5'-3') |
|---|---|---|
| NHEJ AAVS1 | FW | CTTCAGGACAGCATGTTTGC (SEQ ID NO: 52) |
| | RV | GGACTAGAAAGGTGAAGAGCC (SEQ ID NO: 53) |
| AAVS1 3' integration junction ddPCR | FW | GATTGGGAAGACAATAGCAG (SEQ ID NO: 54) |
| | RV | TCTTGGGAAGTGTAAGGAAG (SEQ ID NO: 55) |
| | Probe (FAM) | CCAGATAAGGAATCTGCCTA (SEQ ID NO: 56) |
| ChrX-chr14 translocation ddPCR | FW | GTGGTGACCACCTTAATCCAGTGA |
| | RV | AAGAAATCTAGATTGGGGAG |
| | Probe (FAM) | ATGAAGGCAGGGAGGGAAAGAGAAATGA |
| Human TTC5 ddPCR | (HEX) | PrimePCR ddPCR Copy Number Assay: TTC5, Human (Biorad) |
| CDKN1A | Probe (FAM) | Hs00355782_m1 (Life Technologies) |
| HPRT1 | Probe (FAM) | Hs02800695_m1 (Life Technologies) |
| CDKN2A | Probe (FAM) | Hs00924091_m1 (Life Technologies) |

-continued

| Description | Orientation | Sequence (5'-3') |
|---|---|---|
| APOBEC3H | Probe (FAM) | Hs00419665_m1 (Life Technologies) |
| CDK2 | Probe (FAM) | Hs01548894_m1 (Life Technologies) |

Barcoding Analysis

PCR amplicons for each individual sample were generated by one-step PCR using Taq G2 Hot Start Polymerase (Promega). The forward primer was designed to bind donor template 2 bp upstream the barcode sequence, while the reverse primer annealed outside the homology region, thus amplifying about 350 bp of the on-target integrated cassette. Primers are endowed with tails containing P5/P7 sequence, i5/i7 Illumina tag to allow multiplexed sequencing and R1/R2 primer complementary sequence. PCR library amplicons were separately purified using MinElute PCR Purification kit (QIAGEN) and quality was assessed by Agilent Tapestation (Agilent Technologies). Finally, amplicons were multiplexed and run on Illumina MiSeq paired-end 2×75 bp.

Flow Cytometry

For immunophenotypic analyses (performed on FACSCanto II; BD Pharmingen), we used the antibodies listed below. Single stained and Fluorescence Minus One stained cells were used as controls. LIVE/DEAD Fixable Dead Cell Stain Kit (Thermo Fisher), 7-aminoactinomycin (Sigma Aldrich), were included in the sample preparation for flow cytometry according to the manufacturer's instructions to exclude dead cells from the analysis. Cell sorting was performed using MoFlo XDP Cell Sorter (Beckman Coulter) or FACSAria Fusion (BD Biosciences).

| Anti-Human Antibody | Fluorochrome | Clone | Company |
|---|---|---|---|
| Annexin V | PB | — | Biolegend |
| CD133/2 | PE | 293C3 | Miltenyi Biotec |
| CD34 | PB | AC136 | Miltenyi Biotec |
| CD34 | PECy7 | 8G12 | BD |
| CD90 | APC | 5E10 | BD |
| CD45 | PB | HI30 | Biolegend |
| CD45 | APCH7 | HI30 | eBioscience |
| CD19 | PE | HIB19 | BD |
| CD19 | Pecy7 | HIB19 | Biolegend |
| CD3 | Pecy7 | HIT3a | Biolegend |
| CD3 | PE | SK7 | BD |
| CD13 | APC | WM15 | BD |
| CD33 | PeCy7 | P67.6 | BD |
| CD38 | APC | HB7 | BD |
| CD38 | Percp5.5 | HB7 | Biolegend |
| CD4 | PB | RPA-T4 | BD |
| CD8 | APCH7 | SK1 | BD |

Cell Cycle Analysis

Cell cycle was analysed by flow cytometry (CytoFLEX LX; Beckman Coulter) at 12-24 hours post-editing by collecting $0.5$-$1 \times 10^5$ total HSPCs in culture. Cells were washed with PBS+2% FBS and stained by using 10 μg/ml Hoechst 33342 (Sigma-Aldrich) in PBS+2% FBS for 0.5-1 hour in final volume equal to 200 μl.

Results

Figure 5:
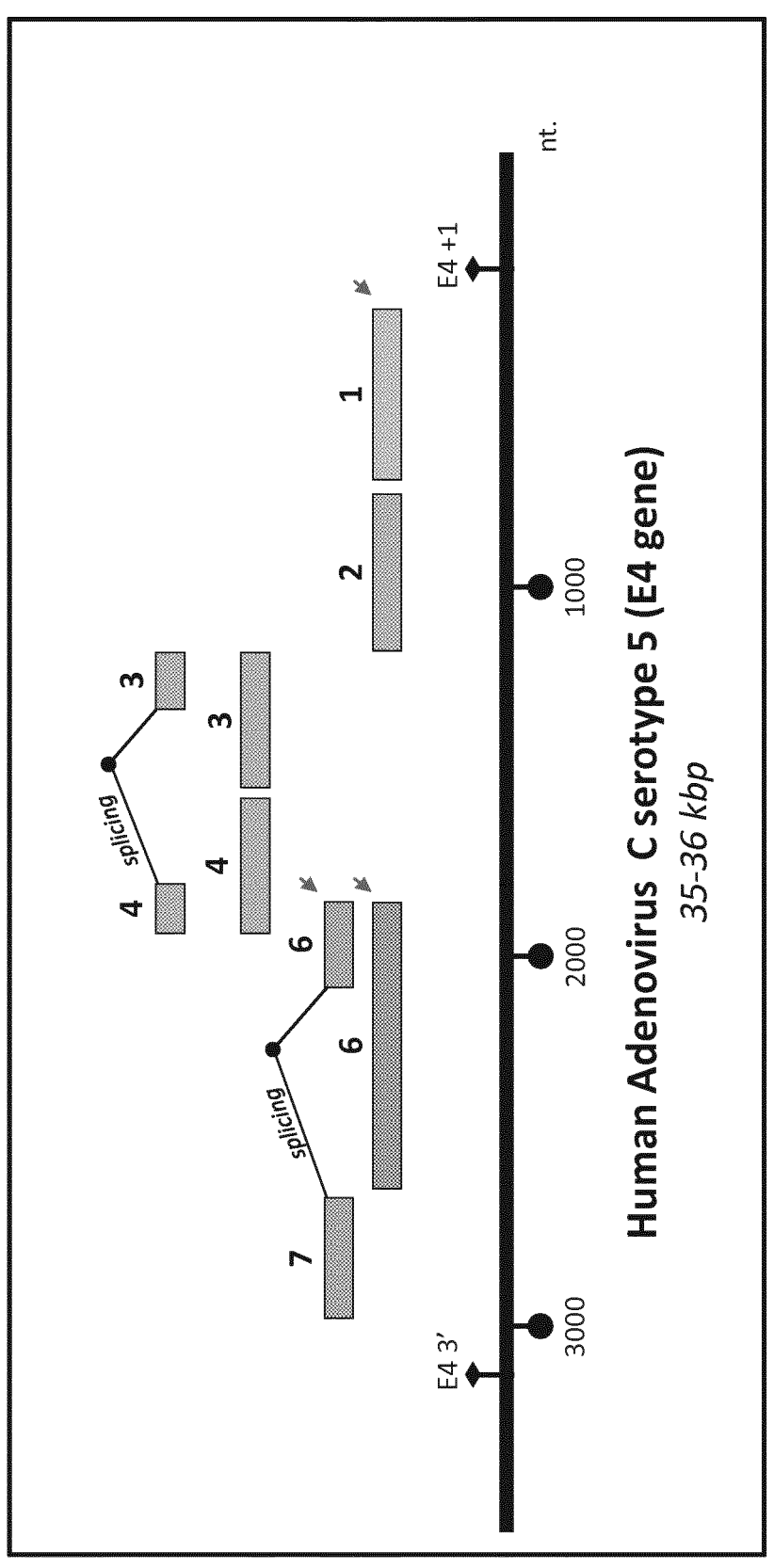
FIG. 5: Scheme of the adenovirus E4 gene. Adenovirus is a natural co-helper of AAV that provides a set of helper genes function (E1a, E1b, E2a, E4) required to optimize AAV infection process. The E4 gene is composed of seven open ORFs that are coding for seven different proteins. We investigated the use of E4orf1 and E4orf6/7 adenoviral proteins to improve gene editing efficiency in HSCs.

Expression of E4Orf1 or E4Orf6/7 During Gene Editing Increases Targeting Efficiency Adenoviruses are natural co-helper of AAV infection and provide a set of helper genes (E1a, E1b, E2a, E4) which function is required to optimize AAV infection process. We were interested to investigate specifically the E4 gene which is composed of 7 open reading frames (ORFs) that are coding for seven different proteins (FIG. 5).

Figure 6:
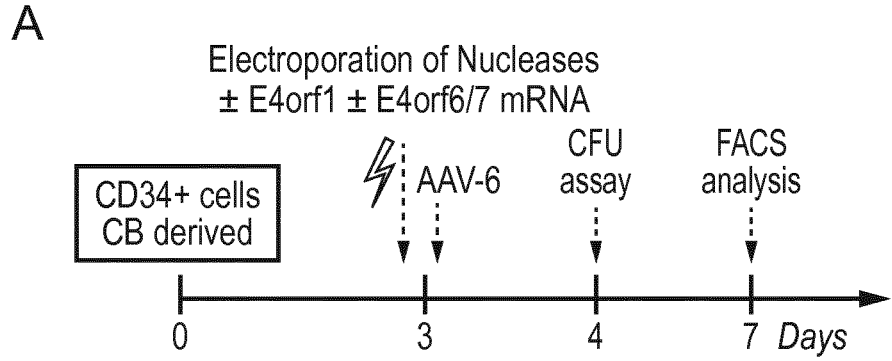
FIG. 6: AAVS1 gene editing in combination with adenoviral E4orf1 and E4orf6/7 proteins. (A) Schematic representation of the gene editing protocol±E4orf1 and/or E4orf6/7 and cell analyses. (B) Percentage of GFP+ cells measured within the indicated subpopulations 4 days after AAVS1 editing of cord blood (CB)-derived CD34+ with Cas9-RNP (25 pmol) in presence (E4orf6/7) or absence (standard) of the adenoviral protein E4orf6/7 mRNA (2 $\mu$g total mRNA) and using increasing doses of AAV6 as donor template, with MOI=$10^4$ vg/cell (n=3), MOI=5×$10^4$ vg/cell (n=12), MOI=$10^5$ vg/cell (n=2). (C) Percentage of GFP+ cells measured within the indicated subpopulations 4 days after AAVS1 editing of CB-derived CD34+ using AAV6 (MOI=5×$10^4$ vg/cell) or IDLV (MOI=200) as donor template, RNP-Cas9 (25 pmol) and supplemented with E4orf6/7 (2 $\mu$g total RNA). (D) Percentage of GFP+ cells measured within the indicated subpopulations 4 days after AAVS1 editing of CB-derived CD34+ using AAV6 as donor template with MOI=5×$10^4$ vg/cell, RNP-Cas9 (25 pmol) and supplemented with crescent dose of E4orf1 (from 1 to 5 $\mu$g total RNA) or E4orf6/7 (from 1 to 5 $\mu$g total RNA).
Figure 6:
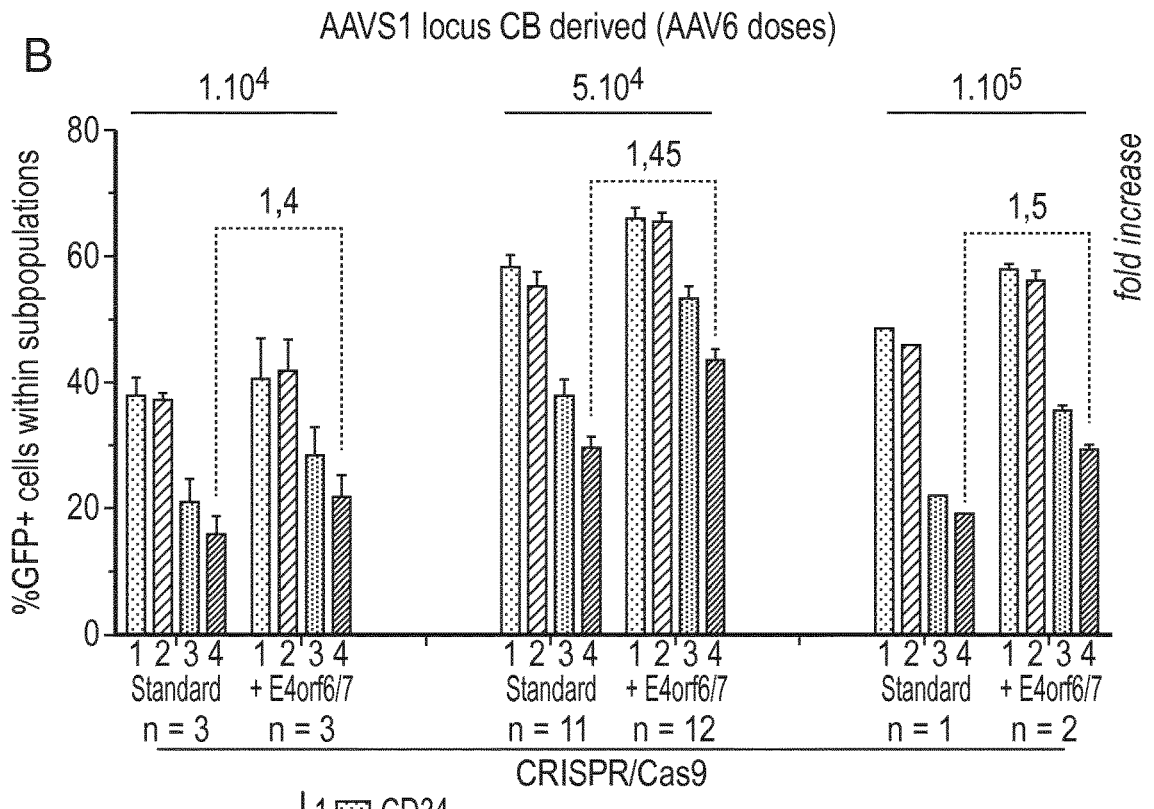
Figure 6:
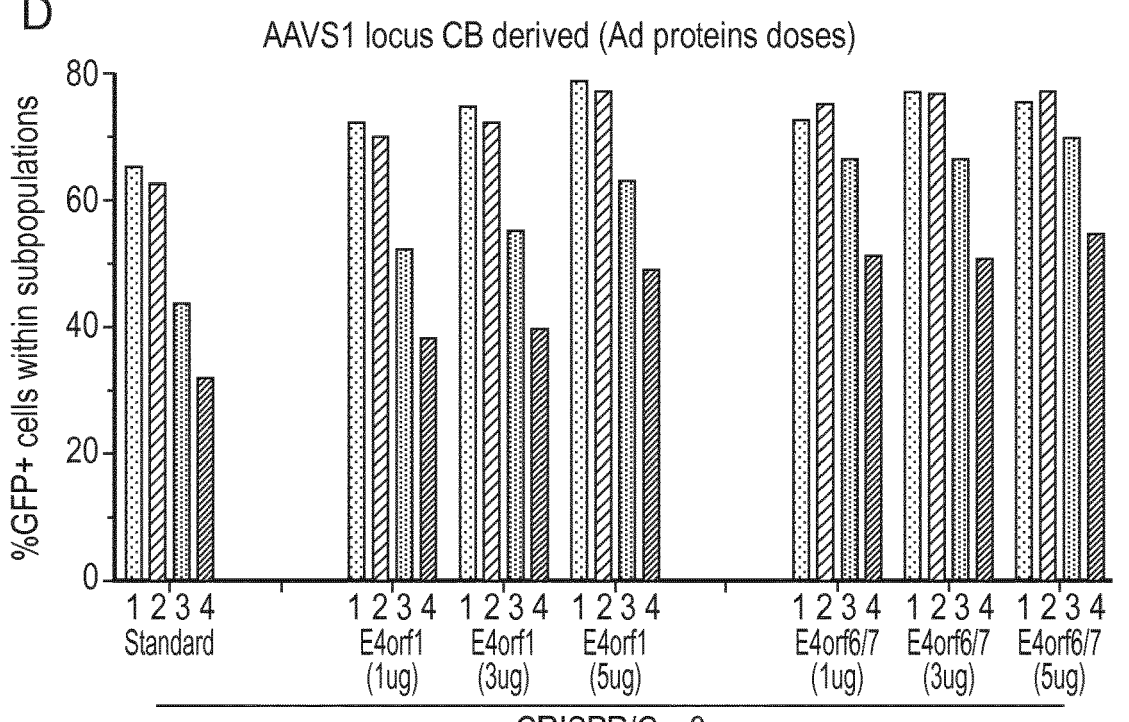

We decided to investigate the use of two adenoviral proteins called E4orf1 and E4orf6/7 derived from the adenovirus serotype 5 (Ad5), which we delivered by electroporation as mRNA together with the Cas9 ribonucleoprotein (RNP) into human HSPC (cord blood derived CD34+ cells) before AAV6 transduction for the delivery of the donor DNA template (FIG. 6A).

By expressing the E4orf6/7 protein during the gene editing procedure, we measured a mean of 1.5-fold increase in the percentage of primitive HSPC that express the GFP reporter gene present in the donor (CD34+CD133+CD90+GFP+). This increase in targeting efficiency was obtained at all the different doses of AAV6 vector used for the transduction of the donor vector (FIG. 6B).

Similar increase in targeted integration was observed in the primitive CD90+ cells also when the donor template was delivered by an Integrase Defective Lentiviral Vector (IDLV; FIG. 6C).

When we delivered different doses of E4orf1 mRNA during the gene editing procedure, we found a dose dependent increase in the targeting efficiency and, with the best performing dose, we measured a mean of 1.5-fold increase in the percentage of targeted primitive HSPC, similar to the increase measured in the conditions with different doses of E4orf6/7 mRNA (FIG. 6D).

Expression of E4Orf1 or E4Orf6/7 Alone and in Combination

We then compared side-by-side the standard gene editing procedure alone or with the addition of the E4orf1, the E4orf6/7 or the combination of both proteins. By cytofluorimetric analysis, we observed that E4orf1 increases the fraction of GFP+ cells to a mean of 1.2-fold compare to the standard and is equivalent in all subpopulations (from the most primitive CD90+ progenitor compartment to the most differentiated CD34− compartment); the E4orf6/7 increases to 1.45-fold the fraction of GFP+ cells mainly in the most primitive HSPC compartment (CD90+); and the combination of them has an additive effect, allowing a mean of 1.55 fold increase in the fraction of GFP+ cells (FIG. 7A).

Figure 7:
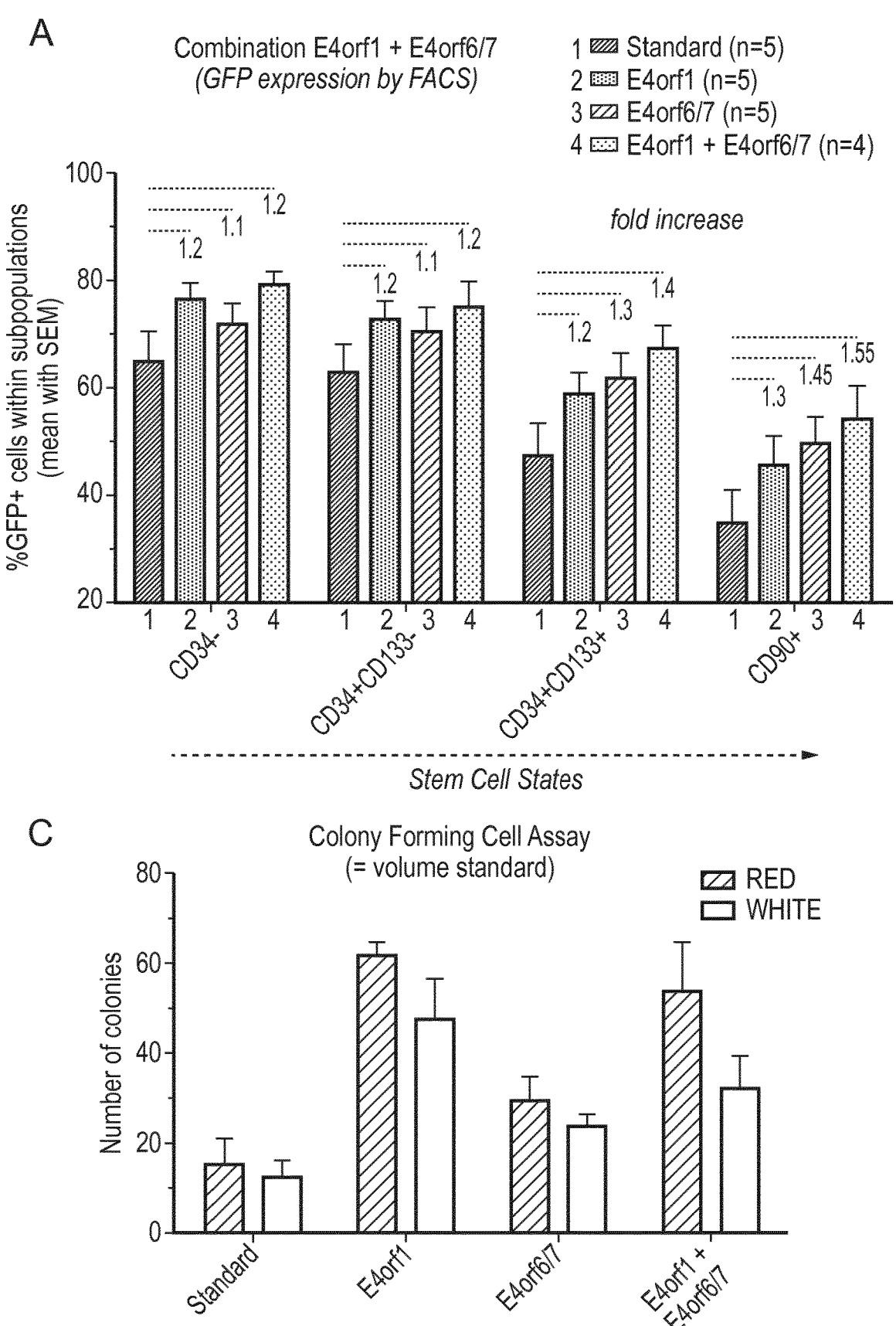
FIG. 7: E4orf1 and E4orf6/7 supplementation to gene editing protocol in human CD34+. (A) Percentage of GFP+ cells measured within the indicated subpopulations 4 days after AAVS1 editing of CB-derived CD34+ using AAV6 as donor template with MOI=5×$10^4$ vg/cell, RNP-Cas9 (25 pmol) and supplemented or not with E4orf1 (3 $\mu$g total RNA) and/or E4orf6/7 (2 $\mu$g total RNA). (B) Percentage of HDR mediated integration measured by ddPCR on the 5' vector-to-genome junction, and GFP+ cells measured by cytofluorimetric analysis within the bulk at 4 days after gene-editing of CB-derived CD34+ using AAV6 as donor template with MOI=5×$10^4$ vg/cell, RNP-Cas9 (25 pmol) and supplemented or not with E4orf1 (3 $\mu$g total RNA) and/or E4orf6/7 (2 $\mu$g total RNA). (C) Colony forming cell assay. Total number of erythroid (n=3), in red, and myeloid (n=3), in white, colonies measured 15 days after plating. (D) Cell growth curve post-electroporation (n=1).
Figure 7:
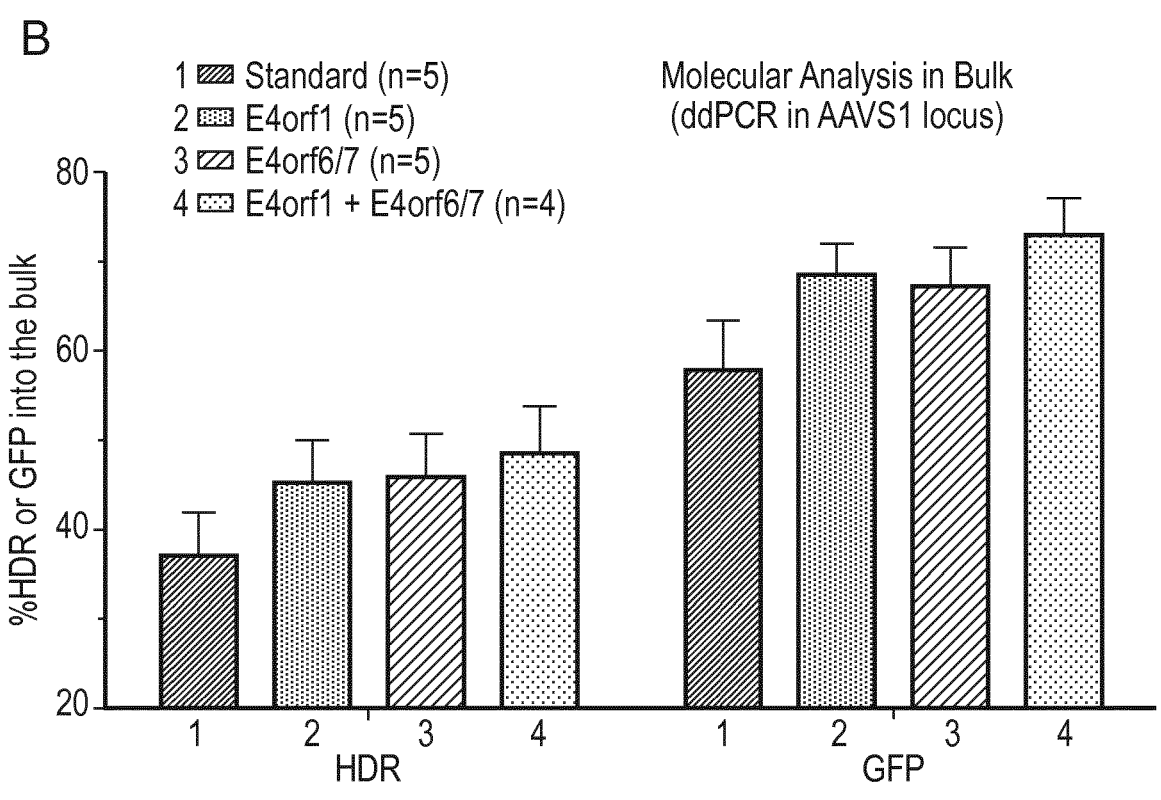
Figure 7:
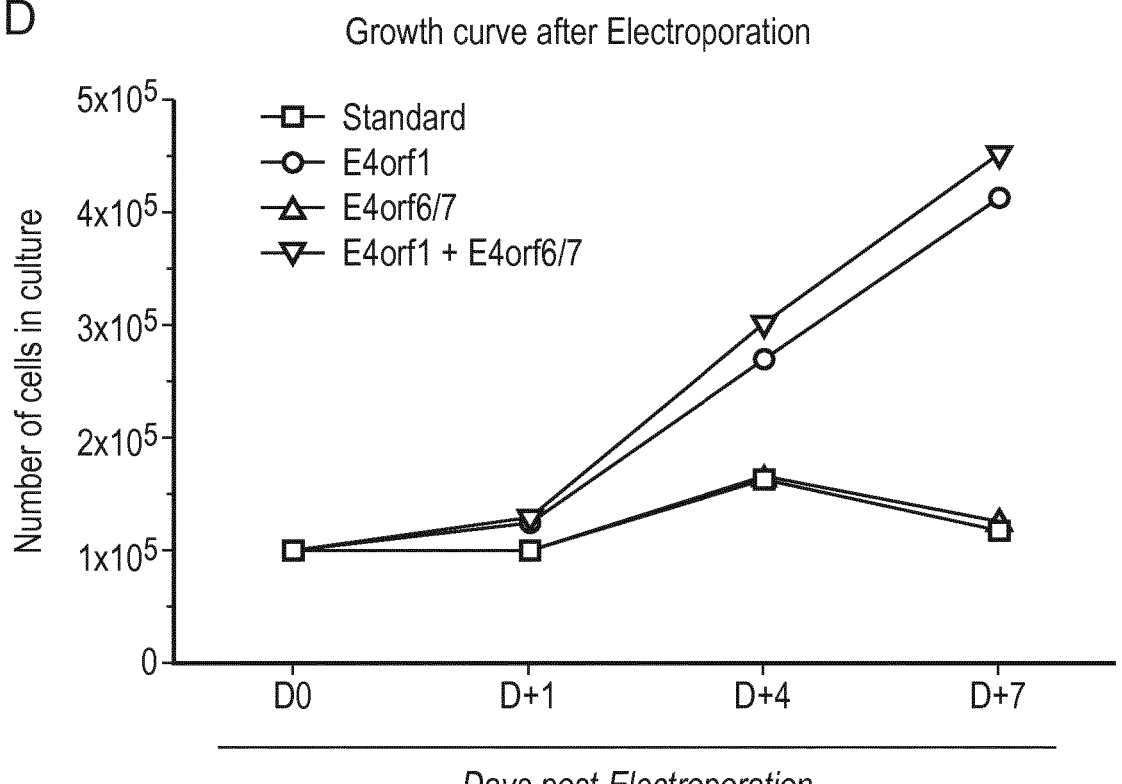

Targeting efficiency was confirmed by digital PCR on the total bulk and compared side-by-side with the total percentage of GFP measured by cytofluorimetric analysis (FIG. 7B).

By performing clonogenic assay, we found that the co-treatment with E4orf1 and E4orf6/7 proteins respectively increase of 3 and 2-fold, the number of both myeloid and erythroid colony forming units (CFU) compared to the standard procedure (FIG. 7C).

Interestingly, the growth curve of the treated cells was 4-fold higher in both the conditions in which E4orf1 was included during the editing compared to the standard and E4orf6/7 alone conditions (FIG. 7D).

A xenotransplantation experiment is on-going in NSG mice to determine long-term engraftment and in-vivo differentiation capacity of edited HSPC treated with these conditions.

Expression of E1B55K and E4Orf6 During Gene Editing

We tested the use of E1B55K and E4orf6 proteins for the editing of human HSPC and compared them in parallel with E4orf1 and E4orf6/7 proteins.

We found that the combination of E1B55K and E4orf6 allow only a transient increase up to 1.45-fold in the fraction of GFP+ cells mainly in the most primitive HSPC compartment, probably due to an increase in transduction that results in a higher expression of the GFP reporter from the nonintegrated vector (FIG. 8A).

Molecular analyses on the genomic DNA extracted from these treated cells confirmed that the E1B55K and E4orf6 proteins are not effective in increasing the editing efficiency on human HSPC, while both E4orf1 and E4orf6/7 proteins were reproducibly able to boost editing in this cell type (FIG. 8B).

By performing clonogenic assay, we did not observe major changes in terms of number of both myeloid and erythroid colony forming units (CFU) compared to the standard condition (FIG. 8C).

Interestingly, the growth curve of the treated cells with the combination E1B55K and E4orf6 was lower compared to the standard, that could point out a certain toxicity due to the use of this combination (FIG. 8D).

Delivery of E4Orf6/7 with Cas9 Improves HDR-Driven Integration in Human Primary T Cells Finally, we tested the delivery of the E4orf6/7 mRNA together with the Cas9 ribonucleoprotein (RNP) into human primary T cells (peripheral blood derived total CD3+ cells) before AAV6 transduction for the delivery of the donor DNA template (FIG. 9A).

By analyzing the cells 20 days after treatment, we found a 1.5-fold increase in the percentage of GFP+ cells expression in the cells treated with the E4orf6/7 compared to standard condition, both in the bulk treated CD3+ cells and in the CD4 and CD8 subpopulation (FIG. 9B).

These results indicate that the E4orf6/7 protein allow boosting HDR-driven integration in different primary human cells.

Edited Cells Treated with E4Orf6/7 mRNA Transplanted into Immunodeficient NSG Mice Increase HDR-Driven Integration in the Most Primitive HSPC Compartments and Preserves Long-Term Repopulation Capacity With the best performing doses of AAV6 donor and E4orf6/7 mRNA, we repeated the gene editing experiment with the aim to perform transplantation of the cells into NSG mice, which represents a surrogate assay for long-term repopulating HSC (FIG. 10A).

Edited cells treated with E4orf6/7 showed a 1.4-fold increase in the percentage of targeted CD90+ cells (FIG. 10B), and without any skew in the culture composition (FIG. 10C).

Molecular analyses performed on the genomic DNA extracted from the treated cells confirmed increase levels of HDR-mediated integration and a similar amount of NHEJ induced mutation, when comparing the E4or6/7 and the standard conditions (FIG. 10D).

These cells were transplanted one day after electroporation into NSG mice, and their engraftment was longitudinally followed by serial blood analyses. The results indicate that while the co-treatment with E4orf6/7 does not affect the overall level of engraftment of the human cells, the mice transplanted with the E4orf6/7 treated cells showed a significant higher fraction of edited cells (measured as percentage of GFP+ or HDR+ cells) in the blood, in the hematopoietic organs and in different blood lineages (FIG. 11).

Overall, these results indicate that transient expression of the E4orf6/7 protein during the gene editing procedure increase the levels of HDR-driven integration in the most primitive HSPC compartments while preserving their long-term repopulation capacity.

Example 3

We investigated whether transient overexpression of the p53 inhibitor (GSE56) during editing procedure altered the proportion of cells in S/G2/M phases of the cell cycle. By performing Hoechst cell-cycle analysis 24 hours after the gene editing procedure, we found a trend towards reduction of the percentage of cells in S/G2/M phases in standard compared to untreated controls, which was partially rescued when cells were edited in presence of GSE56 (FIG. 12A). To evaluate whether the improved yield of HDR-edited cells in vivo was consistent independently of the targeted locus, we transplanted a limited dose ($TO_{eq}=1.5\times10^5$/mouse) of CD34$^+$ cells treated or not with GSE56 mRNA (FIG. 12B). For this experiment, we used our recently developed AAV6 vector targeting the AAVS1 locus and containing a 22-bp highly degenerated molecular region (barcodes). This vector allows in vivo clonal tracking of edited cells and the identification of gene editing protocols which could improve the clonality of the graft. When analysing transplanted NSG mice, we found significantly higher engraftment in the haematopoietic organs (FIG. 12C), despite a similar fraction of gene edited cells than standard protocol (FIG. 12D). To evaluate whether an increased size of the graft was associated with an improved clonality of the edited cells in the presence of GSE56 treatment, we evaluated the number of dominant clones contributing to repopulation of the HDR-edited cells by means of our novel barcoding-based clonal tracking analysis. Indeed, we observed a 6.5-fold higher number of dominant clones in haematopoietic organs (FIG. 12E), which directly correlates with the yield of human edited cells measured by FACS (FIG. 12F). Moreover, we also performed a similar transplantation experiment by targeting the clinically-relevant CD40LG gene which is associated to Hyper IgM syndrome (FIG. 13A). We consistently found a higher percentage of human cells in the peripheral blood of mice transplanted with CD40LG-edited cells in the presence of GSE56 (FIG. 13B), associated with a more stable percentage of gene correction over time (FIG. 13C). At the endpoint of the experiment, the percentage of human cells tended to be improved in all the haematopoietic tissues and organs analysed (FIG. 13D), with 3- to 6-fold higher percentage of corrected cells in sorted cell types, included CD34$^+$ cells (FIG. 13E). Overall, these results confirm and extend those reported in FIGS. 3 and 4, highlighting the relevant role of transient p53-inhibition to robustly improve the yield of edited cells in vivo.

Figure 8:
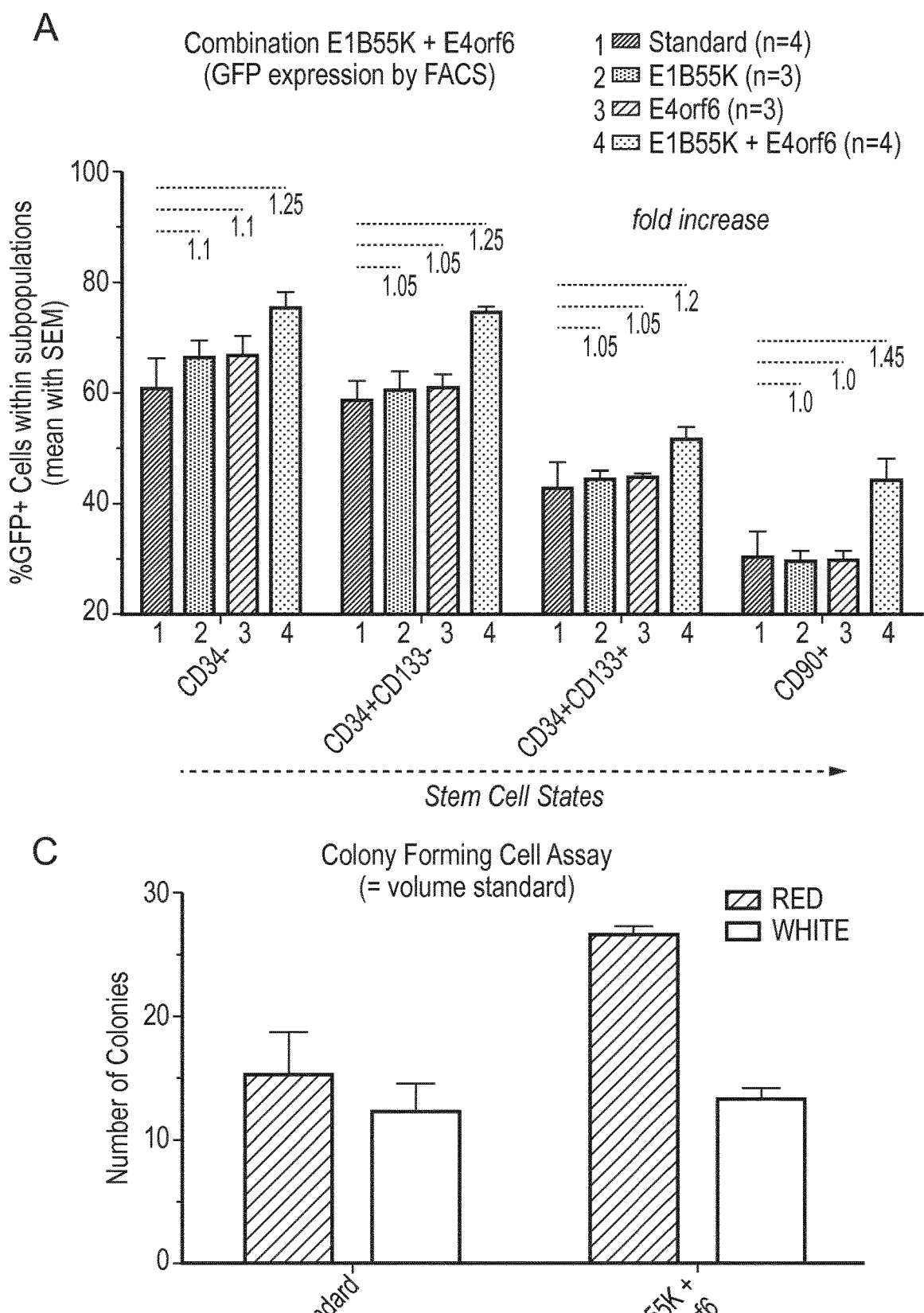
Figure 8:
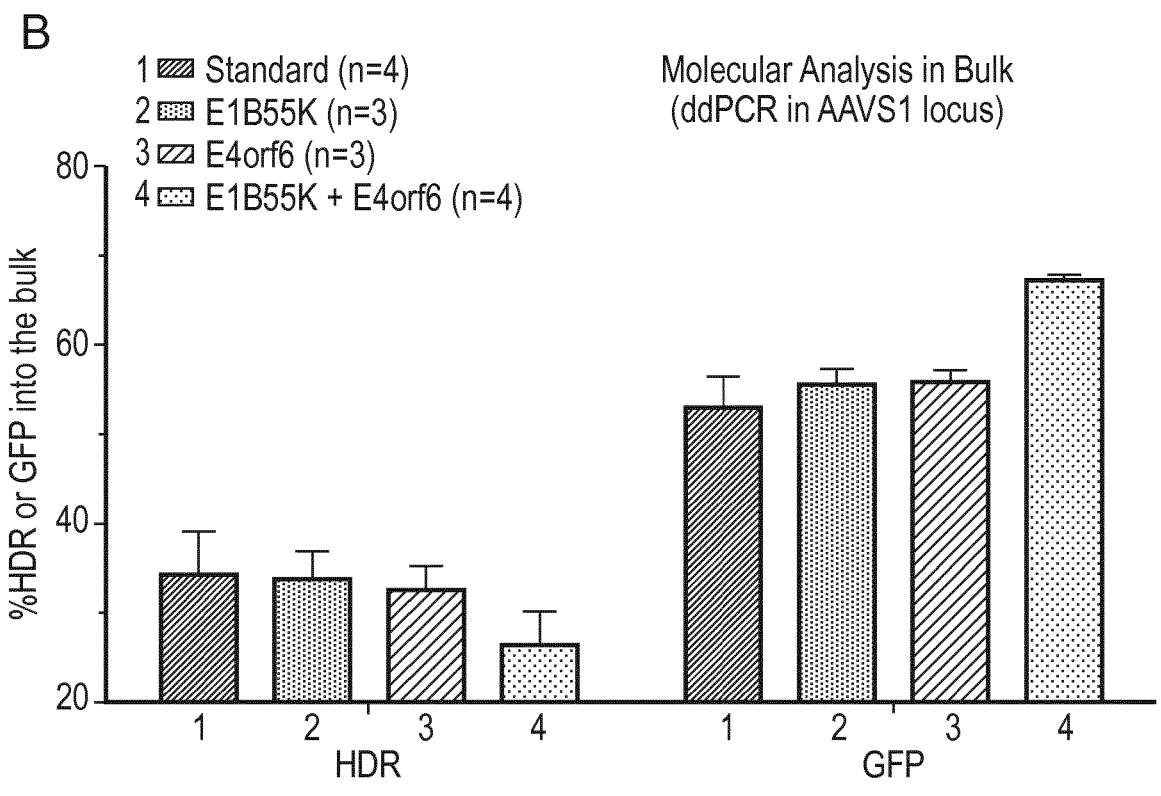
Figure 8:
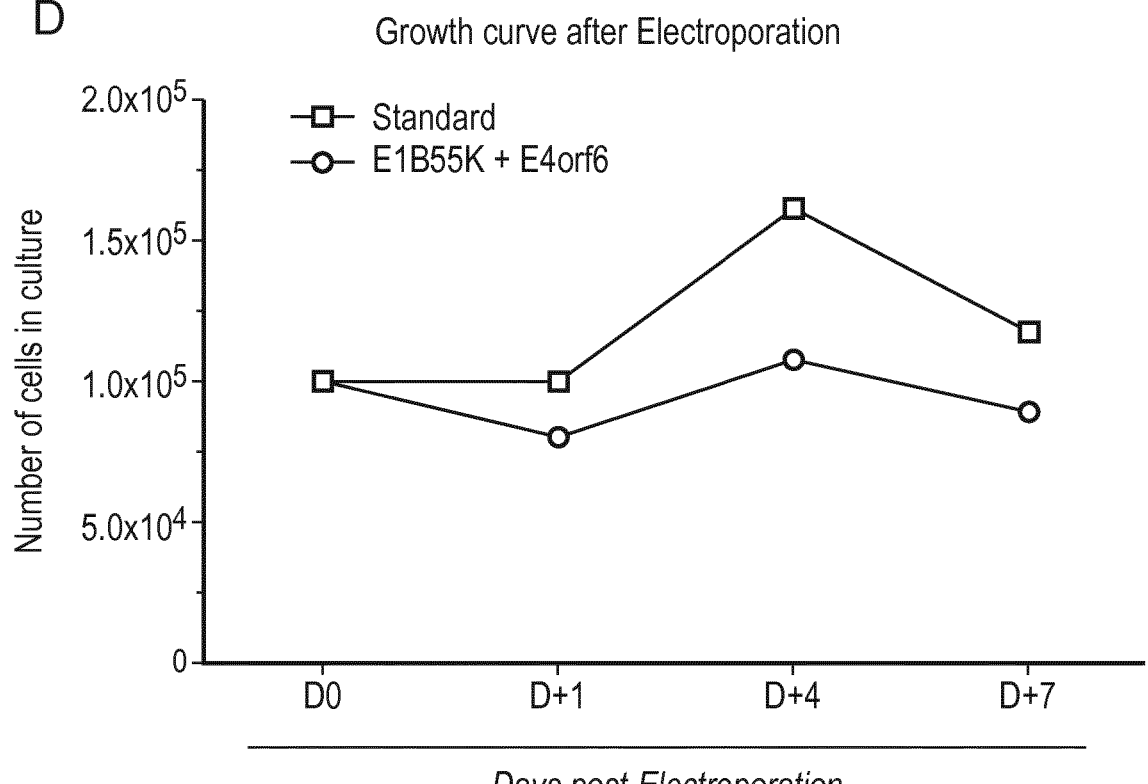

We continued the investigation concerning the potential of adenoviral Ad5-E4orf1 and Ad5-E4orf6/7 to boost HDR efficiency in HSPCs. We performed the targeted gene editing protocol in human cord blood (CB)-derived CD34$^+$ after pre-stimulation with cytokines and drugs (SR1, dmPGE-2 and UM171) and by electroporating at day 3 the pre-assembled RNP-Cas9 followed 15 min later by AAV6 transduction, as our standard editing procedure (RNP+ AAV6). We tested side by side the transient delivery of GFP (as mRNA control), GSE56, Ad5-E4orf1, Ad5-E4orf6/7 or GSE56/Ad5-E4orf6/7 by exploiting mRNA machinery and we characterised various parameters for each condition within the days following the editing protocol (FIG. 14A). We first observed that the standard editing protocol RNP+ AAV6 reduces cell expansion compared to untreated cells (UT). The Ad5-E4orf6/7 had similar trend than standard while both GSE56 and Ad5-E4orf1 increased about 2-fold more the cell growth that correlates with the results in FIGS. 3D and 7D. The combination of GSE56/Ad5-E4orf6/7 shown an intermediate pattern until day 7 post-editing and reached the level of both GSE56 and Ad5-E4orf1 at day 10 (FIG. 14B). Editing efficiency was evaluated by measuring GFP expression within HSPCs subpopulations (FIG. 14C left and right panels). GSE56 shown 1.1-fold increase of GFP expression compared to standard RNP+AAV6, especially in the most primitive compartment (CD34$^+$133$^+$90$^+$) which is slight but significant as described in FIG. 3C, right panel. Similarly, the Ad5-E4orf1 or Ad5-E4orf6/7±GSE56 shown respectively up to 1.3-fold and 1.5-fold increase of GFP expression into the CD90$^+$ cells. We validated these results by looking at promoted HDR-mediated integrations at the targeted AAVS1 locus by digital PCR in bulk culture (FIG. 14D). HDR edited alleles were significantly increased using the Ad5-E4orf6/7±GSE56 while NHEJ fraction remained similar whatever the condition. Moreover, we observed a significant skewing of CD90$^+$ fraction only by adding the Ad5-E4orf6/7±GSE56 that could suggest a possible toxic effect or cells differentiation (FIG. 14E). We then performed a 7-AAD/annexin staining to evaluate the toxicity of our editing protocols. While in the standard we saw a reduced number of live cells compared to UT, we did not observe an extra-toxicity by adding RNAs (FIG. 14F). Interestingly, by performing CFU-C assay, erythroid and myeloid clonogenic output was not affected with the delivery of GFP as mRNA control or the Ad5-E4orf6/7 compared to standard protocol. It was even improved with GSE56 as described in FIG. 3F and Ad5-E4orf1. However, the use of Ad5-E4orf6/7±GSE56 seemed to negatively affect clonogenic properties, even it remained a trend and it was not significant that could correlate with the reduced CD90$^+$ fraction seen in culture composition (FIG. 14G). Finally, we evaluated cell cycle states of HSPCs upon editing protocols. The use of Ad5-E4orf6/7 clearly shown a significant transition from G1 phase to S/G2/M phases of bulk treated cells mainly amplified by combining it with GSE56. We observed a similar pattern by looking into the most primitive compartment. This effect was lower and not significant by using GSE56 or Ad5-E4orf1 (FIG. 14H). To confirm previous results obtained by targeting the bi-allelic AAVS1 locus, we also developed the editing strategy by targeting another genomic mono-allelic IL2RG locus. By measuring the GFP expression within HSPCs subpopulations, we still had a significant editing efficiency increase by using the Ad5-E4orf6/7±GSE56, even the fold was reduced compared to the standard RNP+AAV6. We could speculate this is due to the mono-allelic form of this locus (FIG. 14I). Furthermore, by considering that the Ad5-E4orf6/7 is pushing the cell cycle, we reviewed the timing of the editing protocol during ex-vivo culture to further preserved the HSCPs properties. We evaluated different time points to proceed with the editing protocol from day 0 to day 2 post-thawing (FIG. 14J). Interestingly, we observed that both in total bulk and CD90$^+$ cells fraction, the editing efficiency was increased in presence of Ad5-E4orf6/7 from day 0 to day 2 (FIG. 14K). We confirmed these results by looking at promoted HDR-mediated integrations at the targeted AAVS1 locus by digital PCR in bulk culture (FIG. 14L). We performed a similar characterisation with Ad5-E1B55K and Ad5-E4orf proteins (FIGS. 15A, B, C, D and E). The combination of these two proteins increased significantly the GFP expression from the AAV6 donor as previously described (Gwiazda, K. S. et al. (2016) Mol. Ther. 24:1-11), while it was reducing HDR-mediated integrations at the targeted AAVS1 locus compared to standard procedure, as we already observed (FIG. 8).

We demonstrated that Ad5-E4orf6/7 induced cell cycle progression in HSPCs by cell cycle analysis. In 1989, Huang et al. (Huang, M. M. et al. (1989) Genes Dev. 3:1699-1710) described the direct interaction between Ad5-E4orf6/7 and the E2Fs transcription factor family. We decided to explore E2Fs related gene expression at the RNA level in HSPCs. We selected specific gene targets known to be involved in cell cycle regulation and p53-related. We used TaqMan gene expression assays to quantify specific transcripts upon several editing protocols. CDK2 is known to be a cell cycle progression marker which is specific for transition from G1 to S/G2 phases. We noted that CDK2 was significantly up-regulated in presence of Ad5-E4orf6/7±GSE56 at 24 hours post-editing (FIG. 16A) and it was detectable in a time window from 12 to 24 hours before reducing at 96 hours (FIG. 16B), while in case of RNP+AAV6±GSE56 remained always at basal level. CDKN2A is known as "p14$^{ARF}$" and has been described to be a p53 modulator by inhibiting MDM2, its main repressor. Again, we saw that CDKN2A was significantly up-regulated in the presence of Ad5-E4orf6/7±GSE56 at 24 hours post-editing (FIG. 16C) and similarly to CDK2, it was detectable in a time window from 12 to 24 hours before reducing at 96 hours (FIG. 16D), while RNP+AAV6±GSE56 still remained at basal level. We then investigated the p53 downstream effectors as CDKN1A and APOBEC3H, that are possibly activated by E2Fs. The first one is known as "p21" and it is a direct target of p53 involved in cell cycle arrest. Indeed, CDKN1A was highly up-regulated in the standard protocol RNP+AAV6 at 24 hours post-editing, which is a direct consequence of the editing protocol (FIG. 16E). The use of GSE56, which is a p53 inhibitor, allowed to reduce the amplitude of p21 activation about 3-fold less compared to RNP+AAV6, as described in FIG. 3B. However, by using the Ad5-E4orf6/7 we noted a drop of CDKN1A expression at 12 hours post-editing about 2-fold higher compared to the standard. Interestingly, this drop was not detectable when combining GSE56/Ad5-E4orf6/7, probably due to GSE56 properties that counterbalances the p21 overexpression mediated through Ad5-E4orf6/7 (FIG. 16F). In the end, CDKN1A went back to basal level at 168 hours post-editing. We finally tested APOBEC3H which is involved in anti-viral cell response by inducing C to T mutations in viral genomes. APOBEC3H is highly up-regulated upon editing protocols mainly due to AAV6 transduction in HSPCs (FIG. 3B). However, it was significantly down-regulated in presence of Ad5-E4orf6/7 and/or GSE56 at 24 hours post-editing (FIG. 16G). However, we noted that APOBEC3H went up at 96 hours before reducing at 168 hours (FIG. 16H). To summarise, we demonstrated that the interaction between Ad5-E4orf6/7 and E2Fs is the mechanism involved in HSPCs cell cycle progression and the increase of HDR events upon editing protocol. We also highlighted the presence of p53-mediated feedback loop that allows the cell cycle to be controlled. However, by blocking transiently the p53 activity, we were able to further push the cell cycle progression (FIG. 16I), especially into the most primitive CD90$^+$ cells.

We then planned a first transplantation by using a high number of treated cells (T0$_{eq}$=3×10$^5$/mouse) into an immunodeficient NSG mouse model at 24 hours post-editing (FIG. 17A). Human CD45$^+$ cell engraftment was monitored in bloodstream over the weeks post-transplantation and did not show any statistical significance between several groups RNP+AAV6±Ad5-E4orf1, Ad5-E4orf6/7 or GSE56/Ad5-E4orf6/7 that is probably due to the saturation of engraftment capacity into these recipients (FIG. 17B). Interestingly, the fraction of HDR-edited GFP$^+$ cells slightly decreased during time as described in FIG. 4D, that can be due to the loss of targeted progenitors. However, we noted that protocols RNP+AAV6+Ad5-E4orf6/7 or GSE56/Ad5-E4orf6/7 increased respectively 1.5 and 2-fold the fraction of circulating edited cells. Editing by using the Ad5-E4orf1 remained similar to the standard pattern (FIG. 17C). We confirmed these results at the end of experiments by analysing mice spleen and bone-marrow organs (FIGS. 17D and E). Moreover, we performed clonal tracking by using barcode sequences within our AAV6 cassette. In line with primary transplant, we detected up to 3-fold more edited clones by treating cells with GSE56/Ad5-E4orf6/7 compared to the standard (FIG. 17F).

To further investigate the most primitive cells' long-term repopulation capacity, we decided to perform a secondary transplant by collecting and purifying CD34$^+$ cells from bone-marrow of primary recipients. In order to avoid mouse-dependent heterogenicity, we transplanted around $2 \times 10^6$ cells/mouse from the purify CD34$^+$ pool inside a same group and by considering two primary recipients for one secondary recipient (FIG. 18A). While the engraftment was quite high and similar among each group, we still observed significant differences in terms of circulating edited human cells, especially comparing the standard RNP+AAV6±GSE56/Ad5-E4orf6/7 with more than 2-fold increase of GFP expressing cells (FIGS. 18B and C). This was also true in all the compartments that we analysed (bone marrow and spleen) as well as for all the blood lineages, CD19$^+$, CD33$^+$ and CD3$^+$ (FIGS. 18D, E and F). Overall, these results indicate that GSE56/Ad5-E4orf6/7 allows significant increase in the fraction of edited cells in transplanted mouse model by inducing cell cycle progression during editing protocol and probably reducing the p53-dependent transcriptional response that is helping to better preserve the long-term function of the most primitive HSPC compartment.

We performed a limit cells dose transplantation (T0$_{eq}$=1× 10$^5$/mouse) in order to further elucidate this last point, and including a new group treated with GSE56 in parallel. In these settings, edited cell fractions were similar to the previous experiment, but we better appreciated differences in terms of engraftment capacity between conditions (FIGS. 19A and B). As expected, GSE56 gave rise to 5-6-fold higher engraftment of treated cells compared to standard protocol (also see FIG. 4B). Curiously, the combination of GSE56/Ad5-E4orf6/7 generated about 2-fold higher engraftment compared to standard, but it is still lower compared to GSE56 treatment alone. We could then speculate two hypotheses: in one hand, we know that Ad5-E4orf6/7 induces a transient p53 overexpression during editing protocol, that could even more impair the treated cells. It would require then higher GSE56 dose to counterbalance it. In another hand, we know that the use of p53 inhibitor induces the loss of the feedback loop that allows control of the cell cycle, and which is pushed up by the Ad5-E4orf6/7. Then we could wonder that the stem cells are more prone to performed HDR but as counterpart are also affected about long-term engraftment capacity in mice.

To reinforce previous data, we decided to perform another in vivo experiment by targeting IL2RG locus and transplanting NSG mice similar to FIG. 17 (T0$_{eq}$=3×10$^5$/mouse) by comparing RNP+AAV6±GSE56/Ad5-E4orf6/7. We confirmed then previous results both after primary and secondary transplantation in NSG mice. We observed 2/3-fold increase of edited cells within organs and blood lineages even a secondary transplant, by using the combination GSE56/Ad5-E4orf6/7 compared to the standard protocol (FIGS. 20A, B, C, D, E, F, G and H). To assess potential genotoxicity of the editing procedure by complementing with both GSE56 and Ad5-E4orf6/7, we performed a translocations analysis by targeting the IL2RG locus with our reagents, where we identified one major off-target. Interestingly, we did not observe an increase of genome translocation events frequency by ddPCR compared to the standard protocol. Moreover, for in vivo samples, no event was detectable, suggesting that differentiated cells are probably more prone to this phenomenon (FIG. 20I).

Finally, we also investigated the use of adenoviral proteins variants for both E4orf1 and E4orf6/7 derived from various serotypes of Adenovirus family. We performed protein sequences alignment by using T-coffee algorithm, and we identified specific conserved amino-acids (>95% consensus). We selected the best candidates presenting highest sequence variabilities along the phylogenetic tree of common ancestors. We then choose three variants for each protein, and we evaluated editing efficiency in HSPCs (FIGS. 21/22A and B). E4orf1 variants shown up to 2-fold increase of GFP expression within HSPCs subpopulations comparing to the Ad5-E4orf1 (FIG. 21C). However, Ad5-E4orf1 remained the one that presented the highest number of colonies (FIG. 21D). Surprisingly, TaqMan analyses did not show any impact on E2Fs target genes whatever the E4orf1 variant, suggesting an alternative mechanism to stimulate the cell cycle activity of treated cells (FIG. 21E). Concerning E4orf6/7, only one variant was increasing up to 2-fold the editing efficiency into the most primitive compartment, while two others remained similar to the Ad5-E4orf6/7 (FIG. 22C). However, by looking at colony forming cell assay, all these variants seemed impaired in the clonogenic capacity of treated cells (FIG. 22D). At RNA level, it has been revealed that these variants drastically induced feedback loop response both CDKN1A and CDKN2A revealing a kind of toxicity compared to the use of Ad5-E4orf6/7 (FIG. 22E).

DISCUSSION

We demonstrated that transient expression of both GSE56 and Ad5-E4orf6/7 is able to improve our standard targeted gene editing protocol in HSPCs. In one hand, GSE56 reduces edited cells impairment during the editing protocol by modulation of the p53 response. We observed a higher engraftment capacities post-transplantation and an increased number of abundant clones in NSG mice. Despite of consistent but low increase in terms of HDR efficiency, it revealed that edited cells fraction was more stable at long-term than standard protocol, suggesting that most primitive cells suffered less during the editing protocol thanks to GSE56. Moreover, the transient inhibition of p53 probably wouldn't select naturally p53 deficient HSPCs, avoiding the carry-over of putative tumor-prone clones under transplantation. In the other hand, we discovered that Ad5-E4orf6/7 adenoviral protein was able to push up the cell cycle progression leading to 1.5-fold HDR-events integrations increase in AAVS1 locus of HSPCs. Combined with GSE56, it was possible to directly target the most primitive cells bypassing the feedback loop p53-mediated. Consequently, we were able to increase the long-term edited HSCs fraction in-vivo up to 50% and the number of total abundant clones, even affecting partially the engraftment capacities in this specific case compared to the use of GSE56 alone. This last point could be explained by cell cycle pushing that would induce a kind of cell differentiation into the most primitive compartment. We supposed then that by modulating both GSE56 and Ad5-E4orf6/7 doses, we could balance the HDR vs ENGRAFTMENT capacities.

To summarise, we could distinguish two strategies: in one hand by using the editing protocol with GSE56 alone, we will obtain a higher engraftment of treated cells and long-term stability of the small fraction of both homed and circulating edited cells in-vivo. In the other hand, by using GSE56/Ad5-E4orf6/7 we improved 2/3-fold the percentage of edited cells while the engraftment was reduced compared to the GSE56 alone. To conclude, it is known that recipient capacity is limited during transplantation and a competition between freshly transplanted cells is engaged during homing process. Thus, we can say that the fraction of edited cells is higher and as is the probability that they can reach the bone marrow niche overcoming the competition with non-edited cells. Finally, the combination of GSE56/Ad5-E4orf6/7 could be the best option for diseases in which a high level of edited cells is required.

Example 4

Description

Whereas retro- and lenti-viral vector (LV)-based gene therapy enable clonal tracking studies by monitoring integration sites (Biffi et al. 2013), the site-specific and high-fidelity nature of HDR-mediated targeted insertion impede quantification and monitoring of edited clones. Beside few NHEJ-based tracking analyses (Wu et al. 2019), no data are available about the multilineage repopulation capacity of individual HDR-edited long-term repopulating HSPCs, as well as clonal diversity within the human graft. Therefore, the development of novel and extensive clonal tracking pipelines for gene edited cells would allow to: i) dissect repopulation dynamics; ii) compare clonal richness among different HSPC gene editing protocols, and iii) pave the way for tracking of edited HSPCs in translational settings. Previous works highlighted the value of introducing short random sequences (barcodes) into the genome of viral vectors to track the fate of barcoding-labeled cells upon vector integration into cellular genome (Naik et al. 2014). Integrating barcoded vectors has been previously applied in different fields, e.g. to study hematopoiesis (Verovskaya et al. 2013), T-cell behavior (Schepers et al. 2008) and breast tissue development (Nguyen et al. 2014). Recently, some reports highlighted the possibility of combining genome editing with barcoding technology in order to track the fate of CRISPR-edited *S. cerevisiae* clones (Roy et al. 2018).

Results and Discussion

To enable clonal tracking of targeted HSPCs in vitro and in vivo, we cloned a 22-bp highly degenerated molecular barcode into an HDR-proficient AAV vector targeting the AAVS1 locus (see FIG. 23 and Methods). Theoretically, sequence design allows up to $4.53*10^8$ different barcodes. Since shorter inserts could be preferentially ligated into the backbone during cloning procedure and reduce library complexity, 3 fixed bases were used to avoid cutting during the cloning procedure of the degenerated insert by desired restriction enzymes (Bsu36l and Sphl). Upon site-specific integration of the cassette into the AAVS1 locus, the target sequence containing the barcode can be amplified by PCR and analyzed by deep sequencing to identify number and distribution of HDR-edited clones.

Potentially, this AAV vector/plasmid could be used to perform clonal tracking in whatever cell type (mouse/human HSPCs, T cells, etc.) for pre-clinical and clinical applications. Moreover, as well as the degenerated barcode sequence could be cloned in different type of vectors (short or long naked DNA fragments, IDLVs, etc.) or construct targeting other genomic region of interest (e.g. IL2RG, CD40LG, RAG1, HBB, etc.).

Methods

The barcoded AAV6 donor template targeting the AAVS1 locus was obtained by subcloning the degenerated sequence into the non-barcoded AAVS1 HDR donor template downstream of the polyadenylation sequence (Schiroli et al. 2017). Briefly, a ssODN embedding the random sequence flanked by the unique cloning restriction sites (Bsu36l and Sphl) was purchased from Sigma Aldrich. The degenerated region was designed to avoid any undesired cutting by cloning restriction enzymes. To generate the complementary strand, 50 pmol of the ssODN were amplified with 10 cycle of PCR with Easy-A High-Fidelity enzyme (Agilent Technologies) using the appropriate forward and reverse primers according to manufacturer instruction. The amplified product was purified with MinElute PCR Purification kit (QIAGEN), digested with the restriction enzymes and checked by capillary electrophoresis. 2 μg of the Bsu36l/Sphl-digested AAVS1 HDR donor template were ligated with the digested insert (molar ratio 1:7) using T4 DNA Ligase (NEB) by scaling up the manufacturer protocol. Finally, XL-10 Gold Ultracompetent Cells (Agilent Technologies) were transformed with the ligation product, plated and incubated for 12 hours of incubation at 30° C. to minimize the risk of recombination. Colonies were scraped, mixed, grown in LB medium for additional 6 hours and processed with Nucleo-Bond Xtra MaxiPrep according to manufacturer instruction. Ultimately, the plasmid prep was screened with restriction enzymes for ITR and plasmid integrity.

Sequences

Genomic Insert of the Barcoded AAV (Underlined=Barcoding Sequence)

```
CCACTGAGAACCGGGCAGGTCACGCATCCCCCCCTTCCCTCCCACCCCC

TGCCAAGCTCTCCCTCCCAGGATCCTCTCTGGCTCCATCGTAAGCAAAC

CTTAGAGGTTCTGGCAAGGAGAGAGATGGCTCCAGGAAATGGGGGTGTG

TCACCAGATAAGGAATCTGCCTAACAGGAGGTGGGGGTTAGACCCAATA

TCAGGAGACTAGGAAGGAGGAGGCCTAAGGATGGGGCTTTTCTGTCACC

AATCCTGTCCCTANNYNNNTNTNNNNRTNDNNNHHCCATAGAGCCCACC

GCATCCCCAGCATGCCTGCTATTGTCTTCCCAATCCTCCCCCTTGCTGT

CCTGCCCCACCCCACCCCCCAGAATAGAATGACACCTACTCAGACAATG

CGATGCAATTTCCTCATTTTATTAGGAAAGGACAGTGGGAGTGGCACCT

TCCAGGGTCAAGGAAGGCACGGGGGAGGGGCAAACAACAGATGGCTGGC

AACTAGAAGGCACAGTCGAGGCTGATCAGCGGGTTTAAACGGGCCCTCT

AGACTCGACGCGGCCGCTTTACTTGTACAGCTCGTCCATGCCGAGAGTG

ATCCCGGCGGCGGTCACGAACTCCAGCAGGACCATGTGATCGCGCTTCT

CGTTGGGGTCTTTGCTCAGGGGGGACTGGGTGCTCAGGTAGTGGTTGTC
```

-continued

```
GGGCAGCAGCACGGGGCCGTCGCCGATGGGGGTGTTCTGCTGGTAGTGG

TCGGCGAGCTGCACGCTGCCGTCCTCGATGTTGTGGCGGATCTTGAAGT

TCACCTTGATGCCGTTCTTCTGCTTGTCGGCCATGATATAGACGTTGTG

GCTGTTGTAGTTGTACTCCAGCTTGTGCCCCAGGATGTTGCCGTCCTCC

TTGAAGTCGATGCCCTTCAGCTCGATGCGGTTCACCAGGGTGTCGCCCT

CGAACTTCACCTCGGCGCGGGTCTTGTAGTTGCCGTCGTCCTTGAAGAA

GATGGTGCGCTCCTGGACGTAGCCTTCGGGCATGGCGGACTTGAAGAAG

TCGTGCTGCTTCATGTGGTCGGGGTAGCGGCTGAAGCACTGCACGCCGT

AGGTCAGGGTGGTCACGAGGGTGGGCCAGGGCACGGGCAGCTTGCCGGT

GGTGCAGATGAACTTCAGGGTCAGCTTGCCGTAGGTGGCATCGCCCTCG

CCCTCGCCGGACACGCTGAACTTGTGGCCGTTTACGTCGCCGTCCAGCT

CGACCAGGATGGGCACCACCCCGGTGAACAGCTCCTCGCCCTTGCTCAC

CATGGTGGCGACCGGTGGGGAGAGAGGTCGGTGATTCGGTCAACGAGGG

AGCCGACTGCCGACGTGCGCTCCGGAGGCTTGCAGAATGCGGAACACCG

CGCGGGCAGGAACAGGGCCCACACTACCGCCCCACACCCCGCCTCCCGC

ACCGCCCCTTCCCGGCCGCTGCTCTCGGCGCGCCCTGCTGAGCAGCCGC

TATTGGCCACAGCCCATCGCGGTCGGCGCGCTGCCATTGCTCCCTGGCG

CTGTCCGTCTGCGAGGGTACTAGTGAGACGTGCGGCTTCCGTTTGTCAC

GTCCGGCACGCCGCGAACCGCAAGGAACCTTCCCGACTTAGGGGCGGAG

CAGGAAGCGTCGCCGGGGGGCCCACAAGGGTAGCGGCGAAGATCCGGGT

GACGCTGCGAACGGACGTGAAGAATGTGCGAGACCCAGGGTCGGCGCCG

CTGCGTTTCCCGGAACCACGCCCAGAGCAGCCGCGTCCCTGCGCAAACC

CAGGGCTGCCTTGGAAAAGGCGCAACCCCAACCCCGTGGAAGCTTGCGT

GGGGTGGAGGGGACAGATAAAAGTACCCAGAACCAGAGCCACATTAACC

GGCCCTGGGAATATAAGGTGGTCCCAGCTCGGGGACACAGGATCCCTGG

AGGCAGCAAACATGCTGTCCTGAAGTGGACATAGGGGCCCGGGTTGGAG

GAAGAAGACTAGCTGAGCTCTCGGACCCCTGGAAGATGCCATGACAGGG

GGCTGGAAGAGCTAGCACAGACTAGAGAGGTAAGGGGGGTAGGGGAGCT

GCCCAAATGAAAGGAGTGAGAGGTGACCCGAATCCACAGGAGAACGGGG
```

-continued

```
TGTCCAGGCAAAGAAAGCAAGAGGATGGAGAGGTGGCTAAAGCCAGGGA

GACGGGGTACTTTGGGGTTGTCCAGAAAAACGGTGATGATGCAGGCCTA

CAAGAAGGGGAGGCGGGACGCAAGGGAGACATCCGTCGGAGAAGGCCAT

CCTAAGAAACGAGAGATGGCACAGGCCCCAGAAGGAGAAGGAAAAGGGA

ACCCAGCGAGTGAAGACGGCATGGGGTTGGGTGAGGGAGGAGAGATGCC

CGGAGAGGACCCAGACACGGGGAGGATCCGCTCAGAGGACATCACGTGG

TGCAGCGCCGAGAAGGAAGTGCTCCGGAAAGAGCATCCTTGGGCAGCAA

CACAGCAGAGAGCAAGGGGAAGAGGGGAGTGGAGGAAGACGGAACCTGAA

GGAGGCGGCAGGGAAGGATCTGGGCCAGCCGTAGAGGTGACCCAGGCCA

CAAGCTGCAGACAGAAAGCGGCACAGGCCCAGGGGAGAGAATGCTGGTC

AGAGAAAGCA
``` ssODN Amplification Primers
Bar AAVS1 sense

5'-AGACTAGGAAGGAGGAGGCCTAAGGATG-3'

Bar AAVS1 antisense

5'-ACAATAGCAGGCATGCTGGGGATG-3'

SSODN

```
AGACTAGGAAGGAGGAGGCCTAAGGATGGGGCTTTTCTGTCACCAATCC

TGTCCCTANNYNNNTNTNNNNRTNDNNNHHCCATAGAGCCCACCGCATC

CCCAGCATGCCTGCTATTGT
```

All publications mentioned in the above specification are herein incorporated by reference. Various modifications and variations of the disclosed uses, methods, cells and compositions of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method of haematopoietic cell gene therapy, haematopoietic stem cell gene therapy, and/or haematopoietic progenitor cell gene therapy, wherein said gene therapy comprises gene editing, wherein said method comprises contacting a population of haematopoietic cells, haematopoietic stem cells and/or haematopoietic progenitor cells with an agent that comprises a p53 dominant negative peptide comprising a p53 homo-oligomerisation domain, or that comprises a nucleic acid comprising a nucleotide sequence encoding the p53 dominant negative peptide, wherein the method transiently inhibits p53 in the haematopoietic cells, haematopoietic stem cells and/or haematopoietic progenitor cells.

2. The method of claim 1, wherein the contacting the population of haematopoietic cells, haematopoietic stem cells and/or haematopoietic progenitor cells with the agent increases the survival and/or engraftment of gene edited haematopoietic cells, haematopoietic stem cells and/or haematopoietic progenitor cells, or increases the efficiency of gene editing of haematopoietic cells, haematopoietic stem cells, and/or haematopoietic progenitor cells.

3. The method of claim 1, wherein transient inhibition of p53 occurs during gene editing of the haematopoietic cells, haematopoietic stem cells and/or haematopoietic progenitor cells.

4. The method of claim 1, wherein the agent is added to the haematopoietic cell, haematopoietic stem cell and/or haematopoietic progenitor cells at a concentration of about 1-50 μM.

5. The method of claim 1, wherein the agent further comprises at least one adenoviral protein or a nucleic acid comprising a nucleic acid sequence encoding said at least one adenoviral protein.

6. The method of claim 5, wherein the at least one adenoviral protein is from an Adenovirus of serotype 4, Adenovirus of serotype 5, Adenovirus of serotype 7 and/or Adenovirus of serotype 9.

7. The method of claim 5, wherein the at least one adenoviral protein is: (a) E4ORF1 or (b) E4ORF6/7.

8. The method of claim 5, wherein the nucleic acid encoding the adenoviral protein is an mRNA.

9. The method of claim 5, wherein the adenoviral protein is expressed transiently in the haematopoietic cell, haematopoietic stem cell or haematopoietic progenitor cell.

10. The method of claim 9, wherein the transient expression occurs during gene editing of the haematopoietic cell, haematopoietic stem cell and/or haematopoietic progenitor cell.

11. The method of claim 1, wherein the agent further comprises: adenoviral protein E4ORF1, or a nucleic acid comprising a nucleic acid sequence encoding adenoviral protein E4ORF1; and adenoviral protein E4ORF6/7, or a nucleic acid comprising a nucleic acid sequence encoding adenoviral protein E4ORF6/7.

12. The method of claim 1, wherein the agent comprises:

(a) a p53 dominant negative peptide comprising a p53 homo-oligomerisation domain or a nucleic acid comprising a nucleic acid sequence encoding the p53 dominant negative peptide; and an adenoviral protein, or a nucleic acid comprising a nucleic acid sequence encoding the adenoviral protein;

(b) a p53 dominant negative peptide comprising a p53 homo-oligomerisation domain or a nucleic acid comprising a nucleic acid sequence encoding the p53 dominant negative peptide; and adenoviral protein E4ORF1, or a nucleic acid comprising a nucleic acid sequence encoding the adenoviral protein E4ORF1

(c) a p53 dominant negative peptide comprising a p53 homo-oligomerisation domain or a nucleic acid comprising a nucleic acid sequence encoding the p53 dominant negative peptide; and adenoviral protein E4ORF6/7, or a nucleic acid comprising a nucleic acid sequence encoding the adenoviral protein E4ORF6/7; or (d) a p53 dominant negative peptide comprising a p53 homo-oligomerisation domain or a nucleic acid comprising a nucleic acid sequence encoding the p53 dominant negative peptide; adenoviral protein E4ORF1, or a nucleic acid comprising a nucleic acid sequence encoding the adenoviral protein E4ORF1; and adenoviral protein E4ORF6/7, or a nucleic acid comprising a nucleic acid sequence encoding the adenoviral protein E4ORF6/7.

13. The method of claim 1, wherein a target of the gene editing is selected from the group consisting of CD40L, RAG-1, IL-2RG, CYBA, CYBB, NCF1, NCF2, and NCF4.

14. The method of claim 1, wherein the agent comprises GSE56 or a variant thereof, or a nucleic acid comprising a nucleotide sequence encoding the GSE56.

15. The method of claim 1, wherein the agent comprises a p53 dominant negative peptide comprising an amino acid sequence having at least 80% identity to SEQ ID NO: 9, or a nucleic acid comprising a nucleotide sequence encoding the amino acid sequence.

16. The method of claim 1, wherein the agent is in the form of an mRNA.

* * * * *

SEQUENCE LISTING

```
<160> NUMBER OF SEQ ID NOS: 114

<210> SEQ ID NO 1
<211> LENGTH: 128
<212> TYPE: PRT
<213> ORGANISM: Artificial Sequence
<220> FEATURE:
<223> OTHER INFORMATION: example amino acid sequence of Ad5-E4orf1

<400> SEQUENCE: 1

Met Ala Ala Ala Val Glu Ala Leu Tyr Val Val Leu Glu Arg Glu Gly
1               5                   10                  15

Ala Ile Leu Pro Arg Gln Glu Gly Phe Ser Gly Val Tyr Val Phe Phe
            20                  25                  30
```

```
Ser Pro Ile Asn Phe Val Ile Pro Pro Met Gly Ala Val Met Leu Ser
        35              40              45

Leu Arg Leu Arg Val Cys Ile Pro Pro Gly Tyr Phe Gly Arg Phe Leu
    50              55              60

Ala Leu Thr Asp Val Asn Gln Pro Asp Val Phe Thr Glu Ser Tyr Ile
65              70              75              80

Met Thr Pro Asp Met Thr Glu Glu Leu Ser Val Val Leu Phe Asn His
                85              90              95

Gly Asp Gln Phe Phe Tyr Gly His Ala Gly Met Ala Val Val Arg Leu
            100             105             110

Met Leu Ile Arg Val Val Phe Pro Val Val Arg Gln Ala Ser Asn Val
        115             120             125
```

<210> SEQ ID NO 2
<211> LENGTH: 150
<212> TYPE: PRT
<213> ORGANISM: Artificial Sequence
<220> FEATURE:
<223> OTHER INFORMATION: example amino acid sequence of Ad5-E4orf6/7

<400> SEQUENCE: 2

```
Met Thr Thr Ser Gly Val Pro Phe Gly Met Thr Leu Arg Pro Thr Arg
1               5               10              15

Ser Arg Leu Ser Arg Arg Thr Pro Tyr Ser Arg Asp Arg Leu Pro Pro
            20              25              30

Phe Glu Thr Glu Thr Arg Ala Thr Ile Leu Glu Asp His Pro Leu Leu
        35              40              45

Pro Glu Cys Asn Thr Leu Thr Met His Asn Ala Trp Thr Ser Pro Ser
    50              55              60

Pro Pro Val Lys Gln Pro Gln Val Gly Gln Gln Pro Val Ala Gln Gln
65              70              75              80

Leu Asp Ser Asp Met Asn Leu Ser Glu Leu Pro Gly Glu Phe Ile Asn
                85              90              95

Ile Thr Asp Glu Arg Leu Ala Arg Gln Glu Thr Val Trp Asn Ile Thr
            100             105             110

Pro Lys Asn Met Ser Val Thr His Asp Met Met Leu Phe Lys Ala Ser
        115             120             125

Arg Gly Glu Arg Thr Val Tyr Ser Val Cys Trp Glu Gly Gly Gly Arg
    130             135             140

Leu Asn Thr Arg Val Leu
145             150
```

<210> SEQ ID NO 3
<211> LENGTH: 393
<212> TYPE: PRT
<213> ORGANISM: Homo sapiens

<400> SEQUENCE: 3

```
Met Glu Glu Pro Gln Ser Asp Pro Ser Val Glu Pro Pro Leu Ser Gln
1               5               10              15

Glu Thr Phe Ser Asp Leu Trp Lys Leu Leu Pro Glu Asn Asn Val Leu
            20              25              30

Ser Pro Leu Pro Ser Gln Ala Met Asp Asp Leu Met Leu Ser Pro Asp
        35              40              45

Asp Ile Glu Gln Trp Phe Thr Glu Asp Pro Gly Pro Asp Glu Ala Pro
    50              55              60

Arg Met Pro Glu Ala Ala Pro Pro Val Ala Pro Ala Pro Ala Ala Pro
```

-continued

```
65                     70                      75                      80

Thr Pro Ala Ala Pro Ala Pro Ala Pro Ser Trp Pro Leu Ser Ser Ser
                85                      90                      95

Val Pro Ser Gln Lys Thr Tyr Gln Gly Ser Tyr Gly Phe Arg Leu Gly
                100                     105                     110

Phe Leu His Ser Gly Thr Ala Lys Ser Val Thr Cys Thr Tyr Ser Pro
                115                     120                     125

Ala Leu Asn Lys Met Phe Cys Gln Leu Ala Lys Thr Cys Pro Val Gln
                130                     135                     140

Leu Trp Val Asp Ser Thr Pro Pro Gly Thr Arg Val Arg Ala Met
145                     150                     155                     160

Ala Ile Tyr Lys Gln Ser Gln His Met Thr Glu Val Val Arg Cys
                165                     170                     175

Pro His His Glu Arg Cys Ser Asp Ser Asp Gly Leu Ala Pro Pro Gln
                180                     185                     190

His Leu Ile Arg Val Glu Gly Asn Leu Arg Val Glu Tyr Leu Asp Asp
                195                     200                     205

Arg Asn Thr Phe Arg His Ser Val Val Val Pro Tyr Glu Pro Pro Glu
                210                     215                     220

Val Gly Ser Asp Cys Thr Thr Ile His Tyr Asn Tyr Met Cys Asn Ser
225                     230                     235                     240

Ser Cys Met Gly Gly Met Asn Arg Arg Pro Ile Leu Thr Ile Ile Thr
                245                     250                     255

Leu Glu Asp Ser Ser Gly Asn Leu Leu Gly Arg Asn Ser Phe Glu Val
                260                     265                     270

Arg Val Cys Ala Cys Pro Gly Arg Asp Arg Arg Thr Glu Glu Glu Asn
                275                     280                     285

Leu Arg Lys Lys Gly Glu Pro His His Glu Leu Pro Pro Gly Ser Thr
                290                     295                     300

Lys Arg Ala Leu Pro Asn Asn Thr Ser Ser Ser Pro Gln Pro Lys Lys
305                     310                     315                     320

Lys Pro Leu Asp Gly Glu Tyr Phe Thr Leu Gln Ile Arg Gly Arg Glu
                325                     330                     335

Arg Phe Glu Met Phe Arg Glu Leu Asn Glu Ala Leu Glu Leu Lys Asp
                340                     345                     350

Ala Gln Ala Gly Lys Glu Pro Gly Gly Ser Arg Ala His Ser Ser His
                355                     360                     365

Leu Lys Ser Lys Lys Gly Gln Ser Thr Ser Arg His Lys Lys Leu Met
                370                     375                     380

Phe Lys Thr Glu Gly Pro Asp Ser Asp
385                     390
```

```
<210> SEQ ID NO 4
<211> LENGTH: 3056
<212> TYPE: PRT
<213> ORGANISM: Homo sapiens
```

```
<400> SEQUENCE: 4

Met Ser Leu Val Leu Asn Asp Leu Leu Ile Cys Cys Arg Gln Leu Glu
1                       5                       10                      15

His Asp Arg Ala Thr Glu Arg Lys Lys Glu Val Glu Lys Phe Lys Arg
                20                      25                      30

Leu Ile Arg Asp Pro Glu Thr Ile Lys His Leu Asp Arg His Ser Asp
                35                      40                      45
```

```
Ser Lys Gln Gly Lys Tyr Leu Asn Trp Asp Ala Val Phe Arg Phe Leu
    50              55                  60

Gln Lys Tyr Ile Gln Lys Glu Thr Glu Cys Leu Arg Ile Ala Lys Pro
65              70                  75                  80

Asn Val Ser Ala Ser Thr Gln Ala Ser Arg Gln Lys Lys Met Gln Glu
            85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
            115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
            195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
            245                 250                 255

Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
    275                 280                 285

Ile His His Pro Lys Gly Ala Lys Thr Gln Glu Lys Gly Ala Tyr Glu
    290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
            325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
    355                 360                 365

Ser Tyr Thr Thr Thr Gln Arg Glu Ser Ser Asp Tyr Ser Val Pro Cys
    370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
            405                 410                 415

Thr Gln Leu Ile Ser Lys Tyr Pro Ala Ser Leu Pro Asn Cys Glu Leu
            420                 425                 430

Ser Pro Leu Leu Met Ile Leu Ser Gln Leu Leu Pro Gln Gln Arg His
            435                 440                 445

Gly Glu Arg Thr Pro Tyr Val Leu Arg Cys Leu Thr Glu Val Ala Leu
    450                 455                 460

Cys Gln Asp Lys Arg Ser Asn Leu Glu Ser Ser Gln Lys Ser Asp Leu
```

-continued

```
465                     470                     475                     480

Leu Lys Leu Trp Asn Lys Ile Trp Cys Ile Thr Phe Arg Gly Ile Ser
                485                     490                     495

Ser Glu Gln Ile Gln Ala Glu Asn Phe Gly Leu Leu Gly Ala Ile Ile
                500                     505                     510

Gln Gly Ser Leu Val Glu Val Asp Arg Glu Phe Trp Lys Leu Phe Thr
                515                     520                     525

Gly Ser Ala Cys Arg Pro Ser Cys Pro Ala Val Cys Cys Leu Thr Leu
                530                     535                     540

Ala Leu Thr Thr Ser Ile Val Pro Gly Thr Val Lys Met Gly Ile Glu
545                     550                     555                     560

Gln Asn Met Cys Glu Val Asn Arg Ser Phe Ser Leu Lys Glu Ser Ile
                565                     570                     575

Met Lys Trp Leu Leu Phe Tyr Gln Leu Glu Gly Asp Leu Glu Asn Ser
                580                     585                     590

Thr Glu Val Pro Pro Ile Leu His Ser Asn Phe Pro His Leu Val Leu
                595                     600                     605

Glu Lys Ile Leu Val Ser Leu Thr Met Lys Asn Cys Lys Ala Ala Met
                610                     615                     620

Asn Phe Phe Gln Ser Val Pro Glu Cys Glu His His Gln Lys Asp Lys
625                     630                     635                     640

Glu Glu Leu Ser Phe Ser Glu Val Glu Glu Leu Phe Leu Gln Thr Thr
                645                     650                     655

Phe Asp Lys Met Asp Phe Leu Thr Ile Val Arg Glu Cys Gly Ile Glu
                660                     665                     670

Lys His Gln Ser Ser Ile Gly Phe Ser Val His Gln Asn Leu Lys Glu
                675                     680                     685

Ser Leu Asp Arg Cys Leu Leu Gly Leu Ser Glu Gln Leu Leu Asn Asn
                690                     695                     700

Tyr Ser Ser Glu Ile Thr Asn Ser Glu Thr Leu Val Arg Cys Ser Arg
705                     710                     715                     720

Leu Leu Val Gly Val Leu Gly Cys Tyr Cys Tyr Met Gly Val Ile Ala
                725                     730                     735

Glu Glu Glu Ala Tyr Lys Ser Glu Leu Phe Gln Lys Ala Lys Ser Leu
                740                     745                     750

Met Gln Cys Ala Gly Glu Ser Ile Thr Leu Phe Lys Asn Lys Thr Asn
                755                     760                     765

Glu Glu Phe Arg Ile Gly Ser Leu Arg Asn Met Met Gln Leu Cys Thr
                770                     775                     780

Arg Cys Leu Ser Asn Cys Thr Lys Lys Ser Pro Asn Lys Ile Ala Ser
785                     790                     795                     800

Gly Phe Phe Leu Arg Leu Leu Thr Ser Lys Leu Met Asn Asp Ile Ala
                805                     810                     815

Asp Ile Cys Lys Ser Leu Ala Ser Phe Ile Lys Lys Pro Phe Asp Arg
                820                     825                     830

Gly Glu Val Glu Ser Met Glu Asp Asp Thr Asn Gly Asn Leu Met Glu
                835                     840                     845

Val Glu Asp Gln Ser Ser Met Asn Leu Phe Asn Asp Tyr Pro Asp Ser
                850                     855                     860

Ser Val Ser Asp Ala Asn Glu Pro Gly Glu Ser Gln Ser Thr Ile Gly
865                     870                     875                     880

Ala Ile Asn Pro Leu Ala Glu Glu Tyr Leu Ser Lys Gln Asp Leu Leu
                885                     890                     895
```

-continued

```
Phe Leu Asp Met Leu Lys Phe Leu Cys Leu Cys Val Thr Thr Ala Gln
            900                 905                 910

Thr Asn Thr Val Ser Phe Arg Ala Ala Asp Ile Arg Arg Lys Leu Leu
            915                 920                 925

Met Leu Ile Asp Ser Ser Thr Leu Glu Pro Thr Lys Ser Leu His Leu
            930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
            980                 985                 990

His Val Leu His Val Val Lys Asn  Leu Gly Gln Ser Asn  Met Asp Ser
            995                 1000                1005

Glu Asn  Thr Arg Asp Ala Gln  Gly Gln Phe Leu Thr  Val Ile Gly
    1010                1015                1020

Ala Phe  Trp His Leu Thr Lys  Glu Arg Lys Tyr Ile  Phe Ser Val
    1025                1030                1035

Arg Met  Ala Leu Val Asn Cys  Leu Lys Thr Leu Leu  Glu Ala Asp
    1040                1045                1050

Pro Tyr  Ser Lys Trp Ala Ile  Leu Asn Val Met Gly  Lys Asp Phe
    1055                1060                1065

Pro Val  Asn Glu Val Phe Thr  Gln Phe Leu Ala Asp  Asn His His
    1070                1075                1080

Gln Val  Arg Met Leu Ala Ala  Glu Ser Ile Asn Arg  Leu Phe Gln
    1085                1090                1095

Asp Thr  Lys Gly Asp Ser Ser  Arg Leu Leu Lys Ala  Leu Pro Leu
    1100                1105                1110

Lys Leu  Gln Gln Thr Ala Phe  Glu Asn Ala Tyr Leu  Lys Ala Gln
    1115                1120                1125

Glu Gly  Met Arg Glu Met Ser  His Ser Ala Glu Asn  Pro Glu Thr
    1130                1135                1140

Leu Asp  Glu Ile Tyr Asn Arg  Lys Ser Val Leu Leu  Thr Leu Ile
    1145                1150                1155

Ala Val  Val Leu Ser Cys Ser  Pro Ile Cys Glu Lys  Gln Ala Leu
    1160                1165                1170

Phe Ala  Leu Cys Lys Ser Val  Lys Glu Asn Gly Leu  Glu Pro His
    1175                1180                1185

Leu Val  Lys Lys Val Leu Glu  Lys Val Ser Glu Thr  Phe Gly Tyr
    1190                1195                1200

Arg Arg  Leu Glu Asp Phe Met  Ala Ser His Leu Asp  Tyr Leu Val
    1205                1210                1215

Leu Glu  Trp Leu Asn Leu Gln  Asp Thr Glu Tyr Asn  Leu Ser Ser
    1220                1225                1230

Phe Pro  Phe Ile Leu Leu Asn  Tyr Thr Asn Ile Glu  Asp Phe Tyr
    1235                1240                1245

Arg Ser  Cys Tyr Lys Val Leu  Ile Pro His Leu Val  Ile Arg Ser
    1250                1255                1260

His Phe  Asp Glu Val Lys Ser  Ile Ala Asn Gln Ile  Gln Glu Asp
    1265                1270                1275

Trp Lys  Ser Leu Leu Thr Asp  Cys Phe Pro Lys Ile  Leu Val Asn
    1280                1285                1290
```

-continued

```
Ile Leu  Pro Tyr Phe Ala Tyr  Glu Gly Thr Arg Asp  Ser Gly Met
    1295             1300              1305

Ala Gln  Gln Arg Glu Thr Ala  Thr Lys Val Tyr Asp  Met Leu Lys
    1310             1315              1320

Ser Glu  Asn Leu Leu Gly Lys  Gln Ile Asp His Leu  Phe Ile Ser
    1325             1330              1335

Asn Leu  Pro Glu Ile Val Val  Glu Leu Leu Met Thr  Leu His Glu
    1340             1345              1350

Pro Ala  Asn Ser Ser Ala Ser  Gln Ser Thr Asp Leu  Cys Asp Phe
    1355             1360              1365

Ser Gly  Asp Leu Asp Pro Ala  Pro Asn Pro Pro His  Phe Pro Ser
    1370             1375              1380

His Val  Ile Lys Ala Thr Phe  Ala Tyr Ile Ser Asn  Cys His Lys
    1385             1390              1395

Thr Lys  Leu Lys Ser Ile Leu  Glu Ile Leu Ser Lys  Ser Pro Asp
    1400             1405              1410

Ser Tyr  Gln Lys Ile Leu Leu  Ala Ile Cys Glu Gln  Ala Ala Glu
    1415             1420              1425

Thr Asn  Asn Val Tyr Lys Lys  His Arg Ile Leu Lys  Ile Tyr His
    1430             1435              1440

Leu Phe  Val Ser Leu Leu Leu  Lys Asp Ile Lys Ser  Gly Leu Gly
    1445             1450              1455

Gly Ala  Trp Ala Phe Val Leu  Arg Asp Val Ile Tyr  Thr Leu Ile
    1460             1465              1470

His Tyr  Ile Asn Gln Arg Pro  Ser Cys Ile Met Asp  Val Ser Leu
    1475             1480              1485

Arg Ser  Phe Ser Leu Cys Cys  Asp Leu Leu Ser Gln  Val Cys Gln
    1490             1495              1500

Thr Ala  Val Thr Tyr Cys Lys  Asp Ala Leu Glu Asn  His Leu His
    1505             1510              1515

Val Ile  Val Gly Thr Leu Ile  Pro Leu Val Tyr Glu  Gln Val Glu
    1520             1525              1530

Val Gln  Lys Gln Val Leu Asp  Leu Leu Lys Tyr Leu  Val Ile Asp
    1535             1540              1545

Asn Lys  Asp Asn Glu Asn Leu  Tyr Ile Thr Ile Lys  Leu Leu Asp
    1550             1555              1560

Pro Phe  Pro Asp His Val Val  Phe Lys Asp Leu Arg  Ile Thr Gln
    1565             1570              1575

Gln Lys  Ile Lys Tyr Ser Arg  Gly Pro Phe Ser Leu  Leu Glu Glu
    1580             1585              1590

Ile Asn  His Phe Leu Ser Val  Ser Val Tyr Asp Ala  Leu Pro Leu
    1595             1600              1605

Thr Arg  Leu Glu Gly Leu Lys  Asp Leu Arg Arg Gln  Leu Glu Leu
    1610             1615              1620

His Lys  Asp Gln Met Val Asp  Ile Met Arg Ala Ser  Gln Asp Asn
    1625             1630              1635

Pro Gln  Asp Gly Ile Met Val  Lys Leu Val Val Asn  Leu Leu Gln
    1640             1645              1650

Leu Ser  Lys Met Ala Ile Asn  His Thr Gly Glu Lys  Glu Val Leu
    1655             1660              1665

Glu Ala  Val Gly Ser Cys Leu  Gly Glu Val Gly Pro  Ile Asp Phe
    1670             1675              1680

Ser Thr  Ile Ala Ile Gln His  Ser Lys Asp Ala Ser  Tyr Thr Lys
```

-continued

```
        1685              1690              1695

Ala Leu Lys Leu Phe Glu Asp Lys Glu Leu Gln Trp  Thr Phe Ile
    1700              1705              1710

Met Leu Thr Tyr Leu Asn Asn Thr Leu Val Glu Asp  Cys Val Lys
    1715              1720              1725

Val Arg Ser Ala Ala Val Thr Cys Leu Lys Asn Ile  Leu Ala Thr
    1730              1735              1740

Lys Thr Gly His Ser Phe Trp Glu Ile Tyr Lys Met  Thr Thr Asp
    1745              1750              1755

Pro Met Leu Ala Tyr Leu Gln Pro Phe Arg Thr Ser  Arg Lys Lys
    1760              1765              1770

Phe Leu Glu Val Pro Arg Phe Asp Lys Glu Asn Pro  Phe Glu Gly
    1775              1780              1785

Leu Asp Asp Ile Asn Leu Trp Ile Pro Leu Ser Glu  Asn His Asp
    1790              1795              1800

Ile Trp Ile Lys Thr Leu Thr Cys Ala Phe Leu Asp  Ser Gly Gly
    1805              1810              1815

Thr Lys Cys Glu Ile Leu Gln Leu Leu Lys Pro Met  Cys Glu Val
    1820              1825              1830

Lys Thr Asp Phe Cys Gln Thr Val Leu Pro Tyr Leu  Ile His Asp
    1835              1840              1845

Ile Leu Leu Gln Asp Thr Asn Glu Ser Trp Arg Asn  Leu Leu Ser
    1850              1855              1860

Thr His Val Gln Gly Phe Phe Thr Ser Cys Leu Arg  His Phe Ser
    1865              1870              1875

Gln Thr Ser Arg Ser Thr Thr Pro Ala Asn Leu Asp  Ser Glu Ser
    1880              1885              1890

Glu His Phe Phe Arg Cys Cys Leu Asp Lys Lys Ser  Gln Arg Thr
    1895              1900              1905

Met Leu Ala Val Val Asp Tyr Met Arg Arg Gln Lys  Arg Pro Ser
    1910              1915              1920

Ser Gly Thr Ile Phe Asn Asp Ala Phe Trp Leu Asp  Leu Asn Tyr
    1925              1930              1935

Leu Glu Val Ala Lys Val Ala Gln Ser Cys Ala Ala  His Phe Thr
    1940              1945              1950

Ala Leu Leu Tyr Ala Glu Ile Tyr Ala Asp Lys Lys  Ser Met Asp
    1955              1960              1965

Asp Gln Glu Lys Arg Ser Leu Ala Phe Glu Glu Gly  Ser Gln Ser
    1970              1975              1980

Thr Thr Ile Ser Ser Leu Ser Glu Lys Ser Lys Glu  Glu Thr Gly
    1985              1990              1995

Ile Ser Leu Gln Asp Leu Leu Leu Glu Ile Tyr Arg  Ser Ile Gly
    2000              2005              2010

Glu Pro Asp Ser Leu Tyr Gly Cys Gly Gly Gly Lys  Met Leu Gln
    2015              2020              2025

Pro Ile Thr Arg Leu Arg Thr Tyr Glu His Glu Ala  Met Trp Gly
    2030              2035              2040

Lys Ala Leu Val Thr Tyr Asp Leu Glu Thr Ala Ile  Pro Ser Ser
    2045              2050              2055

Thr Arg Gln Ala Gly Ile Ile Gln Ala Leu Gln Asn  Leu Gly Leu
    2060              2065              2070

Cys His Ile Leu Ser Val Tyr Leu Lys Gly Leu Asp  Tyr Glu Asn
    2075              2080              2085
```

-continued

```
Lys Asp Trp Cys Pro Glu Leu  Glu Glu Leu His Tyr  Gln Ala Ala
    2090             2095              2100

Trp Arg Asn Met Gln Trp Asp  His Cys Thr Ser Val  Ser Lys Glu
    2105             2110              2115

Val Glu Gly Thr Ser Tyr His  Glu Ser Leu Tyr Asn  Ala Leu Gln
    2120             2125              2130

Ser Leu Arg Asp Arg Glu Phe  Ser Thr Phe Tyr Glu  Ser Leu Lys
    2135             2140              2145

Tyr Ala Arg Val Lys Glu Val  Glu Glu Met Cys Lys  Arg Ser Leu
    2150             2155              2160

Glu Ser Val Tyr Ser Leu Tyr  Pro Thr Leu Ser Arg  Leu Gln Ala
    2165             2170              2175

Ile Gly Glu Leu Glu Ser Ile  Gly Glu Leu Phe Ser  Arg Ser Val
    2180             2185              2190

Thr His Arg Gln Leu Ser Glu  Val Tyr Ile Lys Trp  Gln Lys His
    2195             2200              2205

Ser Gln Leu Leu Lys Asp Ser  Asp Phe Ser Phe Gln  Glu Pro Ile
    2210             2215              2220

Met Ala Leu Arg Thr Val Ile  Leu Glu Ile Leu Met  Glu Lys Glu
    2225             2230              2235

Met Asp Asn Ser Gln Arg Glu  Cys Ile Lys Asp Ile  Leu Thr Lys
    2240             2245              2250

His Leu Val Glu Leu Ser Ile  Leu Ala Arg Thr Phe  Lys Asn Thr
    2255             2260              2265

Gln Leu Pro Glu Arg Ala Ile  Phe Gln Ile Lys Gln  Tyr Asn Ser
    2270             2275              2280

Val Ser Cys Gly Val Ser Glu  Trp Gln Leu Glu Glu  Ala Gln Val
    2285             2290              2295

Phe Trp Ala Lys Lys Glu Gln  Ser Leu Ala Leu Ser  Ile Leu Lys
    2300             2305              2310

Gln Met Ile Lys Lys Leu Asp  Ala Ser Cys Ala Ala  Asn Asn Pro
    2315             2320              2325

Ser Leu Lys Leu Thr Tyr Thr  Glu Cys Leu Arg Val  Cys Gly Asn
    2330             2335              2340

Trp Leu Ala Glu Thr Cys Leu  Glu Asn Pro Ala Val  Ile Met Gln
    2345             2350              2355

Thr Tyr Leu Glu Lys Ala Val  Glu Val Ala Gly Asn  Tyr Asp Gly
    2360             2365              2370

Glu Ser Ser Asp Glu Leu Arg  Asn Gly Lys Met Lys  Ala Phe Leu
    2375             2380              2385

Ser Leu Ala Arg Phe Ser Asp  Thr Gln Tyr Gln Arg  Ile Glu Asn
    2390             2395              2400

Tyr Met Lys Ser Ser Glu Phe  Glu Asn Lys Gln Ala  Leu Leu Lys
    2405             2410              2415

Arg Ala Lys Glu Glu Val Gly  Leu Leu Arg Glu His  Lys Ile Gln
    2420             2425              2430

Thr Asn Arg Tyr Thr Val Lys  Val Gln Arg Glu Leu  Glu Leu Asp
    2435             2440              2445

Glu Leu Ala Leu Arg Ala Leu  Lys Glu Asp Arg Lys  Arg Phe Leu
    2450             2455              2460

Cys Lys Ala Val Glu Asn Tyr  Ile Asn Cys Leu Leu  Ser Gly Glu
    2465             2470              2475
```

```
Glu His Asp Met Trp Val Phe  Arg Leu Cys Ser Leu  Trp Leu Glu
    2480             2485             2490

Asn Ser Gly Val Ser Glu Val  Asn Gly Met Met Lys  Arg Asp Gly
    2495             2500             2505

Met Lys Ile Pro Thr Tyr Lys  Phe Leu Pro Leu Met  Tyr Gln Leu
    2510             2515             2520

Ala Ala Arg Met Gly Thr Lys  Met Met Gly Gly Leu  Gly Phe His
    2525             2530             2535

Glu Val Leu Asn Asn Leu Ile  Ser Arg Ile Ser Met  Asp His Pro
    2540             2545             2550

His His Thr Leu Phe Ile Ile  Leu Ala Leu Ala Asn  Ala Asn Arg
    2555             2560             2565

Asp Glu Phe Leu Thr Lys Pro  Glu Val Ala Arg Arg  Ser Arg Ile
    2570             2575             2580

Thr Lys Asn Val Pro Lys Gln  Ser Ser Gln Leu Asp  Glu Asp Arg
    2585             2590             2595

Thr Glu Ala Ala Asn Arg Ile  Ile Cys Thr Ile Arg  Ser Arg Arg
    2600             2605             2610

Pro Gln Met Val Arg Ser Val  Glu Ala Leu Cys Asp  Ala Tyr Ile
    2615             2620             2625

Ile Leu Ala Asn Leu Asp Ala  Thr Gln Trp Lys Thr  Gln Arg Lys
    2630             2635             2640

Gly Ile Asn Ile Pro Ala Asp  Gln Pro Ile Thr Lys  Leu Lys Asn
    2645             2650             2655

Leu Glu Asp Val Val Val Pro  Thr Met Glu Ile Lys  Val Asp His
    2660             2665             2670

Thr Gly Glu Tyr Gly Asn Leu  Val Thr Ile Gln Ser  Phe Lys Ala
    2675             2680             2685

Glu Phe Arg Leu Ala Gly Gly  Val Asn Leu Pro Lys  Ile Ile Asp
    2690             2695             2700

Cys Val Gly Ser Asp Gly Lys  Glu Arg Arg Gln Leu  Val Lys Gly
    2705             2710             2715

Arg Asp Asp Leu Arg Gln Asp  Ala Val Met Gln Gln  Val Phe Gln
    2720             2725             2730

Met Cys Asn Thr Leu Leu Gln  Arg Asn Thr Glu Thr  Arg Lys Arg
    2735             2740             2745

Lys Leu Thr Ile Cys Thr Tyr  Lys Val Val Pro Leu  Ser Gln Arg
    2750             2755             2760

Ser Gly Val Leu Glu Trp Cys  Thr Gly Thr Val Pro  Ile Gly Glu
    2765             2770             2775

Phe Leu Val Asn Asn Glu Asp  Gly Ala His Lys Arg  Tyr Arg Pro
    2780             2785             2790

Asn Asp Phe Ser Ala Phe Gln  Cys Gln Lys Lys Met  Met Glu Val
    2795             2800             2805

Gln Lys Lys Ser Phe Glu Glu  Lys Tyr Glu Val Phe  Met Asp Val
    2810             2815             2820

Cys Gln Asn Phe Gln Pro Val  Phe Arg Tyr Phe Cys  Met Glu Lys
    2825             2830             2835

Phe Leu Asp Pro Ala Ile Trp  Phe Glu Lys Arg Leu  Ala Tyr Thr
    2840             2845             2850

Arg Ser Val Ala Thr Ser Ser  Ile Val Gly Tyr Ile  Leu Gly Leu
    2855             2860             2865

Gly Asp Arg His Val Gln Asn  Ile Leu Ile Asn Glu  Gln Ser Ala
```

```
             2870                2875                2880

Glu Leu  Val His Ile Asp Leu  Gly Val Ala Phe Glu  Gln Gly Lys
    2885                2890                2895

Ile Leu  Pro Thr Pro Glu Thr  Val Pro Phe Arg Leu  Thr Arg Asp
    2900                2905                2910

Ile Val  Asp Gly Met Gly Ile  Thr Gly Val Glu Gly  Val Phe Arg
    2915                2920                2925

Arg Cys  Cys Glu Lys Thr Met  Glu Val Met Arg Asn  Ser Gln Glu
    2930                2935                2940

Thr Leu  Leu Thr Ile Val Glu  Val Leu Leu Tyr Asp  Pro Leu Phe
    2945                2950                2955

Asp Trp  Thr Met Asn Pro Leu  Lys Ala Leu Tyr Leu  Gln Gln Arg
    2960                2965                2970

Pro Glu  Asp Glu Thr Glu Leu  His Pro Thr Leu Asn  Ala Asp Asp
    2975                2980                2985

Gln Glu  Cys Lys Arg Asn Leu  Ser Asp Ile Asp Gln  Ser Phe Asn
    2990                2995                3000

Lys Val  Ala Glu Arg Val Leu  Met Arg Leu Gln Glu  Lys Leu Lys
    3005                3010                3015

Gly Val  Glu Glu Gly Thr Val  Leu Ser Val Gly Gly  Gln Val Asn
    3020                3025                3030

Leu Leu  Ile Gln Gln Ala Ile  Asp Pro Lys Asn Leu  Ser Arg Leu
    3035                3040                3045

Phe Pro  Gly Trp Lys Ala Trp  Val
    3050                3055
```

<210> SEQ ID NO 5
<211> LENGTH: 9171
<212> TYPE: DNA
<213> ORGANISM: Homo sapiens

<400> SEQUENCE: 5

```
atgagtctag tacttaatga tctgcttatc tgctgccgtc aactagaaca tgatagagct       60
acagaacgaa agaaagaagt tgagaaattt aagcgcctga ttcgagatcc tgaaacaatt      120
aaacatctag atcggcattc agattccaaa caaggaaaat atttgaattg ggatgctgtt      180
tttagatttt tacagaaata tattcagaaa gaaacagaat gtctgagaat agcaaaacca      240
aatgtatcag cctcaacaca agcctccagg cagaaaaaga tgcaggaaat cagtagtttg      300
gtcaaatact tcatcaaatg tgcaaacaga agagcaccta ggctaaaatg tcaagaactc      360
ttaaattata tcatggatac agtgaaagat tcatctaatg gtgctattta cggagctgat      420
tgtagcaaca tactactcaa agacattctt tctgtgagaa atactggtg tgaaatatct       480 cagcaacagt ggttagaatt gttctctgtg tacttcaggc tctatctgaa accttcacaa      540
gatgttcata gagtttttagt ggctagaata attcatgctg ttaccaaagg atgctgttct      600
cagactgacg gattaaattc caaatttttg gactttttt ccaaggctat tcagtgtgcg       660
agacaagaaa agagctcttc aggtctaaat catatcttag cagctcttac tatcttcctc      720
aagactttgg ctgtcaactt tcgaattcga gtgtgtgaat taggagatga aattcttccc      780
actttgcttt atatttggac tcaacatagg cttaatgatt ctttaaaaga agtcattatt      840
gaattatttc aactgcaaat ttatatccat catccgaaag agccaaaac ccaagaaaaa       900 ggtgcttatg aatcaacaaa atggagaagt attttataca acttatatga tctgctagtg      960
aatgagataa gtcatatagg aagtagagga aagtattctt caggatttcg taatattgcc     1020
```

-continued

```
gtcaaagaaa atttgattga attgatggca gatatctgtc accaggtttt taatgaagat    1080
accagatcct tggagatttc tcaatcttac actactacac aaagagaatc tagtgattac    1140
agtgtccctt gcaaaaggaa gaaaatagaa ctaggctggg aagtaataaa agatcacctt    1200
cagaagtcac agaatgattt tgatcttgtg ccttggctac agattgcaac ccaattaata    1260
tcaaagtatc ctgcaagttt acctaactgt gagctgtctc cattactgat gatactatct    1320
cagcttctac cccaacagcg acatgggaa cgtacaccat atgtgttacg atgccttacg     1380
gaagttgcat tgtgtcaaga caagaggtca aacctagaaa gctcacaaaa gtcagattta    1440
ttaaaactct ggaataaaat ttggtgtatt acctttcgtg gtataagttc tgagcaaata    1500
caagctgaaa actttggctt acttggagcc ataattcagg gtagtttagt tgaggttgac    1560
agagaattct ggaagttatt tactgggtca gcctgcagac cttcatgtcc tgcagtatgc    1620
tgtttgactt tggcactgac caccagtata gttccaggaa cggtaaaaat gggaatagag    1680
caaaatatgt gtgaagtaaa tagaagcttt tctttaaagg aatcaataat gaaatggctc    1740
ttattctatc agttagaggg tgacttagaa aatagcacag aagtgcctcc aattcttcac    1800
agtaattttc ctcatcttgt actggagaaa attcttgtga gtctcactat gaaaaactgt    1860
aaagctgcaa tgaatttttt ccaaagcgtg ccagaatgtg aacaccacca aaaagataaa    1920
gaagaacttt cattctcaga agtagaagaa ctatttcttc agacaacttt tgacaagatg    1980
gactttttaa ccattgtgag agaatgtggt atagaaaagc accagtccag tattggcttc    2040
tctgtccacc agaatctcaa ggaatcactg gatcgctgtc ttctgggatt atcagaacag    2100
cttctgaata attactcatc tgagattaca aattcagaaa ctcttgtccg gtgttcacgt    2160
cttttggtgg gtgtccttgg ctgctactgt tacatgggtg taatagctga agaggaagca    2220
tataagtcag aattattcca gaaagccaag tctctaatgc aatgtgcagg agaaagtatc    2280 actctgtta aaaataagac aaatgaggaa ttcagaattg gttccttgag aaatatgatg    2340
cagctatgta cacgttgctt gagcaactgt accaagaaga gtccaaataa gattgcatct    2400
ggctttttcc tgcgattgtt aacatcaaag ctaatgaatg acattgcaga tatttgtaaa    2460
agtttagcat ccttcatcaa aaagccattt gaccgtggag aagtagaatc aatggaagat    2520
gatactaatg gaaatctaat ggaggtggag gatcagtcat ccatgaatct atttaacgat    2580
taccctgata gtagtgttag tgatgcaaac gaacctggag agagccaaag taccataggt    2640
gccattaatc ctttagctga agaatatctg tcaaagcaag atctacttt cttagacatg     2700 ctcaagttct tgtgtttgtg tgtaactact gctcagacca atactgtgtc ctttagggca    2760
gctgatattc ggaggaaatt gttaatgtta attgattcta gcacgctaga acctaccaaa    2820
tccctccacc tgcatatgta tctaatgctt ttaaaggagc ttcctggaga agagtacccc    2880
ttgccaatgg aagatgttct tgaacttctg aaaccactat ccaatgtgtg ttctttgtat    2940
cgtcgtgacc aagatgtttg taaaactatt ttaaaccatg tccttcatgt agtgaaaaac    3000
ctaggtcaaa gcaatatgga ctctgagaac acaagggatg ctcaaggaca gtttcttaca    3060
gtaattggag cattttggca tctaacaaag gagaggaaat atatattctc tgtaagaatg    3120
gccctagtaa attgccttaa aactttgctt gaggctgatc cttattcaaa atgggccatt    3180
cttaatgtaa tgggaaaaga ctttcctgta aatgaagtat ttacacaatt tcttgctgac    3240
aatcatcacc aagttcgcat gttggctgca gagtcaatca atagattgtt ccaggacacg    3300
aagggagatt cttccaggtt actgaaagca cttcctttga agcttcagca aacagctttt    3360
```

-continued

```
gaaaatgcat acttgaaagc tcaggaagga atgagagaaa tgtcccatag tgctgagaac    3420
cctgaaactt tggatgaaat ttataataga aaatctgttt tactgacgtt gatagctgtg    3480
gttttatcct gtagccctat ctgcgaaaaa caggctttgt ttgccctgtg taaatctgtg    3540
aaagagaatg gattagaacc tcaccttgtg aaaaaggttt tagagaaagt ttctgaaact    3600
tttggatata gacgtttaga agactttatg gcatctcatt tagattatct ggtttttggaa   3660 tggctaaatc ttcaagatac tgaatacaac ttatcttctt ttccttttat tttattaaac    3720
tacacaaata ttgaggattt ctatagatct tgttataagg ttttgattcc acatctggtg    3780
attagaagtc attttgatga ggtgaagtcc attgctaatc agattcaaga ggactggaaa    3840
agtcttctaa cagactgctt tccaaagatt cttgtaaata ttcttcctta ttttgcctat    3900
gagggtacca gagacagtgg gatggcacag caaagagaga ctgctaccaa ggtctatgat    3960
atgcttaaaa gtgaaaactt attgggaaaa cagattgatc acttattcat tagtaatta    4020 ccagagattg tggtggagtt attgatgacg ttacatgagc cagcaaattc tagtgccagt    4080
cagagcactg acctctgtga cttttcaggg gatttggatc ctgctcctaa tccacctcat    4140
tttccatcgc atgtgattaa agcaacattt gcctatatca gcaattgtca taaaaccaag    4200
ttaaaaagca ttttagaaat tctttccaaa agccctgatt cctatcagaa aattcttctt    4260
gccatatgtg agcaagcagc tgaaacaaat aatgtttata agaagcacag aattcttaaa    4320
atatatcacc tgtttgttag tttattactg aaagatataa aaagtggctt aggaggagct    4380
tgggcctttg ttcttcgaga cgttatttat actttgattc actatatcaa ccaaaggcct    4440
tcttgtatca tggatgtgtc attacgtagc ttctcccttt gttgtgactt attaagtcag    4500
gtttgccaga cagccgtgac ttactgtaag gatgctctag aaaaccatct tcatgttatt    4560
gttggtacac ttatacccct tgtgtatgag caggtggagg ttcagaaaca ggtattggac    4620
ttgttgaaat acttagtgat agataacaag gataatgaaa acctctatat cacgattaag    4680
cttttagatc cttttcctga ccatgttgtt tttaaggatt tgcgtattac tcagcaaaaa    4740
atcaaataca gtagaggacc cttttcactc ttggaggaaa ttaaccattt tctctcagta    4800
agtgtttatg atgcacttcc attgacaaga cttgaaggac taaaggatct tcgaagacaa    4860
ctggaactac ataaagatca gatggtggac attatgagag cttctcagga taatccgcaa    4920
gatgggatta tggtgaaact agttgtcaat ttgttgcagt tatccaagat ggcaataaac    4980
cacactggtg aaaaagaagt tctagaggct gttggaagct gcttgggaga agtgggtcct    5040
atagatttct ctaccatagc tatacaacat agtaaagatg catcttatac caaggccctt    5100
aagttatttg aagataaaga acttcagtgg accttcataa tgctgaccta cctgaataac    5160
acactggtag aagattgtgt caaagttcga tcagcagctg ttacctgttt gaaaaacatt    5220
ttagccacaa agactggaca tagtttctgg gagatttata agatgacaac agatccaatg    5280
ctggcctatc tacagccttt tagaacatca agaaaaaagt ttttagaagt acccagattt    5340
gacaaagaaa acccttttga aggcctggat gatataaatc tgtggattcc tctaagtgaa    5400
aatcatgaca tttggataaa gacactgact tgtgcttttt tggacagtgg aggcacaaaa    5460
tgtgaaattc ttcaattatt aaagccaatg tgtgaagtga aaactgactt ttgtcagact    5520
gtacttccat acttgattca tgatatttta ctccaagata caaatgaatc atggagaaat    5580
ctgctttcta cacatgttca gggatttttt accagctgtc ttcgacactt ctcgcaaacg    5640
agccgatcca caacccctgc aaacttggat tcagagtcag agcacttttt ccgatgctgt    5700
ttggataaaa aatcacaaag aacaatgctt gctgttgtgg actacatgag aagacaaaag    5760
```

-continued

```
agaccttctt caggaacaat ttttaatgat gctttctggc tggatttaaa ttatctagaa    5820
gttgccaagg tagctcagtc ttgtgctgct cactttacag ctttactcta tgcagaaatc    5880
tatgcagata agaaaagtat ggatgatcaa gagaaaagaa gtcttgcatt tgaagaagga    5940
agccagagta caactatttc tagcttgagt gaaaaaagta aagaagaaac tggaataagt    6000
ttacaggatc ttctcttaga aatctacaga agtatagggg agccagatag tttgtatggc    6060
tgtggtggag ggaagatgtt acaacccatt actagactac gaacatatga acacgaagca    6120
atgtggggca aagccctagt aacatatgac ctcgaaacag caatcccctc atcaacacgc    6180
caggcaggaa tcattcaggc cttgcagaat ttgggactct gccatattct ttccgtctat    6240
ttaaaaggat tggattatga aaataaagac tggtgtcctg aactagaaga acttcattac    6300
caagcagcat ggaggaatat gcagtgggac cattgcactt ccgtcagcaa agaagtagaa    6360
ggaaccagtt accatgaatc attgtacaat gctctacaat ctctaagaga cagagaattc    6420
tctacatttt atgaaagtct caaatatgcc agagtaaaag aagtggaaga gatgtgtaag    6480
cgcagccttg agtctgtgta ttcgctctat cccacactta gcaggttgca ggccattgga    6540
gagctggaaa gcattgggga gcttttctca agatcagtca cacatagaca actctctgaa    6600
gtatatatta agtggcagaa acactcccag cttctcaagg acagtgattt tagttttcag    6660
gagcctatca tggctctacg cacagtcatt ttggagatcc tgatggaaaa ggaaatggac    6720
aactcacaaa gagaatgtat taaggacatt ctcaccaaac accttgtaga actctctata    6780
ctggccagaa cttttcaagaa cactcagctc cctgaaaggg caatatttca aattaaacag    6840
tacaattcag ttagctgtgg agtctctgag tggcagctgg aagaagcaca agtattctgg    6900
gcaaaaaagg agcagagtct tgccctgagt attctcaagc aaatgatcaa gaagttggat    6960
gccagctgtg cagcgaacaa tcccagccta aaacttacat acacagaatg tctgagggtt    7020
tgtggcaact ggttagcaga aacgtgctta gaaaatcctg cggtcatcat gcagacctat    7080
ctagaaaagg cagtagaagt tgctggaaat tatgatggag aaagtagtga tgagctaaga    7140
aatgaaaaaa tgaaggcatt tctctcatta gcccggtttt cagatactca ataccaaaga    7200
attgaaaact acatgaaatc atcggaattt gaaaacaagc aagctctcct gaaaagagcc    7260
aaagaggaag taggtctcct tagggaacat aaaattcaga caaacagata cacagtaaag    7320
gttcagcgag agctggagtt ggatgaatta gccctgcgtg cactgaaaga ggatcgtaaa    7380
cgcttcttat gtaaagcagt tgaaaattat atcaactgct tattaagtgg agaagaacat    7440
gatatgtggg tattccgact ttgttccctc tggcttgaaa attctggagt ttctgaagtc    7500
aatggcatga tgaagagaga cggaatgaag attccaacat ataaattttt gcctcttatg    7560
taccaattgg ctgctagaat ggggaccaag atgatgggag gcctaggatt tcatgaagtc    7620
ctcaataatc taatctctag aatttcaatg gatcacccccc atcacacttt gtttattata    7680
ctggccttag caaatgcaaa cagagatgaa tttctgacta aaccagaggt agccagaaga    7740
agcagaataa ctaaaaatgt gcctaaacaa agctctcagc ttgatgagga tcgaacagag    7800
gctgcaaata gaataatatg tactatcaga agtaggagac ctcagatggt cagaagtgtt    7860
gaggcacttt gtgatgctta tattatatta gcaaacttag atgccactca gtggaagact    7920
cagagaaaag gcataaatat tccagcagac cagccaatta ctaaacttaa gaatttagaa    7980
gatgttgttg tccctactat ggaaattaag gtggaccaca caggagaata tggaaatctg    8040
gtgactatac agtcatttaa agcagaattt cgcttagcag gaggtgtaaa tttaccaaaa    8100
```

```
ataatagatt gtgtaggttc cgatggcaag gagaggagac agcttgttaa gggccgtgat      8160
gacctgagac aagatgctgt catgcaacag gtcttccaga tgtgtaatac attactgcag      8220
agaaacacgg aaactaggaa gaggaaatta actatctgta cttataaggt ggttcccctc      8280
tctcagcgaa gtggtgttct tgaatggtgc acaggaactg tccccattgg tgaatttctt      8340
gttaacaatg aagatggtgc tcataaaaga tacaggccaa atgatttcag tgcctttcag      8400
tgccaaaaga aaatgatgga ggtgcaaaaa aagtcttttg aagagaaata tgaagtcttc      8460
atggatgttt gccaaaattt tcaaccagtt ttccgttact tctgcatgga aaaattcttg      8520
gatccagcta tttggtttga aagcgattg gcttatacgc gcagtgtagc tacttcttct      8580
attgttggtt acatacttgg acttggtgat agacatgtac agaatatctt gataaatgag      8640
cagtcagcag aacttgtaca tatagatcta ggtgttgctt ttgaacaggg caaaatcctt      8700
cctactcctg agacagttcc ttttagactc accagagata ttgtggatgg catgggcatt      8760
acgggtgttg aaggtgtctt cagaagatgc tgtgagaaaa ccatggaagt gatgagaaac      8820
tctcaggaaa ctctgttaac cattgtagag gtccttctat atgatccact ctttgactgg      8880
accatgaatc ctttgaaagc tttgtattta cagcagaggc cggaagatga aactgagctt      8940
caccctactc tgaatgcaga tgaccaagaa tgcaaacgaa atctcagtga tattgaccag      9000
agtttcaaca agtagctga acgtgtctta atgagactac aagagaaact gaaaggagtg      9060
gaagaaggca ctgtgctcag tgttggtgga caagtgaatt tgctcataca gcaggccata      9120
gaccccaaaa atctcagccg acttttccca ggatggaaag cttgggtgtg a              9171
```

<210> SEQ ID NO 6
<211> LENGTH: 2644
<212> TYPE: PRT
<213> ORGANISM: Homo sapiens

<400> SEQUENCE: 6

```
Met Gly Glu His Gly Leu Glu Leu Ala Ser Met Ile Pro Ala Leu Arg
1               5                   10                  15

Glu Leu Gly Ser Ala Thr Pro Glu Glu Tyr Asn Thr Val Val Gln Lys
            20                  25                  30

Pro Arg Gln Ile Leu Cys Gln Phe Ile Asp Arg Ile Leu Thr Asp Val
        35                  40                  45

Asn Val Val Ala Val Glu Leu Val Lys Lys Thr Asp Ser Gln Pro Thr
    50                  55                  60

Ser Val Met Leu Leu Asp Phe Ile Gln His Ile Met Lys Ser Ser Pro
65                  70                  75                  80

Leu Met Phe Val Asn Val Ser Gly Ser His Glu Ala Lys Gly Ser Cys
                85                  90                  95

Ile Glu Phe Ser Asn Trp Ile Ile Thr Arg Leu Leu Arg Ile Ala Ala
            100                 105                 110

Thr Pro Ser Cys His Leu Leu His Lys Lys Ile Cys Glu Val Ile Cys
        115                 120                 125

Ser Leu Leu Phe Leu Phe Lys Ser Lys Ser Pro Ala Ile Phe Gly Val
    130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                165                 170                 175

Arg Phe Leu Ser Gln Leu Asp Glu His Met Gly Tyr Leu Gln Ser Ala
            180                 185                 190
```

-continued

```
Pro Leu Gln Leu Met Ser Met Gln Asn Leu Glu Phe Ile Glu Val Thr
        195                 200                 205

Leu Leu Met Val Leu Thr Arg Ile Ile Ala Ile Val Phe Phe Arg Arg
        210                 215                 220

Gln Glu Leu Leu Leu Trp Gln Ile Gly Cys Val Leu Leu Glu Tyr Gly
225                 230                 235                 240

Ser Pro Lys Ile Lys Ser Leu Ala Ile Ser Phe Leu Thr Glu Leu Phe
                245                 250                 255

Gln Leu Gly Gly Leu Pro Ala Gln Pro Ala Ser Thr Phe Phe Ser Ser
        260                 265                 270

Phe Leu Glu Leu Leu Lys His Leu Val Glu Met Asp Thr Asp Gln Leu
        275                 280                 285

Lys Leu Tyr Glu Glu Pro Leu Ser Lys Leu Ile Lys Thr Leu Phe Pro
        290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                325                 330                 335

Leu Lys Ser Asp Leu Leu Lys Ala Ala Leu Cys His Leu Leu Gln Tyr
        340                 345                 350

Phe Leu Lys Phe Val Pro Ala Gly Tyr Glu Ser Ala Leu Gln Val Arg
        355                 360                 365

Lys Val Tyr Val Arg Asn Ile Cys Lys Ala Leu Leu Asp Val Leu Gly
        370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Glu Ile Gln Cys Gln Thr Gln
                405                 410                 415

Gln Glu Asn Leu Ser Ser Asn Ser Asp Gly Ile Ser Pro Lys Arg Arg
        420                 425                 430

Arg Leu Ser Ser Ser Leu Asn Pro Ser Lys Arg Ala Pro Lys Gln Thr
        435                 440                 445

Glu Glu Ile Lys His Val Asp Met Asn Gln Lys Ser Ile Leu Trp Ser
        450                 455                 460

Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
                485                 490                 495

Leu Gln Leu Thr Ala Leu Cys Thr Val His Cys Ser His Gln Asn Met
        500                 505                 510

Asn Cys Arg Thr Phe Lys Asp Cys Gln His Lys Ser Lys Lys Lys Pro
        515                 520                 525

Ser Val Val Ile Thr Trp Met Ser Leu Asp Phe Tyr Thr Lys Val Leu
        530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
                565                 570                 575

Gln Val Asn Ser Ser Phe Glu Asp His Ile Leu Glu Asp Leu Cys Gly
        580                 585                 590

Met Leu Ser Leu Pro Trp Ile Tyr Ser His Ser Asp Asp Gly Cys Leu
        595                 600                 605
```

Lys Leu Thr Thr Phe Ala Ala Asn Leu Leu Thr Leu Ser Cys Arg Ile
    610             615             620

Ser Asp Ser Tyr Ser Pro Gln Ala Gln Ser Arg Cys Val Phe Leu Leu
625             630             635             640

Thr Leu Phe Pro Arg Arg Ile Phe Leu Glu Trp Arg Thr Ala Val Tyr
            645             650             655

Asn Trp Ala Leu Gln Ser Ser His Glu Val Ile Arg Ala Ser Cys Val
            660             665             670

Ser Gly Phe Phe Ile Leu Leu Gln Gln Gln Asn Ser Cys Asn Arg Val
            675             680             685

Pro Lys Ile Leu Ile Asp Lys Val Lys Asp Asp Ser Asp Ile Val Lys
    690             695             700

Lys Glu Phe Ala Ser Ile Leu Gly Gln Leu Val Cys Thr Leu His Gly
705             710             715             720

Met Phe Tyr Leu Thr Ser Ser Leu Thr Glu Pro Phe Ser Glu His Gly
            725             730             735

His Val Asp Leu Phe Cys Arg Asn Leu Lys Ala Thr Ser Gln His Glu
            740             745             750

Cys Ser Ser Ser Gln Leu Lys Ala Ser Val Cys Lys Pro Phe Leu Phe
    755             760             765

Leu Leu Lys Lys Lys Ile Pro Ser Pro Val Lys Leu Ala Phe Ile Asp
    770             775             780

Asn Leu His His Leu Cys Lys His Leu Asp Phe Arg Glu Asp Glu Thr
785             790             795             800

Asp Val Lys Ala Val Leu Gly Thr Leu Leu Asn Leu Met Glu Asp Pro
            805             810             815

Asp Lys Asp Val Arg Val Ala Phe Ser Gly Asn Ile Lys His Ile Leu
            820             825             830

Glu Ser Leu Asp Ser Glu Asp Gly Phe Ile Lys Glu Leu Phe Val Leu
    835             840             845

Arg Met Lys Glu Ala Tyr Thr His Ala Gln Ile Ser Arg Asn Asn Glu
    850             855             860

Leu Lys Asp Thr Leu Ile Leu Thr Thr Gly Asp Ile Gly Arg Ala Ala
865             870             875             880

Lys Gly Asp Leu Val Pro Phe Ala Leu Leu His Leu Leu His Cys Leu
            885             890             895

Leu Ser Lys Ser Ala Ser Val Ser Gly Ala Ala Tyr Thr Glu Ile Arg
            900             905             910

Ala Leu Val Ala Ala Lys Ser Val Lys Leu Gln Ser Phe Phe Ser Gln
    915             920             925

Tyr Lys Lys Pro Ile Cys Gln Phe Leu Val Glu Ser Leu His Ser Ser
    930             935             940

Gln Met Thr Ala Leu Pro Asn Thr Pro Cys Gln Asn Ala Asp Val Arg
945             950             955             960

Lys Gln Asp Val Ala His Gln Arg Glu Met Ala Leu Asn Thr Leu Ser
            965             970             975

Glu Ile Ala Asn Val Phe Asp Phe Pro Asp Leu Asn Arg Phe Leu Thr
            980             985             990

Arg Thr Leu Gln Val Leu Leu Pro  Asp Leu Ala Ala Lys  Ala Ser Pro
    995             1000             1005

Ala Ala  Ser Ala Leu Ile Arg  Thr Leu Gly Lys Gln  Leu Asn Val
    1010             1015             1020

Asn Arg  Arg Glu Ile Leu Ile  Asn Asn Phe Lys Tyr  Ile Phe Ser

-continued

```
        1025                1030                1035

His Leu Val Cys Ser Cys Ser Lys Asp Glu Leu Glu Arg Ala Leu
    1040                1045                1050

His Tyr Leu Lys Asn Glu Thr Glu Ile Glu Leu Gly Ser Leu Leu
    1055                1060                1065

Arg Gln Asp Phe Gln Gly Leu His Asn Glu Leu Leu Leu Arg Ile
    1070                1075                1080

Gly Glu His Tyr Gln Gln Val Phe Asn Gly Leu Ser Ile Leu Ala
    1085                1090                1095

Ser Phe Ala Ser Ser Asp Asp Pro Tyr Gln Gly Pro Arg Asp Ile
    1100                1105                1110

Ile Ser Pro Glu Leu Met Ala Asp Tyr Leu Gln Pro Lys Leu Leu
    1115                1120                1125

Gly Ile Leu Ala Phe Phe Asn Met Gln Leu Leu Ser Ser Ser Val
    1130                1135                1140

Gly Ile Glu Asp Lys Lys Met Ala Leu Asn Ser Leu Met Ser Leu
    1145                1150                1155

Met Lys Leu Met Gly Pro Lys His Val Ser Ser Val Arg Val Lys
    1160                1165                1170

Met Met Thr Thr Leu Arg Thr Gly Leu Arg Phe Lys Asp Asp Phe
    1175                1180                1185

Pro Glu Leu Cys Cys Arg Ala Trp Asp Cys Phe Val Arg Cys Leu
    1190                1195                1200

Asp His Ala Cys Leu Gly Ser Leu Leu Ser His Val Ile Val Ala
    1205                1210                1215

Leu Leu Pro Leu Ile His Ile Gln Pro Lys Glu Thr Ala Ala Ile
    1220                1225                1230

Phe His Tyr Leu Ile Ile Glu Asn Arg Asp Ala Val Gln Asp Phe
    1235                1240                1245

Leu His Glu Ile Tyr Phe Leu Pro Asp His Pro Glu Leu Lys Lys
    1250                1255                1260

Ile Lys Ala Val Leu Gln Glu Tyr Arg Lys Glu Thr Ser Glu Ser
    1265                1270                1275

Thr Asp Leu Gln Thr Thr Leu Gln Leu Ser Met Lys Ala Ile Gln
    1280                1285                1290

His Glu Asn Val Asp Val Arg Ile His Ala Leu Thr Ser Leu Lys
    1295                1300                1305

Glu Thr Leu Tyr Lys Asn Gln Glu Lys Leu Ile Lys Tyr Ala Thr
    1310                1315                1320

Asp Ser Glu Thr Val Glu Pro Ile Ile Ser Gln Leu Val Thr Val
    1325                1330                1335

Leu Leu Lys Gly Cys Gln Asp Ala Asn Ser Gln Ala Arg Leu Leu
    1340                1345                1350

Cys Gly Glu Cys Leu Gly Glu Leu Gly Ala Ile Asp Pro Gly Arg
    1355                1360                1365

Leu Asp Phe Ser Thr Thr Glu Thr Gln Gly Lys Asp Phe Thr Phe
    1370                1375                1380

Val Thr Gly Val Glu Asp Ser Ser Phe Ala Tyr Gly Leu Leu Met
    1385                1390                1395

Glu Leu Thr Arg Ala Tyr Leu Ala Tyr Ala Asp Asn Ser Arg Ala
    1400                1405                1410

Gln Asp Ser Ala Ala Tyr Ala Ile Gln Glu Leu Leu Ser Ile Tyr
    1415                1420                1425
```

```
Asp Cys Arg Glu Met Glu Thr Asn Gly Pro Gly His Gln Leu Trp
    1430              1435              1440

Arg Arg Phe Pro Glu His Val Arg Glu Ile Leu Glu Pro His Leu
    1445              1450              1455

Asn Thr Arg Tyr Lys Ser Ser Gln Lys Ser Thr Asp Trp Ser Gly
    1460              1465              1470

Val Lys Lys Pro Ile Tyr Leu Ser Lys Leu Gly Ser Asn Phe Ala
    1475              1480              1485

Glu Trp Ser Ala Ser Trp Ala Gly Tyr Leu Ile Thr Lys Val Arg
    1490              1495              1500

His Asp Leu Ala Ser Lys Ile Phe Thr Cys Cys Ser Ile Met Met
    1505              1510              1515

Lys His Asp Phe Lys Val Thr Ile Tyr Leu Leu Pro His Ile Leu
    1520              1525              1530

Val Tyr Val Leu Leu Gly Cys Asn Gln Glu Asp Gln Gln Glu Val
    1535              1540              1545

Tyr Ala Glu Ile Met Ala Val Leu Lys His Asp Asp Gln His Thr
    1550              1555              1560

Ile Asn Thr Gln Asp Ile Ala Ser Asp Leu Cys Gln Leu Ser Thr
    1565              1570              1575

Gln Thr Val Phe Ser Met Leu Asp His Leu Thr Gln Trp Ala Arg
    1580              1585              1590

His Lys Phe Gln Ala Leu Lys Ala Glu Lys Cys Pro His Ser Lys
    1595              1600              1605

Ser Asn Arg Asn Lys Val Asp Ser Met Val Ser Thr Val Asp Tyr
    1610              1615              1620

Glu Asp Tyr Gln Ser Val Thr Arg Phe Leu Asp Leu Ile Pro Gln
    1625              1630              1635

Asp Thr Leu Ala Val Ala Ser Phe Arg Ser Lys Ala Tyr Thr Arg
    1640              1645              1650

Ala Val Met His Phe Glu Ser Phe Ile Thr Glu Lys Lys Gln Asn
    1655              1660              1665

Ile Gln Glu His Leu Gly Phe Leu Gln Lys Leu Tyr Ala Ala Met
    1670              1675              1680

His Glu Pro Asp Gly Val Ala Gly Val Ser Ala Ile Arg Lys Ala
    1685              1690              1695

Glu Pro Ser Leu Lys Glu Gln Ile Leu Glu His Glu Ser Leu Gly
    1700              1705              1710

Leu Leu Arg Asp Ala Thr Ala Cys Tyr Asp Arg Ala Ile Gln Leu
    1715              1720              1725

Glu Pro Asp Gln Ile Ile His Tyr His Gly Val Val Lys Ser Met
    1730              1735              1740

Leu Gly Leu Gly Gln Leu Ser Thr Val Ile Thr Gln Val Asn Gly
    1745              1750              1755

Val His Ala Asn Arg Ser Glu Trp Thr Asp Glu Leu Asn Thr Tyr
    1760              1765              1770

Arg Val Glu Ala Ala Trp Lys Leu Ser Gln Trp Asp Leu Val Glu
    1775              1780              1785

Asn Tyr Leu Ala Ala Asp Gly Lys Ser Thr Thr Trp Ser Val Arg
    1790              1795              1800

Leu Gly Gln Leu Leu Leu Ser Ala Lys Lys Arg Asp Ile Thr Ala
    1805              1810              1815
```

-continued

```
Phe Tyr  Asp Ser Leu Lys Leu  Val Arg Ala Glu Gln  Ile Val Pro
    1820             1825             1830

Leu Ser  Ala Ala Ser Phe Glu  Arg Gly Ser Tyr Gln  Arg Gly Tyr
    1835             1840             1845

Glu Tyr  Ile Val Arg Leu His  Met Leu Cys Glu Leu  Glu His Ser
    1850             1855             1860

Ile Lys  Pro Leu Phe Gln His  Ser Pro Gly Asp Ser  Ser Gln Glu
    1865             1870             1875

Asp Ser  Leu Asn Trp Val Ala  Arg Leu Glu Met Thr  Gln Asn Ser
    1880             1885             1890

Tyr Arg  Ala Lys Glu Pro Ile  Leu Ala Leu Arg Arg  Ala Leu Leu
    1895             1900             1905

Ser Leu  Asn Lys Arg Pro Asp  Tyr Asn Glu Met Val  Gly Glu Cys
    1910             1915             1920

Trp Leu  Gln Ser Ala Arg Val  Ala Arg Lys Ala Gly  His His Gln
    1925             1930             1935

Thr Ala  Tyr Asn Ala Leu Leu  Asn Ala Gly Glu Ser  Arg Leu Ala
    1940             1945             1950

Glu Leu  Tyr Val Glu Arg Ala  Lys Trp Leu Trp Ser  Lys Gly Asp
    1955             1960             1965

Val His  Gln Ala Leu Ile Val  Leu Gln Lys Gly Val  Glu Leu Cys
    1970             1975             1980

Phe Pro  Glu Asn Glu Thr Pro  Pro Glu Gly Lys Asn  Met Leu Ile
    1985             1990             1995

His Gly  Arg Ala Met Leu Leu  Val Gly Arg Phe Met  Glu Glu Thr
    2000             2005             2010

Ala Asn  Phe Glu Ser Asn Ala  Ile Met Lys Lys Tyr  Lys Asp Val
    2015             2020             2025

Thr Ala  Cys Leu Pro Glu Trp  Glu Asp Gly His Phe  Tyr Leu Ala
    2030             2035             2040

Lys Tyr  Tyr Asp Lys Leu Met  Pro Met Val Thr Asp  Asn Lys Met
    2045             2050             2055

Glu Lys  Gln Gly Asp Leu Ile  Arg Tyr Ile Val Leu  His Phe Gly
    2060             2065             2070

Arg Ser  Leu Gln Tyr Gly Asn  Gln Phe Ile Tyr Gln  Ser Met Pro
    2075             2080             2085

Arg Met  Leu Thr Leu Trp Leu  Asp Tyr Gly Thr Lys  Ala Tyr Glu
    2090             2095             2100

Trp Glu  Lys Ala Gly Arg Ser  Asp Arg Val Gln Met  Arg Asn Asp
    2105             2110             2115

Leu Gly  Lys Ile Asn Lys Val  Ile Thr Glu His Thr  Asn Tyr Leu
    2120             2125             2130

Ala Pro  Tyr Gln Phe Leu Thr  Ala Phe Ser Gln Leu  Ile Ser Arg
    2135             2140             2145

Ile Cys  His Ser His Asp Glu  Val Phe Val Val Leu  Met Glu Ile
    2150             2155             2160

Ile Ala  Lys Val Phe Leu Ala  Tyr Pro Gln Gln Ala  Met Trp Met
    2165             2170             2175

Met Thr  Ala Val Ser Lys Ser  Ser Tyr Pro Met Arg  Val Asn Arg
    2180             2185             2190

Cys Lys  Glu Ile Leu Asn Lys  Ala Ile His Met Lys  Lys Ser Leu
    2195             2200             2205

Glu Lys  Phe Val Gly Asp Ala  Thr Arg Leu Thr Asp  Lys Leu Leu
```

```
             2210                2215                2220

Glu Leu Cys Asn Lys Pro Val Asp Gly Ser Ser Ser Thr Leu Ser
    2225                2230                2235

Met Ser Thr His Phe Lys Met Leu Lys Lys Leu Val Glu Glu Ala
    2240                2245                2250

Thr Phe Ser Glu Ile Leu Ile Pro Leu Gln Ser Val Met Ile Pro
    2255                2260                2265

Thr Leu Pro Ser Ile Leu Gly Thr His Ala Asn His Ala Ser His
    2270                2275                2280

Glu Pro Phe Pro Gly His Trp Ala Tyr Ile Ala Gly Phe Asp Asp
    2285                2290                2295

Met Val Glu Ile Leu Ala Ser Leu Gln Lys Pro Lys Lys Ile Ser
    2300                2305                2310

Leu Lys Gly Ser Asp Gly Lys Phe Tyr Ile Met Met Cys Lys Pro
    2315                2320                2325

Lys Asp Asp Leu Arg Lys Asp Cys Arg Leu Met Glu Phe Asn Ser
    2330                2335                2340

Leu Ile Asn Lys Cys Leu Arg Lys Asp Ala Glu Ser Arg Arg Arg
    2345                2350                2355

Glu Leu His Ile Arg Thr Tyr Ala Val Ile Pro Leu Asn Asp Glu
    2360                2365                2370

Cys Gly Ile Ile Glu Trp Val Asn Asn Thr Ala Gly Leu Arg Pro
    2375                2380                2385

Ile Leu Thr Lys Leu Tyr Lys Glu Lys Gly Val Tyr Met Thr Gly
    2390                2395                2400

Lys Glu Leu Arg Gln Cys Met Leu Pro Lys Ser Ala Ala Leu Ser
    2405                2410                2415

Glu Lys Leu Lys Val Phe Arg Glu Phe Leu Leu Pro Arg His Pro
    2420                2425                2430

Pro Ile Phe His Glu Trp Phe Leu Arg Thr Phe Pro Asp Pro Thr
    2435                2440                2445

Ser Trp Tyr Ser Ser Arg Ser Ala Tyr Cys Arg Ser Thr Ala Val
    2450                2455                2460

Met Ser Met Val Gly Tyr Ile Leu Gly Leu Gly Asp Arg His Gly
    2465                2470                2475

Glu Asn Ile Leu Phe Asp Ser Leu Thr Gly Glu Cys Val His Val
    2480                2485                2490

Asp Phe Asn Cys Leu Phe Asn Lys Gly Glu Thr Phe Glu Val Pro
    2495                2500                2505

Glu Ile Val Pro Phe Arg Leu Thr His Asn Met Val Asn Gly Met
    2510                2515                2520

Gly Pro Met Gly Thr Glu Gly Leu Phe Arg Arg Ala Cys Glu Val
    2525                2530                2535

Thr Met Arg Leu Met Arg Asp Gln Arg Glu Pro Leu Met Ser Val
    2540                2545                2550

Leu Lys Thr Phe Leu His Asp Pro Leu Val Glu Trp Ser Lys Pro
    2555                2560                2565

Val Lys Gly His Ser Lys Ala Pro Leu Asn Glu Thr Gly Glu Val
    2570                2575                2580

Val Asn Glu Lys Ala Lys Thr His Val Leu Asp Ile Glu Gln Arg
    2585                2590                2595

Leu Gln Gly Val Ile Lys Thr Arg Asn Arg Val Thr Gly Leu Pro
    2600                2605                2610
```

-continued

```
Leu Ser  Ile Glu Gly His Val  His Tyr Leu Ile Gln  Glu Ala Thr
    2615                2620                2625

Asp Glu  Asn Leu Leu Cys Gln  Met Tyr Leu Gly Trp  Thr Pro Tyr
    2630                2635                2640

Met
```

```
<210> SEQ ID NO 7
<211> LENGTH: 7935
<212> TYPE: DNA
<213> ORGANISM: Homo sapiens

<400> SEQUENCE: 7
atgggggaac atggcctgga gctggcttcc atgatccccg ccctgcggga gctgggcagt      60
gccacaccag aggaatataa tacagttgta cagaagccaa gacaaattct gtgtcaattc     120
attgaccgga tacttacaga tgtaaatgtt gttgctgtag aacttgtaaa gaaaactgac     180
tctcagccaa cctccgtgat gttgcttgat ttcatccagc atatcatgaa atcctcccca     240
cttatgtttg taaatgtgag tggaagccat gaggccaaag gcagttgtat tgaattcagt     300
aattggatca taacgagact tctgcggatt gcagcaactc cctcctgtca tttgttacac     360
aagaaaatct gtgaagtcat ctgttcatta ttatttcttt ttaaaagcaa gagtcctgct     420 attttttgggg tactcacaaa agaattatta caactttttg aagacttggt ttacctccat     480
agaagaaatg tgatgggtca tgctgtggaa tggccagtgg tcatgagccg attttttaagt     540 caattagatg aacacatggg atatttacaa tcagctcctt tgcagttgat gagtatgcaa     600
aatttagaat ttattgaagt cactttatta atggttctta ctcgtattat tgcaattgtg     660
ttttttagaa ggcaagaact cttactttgg cagataggtt gtgttctgct agagtatggt     720
agtccaaaaa ttaaatccct agcaattagc ttttttaacag aacttttttca gcttggagga     780 ctaccagcac aaccagctag cactttttttc agctcatttt tggaattatt aaaacacctt     840
gtagaaatgg atactgacca attgaaactc tatgaagagc cattatcaaa gctgataaag     900
acactatttc cctttgaagc agaagcttat agaaatattg aacctgtcta tttaaatatg     960
ctgctggaaa aactctgtgt catgtttgaa gacggtgtgc tcatgcggct taagtctgat    1020
ttgctaaaag cagctttgtg ccatttactg cagtatttcc ttaaatttgt gccagctggg    1080
tatgaatctg ctttacaagt caggaaggtc tatgtgagaa atatttgtaa agctcttttg    1140
gatgtgcttg gaattgaggt agatgcagag tacttgttgg gcccacttta tgcagctttg    1200
aaaatggaaa gtatggaaat cattgaggag attcaatgcc aaactcaaca ggaaaacctc    1260
agcagtaata gtgatggaat atcacccaaa aggcgtcgtc tcagctcgtc tctaaaccct    1320
tctaaaagag caccaaaaca gactgaggaa attaaacatg tggacatgaa ccaaaagagc    1380
atattatgga gtgcactgaa acagaaagct gaatccttc agatttccct tgaatacagt    1440
ggcctaaaga tcctgttat tgagatgtta gaaggaattg ctgttgtctt acaactgact    1500
gctctgtgta ctgttcattg ttctcatcaa aacatgaact gccgtacttt caaggactgt    1560
caacataaat ccaagaagaa accttctgta gtgataactt ggatgtcatt ggatttttac    1620
acaaaagtgc ttaagagctg tagaagtttg ttagaatctg ttcagaaact ggacctggag    1680
gcaaccattg ataaggtggt gaaaatttat gatgctttga tttatatgca agtaaacagt    1740
tcatttgaag atcatatcct ggaagattta tgtggtatgc tctcacttcc atggatttat    1800
tcccattctg atgatggctg tttaaagttg accacatttg ccgctaatct tctaacatta    1860
```

-continued

```
agctgtagga tttcagatag ctattcacca caggcacaat cacgatgtgt gtttcttctg    1920
actctgtttc caagaagaat attccttgag tggagaacag cagtttacaa ctgggccctg    1980
cagagctccc atgaagtaat ccgggctagt tgtgttagtg gattttttat cttattgcag    2040
cagcagaatt cttgtaacag agttcccaag attcttatag ataaagtcaa agatgattct    2100
gacattgtca agaaagaatt tgcttctata cttggtcaac ttgtctgtac tcttcacggc    2160 atgtttatc tgacaagttc tttaacagaa cctttctctg aacacggaca tgtggacctc    2220
ttctgtagga acttgaaagc cacttctcaa catgaatgtt catcttctca actaaaagct    2280
tctgtctgca agccattcct tttcctactg aaaaaaaaaa tacctagtcc agtaaaactt    2340
gctttcatag ataatctaca tcatctttgt aagcatcttg attttagaga agatgaaaca    2400
gatgtaaaag cagttcttgg aactttatta aatttaatgg aagatccaga caaagatgtt    2460
agagtggctt ttagtggaaa tatcaagcac atattggaat ccttggactc tgaagatgga    2520
tttataaagg agcttttgt cttaagaatg aaggaagcat atacacatgc ccaaatatca    2580
agaaataatg agctgaagga taccttgatt cttacaacag gggatattgg aagggccgca    2640
aaaggagatt tggtaccatt tgcactctta cacttattgc attgtttgtt atccaagtca    2700
gcatctgtct ctggagcagc atacacagaa attagagctc tggttgcagc taaaagtgtt    2760
aaactgcaaa gttttttcag ccagtataag aaacccatct gtcagttttt ggtagaatcc    2820
cttcactcta gtcagatgac agcacttccg aatactccat gccagaatgc tgacgtgcga    2880
aaacaagatg tggctcacca gagagaaatg gctttaaata cgttgtctga aattgccaac    2940
gttttcgact ttcctgatct taatcgtttt cttactagga cattacaagt tctactacct    3000
gatcttgctg ccaaagcaag ccctgcagct tctgctctca ttcgaacttt aggaaaacaa    3060
ttaaatgtca atcgtagaga gattttaata aacaacttca aatatatttt ttctcatttg    3120
gtctgttctt gttccaaaga tgaattagaa cgtgcccttc attatctgaa gaatgaaaca    3180
gaaattgaac tggggagcct gttgagacaa gatttccaag gattgcataa tgaattattg    3240
ctgcgtattg gagaacacta tcaacaggtt tttaatggtt tgtcaatact tgcctcattt    3300
gcatccagtg atgatccata tcagggcccg agagatatca tatcacctga actgatggct    3360
gattatttac aacccaaatt gttgggcatt ttggcttttt ttaacatgca gttactgagc    3420
tctagtgttg gcattgaaga taagaaaatg gccttgaaca gtttgatgtc tttgatgaag    3480
ttaatgggac ccaaacatgt cagttctgtg agggtgaaga tgatgaccac actgagaact    3540
ggccttcgat tcaaggatga ttttcctgaa ttgtgttgca gagcttggga ctgctttgtt    3600
cgctgcctgg atcatgcttg tctgggctcc cttctcagtc atgtaatagt agctttgtta    3660
cctcttatac acatccagcc taaagaaact gcagctatct tccactacct cataattgaa    3720
aacagggatg ctgtgcaaga tttttcttcat gaaatatatt ttttacctga tcatccagaa    3780
ttaaaaaaga taaagccgt tctccaggaa tacagaaagg agacctctga gagcactgat    3840
cttcagacaa ctcttcagct ctctatgaag gccattcaac atgaaaatgt cgatgttcgt    3900
attcatgctc ttacaagctt gaaggaaacc ttgtataaaa atcaggaaaa actgataaag    3960
tatgcaacag acagtgaaac agtagaacct attatctcac agttggtgac agtgcttttg    4020
aaaggttgcc aagatgcaaa ctctcaagct cggttgctct gtggggaatg tttaggggaa    4080 ttggggggcga tagatccagg tcgattagat ttctcaacaa ctgaaactca aggaaaagat    4140
tttacatttg tgactggagt agaagattca agctttgcct atggattatt gatggagcta    4200
acaagagctt accttgcgta tgctgataat agccgagctc aagattcagc tgcctatgcc    4260
```

-continued

```
attcaggagt tgctttctat ttatgactgt agagagatgg agaccaacgg cccaggtcac   4320
caattgtgga ggagatttcc tgagcatgtt cgggaaatac tagaacctca tctaaatacc   4380
agatacaaga gttctcagaa gtcaaccgat tggtctggag taaagaagcc aatttactta   4440
agtaaattgg gtagtaactt tgcagaatgg tcagcatctt gggcaggtta tcttattaca   4500
aaggttcgac atgatcttgc cagtaaaatt ttcacctgct gtagcattat gatgaagcat   4560
gatttcaaag tgaccatcta tcttcttcca catattctgg tgtatgtctt actgggttgt   4620
aatcaagaag atcagcagga ggtttatgca gaaattatgg cagttctaaa gcatgacgat   4680
cagcatacca taaataccca agacattgca tctgatctgt gtcaactcag tacacagact   4740
gtgttctcca tgcttgacca tctcacacag tgggcaaggc acaaatttca ggcactgaaa   4800
gctgagaaat gtccacacag caaatcaaac agaaataagg tagactcaat ggtatctact   4860
gtggattatg aagactatca gagtgtaacc cgttttctag acctcatacc ccaggatact   4920
ctggcagtag cttcctttcg ctccaaagca tacacgag ctgtaatgca ctttgaatca   4980
tttattacag aaaagaagca aaatattcag gaacatcttg attttttaca gaaattgtat   5040
gctgctatgc atgaacctga tggagtggcc ggagtcagtg caattagaaa ggcagaacca   5100
tctctaaaag aacagatcct tgaacatgaa agccttggct tgctgaggga tgccactgct   5160
tgttatgaca gggctattca gctagaacca gaccagatca ttcattatca tggtgtagta   5220
aagtccatgt taggtcttgg tcagctgtct actgttatca ctcaggtgaa tggagtgcat   5280
gctaacaggc ccgagtggac agatgaatta aacacgtaca gagtggaagc agcttggaaa   5340
ttgtcacagt gggatttggt ggaaaactat ttggcagcag atggaaaatc tacaacatgg   5400
agtgtcagac tggacagct attattatca gccaaaaaaa gagatatcac agctttttat   5460
gactcactga aactagtgag agcagaacaa attgtacctc tttcagctgc aagctttgaa   5520
agaggctcct accaacgagg atatgaatat attgtgagat tgcacatgtt atgtgagttg   5580
gagcatagca tcaaaccact tttccagcat tctccaggtg acagttctca agaagattct   5640
ctaaactggg tagctcgact agaaatgacc cagaattcct acagagccaa ggagcctatc   5700
ctggctctcc ggagggcttt actaagcctc aacaaaagac cagattacaa tgaaatggtt   5760
ggagaatgct ggctgcagag tgccagggta gctagaaagg ctggtcacca ccagacagcc   5820
tacaatgctc tccttaatgc aggggaatca cgactcgctg aactgtacgt ggaaagggca   5880
aagtggctct ggtccaaggg tgatgttcac caggcactaa ttgttcttca aaaaggtgtt   5940
gaattatgtt ttcctgaaaa tgaaacccca cctgagggta agaacatgtt aatccatggt   6000
cgagctatgc tactagtggg ccgatttatg gaagaaacag ctaactttga aagcaatgca   6060
attatgaaaa aatataagga tgtgaccgcg tgcctgccag aatgggagga tgggcatttt   6120
taccttgcca gtactatga caaattgatg cccatggtca cagacaacaa aatggaaaag   6180
caaggtgatc tcatccggta tatagttctt cattttggca gatctctaca atatggaaat   6240
cagttcatat atcagtcaat gccacgaatg ttaactctat ggcttgatta tggtacaaag   6300
gcatatgaat gggaaaaagc tggccgctcc gatcgtgtac aaatgaggaa tgatttgggt   6360
aaaataaaca aggttatcac agagcataca aactatttag ctccatatca attttttgact   6420 gcttttttcac aattgatctc tcgaatttgt cattctcacg atgaagtttt tgttgtcttg   6480
atggaaataa tagccaaagt atttctagcc tatcctcaac aagcaatgtg gatgatgaca   6540
gctgtgtcaa agtcatctta tcccatgcgt gtgaacagat gcaaggaaat cctcaataaa   6600
```

-continued

```
gctattcata tgaaaaaatc cttagagaag tttgttggag atgcaactcg cctaacagat      6660
aagcttctag aattgtgcaa taaaccggtt gatggaagta gttccacatt aagcatgagc      6720
actcatttta aaatgcttaa aaagctggta gaagaagcaa catttagtga aatcctcatt      6780
cctctacaat cagtcatgat acctacactt ccatcaattc tgggtaccca tgctaaccat      6840
gctagccatg aaccatttcc tggacattgg gcctatattg cagggtttga tgatatggtg      6900
gaaattcttg cttctcttca gaaaccaaag aagatttctt taaaaggctc agatggaaag      6960
ttctacatca tgatgtgtaa gccaaaagat gacctgagaa aggattgtag actaatggaa      7020
ttcaattcct tgattaataa gtgcttaaga aaagatgcag agtctcgtag aagagaactt      7080
catattcgaa catatgcagt tattccacta aatgatgaat gtgggattat tgaatgggtg      7140
aacaacactg ctggtttgag acctattctg accaaactat ataaagaaaa gggagtgtat      7200
atgacaggaa aagaacttcg ccagtgtatg ctaccaaagt cagcagcttt atctgaaaaa      7260
ctcaaagtat tccgagaatt tctcctgccc aggcatcctc ctatttttca tgagtggttt      7320
ctgagaacat tccctgatcc tacatcatgg tacagtagta gatcagctta ctgccgttcc      7380
actgcagtaa tgtcaatggt tggttatatt ctggggcttg gagaccgtca tggtgaaaat      7440
attctctttg attctttgac tggtgaatgc gtacatgtag atttcaattg tcttttcaat      7500
aagggagaaa cctttgaagt tccagaaatt gtgccatttc gcctgactca taatatggtt      7560
aatggaatgg gtcctatggg aacagagggt cttttttcgaa gagcatgtga agttacaatg      7620
aggctgatgc gtgatcagcg agagccttta atgagtgtct taaagacttt tctacatgat      7680
cctcttgtgg aatggagtaa accagtgaaa gggcattcca aagcgccact gaatgaaact      7740
ggagaagttg tcaatgaaaa ggccaagacc catgttcttg acattgagca gcgactacaa      7800
ggtgtaatca agactcgaaa tagagtgaca ggactgccgt tatctattga aggacatgtg      7860
cattacctta tacaggaagc tactgatgaa aacttactat gccagatgta tcttggttgg      7920
actccatata tgtga                                                       7935
```

```
<210> SEQ ID NO 8
<211> LENGTH: 306
<212> TYPE: DNA
<213> ORGANISM: Artificial Sequence
<220> FEATURE:
<223> OTHER INFORMATION: nucleotide sequence for mRNA translation of
      GSE56

<400> SEQUENCE: 8
atggatggat ggtgtcctgg gagagaccgt cggacagagg aagaaaattt ccgcaaaaaa       60
gaagagcatt gcccggagct gcccccaggg agtgcaaaga gagcactgcc caccagcaca      120
agctcctctc cccagcaaaa gaaaaaacca ctcgatggag aatatttcac ccttaagatc      180
cgtgggcgtg agcgcttcga gatgttccga gagctgaatg aggccttgga attaaaggat      240
gcccgtgctg ccgaggagtc aggagacagc agggctcact ccagctaccc gaagatagtt      300
agttag                                                                 306
```

```
<210> SEQ ID NO 9
<211> LENGTH: 101
<212> TYPE: PRT
<213> ORGANISM: Artificial Sequence
<220> FEATURE:
<223> OTHER INFORMATION: amino acid sequence of GSE56

<400> SEQUENCE: 9
```

```
Met Asp Gly Trp Cys Pro Gly Arg Asp Arg Arg Thr Glu Glu Glu Asn
1               5                   10                  15

Phe Arg Lys Lys Glu Glu His Cys Pro Glu Leu Pro Pro Gly Ser Ala
            20                  25                  30

Lys Arg Ala Leu Pro Thr Ser Thr Ser Ser Ser Pro Gln Gln Lys Lys
        35                  40                  45

Lys Pro Leu Asp Gly Glu Tyr Phe Thr Leu Lys Ile Arg Gly Arg Glu
    50                  55                  60

Arg Phe Glu Met Phe Arg Glu Leu Asn Glu Ala Leu Glu Leu Lys Asp
65                  70                  75                  80

Ala Arg Ala Ala Glu Glu Ser Gly Asp Ser Arg Ala His Ser Ser Tyr
                85                  90                  95

Pro Lys Ile Val Ser
            100
```

<210> SEQ ID NO 10
<211> LENGTH: 387
<212> TYPE: DNA
<213> ORGANISM: Artificial Sequence
<220> FEATURE:
<223> OTHER INFORMATION: nucleotide sequence encoding Ad5-E4orf1

<400> SEQUENCE: 10

```
atggccgctg ctgtggaagc cctgtacgtg gtgcttgaaa gagagggcgc catcctgcct        60
agacaagagg gcttttctgg cgtgtacgtg ttcttcagcc ccatcaactt cgtgatccct       120
ccaatgggcg ccgtgatgct gagcctgaga ctgagagtgt gtatccctcc tggctacttc       180
ggccggtttc tggccctgac cgatgtgaac cagcctgacg tgttcaccga gagctacatc       240
atgacccctg acatgaccga ggaactgagc gtggtgctgt tcaaccacgg cgaccagttc       300
ttttatggcc acgccggaat ggccgtcgtg cggctgatgc tgatcagagt ggtgtttccc       360
gtcgtccggc aggccagcaa tgtttga                                          387
```

<210> SEQ ID NO 11
<211> LENGTH: 453
<212> TYPE: DNA
<213> ORGANISM: Artificial Sequence
<220> FEATURE:
<223> OTHER INFORMATION: nucleotide sequence encoding Ad5-E4orf6/7

<400> SEQUENCE: 11

```
atgaccacca gcggcgtgcc cttcggcatg acactcagac ctaccagaag ccggctgagc        60
agaagaaccc cttacagcag agacaggctg cctccattcg agacagagac acgggccacc       120
atcctggaag atcaccctct gctgcccgag tgtaacaccc tgaccatgca caacgcctgg       180
acaagcccat ctcctccagt gaaacagccc caagtgggac agcagcctgt tgctcagcag       240
ctggacagcg acatgaacct gtctgaactg cccggcgagt tcatcaacat caccgacgag       300
agactggccc ggcaagagac agtgtggaac atcacccccta agaacatgag cgtgacccac       360
gacatgatgc tgttcaaggc cagcagaggc gagcggacag tgtacagcgt ttgttgggaa       420
ggcggcggac ggctgaatac cagagtgctg taa                                   453
```

<210> SEQ ID NO 12
<211> LENGTH: 885
<212> TYPE: DNA
<213> ORGANISM: Artificial Sequence
<220> FEATURE:
<223> OTHER INFORMATION: nucleotide sequence encoding E4orf6

```
<400> SEQUENCE: 12
atgacaacca gcggcgtgcc cttcggcatg acactgaggc ctacaagaag ccggctgagc      60
agaagaaccc cttacagcag agacagactg cctccattcg agacagagac acgggccacc     120
atcctggaag atcaccctct gctgcccgag tgcaacaccc tgacaatgca caacgtgtcc     180
tacgtgcggg gcctgccttg tagcgttggc ttcacactga tccaagagtg ggtcgtgccc     240
tgggacatgg tgctgaccag agaggaactg gtcatcctgc ggaagtgtat gcacgtgtgc     300
ctgtgctgcg ccaacatcga catcatgacc agcatgatga tccacggcta cgagagctgg     360
gccctgcact gtcactgttc tagccctggc agcctgcagt gtattgctgg tggacaggtt     420
ctggccagct ggttcagaat ggtggtggac ggcgccatgt tcaaccagag attcatctgg     480
tacagagagg tggtcaacta caacatgccc aaagaagtga tgttcatgag cagcgttttc     540
atgcggggca gacacctgat ctacctgcgg ctttggtacg atggccacgt gggatctgtg     600
gtgcctgcca tgagctttgg ctacagcgcc ctgcattgcg gcatcctgaa caacatcgtg     660
gtgctgtgct gcagctactg cgccgatctg agcgagatca gagtgcggtg ttgtgccaga     720
cggaccagac ggctgatgct gagagccgtg cggatcattg ccgaagagac aaccgccatg     780
ctgtactctt gccggaccga gagaagaagg cagcagttca tcagagccct gctccagcac     840
caccggccta tcctgatgca cgactacgac agcaccccta tgtag                     885
```

```
<210> SEQ ID NO 13
<211> LENGTH: 294
<212> TYPE: PRT
<213> ORGANISM: Artificial Sequence
<220> FEATURE:
<223> OTHER INFORMATION: amino acid sequence of E4orf6

<400> SEQUENCE: 13

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Val Ser Tyr Val Arg Gly
    50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
            100                 105                 110

Met Ile His Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Leu Trp
            180                 185                 190

Tyr Asp Gly His Val Gly Ser Val Val Pro Ala Met Ser Phe Gly Tyr
```

-continued

```
              195                 200                 205
Ser Ala Leu His Cys Gly Ile Leu Asn Asn Ile Val Val Leu Cys Cys
    210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Arg Gln Gln
                260                 265                 270

Phe Ile Arg Ala Leu Leu Gln His His Arg Pro Ile Leu Met His Asp
        275                 280                 285

Tyr Asp Ser Thr Pro Met
    290

<210> SEQ ID NO 14
<211> LENGTH: 1488
<212> TYPE: DNA
<213> ORGANISM: Artificial Sequence
<220> FEATURE:
<223> OTHER INFORMATION: nucleotide sequence encoding E1B55K

<400> SEQUENCE: 14
atggaaagac ggaaccccag cgagagaggc gtgccagctg gattttctgg acacgccagc      60
gtggaaagcg gctgcgagac acaagaaagc cctgccaccg tggtgttcag accacctggc     120
gataataccg atggcggagc tgctgctgca gctggtggat ctcaggcagc agctgcaggc     180
gctgaaccta tggaacctga gagcagacct ggacctagcg catgaatgt ggtgcaggtc      240 gccgagctgt atcccgagct gagaagaatc ctgaccatca ccgaggatgg ccagggactg     300
aagggcgtga agagagaaag aggcgcctgc gaggccacag aggaagccag aaatctggcc     360
ttcagcctga tgaccagaca cagacccgag tgcatcacct tccagcagat caaggacaac     420
tgcgccaacg agctggacct gctggcccag aagtacagca tcgagcagct gaccacctac     480
tggctgcaac ccggcgacga tttcgaagag gccatcagag tgtacgccaa ggtggccctc     540
agacctgact gcaagtacaa gatcagcaag ctggtcaaca tccggaactg ctgctacatc     600
agcggcaatg gcgccgaggt ggaaatcgac acagaggaca gagtggcctt ccggtgcagc     660
atgatcaaca tgtggcctgg cgtgctcggc atggatggcg tggtcattat gaacgtgcgg     720
ttcacaggcc ccaacttcag cggcacagtg tttctggcca acaccaacct gatcctgcac     780
ggcgtgtcct tctacggctt caacaatacc tgcgtggaag cctggaccga cgttcgcgtt     840
agaggctgcg ccttctactg ctgttggaag ggcgtcgtgt gcagacccaa gagcagagcc     900
agcatcaaga gtgcctgtt cgagagatgc accctgggca tcctgagcga gggcaacagc     960
agagtcagac acaacgtggc cagcgactgc ggctgcttca tgctggttaa gagcgtggcc    1020
gtgatcaagc acaacatggt ctgcggcaac tgcgaggata gagccagcca gatgctgacc    1080
tgcagcgacg gcaattgtca tctgctgaaa accatccacg tggcctctca gcagaaaag     1140 gcctggcctg tgttcgagca caatatcctg acacggtgct ccctgcacct gggcaataga    1200
cggggagtgt cctgccttta ccagtgcaac ctgagccaca ccaagatcct gctggaaccc    1260
gagtccatga gcaaagtgaa cctgaatggc gtgttcgaca tgaccatgaa gatctggaaa    1320
gtgctgcgct acgacgagac acggaccaga tgtagacctt gcgagtgtgg cggcaagcac    1380
atcagaaacc agcctgtgat gctggacgtg accgaggaac tgaggcctga tcatctggtg    1440
ctggcctgta ccagagccga gtttggcagc tccgacgagg ataccgat                 1488
```

```
<210> SEQ ID NO 15
<211> LENGTH: 496
<212> TYPE: PRT
<213> ORGANISM: Artificial Sequence
<220> FEATURE:
<223> OTHER INFORMATION: amino acid sequence of E1B55K

<400> SEQUENCE: 15

Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
                20                  25                  30

Thr Val Val Phe Arg Pro Pro Gly Asp Asn Thr Asp Gly Gly Ala Ala
            35                  40                  45

Ala Ala Ala Gly Gly Ser Gln Ala Ala Ala Ala Gly Ala Glu Pro Met
        50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
                100                 105                 110

Thr Glu Glu Ala Arg Asn Leu Ala Phe Ser Leu Met Thr Arg His Arg
            115                 120                 125

Pro Glu Cys Ile Thr Phe Gln Gln Ile Lys Asp Asn Cys Ala Asn Glu
        130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
                180                 185                 190

Asn Ile Arg Asn Cys Cys Tyr Ile Ser Gly Asn Gly Ala Glu Val Glu
            195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
            275                 280                 285

Trp Lys Gly Val Val Cys Arg Pro Lys Ser Arg Ala Ser Ile Lys Lys
    290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
            340                 345                 350

Asp Arg Ala Ser Gln Met Leu Thr Cys Ser Asp Gly Asn Cys His Leu
            355                 360                 365
```

```
Leu Lys Thr Ile His Val Ala Ser His Ser Arg Lys Ala Trp Pro Val
    370             375             380

Phe Glu His Asn Ile Leu Thr Arg Cys Ser Leu His Leu Gly Asn Arg
385             390             395             400

Arg Gly Val Phe Leu Pro Tyr Gln Cys Asn Leu Ser His Thr Lys Ile
            405             410             415

Leu Leu Glu Pro Glu Ser Met Ser Lys Val Asn Leu Asn Gly Val Phe
        420             425             430

Asp Met Thr Met Lys Ile Trp Lys Val Leu Arg Tyr Asp Glu Thr Arg
        435             440             445

Thr Arg Cys Arg Pro Cys Glu Cys Gly Gly Lys His Ile Arg Asn Gln
    450             455             460

Pro Val Met Leu Asp Val Thr Glu Glu Leu Arg Pro Asp His Leu Val
465             470             475             480

Leu Ala Cys Thr Arg Ala Glu Phe Gly Ser Ser Asp Glu Asp Thr Asp
            485             490             495
```

```
<210> SEQ ID NO 16
<211> LENGTH: 131
<212> TYPE: DNA
<213> ORGANISM: Artificial Sequence
<220> FEATURE:
<223> OTHER INFORMATION: AAV donor cassette for adeno-associated virus
      integration site 1 (AAVS1), 3'-ITR

<400> SEQUENCE: 16
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac t                                                          131

<210> SEQ ID NO 17
<211> LENGTH: 796
<212> TYPE: DNA
<213> ORGANISM: Artificial Sequence
<220> FEATURE:
<223> OTHER INFORMATION: AAV donor cassette for AAVS1, Homologous
      arm-left

<400> SEQUENCE: 17
tgctttctct gaccagcatt ctctccctg ggcctgtgcc gctttctgtc tgcagcttgt       60
ggcctgggtc acctctacgg ctggcccaga tccttccctg ccgcctcctt caggttccgt      120
cttcctccac tccctcttcc ccttgctctc tgctgtgttg ctgcccaagg atgctctttc      180
cggagcactt ccttctcggc gctgcaccac gtgatgtcct ctgagcggat cctccccgtg      240
tctgggtcct ctccgggcat ctctcctccc tcacccaacc ccatgccgtc ttcactcgct      300
gggttccctt ttccttctcc ttctggggcc tgtgccatct ctcgtttctt aggatggcct      360
tctccgacgg atgtctccct tgcgtcccgc ctccccttct tgtaggcctg catcatcacc      420
gtttttctgg acaaccccaa agtaccccgt ctccctggct ttagccacct ctccatcctc      480
ttgctttctt tgcctggaca ccccgttctc ctgtggattc gggtcacctc tcactccttt      540
catttgggca gctcccctac cccccttacc tctctagtct gtgctagctc ttccagcccc      600
ctgtcatggc atcttccagg ggtccgagag ctcagctagt cttcttcctc caacccgggc      660
ccctatgtcc acttcaggac agcatgtttg ctgcctccag ggatcctgtg tccccgagct      720
gggaccacct tatattccca gggccggtta atgtggctct ggttctgggt actttttatct     780
```

-continued

```
gtccctcca ccccac                                                        796

<210> SEQ ID NO 18
<211> LENGTH: 514
<212> TYPE: DNA
<213> ORGANISM: Artificial Sequence
<220> FEATURE:
<223> OTHER INFORMATION: AAV donor cassette for AAVS1, hPGK promoter
      (without SA)

<400> SEQUENCE: 18
ccacggggtt ggggttgcgc cttttccaag gcagccctgg gtttgcgcag ggacgcggct        60
gctctgggcg tggttccggg aaacgcagcg gcgccgaccc tgggtctcgc acattcttca       120
cgtccgttcg cagcgtcacc cggatcttcg ccgctaccct tgtgggcccc ccggcgacgc       180
ttcctgctcc gcccctaagt cgggaaggtt ccttgcggtt cgcggcgtgc cggacgtgac       240
aaacggaagc cgcacgtctc actagtaccc tcgcagacgg acagcgccag ggagcaatgg       300
cagcgcgccg accgcgatgg gctgtggcca atagcggctg ctcagcaggg cgcgccgaga       360
gcagcggccg ggaaggggcg gtgcgggagg cggggtgtgg ggcggtagtg tgggccctgt       420
tcctgcccgc gcggtgttcc gcattctgca agcctccgga gcgcacgtcg gcagtcggct       480
ccctcgttga ccgaatcacc gacctctctc ccca                                   514

<210> SEQ ID NO 19
<211> LENGTH: 720
<212> TYPE: DNA
<213> ORGANISM: Artificial Sequence
<220> FEATURE:
<223> OTHER INFORMATION: AAV donor cassette for AAVS1, eGFP

<400> SEQUENCE: 19
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgaccta cggcgtgcag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaagtaa       720

<210> SEQ ID NO 20
<211> LENGTH: 226
<212> TYPE: DNA
<213> ORGANISM: Artificial Sequence
<220> FEATURE:
<223> OTHER INFORMATION: AAV donor cassette for AAVS1, bGH-pA

<400> SEQUENCE: 20
actgtgcctt ctagttgcca gccatctgtt gtttgcccct cccccgtgcc ttccttgacc        60
ctggaaggtg ccactcccac tgtcctttcc taataaaatg aggaaattgc atcgcattgt       120
```

-continued

```
ctgagtaggt gtcattctat tctggggggt ggggtggggc aggacagcaa gggggaggat        180
tgggaagaca atagcaggca tgctggggat gcggtgggct ctatgg                       226
```

```
<210> SEQ ID NO 21
<211> LENGTH: 258
<212> TYPE: DNA
<213> ORGANISM: Artificial Sequence
<220> FEATURE:
<223> OTHER INFORMATION: AAV donor cassette for AAVS1, Homologous
     arm-right

<400> SEQUENCE: 21
tagggacagg attggtgaca gaaaagcccc atccttaggc ctcctccttc ctagtctcct         60
gatattgggt ctaaccccca cctcctgtta ggcagattcc ttatctggtg acacaccccc        120
atttcctgga gccatctctc tccttgccag aacctctaag gtttgcttac gatggagcca        180
gagaggatcc tgggagggag agcttggcag ggggtgggag ggaagggggg gatgcgtgac        240
ctgcccggtt ctcagtgg                                                       258
```

```
<210> SEQ ID NO 22
<211> LENGTH: 120
<212> TYPE: DNA
<213> ORGANISM: Artificial Sequence
<220> FEATURE:
<223> OTHER INFORMATION: AAV donor cassette for AAVS1, 5'-ITR

<400> SEQUENCE: 22
agtgatggag ttggccactc cctctctgcg cgctcgctcg ctcactgagg ccgggcgacc         60
aaaggtcgcc cgacgcccgg gcggcctcag tgagcgagcg agcgcgcagc tgcctgcagg        120
```

```
<210> SEQ ID NO 23
<211> LENGTH: 131
<212> TYPE: DNA
<213> ORGANISM: Artificial Sequence
<220> FEATURE:
<223> OTHER INFORMATION: AAV donor cassette for Interleukin 2 Receptor
     Subunit Gamma (IL2RG), 3'-ITR

<400> SEQUENCE: 23
cctgcaggca gctgcgcgct cgctcgctca ctgaggccgc ccgggcaaag cccgggcgtc         60
gggcgacctt tggtcgcccg gcctcagtga gcgagcgagc gcgcagagag ggagtggcca        120
actccatcac t                                                              131
```

```
<210> SEQ ID NO 24
<211> LENGTH: 290
<212> TYPE: DNA
<213> ORGANISM: Artificial Sequence
<220> FEATURE:
<223> OTHER INFORMATION: AAV donor cassette for IL2RG, Homologous
     arm-left

<400> SEQUENCE: 24
agaggaaacg tgtgggtggg gaggggtagt gggtgaggga cccaggttcc tgacacagac         60
agactacacc cagggaatga agagcaagcg ccatgttgaa gccatcatta ccattcacat        120
ccctcttatt cctgcagctg cccctgctgg gagtggggct gaacacgaca attctgacgc        180
ccaatgggaa tgaagacacc acagctggtg ggaaatctgg gactggaggg ggctggtgag        240
aagggtggct gtgggaaggg gccgtacaga gatctggtgc ctgccactgg                    290
```

```
<210> SEQ ID NO 25
```

<211> LENGTH: 154
<212> TYPE: DNA
<213> ORGANISM: Artificial Sequence
<220> FEATURE:
<223> OTHER INFORMATION: AAV donor cassette for IL2RG, Exon2

<400> SEQUENCE: 25
atttctttct gaccaccatg cccaccgaca gcctgagcgt gagcaccctg cccctgcccg      60
aggtgcagtg cttcgtgttc aacgtggagt acatgaactg cacctggaac agcagcagcg     120
agccccagcc caccaatctg accctgcact actg                                 154

<210> SEQ ID NO 26
<211> LENGTH: 185
<212> TYPE: DNA
<213> ORGANISM: Artificial Sequence
<220> FEATURE:
<223> OTHER INFORMATION: AAV donor cassette for IL2RG, Exon3

<400> SEQUENCE: 26
gtacaagaac agcgacaacg acaaggtgca gaagtgcagc cactacctgt tcagcgagga      60
aatcaccagc ggctgccagc tgcagaagaa agagatccac ctgtaccaga ccttcgtggt     120
gcagctgcag gacccccggg agcccgcag gcaggccacc cagatgctga agctgcagaa      180
cctgg                                                                 185

<210> SEQ ID NO 27
<211> LENGTH: 140
<212> TYPE: DNA
<213> ORGANISM: Artificial Sequence
<220> FEATURE:
<223> OTHER INFORMATION: AAV donor cassette for IL2RG, Exon4

<400> SEQUENCE: 27
tgatcccctg ggcccctgag aacctgacac tgcacaagct gtccgagagc cagctggaac      60
tgaactggaa caaccgcttc ctgaaccact gcctggaaca cctggtgcag taccggaccg     120
actgggacca cagctggacc                                                 140

<210> SEQ ID NO 28
<211> LENGTH: 163
<212> TYPE: DNA
<213> ORGANISM: Artificial Sequence
<220> FEATURE:
<223> OTHER INFORMATION: AAV donor cassette for IL2RG, Exon5

<400> SEQUENCE: 28
gagcagagcg tggactaccg gcacaagttc agcctgccca gcgtggacgg ccagaagcgg      60
tacaccttca gagtgcggag ccggttcaac cccctgtgcg gcagcgccca gcactggtcc     120
gagtggagcc acccatcca ctggggcagc aacaccagca aag                        163

<210> SEQ ID NO 29
<211> LENGTH: 97
<212> TYPE: DNA
<213> ORGANISM: Artificial Sequence
<220> FEATURE:
<223> OTHER INFORMATION: AAV donor cassette for IL2RG, Exon6

<400> SEQUENCE: 29
agaacccctt cctgttcgcc ctggaagccg tggtgatcag cgtgggcagc atgggcctga      60
tcatctccct gctgtgcgtg tacttctggc tggaacg                              97

<210> SEQ ID NO 30
<211> LENGTH: 70
<212> TYPE: DNA
<213> ORGANISM: Artificial Sequence
<220> FEATURE:
<223> OTHER INFORMATION: AAV donor cassette for IL2RG, Exon7

<400> SEQUENCE: 30
gaccatgccc agaatcccca ccctgaagaa cctggaagat ctggtgaccg agtaccacgg      60
caacttcagc                                                              70

<210> SEQ ID NO 31
<211> LENGTH: 186
<212> TYPE: DNA
<213> ORGANISM: Artificial Sequence
<220> FEATURE:
<223> OTHER INFORMATION: AAV donor cassette for IL2RG, Exon8

<400> SEQUENCE: 31
gcctggtccg gcgtgagcaa gggcctggcc gagagcctgc agcccgacta cagcgagcgg      60
ctgtgcctgg tgtccgagat cccccccaaa ggcggagccc tgggcgaagg ccctggcgcc     120
agcccctgca accagcacag cccctactgg gccctcctt gctacaccct gaagcccgag     180
acctga                                                                 186

<210> SEQ ID NO 32
<211> LENGTH: 330
<212> TYPE: DNA
<213> ORGANISM: Artificial Sequence
<220> FEATURE:
<223> OTHER INFORMATION: AAV donor cassette for IL2RG, 3'-UTR

<400> SEQUENCE: 32
tgaaccccaa tcctctgaca gaagaacccc agggtcctgt agccctaagt ggtactaact      60
ttccttcatt caacccactg cgtctcatac tcacctcacc ccactgtggc tgatttggaa     120
ttttgtgccc ccatgtaagc accccttcat ttggcattcc ccacttgaga attacccttt     180
tgccccgaac atgtttttct tctccctcag tctggccctt cctttcgca ggattcttcc     240 tccccccctc tttccctccc ttcctctttc catctacct ccgattgttc ctgaaccgat     300
gagaaataaa gtttctgttg ataatcatcg                                       330

<210> SEQ ID NO 33
<211> LENGTH: 226
<212> TYPE: DNA
<213> ORGANISM: Artificial Sequence
<220> FEATURE:
<223> OTHER INFORMATION: AAV donor cassette for IL2RG, bGH-pA

<400> SEQUENCE: 33
actgtgcctt ctagttgcca gccatctgtt gtttgcccct cccccgtgcc ttccttgacc      60
ctggaaggtg ccactcccac tgccctttcc taataaaatg aggaaattgc atcgcattgt     120
ctgagtaggt gtcattctat tctggggggt ggggtggggc aggacagcaa gggggaggat     180
tgggaagaca atagcaggca tgctggggat gcggtgggct ctatgg                    226

<210> SEQ ID NO 34
<211> LENGTH: 516
<212> TYPE: DNA
<213> ORGANISM: Artificial Sequence
<220> FEATURE:
<223> OTHER INFORMATION: AAV donor cassette for IL2RG, hPGK promoter -continued

```
<400> SEQUENCE: 34
ccacggggtt gggggttgcgc cttttccaag gcagccctgg gtttgcgcag ggacgcggct      60
gctctgggcg tggttccggg aaacgcagcg gcgccgaccc tgggtctcgc acattcttca     120
cgtccgttcg cagcgtcacc cggatcttcg ccgctaccct tgtgggcccc ccggcgacgc     180
ttcctgctcc gcccctaagt cgggaaggtt ccttgcggtt cgcggcgtgc cggacgtgac     240
aaacggaagc cgcacgtctc actagtaccc tcgcagacgg acagcgccag ggagcaatgg     300
cagcgcgccg accgcgatgg gctgtggcca atagcggctg ctcagcaggg cgcgccgaga     360
gcagcggccg ggaaggggcg gtgcgggagg cggggtgtgg ggcggtagtg tgggccctgt     420
tcctgcccgc gcggtgttcc gcattctgca agcctccgga gcgcacgtcg gcagtcggct     480
ccctcgttga ccgaatcacc gacctctctc cccagg                              516

<210> SEQ ID NO 35
<211> LENGTH: 720
<212> TYPE: DNA
<213> ORGANISM: Artificial Sequence
<220> FEATURE:
<223> OTHER INFORMATION: AAV donor cassette for IL2RG, eGFP

<400> SEQUENCE: 35
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 36
<211> LENGTH: 244
<212> TYPE: DNA
<213> ORGANISM: Artificial Sequence
<220> FEATURE:
<223> OTHER INFORMATION: AAV donor cassette for IL2RG, SV40-pA

<400> SEQUENCE: 36
tgagatccag acatgataag atacattgat gagtttggac aaaccaaaac tagaatgcag      60
tgaaaaaaat gccttatttg tgaaatttgt gatgctattg ccttatttgt aaccattata     120
agctgcaata aacaagttaa caacaacaat tgcattcatt ttatgtttca ggttcagggg     180
gaggtgtggg aggtttttta aagcaagtaa aacctctaca aatgtggtat ggctgattat     240
gatc                                                                244

<210> SEQ ID NO 37
<211> LENGTH: 267
<212> TYPE: DNA
<213> ORGANISM: Artificial Sequence
```

-continued

<220> FEATURE:
<223> OTHER INFORMATION: AAV donor cassette for IL2RG, Homologous
      arm-right

<400> SEQUENCE: 37
tacaatcatg tgggcagaat tgaaaagtgg agtgggaagg gcaaggggga gggttccctg      60
cctcacgcta cttcttcttt ctttcttgtt tgtttgtttc tttctttctt ttgaggcagg     120
gtctcactat gttgcctagg ctggtctcaa actcctggcc tctagtgatc ctcctgcctc     180
agcctttcaa agcaccagga ttacagacat gagccaccgt gcttggcctc ctccttctga     240
ccatcatttc tctttccctc cctgcct                                         267

<210> SEQ ID NO 38
<211> LENGTH: 120
<212> TYPE: DNA
<213> ORGANISM: Artificial Sequence
<220> FEATURE:
<223> OTHER INFORMATION: AAV donor cassette for IL2RG, 5'-ITR

<400> SEQUENCE: 38
agtgatggag ttggccactc cctctctgcg cgctcgctcg ctcactgagg ccgggcgacc      60
aaaggtcgcc cgacgcccgg gcggcctcag tgagcgagcg agcgcgcagc tgcctgcagg     120

<210> SEQ ID NO 39
<211> LENGTH: 23
<212> TYPE: DNA
<213> ORGANISM: Artificial Sequence
<220> FEATURE:
<223> OTHER INFORMATION: AAVS1 guide RNA (gRNA)

<400> SEQUENCE: 39
gtcaccaatc ctgtccctag tgg                                              23

<210> SEQ ID NO 40
<211> LENGTH: 23
<212> TYPE: DNA
<213> ORGANISM: Artificial Sequence
<220> FEATURE:
<223> OTHER INFORMATION: IL2RG gRNA

<400> SEQUENCE: 40
actggccatt acaatcatgt ggg                                              23

<210> SEQ ID NO 41
<211> LENGTH: 20
<212> TYPE: DNA
<213> ORGANISM: Artificial Sequence
<220> FEATURE:
<223> OTHER INFORMATION: NHEJ AAVS1 FW primer

<400> SEQUENCE: 41
cttcaggaca gcatgtttgc                                                  20

<210> SEQ ID NO 42
<211> LENGTH: 20
<212> TYPE: DNA
<213> ORGANISM: Artificial Sequence
<220> FEATURE:
<223> OTHER INFORMATION: NHEJ AAVS1 RV primer

<400> SEQUENCE: 42
acaggaggtg ggggttagac                                                  20

<210> SEQ ID NO 43
<211> LENGTH: 20
<212> TYPE: DNA
<213> ORGANISM: Artificial Sequence
<220> FEATURE:
<223> OTHER INFORMATION: NHEJ Intron 1 IL2RG FW primer

<400> SEQUENCE: 43
caccctctgt aaagccctgg                                                                                       20

<210> SEQ ID NO 44
<211> LENGTH: 20
<212> TYPE: DNA
<213> ORGANISM: Artificial Sequence
<220> FEATURE:
<223> OTHER INFORMATION: NHEJ Intron 1 IL2RG RV primer

<400> SEQUENCE: 44
aagaaatcta gattggggag                                                                                       20

<210> SEQ ID NO 45
<211> LENGTH: 20
<212> TYPE: DNA
<213> ORGANISM: Artificial Sequence
<220> FEATURE:
<223> OTHER INFORMATION: Intron 1 IL2RG 3' integration junction ddPCR FW
     primer

<400> SEQUENCE: 45
ctagattggg gagaaaatga                                                                                       20

<210> SEQ ID NO 46
<211> LENGTH: 19
<212> TYPE: DNA
<213> ORGANISM: Artificial Sequence
<220> FEATURE:
<223> OTHER INFORMATION: Intron 1 IL2RG 3' integration junction ddPCR RV
     primer

<400> SEQUENCE: 46
gtgggaaggg gccgtacag                                                                                        19

<210> SEQ ID NO 47
<211> LENGTH: 24
<212> TYPE: DNA
<213> ORGANISM: Artificial Sequence
<220> FEATURE:
<223> OTHER INFORMATION: Intron 1 IL2RG 3' integration junction ddPCR
     probe

<400> SEQUENCE: 47
gtagctccta tgctaggcgt agcc                                                                                  24

<210> SEQ ID NO 48
<211> LENGTH: 20
<212> TYPE: DNA
<213> ORGANISM: Artificial Sequence
<220> FEATURE:
<223> OTHER INFORMATION: AAVS1 3' integration junction ddPCR FW primer

<400> SEQUENCE: 48
gattgggaag acaatagcag                                                                                       20

<210> SEQ ID NO 49
<211> LENGTH: 20
<212> TYPE: DNA
<213> ORGANISM: Artificial Sequence

```
<220> FEATURE:
<223> OTHER INFORMATION: AAVS1 3' integration junction ddPCR RV primer

<400> SEQUENCE: 49
tcttgggaag tgtaaggaag                                                      20

<210> SEQ ID NO 50
<211> LENGTH: 20
<212> TYPE: DNA
<213> ORGANISM: Artificial Sequence
<220> FEATURE:
<223> OTHER INFORMATION: AAVS1 3' integration junction ddPCR FW probe

<400> SEQUENCE: 50
ccagataagg aatctgccta                                                      20

<210> SEQ ID NO 51
<211> LENGTH: 23
<212> TYPE: DNA
<213> ORGANISM: Artificial Sequence
<220> FEATURE:
<223> OTHER INFORMATION: AAVS1 gRNA

<400> SEQUENCE: 51
gtcaccaatc ctgtccctag tgg                                                  23

<210> SEQ ID NO 52
<211> LENGTH: 20
<212> TYPE: DNA
<213> ORGANISM: Artificial Sequence
<220> FEATURE:
<223> OTHER INFORMATION: NHEJ AAVS1 FW primer

<400> SEQUENCE: 52
cttcaggaca gcatgtttgc                                                      20

<210> SEQ ID NO 53
<211> LENGTH: 21
<212> TYPE: DNA
<213> ORGANISM: Artificial Sequence
<220> FEATURE:
<223> OTHER INFORMATION: NHEJ AAVS1 RV primer

<400> SEQUENCE: 53
ggactagaaa ggtgaagagc c                                                    21

<210> SEQ ID NO 54
<211> LENGTH: 20
<212> TYPE: DNA
<213> ORGANISM: Artificial Sequence
<220> FEATURE:
<223> OTHER INFORMATION: AAVS1 3' integration junction ddPCR FW primer

<400> SEQUENCE: 54
gattgggaag acaatagcag                                                      20

<210> SEQ ID NO 55
<211> LENGTH: 20
<212> TYPE: DNA
<213> ORGANISM: Artificial Sequence
<220> FEATURE:
<223> OTHER INFORMATION: AAVS1 3' integration junction ddPCR RV primer

<400> SEQUENCE: 55
tcttgggaag tgtaaggaag                                                      20
```

<210> SEQ ID NO 56
<211> LENGTH: 20
<212> TYPE: DNA
<213> ORGANISM: Artificial Sequence
<220> FEATURE:
<223> OTHER INFORMATION: AAVS1 3' integration junction ddPCR probe

<400> SEQUENCE: 56
ccagataagg aatctgccta                                                                                     20

<210> SEQ ID NO 57
<211> LENGTH: 128
<212> TYPE: PRT
<213> ORGANISM: Artificial Sequence
<220> FEATURE:
<223> OTHER INFORMATION: E4orf1 amino acid sequence, Ad1-E4orf1

<400> SEQUENCE: 57

Met Ala Ala Ala Val Glu Ala Leu Tyr Val Val Leu Glu Arg Glu Gly
1               5                   10                  15

Ala Ile Leu Pro Arg Gln Glu Gly Phe Ser Gly Val Tyr Val Phe Phe
            20                  25                  30

Ser Pro Ile Asn Phe Val Ile Pro Pro Met Gly Ala Val Met Leu Pro
        35                  40                  45

Leu Arg Leu Arg Val Cys Ile Pro Pro Gly Tyr Phe Gly Arg Phe Leu
    50                  55                  60

Ala Leu Thr Asp Val Asn Gln Pro Asp Val Phe Thr Glu Ser Tyr Ile
65                  70                  75                  80

Met Thr Pro Asp Met Thr Glu Glu Leu Ser Val Val Leu Phe Asn His
                85                  90                  95

Gly Asp Gln Phe Phe Tyr Gly His Ala Gly Met Ala Val Val Arg Leu
            100                 105                 110

Met Leu Ile Arg Val Val Phe Pro Val Val Arg Gln Ala Ser Asn Val
        115                 120                 125

<210> SEQ ID NO 58
<211> LENGTH: 128
<212> TYPE: PRT
<213> ORGANISM: Artificial Sequence
<220> FEATURE:
<223> OTHER INFORMATION: E4orf1 amino acid sequence, Ad2-E4orf1

<400> SEQUENCE: 58

Met Ala Ala Ala Val Glu Ala Leu Tyr Val Val Leu Glu Arg Glu Gly
1               5                   10                  15

Ala Ile Leu Pro Arg Gln Glu Gly Phe Ser Gly Val Tyr Val Phe Phe
            20                  25                  30

Ser Pro Ile Asn Phe Val Ile Pro Pro Met Gly Ala Val Met Leu Ser
        35                  40                  45

Leu Arg Leu Arg Val Cys Ile Pro Pro Gly Tyr Phe Gly Arg Phe Leu
    50                  55                  60

Ala Leu Thr Asp Val Asn Gln Pro Asp Val Phe Thr Glu Ser Tyr Ile
65                  70                  75                  80

Met Thr Pro Asp Met Ile Glu Glu Leu Ser Val Val Leu Phe Asn His
                85                  90                  95

Gly Asp Gln Phe Phe Tyr Gly His Ala Gly Met Ala Val Val Arg Leu
            100                 105                 110

Met Leu Ile Arg Val Val Phe Pro Val Val Arg Gln Ala Ser Asn Val
        115                 120                 125

```
<210> SEQ ID NO 59
<211> LENGTH: 125
<212> TYPE: PRT
<213> ORGANISM: Artificial Sequence
<220> FEATURE:
<223> OTHER INFORMATION: E4orf1 amino acid sequence, Ad3-E4orf1

<400> SEQUENCE: 59

Met Ala Asp Glu Ala Leu Tyr Val Tyr Leu Glu Gly Pro Gly Ala Thr
1               5                   10                  15

Leu Pro Glu Gln Gln Gln Arg Asn Asn Tyr Ile Phe Tyr Ser Pro Val
                20                  25                  30

Pro Phe Thr Leu Tyr Pro Arg Gly Val Ala Leu Leu Tyr Leu Lys Leu
            35                  40                  45

Ser Ile Ile Ile Pro Arg Gly Tyr Val Gly Cys Phe Phe Ser Leu Thr
            50                  55                  60

Asp Ala Asn Met Ser Gly Leu Tyr Ala Ser Ser Arg Ile Ile His Ala
65                  70                  75                  80

Gly His Arg Glu Glu Leu Ser Val Leu Leu Phe Asn His Asn Asp Arg
                85                  90                  95

Phe Tyr Glu Gly Arg Ala Gly Asp Pro Val Ala Cys Leu Val Met Glu
                100                 105                 110

Arg Leu Ile Phe Pro Pro Val Arg Gln Ala Thr Met Ile
            115                 120                 125

<210> SEQ ID NO 60
<211> LENGTH: 124
<212> TYPE: PRT
<213> ORGANISM: Artificial Sequence
<220> FEATURE:
<223> OTHER INFORMATION: E4orf1 amino acid sequence, Ad4-E4orf1

<400> SEQUENCE: 60

Met Asp Ala Gln Val Leu Tyr Val Phe Leu Glu Gly Ala Gly Ala Leu
1               5                   10                  15

Leu Pro Val Gln Lys Gly Ser Asn Tyr Ile Phe Tyr Ala Pro Ala Asn
                20                  25                  30

Phe Val Leu His Pro His Gly Val Ala Leu Leu Glu Leu Arg Leu Ser
            35                  40                  45

Ile Val Val Pro Gln Gly Phe Ile Gly Arg Phe Phe Ser Leu Thr Asp
        50                  55                  60

Ala Asn Val Pro Gly Val Tyr Ala Ser Ser Arg Ile Ile His Ala Gly
65                  70                  75                  80

His Arg Glu Gly Leu Ser Val Met Leu Phe Asn His Asn Val Ser Phe
                85                  90                  95

Tyr Asn Gly Arg Ala Gly Asp Pro Val Ala Cys Leu Val Leu Glu Arg
                100                 105                 110

Val Ile Tyr Pro Pro Val Arg Gln Ala Ser Met Val
            115                 120

<210> SEQ ID NO 61
<211> LENGTH: 128
<212> TYPE: PRT
<213> ORGANISM: Artificial Sequence
<220> FEATURE:
<223> OTHER INFORMATION: E4orf1 amino acid sequence, Ad6-E4orf1

<400> SEQUENCE: 61
```

-continued

```
Met Ala Ala Ala Val Glu Ala Leu Tyr Val Val Leu Glu Arg Glu Gly
1               5                   10                  15

Ala Ile Leu Pro Arg Gln Glu Gly Phe Ser Gly Val Tyr Val Phe Phe
            20                  25                  30

Ser Pro Ile Asn Phe Val Ile Pro Pro Met Gly Ala Val Met Leu Ser
        35                  40                  45

Leu Arg Leu Arg Val Cys Ile Pro Pro Gly Tyr Phe Gly Arg Phe Leu
    50                  55                  60

Ala Leu Thr Asp Val Ser Gln Pro Asp Val Phe Thr Glu Ser Tyr Ile
65                  70                  75                  80

Met Thr Pro Asp Met Thr Glu Glu Leu Ser Val Val Leu Phe Asn His
                85                  90                  95

Gly Asp Gln Phe Phe Tyr Gly His Ala Gly Met Ala Val Val Arg Leu
                100                 105                 110

Met Leu Ile Arg Val Val Phe Pro Val Val Arg Gln Ala Ser Asn Val
                115                 120                 125
```

<210> SEQ ID NO 62
<211> LENGTH: 125
<212> TYPE: PRT
<213> ORGANISM: Artificial Sequence
<220> FEATURE:
<223> OTHER INFORMATION: E4orf1 amino acid sequence, Ad7-E4orf1

<400> SEQUENCE: 62

```
Met Ala Asp Glu Ala Leu Tyr Val Tyr Leu Glu Gly Pro Gly Ala Thr
1               5                   10                  15

Leu Pro Glu Gln Gln Gln Arg Asn Asn Tyr Ile Phe Tyr Ser Pro Val
            20                  25                  30

Pro Phe Thr Leu Tyr Pro Arg Gly Val Ala Leu Leu Tyr Leu Arg Leu
        35                  40                  45

Ser Ile Ile Ile Pro Arg Gly Tyr Val Gly Cys Phe Phe Ser Leu Thr
    50                  55                  60

Asp Ala Asn Met Ser Gly Leu Tyr Ala Ser Ser Arg Ile Ile His Ala
65                  70                  75                  80

Gly His Arg Glu Glu Leu Ser Val Leu Leu Phe Asn His Asp Asp Arg
                85                  90                  95

Phe Tyr Glu Gly Arg Ala Gly Asp Pro Val Ala Cys Leu Val Met Glu
                100                 105                 110

Arg Leu Ile Tyr Pro Pro Val Arg Gln Ala Thr Met Ile
        115                 120                 125
```

<210> SEQ ID NO 63
<211> LENGTH: 125
<212> TYPE: PRT
<213> ORGANISM: Artificial Sequence
<220> FEATURE:
<223> OTHER INFORMATION: E4orf1 amino acid sequence, Ad9-E4orf1

<400> SEQUENCE: 63

```
Met Ala Glu Ser Leu Tyr Ala Phe Ile Asp Ser Pro Gly Gly Ile Ala
1               5                   10                  15

Pro Val Gln Glu Gly Thr Ser Asn Arg Tyr Thr Phe Phe Cys Pro Glu
            20                  25                  30

Ser Phe His Ile Pro Pro His Gly Val Val Leu Leu His Leu Lys Val
        35                  40                  45

Ser Val Leu Val Pro Thr Gly Tyr Gln Gly Arg Phe Met Ala Leu Asn
    50                  55                  60
```

```
Asp Tyr His Ala Arg Asp Ile Leu Thr Gln Ser Asp Val Ile Phe Ala
65                  70                  75                  80

Gly Arg Arg Gln Glu Leu Thr Val Leu Leu Phe Asn His Thr Asp Arg
                85                  90                  95

Phe Leu Tyr Val Arg Lys Gly His Pro Val Gly Thr Leu Leu Leu Glu
            100                 105                 110

Arg Val Ile Phe Pro Ser Val Lys Ile Ala Thr Leu Val
        115                 120                 125

<210> SEQ ID NO 64
<211> LENGTH: 125
<212> TYPE: PRT
<213> ORGANISM: Artificial Sequence
<220> FEATURE:
<223> OTHER INFORMATION: E4orf1 amino acid sequence, Ad14-E4orf1

<400> SEQUENCE: 64

Met Ala Asp Glu Ala Leu Tyr Val Tyr Leu Glu Gly Pro Gly Ala Thr
1               5                   10                  15

Leu Pro Glu Gln Gln Gln Arg Asn Asn Tyr Ile Phe Tyr Ser Pro Val
                20                  25                  30

Pro Phe Thr Leu Tyr Pro Arg Gly Val Ala Leu Leu Tyr Leu Arg Leu
            35                  40                  45

Ser Ile Ile Ile Pro Arg Gly Tyr Ile Gly Cys Phe Leu Ser Leu Thr
        50                  55                  60

Asp Ala Asn Met Phe Gly Leu Tyr Ala Ser Ser Arg Ile Ile His Ala
65                  70                  75                  80

Gly His Arg Glu Glu Leu Ser Val Leu Leu Phe Asn His Asp Asp Arg
                85                  90                  95

Phe Tyr Glu Gly Arg Ala Gly Asp Pro Val Ala Cys Leu Val Met Glu
            100                 105                 110

Arg Leu Ile Tyr Pro Pro Val Arg Gln Ala Thr Leu Ile
        115                 120                 125

<210> SEQ ID NO 65
<211> LENGTH: 126
<212> TYPE: PRT
<213> ORGANISM: Artificial Sequence
<220> FEATURE:
<223> OTHER INFORMATION: E4orf1 amino acid sequence, Ad16-E4orf1

<400> SEQUENCE: 65

Met Ala Asp Glu Ala Leu Tyr Val Tyr Phe Arg Gly Pro Gly Ala Thr
1               5                   10                  15

Leu Pro Glu Gln Gln Gln Gln Arg Asn Asn Tyr Ile Phe Tyr Ser Pro
                20                  25                  30

Val Pro Phe Thr Leu Tyr Pro Arg Gly Val Ala Leu Leu Tyr Leu Arg
            35                  40                  45

Leu Ser Ile Ile Ile Pro Arg Gly Tyr Val Gly Cys Phe Phe Ser Leu
        50                  55                  60

Thr Asp Ala Asn Met Ser Gly Leu Tyr Ala Ser Ser Arg Ile Ile His
65                  70                  75                  80

Ala Gly His Arg Glu Glu Leu Ser Val Leu Leu Phe Asn His Asp Asp
                85                  90                  95

Arg Phe Tyr Glu Gly Arg Ala Gly Asp Pro Val Ala Cys Leu Val Met
            100                 105                 110

Glu Arg Leu Ile Tyr Pro Pro Val Arg Gln Ala Thr Met Ile
```

-continued

```
         115              120              125
```

<210> SEQ ID NO 66
<211> LENGTH: 127
<212> TYPE: PRT
<213> ORGANISM: Artificial Sequence
<220> FEATURE:
<223> OTHER INFORMATION: E4orf1 amino acid sequence, Ad18-E4orf1

<400> SEQUENCE: 66

Met Ala Ala Leu Gln Ala Leu Tyr Val Tyr Phe Lys Gly Pro Gly Ala
1               5                   10                  15

Met Leu Pro Glu Gln Glu Gly Tyr Ser Asn Ala Tyr Val Leu Phe Ser
            20                  25                  30

Pro Ala Asn Phe Val Ile Pro Pro His Gly Val Val Leu Leu Tyr Leu
        35                  40                  45

His Ile Ala Val Asp Ile Pro Pro Gly Tyr Leu Gly Thr Leu Phe Ser
    50                  55                  60

Leu Ser Asp Met Asn Ala Arg Gly Val Phe Val Gly Ala Glu Thr Leu
65                  70                  75                  80

Tyr Pro Gly Ser Arg Met Glu Leu Ser Val Leu Leu Phe Asn His Ser
                85                  90                  95

Asp Val Phe Cys Asp Val Arg Ala Lys Gln Pro Val Ala Arg Leu Leu
                100                 105                 110

Leu Ser Arg Val Ile Phe Pro Pro Val Arg Gln Ala Ser Leu Leu
            115                 120                 125

<210> SEQ ID NO 67
<211> LENGTH: 125
<212> TYPE: PRT
<213> ORGANISM: Artificial Sequence
<220> FEATURE:
<223> OTHER INFORMATION: E4orf1 amino acid sequence, Ad20-E4orf1

<400> SEQUENCE: 67

Met Ala Glu Ser Leu Tyr Ala Phe Ile Asp Ser Pro Gly Gly Ile Ala
1               5                   10                  15

Pro Val Gln Glu Gly Thr Ser Asn Arg Tyr Asn Phe Phe Cys Pro Gln
            20                  25                  30

Ser Phe His Ile Pro Pro His Gly Val Val Leu Leu His Leu Lys Val
        35                  40                  45

Ser Val Leu Val Pro Thr Gly Tyr Gln Gly Arg Phe Met Ala Leu Asn
    50                  55                  60

Asp Tyr His Ala Arg Asp Ile Leu Thr Gln Ser Asp Val Ile Phe Ala
65                  70                  75                  80

Gly Arg Arg Gln Glu Leu Thr Val Leu Leu Phe Asn His Thr Asp Arg
                85                  90                  95

Phe Leu Tyr Val Arg Lys Gly His Pro Val Gly Thr Leu Leu Leu Glu
            100                 105                 110

Arg Val Ile Phe Pro Ser Val Lys Ile Ala Thr Leu Val
            115                 120                 125

<210> SEQ ID NO 68
<211> LENGTH: 123
<212> TYPE: PRT
<213> ORGANISM: Artificial Sequence
<220> FEATURE:
<223> OTHER INFORMATION: E4orf1 amino acid sequence, Ad21-E4orf1

<400> SEQUENCE: 68

-continued

```
Met Ala Glu Val Leu Tyr Val Ile Leu Glu Gly Pro Gly Ala Arg Leu
1               5                   10                  15

Pro Val Gln Glu Gly Asn Asn Tyr Ile Phe Tyr Ala Pro Val Asp Phe
            20                  25                  30

Thr Leu His Pro Arg Gly Val Ala Leu Leu His Leu Arg Leu Ser Ile
        35                  40                  45

Ile Val Pro Arg Cys Tyr Ile Gly Arg Phe Phe Ser Leu Thr Asp Thr
    50                  55                  60

Asn Thr Ser Gly Leu Tyr Ala Ser Ser Gln Ile Ile Phe Ala Ala His
65                  70                  75                  80

Gln Gln Pro Leu Ser Val Met Leu Phe Asn His Thr Asp Arg Phe Tyr
                85                  90                  95

Glu Gly Arg Val Gly Asp Pro Val Ala Cys Leu Val Leu Glu Arg Val
                100                 105                 110

Ile Tyr Pro Ser Val Arg Gln Ala Ser Met Met
            115                 120
```

```
<210> SEQ ID NO 69
<211> LENGTH: 125
<212> TYPE: PRT
<213> ORGANISM: Artificial Sequence
<220> FEATURE:
<223> OTHER INFORMATION: E4orf1 amino acid sequence, Ad23-E4orf1

<400> SEQUENCE: 69
```

```
Met Ala Glu Ser Leu Tyr Ala Phe Ile Asp Ser Pro Gly Gly Ile Ala
1               5                   10                  15

Pro Val Gln Glu Gly Ser Ser Asn Arg Tyr Asn Phe Phe Cys Pro Glu
            20                  25                  30

Ser Phe His Ile Pro Pro His Gly Val Val Leu Leu His Leu Arg Val
        35                  40                  45

Ser Val Leu Ile Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Glu Leu Thr Val Leu Leu Phe Asn His Thr Asp Arg
                85                  90                  95

Phe Leu Tyr Val Arg Glu Gly His Pro Val Gly Thr Leu Leu Leu Glu
                100                 105                 110

Arg Val Ile Phe Pro Ser Val Arg Leu Ala Thr Leu Val
            115                 120                 125
```

```
<210> SEQ ID NO 70
<211> LENGTH: 125
<212> TYPE: PRT
<213> ORGANISM: Artificial Sequence
<220> FEATURE:
<223> OTHER INFORMATION: E4orf1 amino acid sequence, Ad25-E4orf1

<400> SEQUENCE: 70
```

```
Met Ala Glu Ser Leu Tyr Ala Phe Ile Asp Ser Pro Gly Gly Ile Ala
1               5                   10                  15

Pro Val Gln Glu Gly Thr Ser Asn Arg Tyr Thr Phe Phe Cys Pro Glu
            20                  25                  30

Ser Phe His Ile Pro Pro His Gly Val Val Leu Val His Leu Arg Val
        35                  40                  45

Ser Val Leu Ile Pro Asn Gly Tyr Gln Gly Arg Phe Met Ala Leu Asn
```

-continued

```
        50                55                60

Asp Tyr His Ser Arg Gly Ile Leu Thr Gln Ser Asp Val Ile Phe Ala
65                70                75                80

Gly Arg Arg Gln Glu Leu Thr Val Leu Leu Phe Asn His Thr Asp Arg
                85                90                95

Phe Leu Tyr Val Arg Glu Gly His Pro Val Gly Thr Leu Leu Leu Glu
                100               105               110

Arg Val Ile Phe Pro Ser Val Arg Leu Ala Thr Leu Val
        115               120               125

<210> SEQ ID NO 71
<211> LENGTH: 125
<212> TYPE: PRT
<213> ORGANISM: Artificial Sequence
<220> FEATURE:
<223> OTHER INFORMATION: E4orf1 amino acid sequence, Ad30-E4orf1

<400> SEQUENCE: 71

Met Ala Glu Ser Leu Tyr Ala Phe Ile Asp Ser Pro Gly Gly Ile Ala
1                5                10                15

Pro Val Gln Glu Gly Ala Ser Asn Arg Tyr Thr Phe Phe Cys Pro Glu
                20                25                30

Ser Phe His Ile Pro Pro His Gly Val Ile Leu Leu His Leu Arg Val
        35                40                45

Ser Val Leu Val Pro Thr Gly Tyr Gln Gly Arg Phe Met Ala Leu Asn
    50                55                60

Asp Tyr His Ala Arg Gly Ile Leu Thr Gln Ser Asp Val Ile Phe Ala
65                70                75                80

Gly Arg Arg His Asp Leu Ser Val Leu Leu Phe Asn His Thr Asp Arg
                85                90                95

Phe Leu Tyr Val Arg Glu Gly His Pro Val Gly Thr Leu Leu Leu Glu
                100               105               110

Arg Val Ile Phe Pro Ser Val Arg Leu Ala Thr Leu Val
        115               120               125

<210> SEQ ID NO 72
<211> LENGTH: 125
<212> TYPE: PRT
<213> ORGANISM: Artificial Sequence
<220> FEATURE:
<223> OTHER INFORMATION: E4orf1 amino acid sequence, Ad36-E4orf1

<400> SEQUENCE: 72

Met Ala Glu Ser Leu Tyr Ala Phe Ile Asp Ser Pro Gly Gly Ile Ala
1                5                10                15

Pro Val Gln Glu Gly Ala Ser Asn Arg Tyr Ile Phe Phe Cys Pro Glu
                20                25                30

Ser Phe His Ile Pro Pro His Gly Val Ile Leu Leu His Leu Arg Val
        35                40                45

Ser Val Leu Val Pro Thr Gly Tyr Gln Gly Arg Phe Met Ala Leu Asn
    50                55                60

Asp Tyr His Ala Arg Gly Ile Leu Thr Gln Ser Asp Val Ile Phe Ala
65                70                75                80

Gly Arg Arg His Asp Leu Ser Val Leu Leu Phe Asn His Thr Asp Arg
                85                90                95

Phe Leu Tyr Val Arg Glu Gly His Pro Val Gly Thr Leu Leu Leu Glu
                100               105               110
```

-continued

```
Arg Val Ile Phe Pro Ser Val Arg Ile Ala Thr Leu Val
        115                 120                 125

<210> SEQ ID NO 73
<211> LENGTH: 125
<212> TYPE: PRT
<213> ORGANISM: Artificial Sequence
<220> FEATURE:
<223> OTHER INFORMATION: E4orf1 amino acid sequence, Ad50-E4orf1

<400> SEQUENCE: 73

Met Ala Asp Glu Ala Leu Tyr Val Tyr Leu Asp Gly Pro Gly Ala Thr
1               5                   10                  15

Leu Pro Glu Gln Gln Gln Arg Asn Asn Tyr Ile Phe Tyr Ser Pro Val
            20                  25                  30

Pro Phe Thr Leu Tyr Pro Arg Gly Val Ala Leu Leu Tyr Leu Arg Leu
            35                  40                  45

Ser Ile Ile Ile Pro Arg Gly Tyr Val Gly Cys Phe Phe Ser Leu Thr
        50                  55                  60

Asp Ala Asn Met Ser Gly Leu Tyr Ala Ser Ser Arg Ile Ile His Ala
65                  70                  75                  80

Gly His Arg Glu Glu Leu Ser Val Leu Leu Phe Asn His Asp Asp Arg
                85                  90                  95

Phe Tyr Glu Gly Arg Ala Gly Asp Pro Val Ala Cys Leu Val Met Glu
                100                 105                 110

Arg Leu Ile Tyr Pro Pro Val Arg Gln Ala Thr Met Ile
        115                 120                 125

<210> SEQ ID NO 74
<211> LENGTH: 125
<212> TYPE: PRT
<213> ORGANISM: Artificial Sequence
<220> FEATURE:
<223> OTHER INFORMATION: E4orf1 amino acid sequence, Ad55-E4orf1

<400> SEQUENCE: 74

Met Ala His Glu Ala Leu Tyr Val Tyr Leu Glu Gly Pro Gly Ala Thr
1               5                   10                  15

Leu Pro Glu Gln Gln Gln Arg Asn Asn Tyr Ile Phe Tyr Ser Pro Val
            20                  25                  30

Pro Phe Thr Leu Tyr Pro Arg Gly Val Ala Leu Leu Tyr Leu Arg Leu
            35                  40                  45

Ser Ile Ile Ile Pro Arg Gly Tyr Ile Gly Cys Phe Leu Ser Leu Thr
        50                  55                  60

Asp Ala Asn Met Phe Gly Leu Tyr Ala Ser Ser Arg Ile Ile His Ala
65                  70                  75                  80

Gly His Arg Glu Glu Leu Ser Val Leu Leu Phe Asn His Asp Asp Arg
                85                  90                  95

Phe Tyr Glu Gly Arg Ala Gly Asp Pro Val Ala Cys Leu Val Met Glu
                100                 105                 110

Arg Leu Ile Tyr Pro Pro Val Arg Gln Ala Thr Leu Ile
        115                 120                 125

<210> SEQ ID NO 75
<211> LENGTH: 125
<212> TYPE: PRT
<213> ORGANISM: Artificial Sequence
<220> FEATURE:
<223> OTHER INFORMATION: E4orf1 amino acid sequence, Ad62-E4orf1
```

<400> SEQUENCE: 75

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
            20                  25                  30

Ser Phe His Ile Pro Pro His Gly Val Ile Leu Leu His Leu Arg Val
        35                  40                  45

Ser Val Met Val Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
            85                  90                  95

Phe Leu Tyr Val Arg Glu Gly His Pro Val Gly Thr Leu Leu Leu Glu
            100                 105                 110

Arg Val Ile Phe Pro Ser Val Arg Ile Ala Thr Leu Val
        115                 120                 125

<210> SEQ ID NO 76
<211> LENGTH: 125
<212> TYPE: PRT
<213> ORGANISM: Artificial Sequence
<220> FEATURE:
<223> OTHER INFORMATION: E4orf1 amino acid sequence, Ad71-E4orf1

<400> SEQUENCE: 76

Met Ala Glu Ser Leu Tyr Ala Phe Ile Asp Ser Pro Gly Gly Ile Ala
1               5                   10                  15

Pro Val Gln Glu Gly Thr Ser Asn Arg Tyr Asp Phe Phe Cys Pro Glu
            20                  25                  30

Ser Phe His Ile Pro Pro His Gly Val Val Leu Leu His Leu Arg Val
        35                  40                  45

Ser Val Leu Ile Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Glu Leu Thr Val Leu Leu Phe Asn His Thr Asp Arg
            85                  90                  95

Phe Leu Tyr Val Arg Glu Gly His Pro Val Gly Thr Leu Leu Leu Glu
            100                 105                 110

Arg Val Ile Phe Pro Ser Val Arg Leu Ala Thr Leu Val
        115                 120                 125

<210> SEQ ID NO 77
<211> LENGTH: 150
<212> TYPE: PRT
<213> ORGANISM: Artificial Sequence
<220> FEATURE:
<223> OTHER INFORMATION: E4orf6/7 amino acid sequence, Ad1-E4orf6/7

<400> SEQUENCE: 77

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

```
Pro Glu Cys Asn Thr Leu Thr Met His Asn Ala Trp Thr Ser Pro Ser
    50                  55                  60

Pro Pro Val Glu Gln Pro Gln Val Gly Gln Gln Pro Val Ala Gln Gln
65                  70                  75                  80

Leu Asp Ser Asn Met Asn Leu Arg Glu Leu Pro Gly Glu Phe Ile Asn
                85                  90                  95

Ile Thr Asp Glu Arg Leu Ala Arg Gln Glu Thr Val Trp Asn Ile Thr
            100                 105                 110

Pro Lys Asn Met Ser Val Thr His Asp Met Met Leu Phe Lys Ala Ser
        115                 120                 125

Arg Gly Glu Arg Thr Val Tyr Ser Val Cys Trp Glu Gly Gly Gly Arg
    130                 135                 140

Leu Asn Thr Arg Val Leu
145                 150

<210> SEQ ID NO 78
<211> LENGTH: 150
<212> TYPE: PRT
<213> ORGANISM: Artificial Sequence
<220> FEATURE:
<223> OTHER INFORMATION: E4orf6/7 amino acid sequence, Ad2-E4orf6/7

<400> SEQUENCE: 78

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
                20                  25                  30

Phe Glu Thr Glu Thr Arg Ala Thr Ile Leu Glu Asp His Pro Leu Leu
            35                  40                  45

Pro Glu Cys Asn Thr Leu Thr Met His Asn Ala Trp Thr Ser Pro Ser
    50                  55                  60

Pro Pro Val Glu Gln Pro Gln Val Gly Gln Gln Pro Val Ala Gln Gln
65                  70                  75                  80

Leu Asp Ser Asp Met Asn Leu Ser Glu Leu Pro Gly Glu Phe Ile Asn
                85                  90                  95

Ile Thr Asp Glu Arg Leu Ala Arg Gln Glu Thr Val Trp Asn Ile Thr
            100                 105                 110

Pro Lys Asn Met Ser Val Thr His Asp Met Met Leu Phe Lys Ala Ser
        115                 120                 125

Arg Gly Glu Arg Thr Val Tyr Ser Val Cys Trp Glu Gly Gly Gly Arg
    130                 135                 140

Leu Asn Thr Arg Val Leu
145                 150

<210> SEQ ID NO 79
<211> LENGTH: 141
<212> TYPE: PRT
<213> ORGANISM: Artificial Sequence
<220> FEATURE:
<223> OTHER INFORMATION: E4orf6/7 amino acid sequence, Ad3-E4orf6/7

<400> SEQUENCE: 79

Met Ser Gly Ser Asn Ser Ile Met Thr Arg Leu Arg Ala Arg Ser Thr
1               5                   10                  15

Ser Cys Ala Arg His His Pro Tyr Thr Arg Ala Gln Leu Pro Arg Cys
                20                  25                  30

Glu Glu Asn Glu Thr Arg Ala Ser Met Thr Glu Asp His Pro Leu Leu
            35                  40                  45
```

-continued

```
Pro Asp Cys Asp Thr Met Thr Met His Ser Met Thr Val Ile Gln Thr
    50              55              60

Pro Glu Ser His Pro Gln Gln Leu Asp Cys Glu Ser Ala Leu Lys Asp
65              70              75              80

Tyr Pro Asp Ala Phe Leu Cys Ile Thr Asp Pro Arg Leu Ala Arg Ser
                85              90              95

Glu Thr Val Trp Asn Val Glu Ser Lys Thr Met Ser Ile Ser Asn Gly
            100             105             110

Ile Gln Met Phe Lys Ala Val Arg Gly Glu Arg Leu Val Tyr Ser Val
        115             120             125

Lys Trp Glu Gly Gly Gly Lys Ile Thr Thr Arg Ile Leu
    130             135             140
```

```
<210> SEQ ID NO 80
<211> LENGTH: 141
<212> TYPE: PRT
<213> ORGANISM: Artificial Sequence
<220> FEATURE:
<223> OTHER INFORMATION: E4orf6/7 amino acid sequence, Ad4-E4orf6/7

<400> SEQUENCE: 80
```

```
Met Ser Gly Asn Ser Ser Ile Met Thr Arg Ser Arg Thr Arg Leu Ala
1               5               10              15

Leu Ser Arg His His Pro Tyr Gln Pro Pro Ala Thr Leu Pro Arg Cys
            20              25              30

Glu Glu Thr Glu Ser Arg Ala Ser Leu Val Glu Asp His Pro Val Leu
        35              40              45

Pro Asp Cys Asp Thr Leu Ser Met His Asn Ile Thr Val Ile Pro Ile
    50              55              60

Thr Glu Asp Ser Pro Gln Leu Leu Asn Cys Glu Val Gln Met Gln Glu
65              70              75              80

Cys Pro Glu Gly Phe Ile Ser Leu Thr Asp Pro Arg Leu Ser Arg Ser
                85              90              95

Glu Thr Val Trp Asn Val Glu Ile Lys Thr Met Ser Ile Thr Asn Ser
            100             105             110

Ile Gln Met Phe Lys Ala Val Arg Gly Glu Arg Ile Val Tyr Ser Met
        115             120             125

Arg Trp Glu Gly Gly Gly Lys Ile Thr Thr Arg Ile Leu
    130             135             140
```

```
<210> SEQ ID NO 81
<211> LENGTH: 150
<212> TYPE: PRT
<213> ORGANISM: Artificial Sequence
<220> FEATURE:
<223> OTHER INFORMATION: E4orf6/7 amino acid sequence, Ad6-E4orf6/7

<400> SEQUENCE: 81
```

```
Met Thr Thr Ser Gly Val Pro Phe Gly Met Thr Leu Arg Pro Thr Arg
1               5               10              15

Ser Arg Leu Ser Arg Arg Thr Pro Tyr Ser Arg Asp Arg Leu Pro Pro
            20              25              30

Phe Glu Thr Glu Thr Arg Ala Thr Ile Leu Glu Asp His Pro Leu Leu
        35              40              45

Pro Glu Cys Asn Thr Leu Thr Met His Asn Ala Trp Thr Ser Pro Ser
    50              55              60

Pro Ser Val Lys Arg Pro Gln Val Gly Gln Gln Pro Val Ala Gln Gln
```

```
65                    70                    75                    80

Leu Asp Ser Asp Met Asn Leu Ser Glu Leu Pro Gly Glu Phe Ile Asn
                85                    90                    95

Ile Thr Asp Glu Arg Leu Ala Arg Gln Glu Thr Val Trp Asn Ile Thr
                100                   105                   110

Pro Lys Asn Met Ser Val Thr His Asp Met Met Leu Phe Lys Ala Ser
                115                   120                   125

Arg Gly Glu Arg Thr Val Tyr Ser Val Cys Trp Glu Gly Gly Gly Arg
        130                   135                   140

Leu Asn Thr Arg Val Leu
145                   150

<210> SEQ ID NO 82
<211> LENGTH: 141
<212> TYPE: PRT
<213> ORGANISM: Artificial Sequence
<220> FEATURE:
<223> OTHER INFORMATION: E4orf6/7 amino acid sequence, Ad7-E4orf6/7

<400> SEQUENCE: 82

Met Ser Gly Ser Asn Ser Ile Met Thr Arg Leu Arg Ala Arg Ser Thr
1                    5                    10                    15

Ser Cys Ala Arg His His Pro Tyr Thr Arg Ala Gln Leu Pro Arg Cys
                20                    25                    30

Glu Glu Asn Glu Thr Arg Ala Ser Met Thr Glu Asp His Pro Leu Leu
                35                    40                    45

Pro Asp Cys Asp Thr Met Thr Met His Ser Met Thr Val Ile Gln Thr
        50                    55                    60

Pro Glu Ser His Pro Gln Gln Leu Asp Cys Glu Ser Ala Leu Lys Asp
65                    70                    75                    80

Tyr Pro Asp Ala Phe Leu Cys Ile Thr Asp Pro Arg Leu Ala Arg Phe
                85                    90                    95

Glu Thr Val Trp Asn Val Glu Ser Lys Thr Met Ser Ile Cys Asn Gly
                100                   105                   110

Ile Gln Met Phe Lys Ala Val Arg Gly Glu Arg Leu Val Tyr Ser Val
        115                   120                   125

Lys Trp Glu Gly Gly Gly Lys Ile Thr Thr Arg Ile Leu
        130                   135                   140

<210> SEQ ID NO 83
<211> LENGTH: 141
<212> TYPE: PRT
<213> ORGANISM: Artificial Sequence
<220> FEATURE:
<223> OTHER INFORMATION: E4orf6/7 amino acid sequence, Ad11-E4orf6/7

<400> SEQUENCE: 83

Met Ser Gly Ser Asn Ser Ile Met Thr Arg Leu Arg Ala Arg Ser Thr
1                    5                    10                    15

Ser Cys Ala Arg His His Pro Tyr Thr Arg Ala Gln Leu Pro Arg Cys
                20                    25                    30

Glu Glu Asn Glu Thr Arg Ala Ser Met Thr Glu Asp His Pro Leu Leu
        35                    40                    45

Pro Asp Cys Asp Thr Met Thr Met His Ser Met Thr Val Ile Gln Thr
        50                    55                    60

Pro Glu Ser Gln Pro Gln Gln Leu Asp Cys Glu Ser Ala Leu Lys Asp
65                    70                    75                    80
```

```
Tyr Pro Asp Ala Phe Leu Ser Ile Thr Asp Pro Arg Leu Ala Arg Ser
                85                  90                  95

Glu Thr Val Trp Asn Val Glu Ser Lys Thr Met Ser Ile Ser Asn Gly
                100                 105                 110

Ile Gln Met Phe Lys Ala Val Arg Gly Glu Arg Leu Val Tyr Ser Val
            115                 120                 125

Lys Trp Glu Gly Gly Gly Lys Ile Thr Thr Arg Ile Leu
    130                 135                 140

<210> SEQ ID NO 84
<211> LENGTH: 141
<212> TYPE: PRT
<213> ORGANISM: Artificial Sequence
<220> FEATURE:
<223> OTHER INFORMATION: E4orf6/7 amino acid sequence, Ad14-E4orf6/7

<400> SEQUENCE: 84

Met Ser Gly Ser Asn Ser Ile Met Thr Arg Leu Cys Ala Arg Ser Thr
1               5                   10                  15

Ser Cys Ala Arg His His Pro Tyr Thr Arg Ala Gln Leu Pro Arg Cys
                20                  25                  30

Glu Glu Asn Glu Thr Arg Ala Ser Met Thr Glu Asp His Pro Leu Leu
            35                  40                  45

Pro Asp Cys Asp Thr Met Thr Met His Ser Met Thr Val Ile Gln Thr
    50                  55                  60

Pro Glu Ser His Pro Gln Gln Leu Asp Cys Glu Ser Ala Leu Lys Asp
65                  70                  75                  80

Tyr Pro Ala Gly Phe Leu Ser Ile Thr Asp Pro Arg Leu Ala Arg Tyr
                85                  90                  95

Glu Thr Val Trp Asn Val Glu Ser Lys Thr Met Ser Ile Ser Asn Gly
                100                 105                 110

Ile Gln Met Phe Lys Ala Val Arg Gly Glu Arg Leu Val Tyr Ser Val
            115                 120                 125

Lys Trp Glu Gly Gly Gly Lys Ile Thr Thr Arg Ser Leu
    130                 135                 140

<210> SEQ ID NO 85
<211> LENGTH: 126
<212> TYPE: PRT
<213> ORGANISM: Artificial Sequence
<220> FEATURE:
<223> OTHER INFORMATION: E4orf6/7 amino acid sequence, Ad18-E4orf6/7

<400> SEQUENCE: 85

Met Gln Arg Asn Arg Arg Tyr Pro Tyr Arg Leu Ala Pro Tyr Gly Lys
1               5                   10                  15

Tyr Pro Leu Pro Pro Cys Glu Lys Glu Met Arg Ala Ser Leu Phe Gly
                20                  25                  30

Pro Glu Asn Ser Ser Val Ser Glu Cys Asn Ser Leu Thr Leu His Asn
            35                  40                  45

Val Ile Asn Met Asp Leu Val Leu Asp Gly Glu Ser Tyr Leu Ser Asp
    50                  55                  60

Cys Val Gly Glu Gly Phe Val Ser Ile Ile Asp His Arg Phe Ala Arg
65                  70                  75                  80

Lys Glu Thr Ile Trp Thr Val Thr Pro Lys Asn Leu Ser Arg Asn Met
                85                  90                  95

His Met Gln Leu Phe Ser Ala Ile Lys Gly Glu Arg Val Val Tyr Lys
                100                 105                 110
```

```
Ile Lys Trp Glu Gly Gly Gly Ser Leu Thr Thr Arg Ile Val
        115                 120                 125

<210> SEQ ID NO 86
<211> LENGTH: 130
<212> TYPE: PRT
<213> ORGANISM: Artificial Sequence
<220> FEATURE:
<223> OTHER INFORMATION: E4orf6/7 amino acid sequence, Ad19-E4orf6/7

<400> SEQUENCE: 86

Met Gln Thr Glu Asp Gln Ser Ser Leu Leu Arg His His Pro Tyr Arg
1               5                   10                  15

Arg Ala Arg Leu Pro Arg Ser Asp Glu Glu Thr Arg Ala Ser Leu Thr
            20                  25                  30

Glu Gln His Pro Leu Leu Pro Asp Cys Asp His Ala Asp Tyr His Asn
        35                  40                  45

Thr Val Thr Leu Asp Cys Glu Ala Arg Leu Asp Asp Phe Ser Glu Asp
    50                  55                  60

Gly Phe Ile Ser Ile Thr Asp Pro Arg Leu Ala Arg Gln Glu Thr Val
65                  70                  75                  80

Trp Ile Ile Asp Pro Lys Leu Ser Ser Arg Thr Asn Gln Asn Ile Pro
                85                  90                  95

Leu Phe Lys Ala Thr Arg Ala Glu Arg Thr Val Tyr Thr Val Lys Trp
            100                 105                 110

Ala Gly Gly Gly Arg Leu Thr Thr Arg Ala Gly Val Lys Ile Asn Lys
        115                 120                 125

Asp Thr
    130

<210> SEQ ID NO 87
<211> LENGTH: 130
<212> TYPE: PRT
<213> ORGANISM: Artificial Sequence
<220> FEATURE:
<223> OTHER INFORMATION: E4orf6/7 amino acid sequence, Ad20-E4orf6/7

<400> SEQUENCE: 87

Met Gln Thr Glu Ile Gln Ser Ser Ser Leu Arg His His Pro Tyr Arg
1               5                   10                  15

Arg Ala Arg Leu Pro Arg Ser Asp Glu Glu Thr Arg Ala Ser Leu Thr
            20                  25                  30

Glu Gln His Pro Leu Leu Pro Asp Cys Asp His Ala Asp Tyr His Asn
        35                  40                  45

Thr Val Thr Leu Asp Cys Glu Ala Arg Leu Asp Asp Phe Ser Glu Asp
    50                  55                  60

Gly Phe Ile Ser Ile Thr Asp Pro Arg Leu Ala Arg Gln Glu Thr Val
65                  70                  75                  80

Trp Ile Ile Asp Pro Lys Ser Ser Ser Arg Thr Asn Gln Asn Ile Ser
                85                  90                  95

Leu Phe Lys Ala Thr Arg Ala Glu Arg Thr Val Tyr Thr Val Lys Trp
            100                 105                 110

Ala Gly Gly Gly Arg Leu Thr Thr Arg Ala Gly Val Lys Ile Asn Lys
        115                 120                 125

Asp Thr
    130
```

-continued

```
<210> SEQ ID NO 88
<211> LENGTH: 130
<212> TYPE: PRT
<213> ORGANISM: Artificial Sequence
<220> FEATURE:
<223> OTHER INFORMATION: E4orf6/7 amino acid sequence, Ad23-E4orf6/7

<400> SEQUENCE: 88

Met Ser Thr Glu Glu Gln Ser Ser Ser Leu Arg His His Pro Tyr Arg
1               5                   10                  15

Arg Ala Arg Leu Pro Arg Cys Glu Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Phe Ser Glu Asp
        50                  55                  60

Gly Phe Ile Ser Ile Thr Asp Pro Arg Leu Ala Arg Gln Glu Thr Val
65                  70                  75                  80

Trp Ile Ile Asp Thr Lys Thr Ser Ser Arg Thr Asn Asn Asn Ile Pro
                85                  90                  95

Leu Phe Lys Ala Thr Arg Ala Glu Arg Ile Val Tyr Thr Val Lys Trp
                100                 105                 110

Ala Gly Gly Gly Arg Leu Thr Thr Arg Ala Gly Val Lys Ile Asn Lys
            115                 120                 125

Asp Thr
    130

<210> SEQ ID NO 89
<211> LENGTH: 130
<212> TYPE: PRT
<213> ORGANISM: Artificial Sequence
<220> FEATURE:
<223> OTHER INFORMATION: E4orf6/7 amino acid sequence, Ad25-E4orf6/7

<400> SEQUENCE: 89

Met Ser Thr Glu Glu Gln Ser Ser Ser Leu Arg His His Pro Tyr Arg
1               5                   10                  15

Arg Ala Arg Leu Pro Arg Cys Glu Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Phe Ser Glu Asp
        50                  55                  60

Gly Phe Ile Ser Ile Thr Asp Pro Arg Leu Ala Arg Gln Glu Thr Val
65                  70                  75                  80

Trp Ile Ile Asp Pro Lys Ser Ser Ser Arg Thr Asn Gln Asn Ile Ser
                85                  90                  95

Leu Phe Lys Ala Thr Arg Ala Glu Arg Thr Val Tyr Thr Val Lys Trp
                100                 105                 110

Ala Gly Gly Gly Arg Leu Thr Thr Arg Ala Gly Val Lys Ile Asn Lys
            115                 120                 125

Asp Thr
    130

<210> SEQ ID NO 90
<211> LENGTH: 130
<212> TYPE: PRT
<213> ORGANISM: Artificial Sequence
<220> FEATURE:
```

-continued

<223> OTHER INFORMATION: E4orf6/7 amino acid sequence, Ad27-E4orf6/7

<400> SEQUENCE: 90

```
Met Gln Thr Glu Asp Gln Ser Ser Leu Leu Arg His His Pro Tyr Arg
1               5                   10                  15

Arg Ala Arg Leu Pro Arg Ser Asp Glu Glu Thr Arg Ala Ser Leu Thr
            20                  25                  30

Glu Gln His Pro Leu Leu Pro Asp Cys Asp His Ala Asp Tyr His Asn
        35                  40                  45

Thr Val Thr Leu Asp Cys Glu Ala Arg Leu Asp Asp Phe Ser Glu Asp
    50                  55                  60

Gly Phe Ile Ser Ile Thr Asp Pro Arg Leu Ala Arg Gln Glu Thr Val
65                  70                  75                  80

Trp Ile Ile Asp Pro Lys Phe Ser Ser Arg Thr Asn Gln Asn Ile Pro
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
        115                 120                 125

Asp Thr
    130
```

<210> SEQ ID NO 91
<211> LENGTH: 130
<212> TYPE: PRT
<213> ORGANISM: Artificial Sequence
<220> FEATURE:
<223> OTHER INFORMATION: E4orf6/7 amino acid sequence, Ad29-E4orf6/7

<400> SEQUENCE: 91

```
Met Gln Thr Glu Asp Gln Ser Ser Leu Leu Arg His His Pro Tyr Arg
1               5                   10                  15

Arg Ala Arg Leu Pro Arg Ser Asp Glu Glu Thr Arg Ala Ser Leu Thr
            20                  25                  30

Glu Gln His Pro Leu Leu Pro Asp Cys Asp His Ala Glu Tyr His Asn
        35                  40                  45

Thr Val Thr Leu Asp Cys Glu Ala Arg Leu Asp Asp Phe Ser Glu Asp
    50                  55                  60

Gly Phe Ile Ser Ile Thr Asp Pro Arg Leu Ala Arg Gln Glu Thr Val
65                  70                  75                  80

Trp Leu Ile Asp Thr Lys Ser Ser Ser Arg Ala Asn Gln Asn Ile Pro
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
        115                 120                 125

Asp Thr
    130
```

<210> SEQ ID NO 92
<211> LENGTH: 130
<212> TYPE: PRT
<213> ORGANISM: Artificial Sequence
<220> FEATURE:
<223> OTHER INFORMATION: E4orf6/7 amino acid sequence, Ad30-E4orf6/7

<400> SEQUENCE: 92

```
Met Ser Thr Glu Glu Gln Ser Ser Ser Leu Arg His His Pro Tyr Arg
```

```
1               5                    10                   15

Arg Ala Arg Leu Pro Arg Cys Glu Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Phe Ser Glu Asp
        50                  55                  60

Gly Phe Ile Ser Ile Thr Asp Pro Arg Leu Ala Arg Gln Glu Thr Val
65                  70                  75                  80

Trp Ile Ile Asp Ser Lys Ser Ser Ser Arg Thr Asn Gln Asn Ile Pro
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
            115                 120                 125

Asp Pro
    130
```

```
<210> SEQ ID NO 93
<211> LENGTH: 130
<212> TYPE: PRT
<213> ORGANISM: Artificial Sequence
<220> FEATURE:
<223> OTHER INFORMATION: E4orf6/7 amino acid sequence, Ad32-E4orf6/7

<400> SEQUENCE: 93
```

```
Met Ser Thr Glu Glu Gln Ser Ser Ser Leu Arg His His Pro Tyr Arg
1               5                    10                   15

Arg Ala Arg Leu Pro Arg Cys Asp Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Phe Ser Glu Asp
        50                  55                  60

Gly Phe Ile Ser Ile Thr Asp Pro Arg Leu Ala Arg Gln Glu Thr Val
65                  70                  75                  80

Trp Ile Ile Asp Pro Lys Ser Ser Ser Arg Thr Asn Gln Asn Ile Phe
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
            115                 120                 125

Asp Thr
    130
```

```
<210> SEQ ID NO 94
<211> LENGTH: 141
<212> TYPE: PRT
<213> ORGANISM: Artificial Sequence
<220> FEATURE:
<223> OTHER INFORMATION: E4orf6/7 amino acid sequence, Ad34-E4orf6/7

<400> SEQUENCE: 94
```

```
Met Ser Gly Ser Asn Ser Ile Met Thr Arg Leu Arg Ala Arg Ser Thr
1               5                    10                   15

Ser Cys Ala Arg His His Pro Tyr Thr Arg Ala Gln Leu Pro Arg Cys
                20                  25                  30
```

-continued

```
Glu Glu Asn Glu Thr Arg Ala Ser Met Thr Glu Asp His Pro Leu Leu
        35                  40                  45

Pro Asp Cys Asp Thr Met Thr Met His Ser Met Thr Val Ile Gln Thr
    50                  55                  60

Pro Glu Ser His Pro Gln Gln Leu Asp Cys Glu Ser Ala Leu Lys Asp
65                  70                  75                  80

Tyr Pro Asp Ala Phe Leu Ser Ile Thr Asp Pro Arg Leu Ala Arg Ser
                85                  90                  95

Glu Thr Val Trp Asn Val Glu Ser Lys Thr Met Ser Ile Ser Asn Gly
                100                 105                 110

Ile Gln Met Phe Lys Ala Val Arg Gly Glu Arg Leu Val Tyr Ser Val
            115                 120                 125

Lys Trp Glu Gly Gly Gly Lys Ile Thr Thr Arg Ile Leu
    130                 135                 140
```

<210> SEQ ID NO 95
<211> LENGTH: 130
<212> TYPE: PRT
<213> ORGANISM: Artificial Sequence
<220> FEATURE:
<223> OTHER INFORMATION: E4orf6/7 amino acid sequence, Ad36-E4orf6/7

<400> SEQUENCE: 95

```
Met Ser Thr Glu Glu Gln Ser Thr Ser Leu Arg His His Pro Tyr Arg
1               5                   10                  15

Arg Ala Arg Leu Pro Arg Ser Glu Glu Glu Thr Arg Ala Ser Leu Thr
                20                  25                  30

Glu Gln His Pro Leu Leu Pro Asp Cys Asp His Ala Glu Tyr His Asn
        35                  40                  45

Thr Val Thr Leu Asp Cys Glu Ala Arg Leu Glu Asp Phe Ser Glu Asp
    50                  55                  60

Gly Phe Ile Ser Ile Thr Asp Pro Arg Leu Ala Arg Gln Glu Thr Val
65                  70                  75                  80

Trp Ile Ile Asp Thr Lys Ser Ser Ser Arg Thr Asn Gln Asn Ile Pro
                85                  90                  95

Leu Phe Lys Ala Thr Arg Ala Glu Arg Ile Val Tyr Thr Val Lys Trp
                100                 105                 110

Ala Gly Gly Gly Arg Leu Thr Thr Arg Ala Gly Val Lys Ile Asn Lys
        115                 120                 125

Asp Thr
    130
```

<210> SEQ ID NO 96
<211> LENGTH: 130
<212> TYPE: PRT
<213> ORGANISM: Artificial Sequence
<220> FEATURE:
<223> OTHER INFORMATION: E4orf6/7 amino acid sequence, Ad38-E4orf6/7

<400> SEQUENCE: 96

```
Met Ser Thr Glu Glu Gln Ser Ser Leu Leu Arg His His Pro Tyr Arg
1               5                   10                  15

Arg Ala Arg Leu Pro Arg Cys Glu Glu Glu Thr Arg Ala Ser Leu Thr
                20                  25                  30

Glu Gln His Pro Leu Leu Pro Asp Cys Asp His Ala Asp Tyr His Asn
        35                  40                  45

Thr Val Thr Leu Asp Cys Glu Ala Arg Leu Asp Asp Phe Ser Glu Asp
    50                  55                  60
```

```
Gly Phe Ile Ser Ile Thr Asp Pro Arg Leu Ala Arg Gln Glu Thr Val
65                  70                  75                  80

Trp Ile Ile Asp Thr Lys Ser Ser Ser Arg Ser Asn Asn Asn Ile Pro
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
        115                 120                 125

Asp Ser
    130

<210> SEQ ID NO 97
<211> LENGTH: 130
<212> TYPE: PRT
<213> ORGANISM: Artificial Sequence
<220> FEATURE:
<223> OTHER INFORMATION: E4orf6/7 amino acid sequence, Ad39-E4orf6/7

<400> SEQUENCE: 97

Met Ser Thr Glu Glu Gln Ser Ser Leu Leu Arg His His Pro Tyr Arg
1               5                   10                  15

Arg Ala Arg Leu Pro Arg Cys Glu Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Glu Asp Phe Ser Glu Asp
        50                  55                  60

Gly Phe Ile Ser Ile Thr Asp Pro Arg Leu Ala Arg Gln Glu Thr Val
65                  70                  75                  80

Trp Ile Ile Asp Thr Lys Ser Ser Ser Arg Thr Asn Gln Asn Ile Pro
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
        115                 120                 125

Asp Thr
    130

<210> SEQ ID NO 98
<211> LENGTH: 130
<212> TYPE: PRT
<213> ORGANISM: Artificial Sequence
<220> FEATURE:
<223> OTHER INFORMATION: E4orf6/7 amino acid sequence, Ad43-E4orf6/7

<400> SEQUENCE: 98

Met Ser Thr Glu Glu Gln Ser Ser Leu Leu Arg His His Pro Tyr Arg
1               5                   10                  15

Arg Ala Arg Leu Pro Arg Cys Glu Gln Glu Thr Arg Ala Ser Leu Thr
                20                  25                  30

Glu Gln His Pro Leu Leu Pro Asp Cys Asp His Ala Glu Tyr His Asn
            35                  40                  45

Thr Val Thr Leu Asp Cys Glu Pro Arg Leu Glu Asp Phe Ser Glu Asp
        50                  55                  60

Gly Phe Ile Ser Ile Thr Asp Pro Arg Leu Ala Arg Gln Glu Thr Val
65                  70                  75                  80

Trp Leu Ile Asp Thr Lys Thr Ser Ser Arg Thr Asn Gln Asn Ile Pro
```

-continued

```
                    85                    90                    95

Leu Phe Lys Ala Thr Arg Ala Glu Arg Thr Val Tyr Thr Val Lys Trp
            100                   105                   110

Ala Gly Gly Gly Arg Leu Thr Thr Arg Ala Gly Val Lys Ile Asn Lys
            115                   120                   125

Asp Thr
    130

<210> SEQ ID NO 99
<211> LENGTH: 130
<212> TYPE: PRT
<213> ORGANISM: Artificial Sequence
<220> FEATURE:
<223> OTHER INFORMATION: E4orf6/7 amino acid sequence, Ad44-E4orf6/7

<400> SEQUENCE: 99

Met Gln Thr Glu Asp Gln Ser Ser Leu Leu Arg His His Pro Tyr Arg
1                   5                    10                   15

Arg Ala Arg Leu Pro Arg Cys Glu Glu Glu Thr Arg Ala Ser Leu Thr
            20                    25                   30

Glu Gln His Pro Leu Leu Pro Asp Cys Asp His Ala Asp Tyr His Asn
        35                    40                    45

Thr Val Thr Leu Asp Cys Glu Ala Arg Leu Glu Asp Phe Ser Glu Asp
    50                    55                    60

Gly Phe Ile Ser Ile Thr Asp Pro Arg Leu Ala Arg Gln Glu Thr Val
65                    70                    75                    80

Trp Leu Ile Asp Thr Lys Ser Ser Ser Arg Thr Asn Gln Asn Ile Pro
                    85                    90                    95

Leu Phe Lys Ala Thr Arg Ala Glu Arg Thr Val Tyr Thr Val Lys Trp
            100                   105                   110

Ala Gly Gly Gly Arg Leu Thr Thr Arg Ala Gly Val Lys Ile Asn Lys
            115                   120                   125

Asp Thr
    130

<210> SEQ ID NO 100
<211> LENGTH: 130
<212> TYPE: PRT
<213> ORGANISM: Artificial Sequence
<220> FEATURE:
<223> OTHER INFORMATION: E4orf6/7 amino acid sequence, Ad45-E4orf6/7

<400> SEQUENCE: 100

Met Ser Thr Glu Glu Gln Ser Ser Leu Leu Arg His His Pro Tyr Arg
1                   5                    10                   15

Arg Ala Arg Leu Pro Arg Cys Glu Glu Glu Thr Arg Ala Ser Leu Thr
            20                    25                   30

Glu Gln His Pro Leu Leu Pro Asp Cys Asp His Ala Asp Tyr His Asn
        35                    40                    45

Thr Val Thr Leu Asp Cys Glu Ala Arg Leu Asp Asp Phe Ser Glu Asp
    50                    55                    60

Gly Phe Ile Ser Ile Thr Asp Pro Arg Leu Ala Arg Gln Glu Thr Val
65                    70                    75                    80

Trp Ile Ile Asp Pro Lys Ser Ser Ser Arg Thr Asn Gln Asn Ile Ser
                    85                    90                    95

Leu Phe Lys Ala Thr Arg Ala Glu Arg Ile Val Tyr Thr Val Lys Trp
            100                   105                   110
```

```
Ala Gly Gly Gly Arg Leu Thr Thr Arg Ala Gly Val Lys Ile Asn Lys
        115                 120                 125

Asp Thr
    130

<210> SEQ ID NO 101
<211> LENGTH: 130
<212> TYPE: PRT
<213> ORGANISM: Artificial Sequence
<220> FEATURE:
<223> OTHER INFORMATION: E4orf6/7 amino acid sequence, Ad47-E4orf6/7

<400> SEQUENCE: 101

Met Ser Thr Glu Glu Gln Ser Ser Leu Leu Arg His His Pro Tyr Arg
1               5                   10                  15

Arg Ala Arg Leu Pro Arg Ser Asp Glu Glu Thr Arg Ala Ser Leu Thr
        20                  25                  30

Glu Gln His Pro Leu Leu Pro Asp Cys Asp His Ala Asp Tyr His Asn
        35                  40                  45

Thr Val Thr Leu Asp Cys Glu Ala Arg Leu Glu Asp Phe Ser Glu Asp
    50                  55                  60

Gly Phe Ile Ser Ile Thr Asp Pro Arg Leu Ala Arg Gln Glu Thr Val
65                  70                  75                  80

Trp Ile Ile Asp Pro Lys Ser Ser Ser Arg Thr Asn Gln Asn Ile Pro
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
        115                 120                 125

Asp Thr
    130

<210> SEQ ID NO 102
<211> LENGTH: 141
<212> TYPE: PRT
<213> ORGANISM: Artificial Sequence
<220> FEATURE:
<223> OTHER INFORMATION: E4orf6/7 amino acid sequence, Ad50-E4orf6/7

<400> SEQUENCE: 102

Met Ser Gly Asn Asn Ser Ile Met Thr Arg Leu Arg Ala Arg Ser Thr
1               5                   10                  15

Ser Cys Ala Arg His His Pro Tyr Thr Arg Ala Gln Leu Pro Arg Cys
        20                  25                  30

Glu Glu Asn Glu Thr Arg Ala Ser Met Thr Glu Asp His Pro Leu Leu
        35                  40                  45

Pro Asp Cys Asp Thr Met Thr Met His Ser Met Thr Val Ile Gln Thr
    50                  55                  60

Pro Glu Ser His Pro Gln Gln Leu Asp Cys Glu Ser Ala Leu Lys Asp
65                  70                  75                  80

Tyr Pro Asp Ala Phe Leu Cys Ile Thr Asp Pro Arg Leu Ala Arg Ser
                85                  90                  95

Glu Thr Val Trp Asn Val Glu Thr Lys Thr Met Ser Ile Ser Asn Gly
            100                 105                 110

Ile Gln Met Phe Lys Ala Val Arg Gly Glu Arg Leu Val Tyr Ser Val
        115                 120                 125

Lys Trp Glu Gly Gly Gly Lys Ile Thr Thr Arg Ile Leu
        130                 135                 140
```

<210> SEQ ID NO 103
<211> LENGTH: 130
<212> TYPE: PRT
<213> ORGANISM: Artificial Sequence
<220> FEATURE:
<223> OTHER INFORMATION: E4orf6/7 amino acid sequence, Ad53-E4orf6/7

<400> SEQUENCE: 103

Met Gln Thr Glu Ile Gln Ser Ser Ser Leu Arg His His Pro Tyr Arg
1               5                   10                  15

Arg Ala Arg Leu Pro Arg Ser Asp Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Phe Ser Glu Asp
        50                  55                  60

Gly Phe Ile Ser Ile Thr Asp Pro Arg Leu Ala Arg Gln Glu Thr Val
65                  70                  75                  80

Trp Ile Ile Asn Pro Lys Ser Ser Ser Arg Thr Asn Glu Asn Phe Pro
                85                  90                  95

Leu Phe Lys Ala Thr Arg Ala Glu Arg Ile Val Tyr Thr Val Lys Trp
                100                 105                 110

Ala Gly Gly Gly Arg Met Cys Thr Arg Ala Gly Val Lys Ile Asn Lys
            115                 120                 125

Asp Thr
    130

<210> SEQ ID NO 104
<211> LENGTH: 130
<212> TYPE: PRT
<213> ORGANISM: Artificial Sequence
<220> FEATURE:
<223> OTHER INFORMATION: E4orf6/7 amino acid sequence, Ad54-E4orf6/7

<400> SEQUENCE: 104

Met Ser Thr Glu Glu Gln Ser Thr Leu Leu Arg His His Pro Tyr Arg
1               5                   10                  15

Arg Ala Arg Leu Ser Arg Tyr Asp Lys Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Leu Ser Lys Asp
        50                  55                  60

Gly Phe Ile Ser Ile Thr Asp Pro Arg Leu Ala Arg Gln Glu Thr Val
65                  70                  75                  80

Trp Ile Ile Asp Pro Lys Ser Ser Ser Arg Thr Asn Glu Asn Phe Pro
                85                  90                  95

Leu Phe Lys Ala Thr Arg Thr Glu Arg Ile Val Tyr Thr Val Lys Trp
                100                 105                 110

Ala Gly Gly Gly Arg Met Cys Thr Arg Ala Gly Val Lys Ile Asn Lys
            115                 120                 125

Asp Thr
    130

<210> SEQ ID NO 105
<211> LENGTH: 130
<212> TYPE: PRT

```
<213> ORGANISM: Artificial Sequence
<220> FEATURE:
<223> OTHER INFORMATION: E4orf6/7 amino acid sequence, Ad58-E4orf6/7

<400> SEQUENCE: 105

Met Gln Thr Glu Ile Gln Ser Ser Leu Leu Arg His His Pro Tyr Arg
1               5                   10                  15

Arg Ala Arg Leu Pro Arg Ser Asp Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Phe Ser Glu Asp
        50                  55                  60

Gly Phe Ile Ser Ile Thr Asp Pro Arg Leu Ala Arg Gln Glu Thr Val
65                  70                  75                  80

Trp Leu Ile Asp Thr Lys Ser Ser Ser Arg Ala Asn Gln Asn Ile Pro
                    85                  90                  95

Leu Phe Lys Ala Thr Arg Ala Glu Arg Ile Val Tyr Thr Val Lys Trp
                100                 105                 110

Ala Gly Gly Gly Arg Leu Thr Thr Arg Ala Gly Val Lys Ile Asn Lys
            115                 120                 125

Asp Thr
    130

<210> SEQ ID NO 106
<211> LENGTH: 130
<212> TYPE: PRT
<213> ORGANISM: Artificial Sequence
<220> FEATURE:
<223> OTHER INFORMATION: E4orf6/7 amino acid sequence, Ad64-E4orf6/7

<400> SEQUENCE: 106

Met Gln Thr Glu Ile Gln Ser Ser Ser Leu Arg His His Pro Tyr Arg
1               5                   10                  15

Arg Ala Arg Leu Pro Arg Ser Asp Glu Glu Thr Arg Ala Ser Leu Thr
                20                  25                  30

Glu Gln His Pro Leu Leu Pro Asp Cys Asp His Ala Asp Tyr His Asn
            35                  40                  45

Thr Val Thr Leu Asp Cys Glu Ala Arg Leu Asp Asp Phe Ser Glu Asp
        50                  55                  60

Gly Phe Ile Ser Ile Thr Asp Pro Arg Leu Ala Arg Gln Glu Thr Val
65                  70                  75                  80

Trp Ile Ile Asp Pro Lys Ser Asn Ser Arg Thr Asn Glu Asn Ile Ser
                    85                  90                  95

Leu Phe Lys Ala Thr Arg Ala Glu Arg Thr Val Tyr Thr Val Lys Trp
                100                 105                 110

Ala Gly Gly Gly Arg Leu Ser Thr Arg Ala Gly Val Lys Ile Asn Lys
            115                 120                 125

Asp Thr
    130

<210> SEQ ID NO 107
<211> LENGTH: 130
<212> TYPE: PRT
<213> ORGANISM: Artificial Sequence
<220> FEATURE:
<223> OTHER INFORMATION: E4orf6/7 amino acid sequence, Ad69-E4orf6/7

<400> SEQUENCE: 107
```

```
Met Gln Thr Glu Ile Gln Ser Ser Ser Leu Arg His His Pro Tyr Arg
1               5                   10                  15

Arg Ala Arg Leu Pro Arg Ser Asp Glu Glu Thr Arg Ala Ser Leu Thr
            20                  25                  30

Glu Gln His Pro Leu Leu Pro Asp Cys Asp His Ala Asp Tyr His Asn
        35                  40                  45

Thr Val Thr Leu Asp Cys Glu Ala Arg Leu Asp Asp Phe Ser Glu Asp
    50                  55                  60

Gly Phe Ile Ser Ile Thr Asp Pro Arg Leu Ala Arg Gln Glu Thr Val
65                  70                  75                  80

Trp Ile Ile Asp Pro Lys Ser Ser Ser Arg Thr Asn Gln Asn Ile Ser
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
        115                 120                 125

Asp Thr
    130
```

<210> SEQ ID NO 108
<211> LENGTH: 2607
<212> TYPE: DNA
<213> ORGANISM: Artificial Sequence
<220> FEATURE:
<223> OTHER INFORMATION: Adeno-associated virus (AAV) vector sequence
<220> FEATURE:
<221> NAME/KEY: misc_feature
<222> LOCATION: (259)..(260)
<223> OTHER INFORMATION: n is a, c, g, or t
<220> FEATURE:
<221> NAME/KEY: misc_feature
<222> LOCATION: (262)..(264)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (268)..(271)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (276)..(278)
<223> OTHER INFORMATION: n is a, c, g, or t

<400> SEQUENCE: 108

```
ccactgagaa ccgggcaggt cacgcatccc ccccttccct cccacccct gccaagctct        60 ccctcccagg atcctctctg gctccatcgt aagcaaacct tagaggttct ggcaaggaga       120
gagatggctc caggaaatgg gggtgtgtca ccagataagg aatctgccta acaggaggtg       180
ggggttagac ccaatatcag gagactagga aggaggaggc ctaaggatgg ggcttttctg       240
tcaccaatcc tgtccctann ynnntntnnn nrtndnnnhh ccatagagcc caccgcatcc       300
ccagcatgcc tgctattgtc ttcccaatcc tcccccttgc tgtcctgccc cacccacc         360 cccagaatag aatgacacct actcagacaa tgcgatgcaa tttcctcatt ttattaggaa       420
aggacagtgg gagtggcacc ttccagggtc aaggaaggca cggggagggg gcaaacaaca       480
gatggctggc aactagaagg cacagtcgag gctgatcagc gggtttaaac gggccctcta       540
```

-continued

```
gactcgacgc ggccgcttta cttgtacagc tcgtccatgc cgagagtgat cccggcggcg      600
gtcacgaact ccagcaggac catgtgatcg cgcttctcgt tggggtcttt gctcagggcg      660
gactgggtgc tcaggtagtg gttgtcgggc agcagcacgg ggccgtcgcc gatgggggtg      720
ttctgctggt agtggtcggc gagctgcacg ctgccgtcct cgatgttgtg gcggatcttg      780
aagttcacct tgatgccgtt cttctgcttg tcggccatga tatagacgtt gtggctgttg      840
tagttgtact ccagcttgtg ccccaggatg ttgccgtcct ccttgaagtc gatgcccttc      900
agctcgatgc ggttcaccag ggtgtcgccc tcgaacttca cctcggcgcg ggtcttgtag      960
ttgccgtcgt ccttgaagaa gatggtgcgc tcctggacgt agccttcggg catggcggac     1020
ttgaagaagt cgtgctgctt catgtggtcg gggtagcggc tgaagcactg cacgccgtag     1080
gtcagggtgg tcacgagggt gggccagggc acgggcagct tgccggtggt gcagatgaac     1140
ttcagggtca gcttgccgta ggtggcatcg ccctcgccct cgccggacac gctgaacttg     1200
tggccgttta cgtcgccgtc cagctcgacc aggatgggca ccaccccggt gaacagctcc     1260
tcgcccttgc tcaccatggt ggcgaccggt ggggagagag gtcggtgatt cggtcaacga     1320
gggagccgac tgccgacgtg cgctccggag gcttgcagaa tgcggaacac cgcgcgggca     1380
ggaacagggc ccacactacc gccccacacc ccgcctcccg caccgcccct tcccggccgc     1440
tgctctcggc gcgccctgct gagcagccgc tattggccac agcccatcgc ggtcggcgcg     1500
ctgccattgc tccctggcgc tgtccgtctg cgagggtact agtgagacgt gcggcttccg     1560
tttgtcacgt ccggcacgcc gcgaaccgca aggaaccttc ccgacttagg ggcggagcag     1620
gaagcgtcgc cggggggccc acaagggtag cggcgaagat ccgggtgacg ctgcgaacgg     1680
acgtgaagaa tgtgcgagac ccagggtcgg cgccgctgcg tttcccggaa ccacgcccag     1740
agcagccgcg tccctgcgca aacccagggc tgccttggaa aaggcgcaac cccaaccccg     1800
tggaagcttg cgtggggtgg aggggacaga taaaagtacc cagaaccaga gccacattaa     1860
ccggccctgg gaatataagg tggtcccagc tcggggacac aggatccctg gaggcagcaa     1920
acatgctgtc ctgaagtgga catagggggcc cgggttggag gaagaagact agctgagctc     1980
tcggacccct ggaagatgcc atgacagggg gctggaagag ctagcacaga ctagagaggt     2040
aaggggggta ggggagctgc ccaaatgaaa ggagtgagag gtgacccgaa tccacaggag     2100 aacgggtgt ccaggcaaag aaagcaagag gatggagagg tggctaaagc cagggagacg      2160
gggtactttg gggttgtcca gaaaaacggt gatgatgcag gcctacaaga aggggaggcg     2220
ggacgcaagg gagacatccg tcggagaagg ccatcctaag aaacgagaga tggcacaggc     2280
cccagaagga gaaggaaaag ggaacccagc gagtgaagac ggcatggggt tgggtgaggg     2340
aggagagatg cccggagagg acccagacac ggggaggatc cgctcagagg acatcacgtg     2400
gtgcagcgcc gagaaggaag tgctccggaa agagcatcct tgggcagcaa cacagcagag     2460
agcaagggga agagggagtg gaggaagacg gaacctgaag gaggcggcag ggaaggatct     2520
gggccagccg tagaggtgac ccaggccaca agctgcagac agaaagcggc acaggcccag     2580
gggagagaat gctggtcaga gaaagca                                        2607
```

```
<210> SEQ ID NO 109
<211> LENGTH: 24
<212> TYPE: DNA
<213> ORGANISM: Artificial Sequence
<220> FEATURE:
<223> OTHER INFORMATION: ChrX-chr14 translocation ddPCR FW primer
```

<400> SEQUENCE: 109
gtggtgacca ccttaatcca gtga                                          24

<210> SEQ ID NO 110
<211> LENGTH: 28
<212> TYPE: DNA
<213> ORGANISM: Artificial Sequence
<220> FEATURE:
<223> OTHER INFORMATION: ChrX-chr14 translocation ddPCR probe

<400> SEQUENCE: 110
atgaaggcag ggagggaaag agaaatga                                      28

<210> SEQ ID NO 111
<211> LENGTH: 28
<212> TYPE: DNA
<213> ORGANISM: Artificial Sequence
<220> FEATURE:
<223> OTHER INFORMATION: ssODN amplification primer, Bar AAVS1 sense

<400> SEQUENCE: 111
agactaggaa ggaggaggcc taaggatg                                      28

<210> SEQ ID NO 112
<211> LENGTH: 24
<212> TYPE: DNA
<213> ORGANISM: Artificial Sequence
<220> FEATURE:
<223> OTHER INFORMATION: ssODN amplification primer, Bar AAVS1 antisense

<400> SEQUENCE: 112
acaatagcag gcatgctggg gatg                                          24

<210> SEQ ID NO 113
<211> LENGTH: 118
<212> TYPE: DNA
<213> ORGANISM: Artificial Sequence
<220> FEATURE:
<223> OTHER INFORMATION: ssODN sequence
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(63)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (67)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (75)..(77)
<223> OTHER INFORMATION: n is a, c, g, or t

<400> SEQUENCE: 113
agactaggaa ggaggaggcc taaggatggg gcttttctgt caccaatcct gtccctanny     60
nnntntnnnn rtndnnnhhc catagagccc accgcatccc cagcatgcct gctattgt      118

-continued

```
<210> SEQ ID NO 114
<211> LENGTH: 22
<212> TYPE: DNA
<213> ORGANISM: Artificial Sequence
<220> FEATURE:
<223> OTHER INFORMATION: barcode sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 114
nnynnntntn nnnrtndnnn hh                                              22
```